US012240843B2

(12) United States Patent
Lian et al.

(10) Patent No.: US 12,240,843 B2
(45) Date of Patent: Mar. 4, 2025

(54) SUBSTITUTED 1,2,4-TRIAZOLO[4,3-A]PYRIDINE DERIVATIVE AND PREPARATION METHOD, HERBICIDAL COMPOSITION AND APPLICATION THEREOF

(71) Applicant: Qingdao Kingagroot Chemical Compound Co., Ltd., Qingdao (CN)

(72) Inventors: Lei Lian, Qingdao (CN); Xuegang Peng, Qingdao (CN); Rongbao Hua, Qingdao (CN); De Zhao, Qingdao (CN); Qi Cui, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 425 days.

(21) Appl. No.: 17/414,501

(22) PCT Filed: Jul. 17, 2020

(86) PCT No.: PCT/CN2020/102660
§ 371 (c)(1),
(2) Date: Jun. 16, 2021

(87) PCT Pub. No.: WO2021/008607
PCT Pub. Date: Jan. 21, 2021

(65) Prior Publication Data
US 2023/0075221 A1    Mar. 9, 2023

(30) Foreign Application Priority Data
Jul. 18, 2019   (CN) .......................... 201910650905.6

(51) Int. Cl.
*C07D 471/04*   (2006.01)
*A01N 43/90*   (2006.01)

(52) U.S. Cl.
CPC ........... *C07D 471/04* (2013.01); *A01N 43/90* (2013.01)

(58) Field of Classification Search
CPC .................................................. C07D 471/04
See application file for complete search history.

(56) References Cited

U.S. PATENT DOCUMENTS

| 5,013,659 A | 5/1991 | Bedbrook et al. | |
| 2010/0035756 A1* | 2/2010 | Luthy | A01N 43/90 504/246 |
| 2023/0075221 A1* | 3/2023 | Lian | C07D 471/04 |

FOREIGN PATENT DOCUMENTS

| CN | 1053792 A | 8/1991 |
| CN | 101778832 A | 7/2010 |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

(Continued)

*Primary Examiner* — Nizal S Chandrakumar
(74) *Attorney, Agent, or Firm* — FINNEGAN, HENDERSON, FARABOW, GARRETT & DUNNER LLP

(57) ABSTRACT

The invention relates to the field of pesticide technology, and in particular a type of substituted 1,2,4-triazolo[4,3-a]pyridine derivatives, preparation method, herbicidal composition and use thereof. A substituted 1,2,4-triazolo[4,3-a] pyridine derivative, as shown in Formula I:

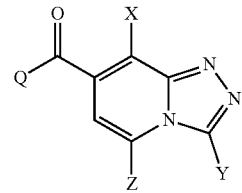

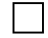

wherein, Q represents

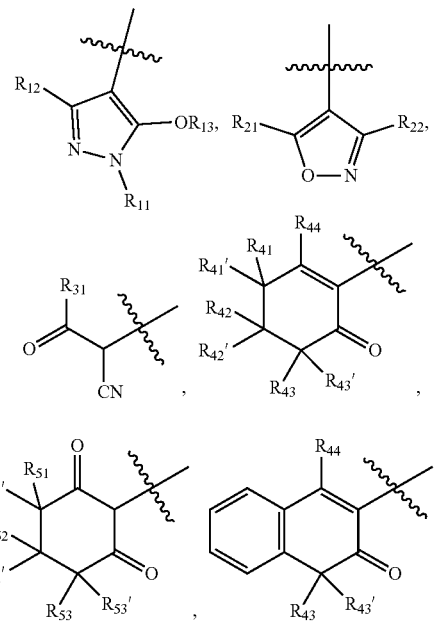

(Continued)

-continued

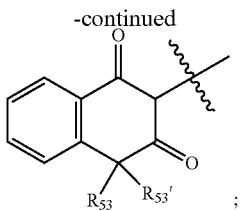

X and Z each independently represent hydrogen, halogen, cyano or nitro, etc.; Y represents hydrogen, halogen, formyl, cyanoalkyl; or an alkyl, alkenyl or alkynyl, each of which contains or does not contain a halogen, etc. The compound and its composition have excellent herbicidal activity and higher crop safety, especially good selectivity for key crops such as rice.

9 Claims, No Drawings

(56) References Cited

FOREIGN PATENT DOCUMENTS

| CN | 102870791 | A |   | 1/2013 |
|---|---|---|---|---|
| EP | 0131624 | A1 |   | 1/1985 |
| EP | 0142924 | A2 |   | 5/1985 |
| EP | 0193259 | A1 |   | 9/1986 |
| EP | 0221044 | A1 |   | 5/1987 |
| EP | 0242236 | A1 |   | 10/1987 |
| EP | 0242246 | A1 |   | 10/1987 |
| EP | 0257993 | A2 |   | 3/1988 |
| EP | 20100035756 |   | * | 1/2008 |
| JP | 2000178268 | A |   | 6/2000 |
| JP | 2002544132 | A |   | 12/2002 |
| WO | WO 91/13972 | A1 |   | 9/1991 |
| WO | WO 91/19806 | A1 |   | 12/1991 |
| WO | WO 92/00377 | A1 |   | 1/1992 |
| WO | WO 92/11376 | A1 |   | 7/1992 |
| WO | WO 92/14827 | A1 |   | 9/1992 |
| WO | WO 00/15615 | A1 |   | 3/2000 |
| WO | WO 2008/006540 | A1 |   | 1/2008 |

OTHER PUBLICATIONS

"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/ZREGISTRY (CAS REGISTRYTM) Sep. 2016 2 pages.*
K. Naumann, Influence of chlorine substituents on biological activity of chemicals: a review, *Pest Management Science*, 56(1), pp. 3-21 (2000).
P. Christou, Transformation Technology, *Trends in Plant Science*, 1:423-431 (1996).
H. Braun et al., The General Mitochondrial Processing Peptidase from Potato Is an Integral Part of Cytochrome C Reductase of The Respiratory Chain, *EMBO J.* 11:3219-3227 (1992).
F. Wolter et al., Rbcs Genes in Solanum Tuberosum: Conservation of Transit Peptide and Exon Shuffling During Evolution, *Proc. Natl. Acad. Sci. USA*, 85:846-850 (1988).
U. Sonnewald et al., Transgenic Tobacco Plants Expressing Yeast-Derived Invertase in Either the Cytosol, Vacuole or Apoplast: A Powerful Tool for Studying Sucrose Metabolism and Sink/Source Interactions, *Plant J.* 1:95-106 (1991).
International Search Report and Written Opinion of counterpart International Application No. PCT/CN2020/102660, dated Oct. 21, 2020.

* cited by examiner

SUBSTITUTED 1,2,4-TRIAZOLO[4,3-A]PYRIDINE DERIVATIVE AND PREPARATION METHOD, HERBICIDAL COMPOSITION AND APPLICATION THEREOF

CROSS-REFERENCE TO RELATED APPLICATION

This application is a national stage filing under 35 U.S.C. § 371 of International Application No. PCT/CN2020/102660, filed Jul. 17, 2020, which is incorporated herein by reference in its entirety.

TECHNICAL FIELD

The invention relates to the field of pesticide technology, and in particular a type of substituted 1,2,4-triazolo[4,3-a]pyridine derivatives, preparation method, herbicidal composition and use thereof.

TECHNICAL BACKGROUND

Weed control is one of the most important links in the course of achieving high-efficiency agriculture. Various herbicides are available in the market, for example, patent WO2008006540A1 discloses that the triazolopyridine derivative represented by the following general formula (I) is used as a herbicide

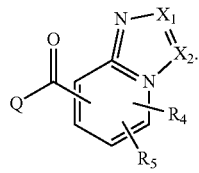

(I)

However, there is still a need to develop new herbicides with high efficacy, safety, economics and different modes of action.

INVENTION CONTENTS

Based on this, the present invention provides a type of substituted 1,2,4-triazolo[4,3-a]pyridine derivatives, preparation method, herbicidal composition and use thereof. The compound and its composition have excellent herbicidal activity and higher crop safety, especially good selectivity for key crops such as rice.

The technical solution adopted by the invention is as follows:

A substituted 1,2,4-triazolo[4,3-a]pyridine derivative, as shown in Formula I:

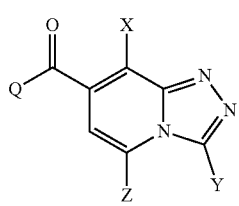

I wherein, Q represents

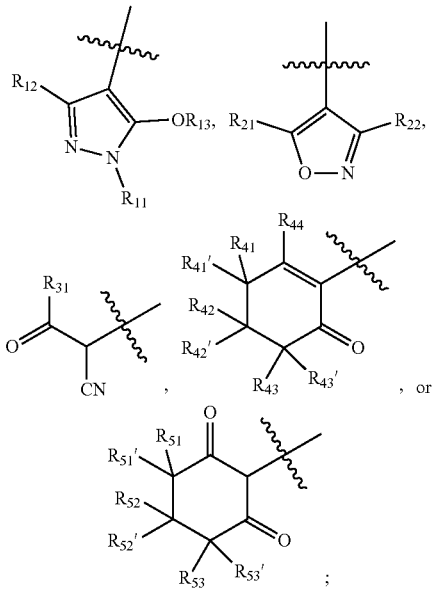

$R_{11}$ represents an alkyl, a halogenated alkyl or an aryl;

$R_{12}$ represents hydrogen; an alkyl, alkenyl or alkynyl, each of which contains or does not contain a halogen; a cycloalkyl, which is unsubstituted or substituted with at least one group selected from an alkyl, cyano and halogen;

$R_{21}$ and $R_{22}$ each independently represent hydrogen; an alkyl, alkenyl, alkynyl, alkoxy, alkylthio, alkylsulfoxide, alkylsulfonyl, alkoxyalkyl, alkylcarbonyl or alkoxycarbonyl, each of which contains or does not contain a halogen; a cycloalkyl, which is unsubstituted or substituted with at least one group selected from an alkyl, cyano and halogen; aryl or heterocyclyl;

$R_{31}$ represents hydrogen; an alkyl, alkenyl or alkynyl, each of which contains or does not contain a halogen; a cycloalkyl, which is unsubstituted or substituted with at least one group selected from an alkyl, cyano and halogen; aryl or heterocyclyl;

$R_{41}$, $R_{41}'$, $R_{42}$, $R_{42}'$, $R_{43}$ and $R_{43}'$ each independently represent hydrogen, alkyl, alkenyl, alkynyl, cycloalkyl; alkoxy, alkylthio, alkoxyalkyl, alkylthioalkyl, alkylcarbonyl, alkoxycarbonyl, aryl or heterocyclyl; or two of $R_{41}$, $R_{41}'$, $R_{42}$, $R_{42}'$, $R_{43}$ and $R_{43}'$ that are on different carbon atoms connect to form $CH_2$, $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$; or two of $R_{41}$, $R_{41}'$, $R_{42}$, $R_{42}'$, $R_{43}$ and $R_{43}'$ that are on the same carbon atom connect to form $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$;

$R_{44}$ is selected from $-OR_{45}$ and $-SR_{45}$;

$R_{51}$, $R_{51}'$, $R_{52}$, $R_{52}'$, $R_{53}$ and $R_{53}'$ each independently represent hydrogen, alkyl, alkenyl, alkynyl, cycloalkyl, alkoxy, alkylthio, alkoxyalkyl, alkylthioalkyl, alkylcarbonyl, alkoxycarbonyl, aryl or a heterocyclyl; or two of $R_{51}$, $R_{51}'$, $R_{52}$, $R_{52}'$, $R_{53}$ and $R_{53}'$ that are on different carbon atoms connect to form $CH_2$, $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$; or two of $R_{51}$, $R_{51}'$, $R_{52}$, $R_{52}'$, $R_{53}$ and $R_{53}'$ that are on the same carbon atom connect to form (CH$_2$)$_2$, (CH$_2$)$_3$, (CH$_2$)$_4$, (CH$_2$)$_5$, (CH$_2$)$_6$, O, O(CH$_2$)$_2$O, O(CH$_2$)$_3$O, O(CH$_2$)$_4$O, S(CH$_2$)$_2$S or S(CH$_2$)$_3$S;

R$_{13}$ and R$_{45}$ each independently represent hydrogen, —R$_{61}$, —S(O)$_n$R$_{62}$, —CH$_2$R$_{63}$, —(C=O)R$_{64}$, —PO(OR$_{65}$)$_2$ or —Si(OR$_{66}$)$_3$, wherein, R$_{61}$ represents metal ion; ammonium ion; an alkyl, alkenyl or alkynyl, each of which contains or does not contain a halogen; aryl or heterocyclyl;

R$_{62}$ represents an alkyl, alkenyl or alkynyl, each of which contains or does not contain a halogen; aryl or heterocyclyl; n represents 1, 2 or 3;

R$_{63}$ represents halogen; nitro; cyano; an alkyl, alkenyl, alkynyl, alkoxy, alkoxycarbonyl or alkylthio, each of which contains or does not contain a halogen; a cycloalkyl, which is unsubstituted or substituted with at least one group selected from alkyl, cyano and halogen; an amino or aminocarbonyl, each of which is unsubstituted or substituted with at least one group selected from alkyl, alkylcarbonyl and halogenated alkyl; aryl; heterocyclyl; arylcarbonyl or heterocyclylcarbonyl;

R$_{64}$ represents halogen; nitro; cyano; an alkyl, alkenyl, alkynyl, alkoxy, alkylthio, alkoxyalkyl or alkylthioalkyl, each of which contains or does not contain a halogen; an amino or aminoalkyl, each of which is unsubstituted or substituted with at least one group selected from alkyl, alkylcarbonyl and halogenated alkyl; aryl; heterocyclyl; arylalkyl; heterocyclylalkyl; aryloxy; heterocyclyloxy; aryloxyalkyl or heterocyclyloxyalkyl;

R$_{65}$ and R$_{66}$ each independently represent hydrogen, alkyl, halogenated alkyl, cycloalkyl, aryl or heterocyclyl;

X and Z each independently represent hydrogen; halogen; cyano; nitro; —NR$_1$R$_2$; an alkenyl, alkynyl, cycloalkyl, alkoxy, alkylthio, alkylsulfoxide, alkylsulfonyl, alkoxyalkyl, alkylthioalkyl, alkylsulfoxyalkyl or alkylsulfonylalkyl, each of which contains or does not contain a halogen;

R$_1$ and R$_2$ each independently represent hydrogen, alkyl or halogenated alkyl, or —NR$_1$R$_2$ represents a 5- to 8-membered lactam group;

Y represents hydrogen; halogen; formyl; an alkyl, alkenyl, alkynyl, alkoxy, alkylthio, alkylsulfoxide, alkylsulfonyl, alkylacyl, cyanoalkyl, alkoxyalkyl, alkylthioalkyl, alkylsulfoxyalkyl or alkylsulfonylalkyl, each of which contains or does not contain a halogen; an aminoalkyl or aminoacyl, each of which is unsubstituted or substituted with at least one group selected from alkyl, alkenyl, alkynyl, alkylacyl, halogenated alkyl, halogenated alkenyl, halogenated alkynyl, halogenated alkylacyl and aryl; a cycloalkyl, cycloalkylalkyl, cycloalkenyl or cycloalkenylalkyl, each of which is unsubstituted or substituted with at least one group selected from alkyl, cyano and halogen; aryl; heterocyclyl; arylalkyl or heterocyclylalkyl;

the aryl or heterocyclyl is substituted or unsubstituted, respectively, and said "substituted" refers to being substituted with at least one group selected from halogen; nitro; cyano; thiocyano; cyanoalkyl; mercapto; hydroxy; hydroxyalkyl; carboxyl; formyl; azido; trialkylsilyl; dialkylphosphono; a heterocyclyl, heterocyclylalkyl, aryl or arylalkyl, each of which is unsubstituted or substituted with at least one group selected from alkyl, halogenated alkyl, alkylsulfonyl, alkylacyl, alkylacyloxy, alkoxyacyl, halogen, alkoxy, alkylthio, cyano, amino and alkylamino; an alkyl, alkenyl, alkynyl, cycloalkyl, cycloalkenyl, cycloalkylalkyl, cycloalkenylalkyl, alkyl-substituted cycloalkyl, OR", SR", -alkyl-OR", —O-alkyl-OR", -alkyl-SR", COR", -alkyl-COR", —O-alkyl-COR", COOR", -alkyl-COOR", —O-alkyl-COOR", COSR", SOR", SO$_2$R", —O—SO$_2$R", -alkyl-SO$_2$R", OCOR", -alkyl-OCOR" or SCOR", each of which contains or does not contain a halogen; an amino, aminocarbonyl, aminocarbonylalkyl or aminosulfonyl, each of which is unsubstituted or substituted with 1 or 2 groups selected from R", COR", COOR", SO$_2$R", -alkyl-SO$_2$R" and OR", wherein each of the group contains or does not contain a halogen; or forming a fused ring by connecting any two adjacent carbon atoms in the ring with the group —CH$_2$CH$_2$CH$_2$—, —OCH$_2$CH$_2$—, —OCH$_2$O—, —OCH$_2$CH$_2$O— or —CH=CH—CH=CH—;

R" each independently represents alkyl; alkenyl; alkynyl; cycloalkyl; cycloalkylalkyl; cycloalkenyl; cycloalkenylalkyl; or a heterocyclyl, heterocyclylalkyl, aryl or arylalkyl, each of which is unsubstituted or substituted.

In another embodiment, wherein, Q represents

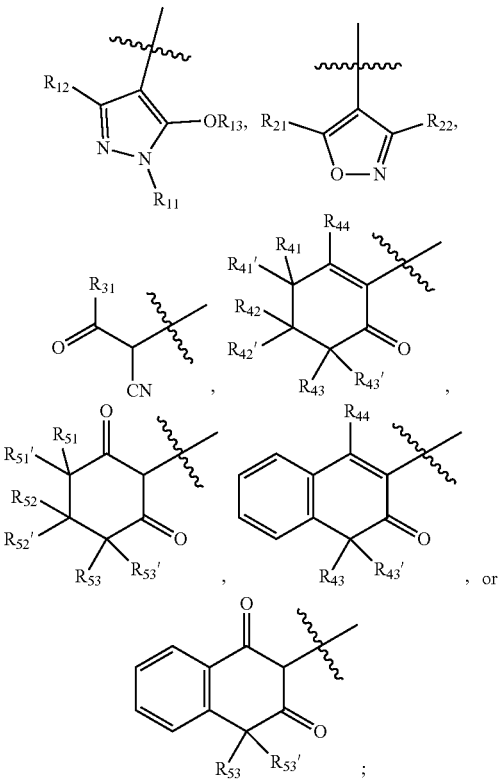

R$_{11}$ represents an alkyl, a halogenated alkyl or an aryl;

R$_{12}$ represents hydrogen; an alkyl, alkenyl or alkynyl, each of which contains or does not contain a halogen; a cycloalkyl, which is unsubstituted or substituted with at least one group selected from an alkyl, cyano and halogen;

R$_{21}$ and R$_{22}$ each independently represent hydrogen; an alkyl, alkenyl, alkynyl, alkoxy, alkylthio, alkylsulfoxide, alkylsulfonyl, alkoxyalkyl, alkylcarbonyl or alkoxycarbonyl, each of which contains or does not contain a halogen; a cycloalkyl, which is unsubstituted or substituted with at least one group selected from an alkyl, cyano and halogen; aryl or heterocyclyl;

$R_{31}$ represents hydrogen; an alkyl, alkenyl or alkynyl, each of which contains or does not contain a halogen; a cycloalkyl, which is unsubstituted or substituted with at least one group selected from an alkyl, cyano and halogen; aryl or heterocyclyl;

$R_{41}$, $R_{41}'$, $R_{42}$, $R_{42}'$, $R_{43}$ and $R_{43}'$ each independently represent hydrogen; an alkyl, alkenyl, alkynyl or cycloalkyl, each of which contains or does not contain a halogen; alkoxy; alkylthio; alkoxyalkyl; alkylthioalkyl; alkylcarbonyl; alkoxycarbonyl; aryl or heterocyclyl; or two of $R_{41}$, $R_{41}'$, $R_{42}$, $R_{42}'$, $R_{43}$ and $R_{43}'$ that are on different carbon atoms connect to form $CH_2$, $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$; or two of $R_{41}$, $R_{41}'$, $R_{42}$, $R_{42}'$, $R_{43}$ and $R_{43}'$ that are on the same carbon atom connect to form $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$;

$R_{44}$ is selected from $-OR_{45}$ and $-SR_{45}$;

$R_{51}$, $R_{51}'$, $R_{52}$, $R_{52}'$, $R_{53}$ and $R_{53}'$ each independently represent hydrogen; an alkyl, alkenyl, alkynyl or cycloalkyl, each of which contains or does not contain a halogen; alkoxy; alkylthio; alkoxyalkyl; alkylthioalkyl; alkylcarbonyl; alkoxycarbonyl; aryl or a heterocyclyl; or two of $R_{51}$, $R_{51}'$, $R_{52}$, $R_{52}'$, $R_{53}$ and $R_{53}'$ that are on different carbon atoms connect to form $CH_2$, $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$; or two of $R_{51}$, $R_{51}'$, $R_{52}$, $R_{52}'$, $R_{53}$ and $R_{53}'$ that are on the same carbon atom connect to form $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$;

$R_{13}$ and $R_{45}$ each independently represent hydrogen, $-R_{61}$, $-S(O)_nR_{62}$, $-CH_2R_{63}$, $-(C=O)R_{64}$, $-PO(OR_{65})_2$ or $-Si(OR_{66})_3$, wherein, $R_{61}$ represents metal ion; ammonium ion; an alkyl, alkenyl or alkynyl, each of which contains or does not contain a halogen; aryl or heterocyclyl;

$R_{62}$ represents an alkyl, alkenyl or alkynyl, each of which contains or does not contain a halogen; aryl or heterocyclyl; n represents 1, 2 or 3;

$R_{63}$ represents halogen; nitro; cyano; an alkyl, alkenyl, alkynyl, alkoxy, alkoxycarbonyl or alkylthio, each of which contains or does not contain a halogen; a cycloalkyl, which is unsubstituted or substituted with at least one group selected from alkyl, cyano and halogen; an amino or aminocarbonyl, each of which is unsubstituted or substituted with at least one group selected from alkyl, alkylcarbonyl and halogenated alkyl; aryl; heterocyclyl; arylcarbonyl or heterocyclylcarbonyl;

$R_{64}$ represents halogen; nitro; cyano; an alkyl, alkenyl, alkynyl, alkoxy, alkylthio, alkoxyalkyl or alkylthioalkyl, each of which contains or does not contain a halogen; an amino or aminoalkyl, each of which is unsubstituted or substituted with at least one group selected from alkyl, alkylcarbonyl and halogenated alkyl; aryl; heterocyclyl; arylalkyl; heterocyclylalkyl; aryloxy; heterocyclyloxy; aryloxyalkyl or heterocyclyloxyalkyl;

$R_{65}$ and $R_{66}$ each independently represent hydrogen, alkyl, halogenated alkyl, cycloalkyl, aryl or heterocyclyl;

X and Z each independently represent hydrogen; halogen; cyano; nitro; $-NR_1R_2$; an alkenyl, alkynyl, cycloalkyl, alkoxy, alkylthio, alkylsulfoxide, alkylsulfonyl, alkoxyalkyl, alkylthioalkyl, alkylsulfoxyalkyl or alkylsulfonylalkyl, each of which contains or does not contain a halogen;

$R_1$ and $R_2$ each independently represent hydrogen, alkyl or halogenated alkyl, or $-NR_1R_2$ represents a 5- to 8-membered lactam group;

Y represents hydrogen; halogen; formyl; cyanoalkyl; an alkyl, alkenyl or alkynyl, each of which contains or does not contain a halogen; $-OR_3$; $-OCOR_4$; $-COR_4$; $-SR_3$; $-SOR_4$; $-SO_2R_4$; -alkyl-$OR_3$; -alkyl-$OCOR_4$; -alkyl-$COR_4$; -alkyl-$SR_3$; -alkyl-$SOR_4$; -alkyl-$SO_2R_4$; an amino, aminoalkyl or aminoacyl, each of which is unsubstituted or substituted with at least one group selected from alkyl, alkenyl, alkynyl, alkylacyl, halogenated alkyl, halogenated alkenyl, halogenated alkynyl, halogenated alkylacyl and aryl; a cycloalkyl, cycloalkylalkyl, cycloalkenyl or cycloalkenylalkyl, each of which is unsubstituted or substituted with at least one group selected from alkyl, cyano and halogen; aryl; heterocyclyl; arylalkyl or heterocyclylalkyl;

$R_3$ each independently represents hydrogen; metal ion; an alkyl, alkenyl, alkynyl or cycloalkyl, each of which contains or does not contain a halogen;

$R_4$ each independently represents an alkyl, alkenyl, alkynyl or cycloalkyl, each of which contains or does not contain a halogen;

the aryl or heterocyclyl is substituted or unsubstituted, respectively, and said "substituted" refers to being substituted with at least one group selected from halogen; nitro; cyano; thiocyano; cyanoalkyl; mercapto; hydroxy; hydroxyalkyl; carboxyl; formyl; azido; trialkylsilyl; dialkylphosphono; a heterocyclyl, heterocyclylalkyl, aryl or arylalkyl, each of which is unsubstituted or substituted with at least one group selected from alkyl, halogenated alkyl, alkylsulfonyl, alkylacyl, alkylacyloxy, alkoxyacyl, halogen, alkoxy, alkylthio, cyano, amino and alkylamino; an alkyl, alkenyl, alkynyl, cycloalkyl, cycloalkenyl, cycloalkylalkyl, cycloalkenylalkyl, alkyl-substituted cycloalkyl, OR", SR", -alkyl-OR", $-$O-alkyl-OR", -alkyl-SR", COR", -alkyl-COR", $-$O-alkyl-COR", COOR", -alkyl-COOR", $-$O-alkyl-COOR", COSR", SOR", $SO_2R''$, $-SO_2R''$, -alkyl-$SO_2R''$, OCOR", -alkyl-OCOR" or SCOR", each of which contains or does not contain a halogen; an amino, aminocarbonyl, aminocarbonylalkyl or aminosulfonyl, each of which is unsubstituted or substituted with 1 or 2 groups selected from R", COR", COOR", $SO_2R''$, -alkyl-$SO_2R''$ and OR", wherein each of the group contains or does not contain a halogen; or forming a fused ring by connecting any two adjacent carbon atoms in the ring with the group $-CH_2CH_2CH_2-$, $-OCH_2CH_2-$, $-OCH_2O-$, $-OCH_2CH_2O-$ or $-CH=CH-CH=CH-$;

R" each independently represents alkyl; alkenyl; alkynyl; cycloalkyl; cycloalkylalkyl; cycloalkenyl; cycloalkenylalkyl; or a heterocyclyl, heterocyclylalkyl, aryl or arylalkyl, each of which is unsubstituted or substituted.

Preferably, $R_{11}$ represents a $C_1$-$C_8$ alkyl, a halogenated $C_1$-$C_8$ alkyl or an aryl;

$R_{12}$ represents hydrogen; a $C_1$-$C_8$ alkyl, $C_2$-$C_8$ alkenyl or $C_2$-$C_8$ alkynyl, each of which contains or does not contain a halogen; a $C_3$-$C_8$ cycloalkyl, which is unsubstituted or substituted with 1 to 3 groups selected from $C_1$-$C_8$ alkyl, cyano and halogen;

$R_{21}$ and $R_{22}$ each independently represent hydrogen; a $C_1$-$C_8$ alkyl, $C_2$-$C_8$ alkenyl, $C_2$-$C_8$ alkynyl, $C_1$-$C_8$ alkoxy, $C_1$-$C_8$ alkylthio, $C_1$-$C_8$ alkylsulfoxide, $C_1$-$C_8$ alkylsulfonyl, $C_1$-$C_8$ alkoxy-$C_1$-$C_8$ alkyl, $C_1$-$C_8$ alkylcarbonyl or $C_1$-$C_8$ alkoxycarbonyl, each of which contains or does not contain a halogen; a $C_3$-$C_8$ cycloalkyl, which is unsubstituted or substituted with 1 to 3 groups selected from $C_1$-$C_8$ alkyl, cyano and halogen; aryl or heterocyclyl;

$R_{31}$ represents hydrogen; a $C_1$-$C_8$ alkyl, $C_2$-$C_8$ alkenyl or $C_2$-$C_8$ alkynyl, each of which contains or does not contain a halogen; a $C_3$-$C_8$ cycloalkyl, which is unsubstituted or substituted with 1~3 selected from $C_1$-$C_8$ alkyl, cyano and halogen; aryl, heterocyclyl;

$R_{41}$, $R_{41}'$, $R_{42}$, $R_{42}'$, $R_{43}$ and $R_{43}'$ each independently represent hydrogen, a $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ alkylthio, $C_1$-$C_8$ alkoxy-$C_1$-$C_8$ alkyl, $C_1$-$C_8$ alkylthio-$C_1$-$C_8$ alkyl, $C_1$-$C_8$ alkylcarbonyl, $C_1$-$C_8$ alkoxycarbonyl, aryl, or heterocyclyl; or two of $R_{41}$, $R_{41}'$, $R_{42}$, $R_{42}'$, $R_{43}$ and $R_{43}'$ that are on different carbon atoms connect to form $CH_2$, $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$, or two of $R_{41}$, $R_{41}'$, $R_{42}$, $R_{42}'$, $R_{43}$ and $R_{43}'$ that are the same carbon atoms connect to form $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$;

$R_{44}$ is selected from $-OR_{45}$ or $-SR_{45}$;

$R_{51}$, $R_{51}'$, $R_{52}$, $R_{52}'$, $R_{53}$ and $R_{53}'$ each independently represent hydrogen, a $C_1$-$C_8$ alkyl, $C_2$-$C_8$ alkenyl, $C_2$-$C_8$ alkynyl, $C_3$-$C_8$ cycloalkyl, $C_1$-$C_8$ alkoxy, $C_1$-$C_8$ alkylthio, $C_1$-$C_8$ alkoxy-$C_1$-$C_8$ alkyl, $C_1$-$C_8$ alkylthio-$C_1$-$C_8$ alkyl, $C_1$-$C_8$ alkylcarbonyl, $C_1$-$C_8$ alkoxycarbonyl, aryl or heterocyclyl; or two of $R_{51}$, $R_{51}'$, $R_{52}$, $R_{52}'$, $R_{53}$ and $R_{53}'$ that are on different carbon atoms connect to form $CH_2$, $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$, or two of $R_{51}$, $R_{51}'$, $R_{52}$, $R_{52}'$, $R_{53}$ and $R_{53}'$ that are on the same carbon atoms connect to form $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$;

$R_{13}$ and $R_{45}$ each independently represent hydrogen, $-R_{61}$, $-S(O)_nR_{62}$, $-CH_2R_{63}$, $-(C=O)R_{64}$, $-PO(OR_{65})_2$ or $-Si(OR_{66})_3$, wherein, $R_{61}$ represents metal ion; ammonium ion; a $C_1$-$C_8$ alkyl, $C_2$-$C_8$ alkenyl or $C_2$-$C_8$ alkynyl, each of which contains or does not contain a halogen; aryl or heterocyclyl;

$R_{62}$ represents a $C_1$-$C_8$ alkyl, $C_2$-$C_8$ alkenyl or $C_2$-$C_8$ alkynyl, each of which contains or does not contain a halogen; aryl or heterocyclyl; n represents 1, 2 or 3;

$R_{63}$ represents halogen; nitro; cyano; a $C_1$-$C_8$ alkyl, $C_2$-$C_8$ alkenyl, $C_2$-$C_8$ alkynyl, $C_1$-$C_8$ alkoxy, $C_1$-$C_8$ alkoxycarbonyl or $C_1$-$C_8$ alkylthio, each of which contains or does not contain a halogen; a $C_3$-$C_8$ cycloalkyl, which is unsubstituted or substituted with 1 to 3 groups selected from $C_1$-$C_8$ alkyl, cyano and halogen; an amino or aminocarbonyl, each of which is unsubstituted or substituted with one or two groups selected from $C_1$-$C_8$ alkyl, $C_1$-$C_8$ alkylcarbonyl and halogenated $C_1$-$C_8$ alkyl; aryl; heterocyclyl; arylcarbonyl or heterocyclylcarbonyl;

$R_{64}$ represents halogen; nitro; cyano; a $C_1$-$C_8$ alkyl, $C_2$-$C_8$ alkenyl, $C_2$-$C_8$ alkynyl, $C_1$-$C_8$ alkoxy, $C_1$-$C_8$ alkylthio, $C_1$-$C_8$ alkoxy-$C_1$-$C_8$ alkyl or $C_1$-$C_8$ alkylthio-$C_1$-$C_8$ alkyl, each of which contains or does not contain a halogen; an amino or amino-$C_1$-$C_8$ alkyl, each of which is unsubstituted or substituted with 1 or 2 groups selected from $C_1$-$C_8$ alkyl, $C_1$-$C_8$ alkylcarbonyl and halogenated $C_1$-$C_8$ alkyl; aryl; heterocyclyl; aryl-$C_1$-$C_8$ alkyl; heterocyclyl-$C_1$-$C_8$ alkyl; aryloxy; heterocyclyloxy; aryloxy-$C_1$-$C_8$ alkyl or heterocyclyloxy-$C_1$-$C_8$ alkyl;

$R_{65}$ and $R_{66}$ each independently represent hydrogen, $C_1$-$C_8$ alkyl, halogenated $C_1$-$C_8$ alkyl, $C_3$-$C_8$ cycloalkyl, aryl or heterocyclyl;

X and Z each independently represent hydrogen; halogen; cyano; nitro; $-NR_1R_2$; a $C_2$-$C_8$ alkenyl, $C_2$-$C_8$ alkynyl, $C_3$-$C_8$ cycloalkyl, $C_1$-$C_8$ alkoxy, $C_1$-$C_8$ alkylthio, $C_1$-$C_8$ alkylsulfoxide, $C_1$-$C_8$ alkylsulfonyl, $C_1$-$C_8$ alkoxy-$C_1$-$C_8$ alkyl, $C_1$-$C_8$ alkylthio-$C_1$-$C_8$ alkyl, $C_1$-$C_8$ alkylsulfoxide-$C_1$-$C_8$ alkyl or $C_1$-$C_8$ alkylsulfonyl-$C_1$-$C_8$ alkyl, each of which contains or does not contain a halogen;

$R_1$ and $R_2$ each independently represent hydrogen, $C_1$-$C_8$ alkyl or halogenated $C_1$-$C_8$ alkyl, or $-NR_1R_2$ represents a 5- to 8-membered lactam group;

Y represents hydrogen; halogen; formyl; a $C_1$-$C_{18}$ alkyl, $C_2$-$C_8$ alkenyl, $C_2$-$C_8$ alkynyl, $C_1$-$C_8$ alkoxy, $C_1$-$C_8$ alkylthio, $C_1$-$C_8$ alkylsulfoxide, $C_1$-$C_8$ alkylsulfonyl, $C_1$-$C_8$ alkylacyl, cyano-$C_1$-$C_8$ alkyl, $C_1$-$C_8$ alkoxy-$C_1$-$C_8$ alkyl, $C_1$-$C_8$ alkylthio-$C_1$-$C_8$ alkyl, $C_1$-$C_8$ alkylsulfoxide-$C_1$-$C_8$ alkyl or $C_1$-$C_8$ alkylsulfonyl-$C_1$-$C_8$ alkyl, each of which contains or does not contain a halogen; an amino-$C_1$-$C_8$ alkyl or aminoacyl, each of which is unsubstituted or substituted with 1 or 2 groups selected from $C_1$-$C_8$ alkyl, $C_2$-$C_8$ alkenyl, $C_2$-$C_8$ alkynyl, $C_1$-$C_8$ alkylacyl, halogenated $C_1$-$C_8$ alkyl, halogenated $C_2$-$C_8$ alkenyl, halogenated $C_2$-$C_8$ alkynyl, halogenated $C_1$-$C_8$ alkylacyl and aryl; a $C_3$-$C_8$ cycloalkyl, $C_3$-$C_8$ cycloalkyl-$C_1$-$C_8$ alkyl, $C_3$-$C_8$ cycloalkenyl or $C_3$-$C_8$ cycloalkenyl-$C_1$-$C_8$ alkyl, each of which is unsubstituted or substituted with 1 to 3 groups selected from $C_1$-$C_8$ alkyl, cyano and halogen; aryl; heterocyclyl; aryl-$C_1$-$C_8$ alkyl or heterocyclyl-$C_1$-$C_8$ alkyl;

the aryl or heterocyclyl is substituted or unsubstituted, respectively, and said "substituted" refers to being substituted with 1 to 3 groups selected from halogen; nitro; cyano; thiocyano; cyano-$C_1$-$C_8$ alkyl; mercapto; hydroxyl; hydroxy-$C_1$-$C_8$ alkyl; carboxyl; formyl; azido; tri-$C_1$-$C_8$ alkylsilyl; di-$C_1$-$C_8$ alkylphosphono; a heterocyclyl, heterocyclyl-$C_1$-$C_8$ alkyl, aryl or aryl-$C_1$-$C_8$ alkyl, each of which is unsubstituted or substituted with 1 to 3 groups selected from $C_1$-$C_8$ alkyl, halogenated $C_1$-$C_8$ alkyl, $C_1$-$C_8$ alkylsulfonyl, $C_1$-$C_8$ alkylacyl, $C_1$-$C_8$ alkylacyloxy, $C_1$-$C_8$ alkoxyacyl, halogen, $C_1$-$C_8$ alkoxy, $C_1$-$C_8$ alkylthio, cyano, amino and $C_1$-$C_8$ alkylamino; a $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, $C_3$-$C_8$ cycloalkyl-$C_1$-$C_8$ alkyl, $C_3$-$C_8$ cycloalkenyl-$C_1$-$C_8$ alkyl or $C_1$-$C_8$ alkyl-substituted $C_3$-$C_8$ cycloalkyl, OR", SR", $-(C_1$-$C_8)$alkyl-OR", $-O-(C_1$-$C_8)$alkyl-OR", $-(C_1$-$C_8)$alkyl-SR", COR", $-(C_1$-$C_8)$alkyl-COR", $-O-(C_1$-$C_8)$alkyl-COR", COOR", $-(C_1$-$C_8)$alkyl-COOR", $-O-(C_1$-$C_8)$alkyl-COOR", COSR", SOR", $SO_2R"$, $-O-SO_2R"$, $-(C_1$-$C_8)$alkyl-$SO_2R"$, OCOR", $-(C_1$-$C_8)$alkyl-OCOR" or SCOR", each of which contains or does not contain a halogen; an amino, aminocarbonyl, aminocarbonyl-$C_1$-$C_8$ alkyl or aminosulfonyl, each of which is unsubstituted or substituted with 1 or 2 groups selected from R", COR", COOR", $SO_2R"$, $-(C_1$-$C_8)$alkyl-$SO_2R"$ or OR", wherein each of the group contains or does not contain a halogen; or forming a fused ring by connecting any two adjacent carbon atoms in the ring with the group $-CH_2CH_2CH_2-$, $-OCH_2CH_2-$, $-OCH_2O-$, $-OCH_2CH_2O-$ or $-CH=CH-CH=CH-$;

R" each independently represents $C_1$-$C_8$ alkyl; $C_2$-$C_8$ alkenyl; $C_2$-$C_8$ alkynyl; $C_3$-$C_8$ cycloalkyl; $C_3$-$C_8$ cycloalkyl-$C_1$-$C_8$ alkyl; $C_3$-$C_8$ cycloalkenyl; $C_3$-$C_8$ cycloalkenyl-$C_1$-$C_8$ alkyl; or a heterocyclyl, heterocyclyl-$C_1$-$C_8$ alkyl, aryl or aryl-$C_1$-$C_8$ alkyl, each of which is unsubstituted or substituted with 1 to 3 groups selected from halogen, $C_1$-$C_8$ alkyl, halogenated $C_1$-$C_8$ alkyl, $C_1$-$C_8$ alkoxy and amino.

In another embodiment, $R_{11}$ represents a $C_1$-$C_8$ alkyl, a halogenated $C_1$-$C_8$ alkyl or an aryl;

$R_{12}$ represents hydrogen; a $C_1$-$C_8$ alkyl, $C_2$-$C_8$ alkenyl or $C_2$-$C_8$ alkynyl, each of which contains or does not contain a halogen; a $C_3$-$C_8$ cycloalkyl, which is unsubstituted or substituted with at least one group selected from $C_1$-$C_8$ alkyl, cyano and halogen;

$R_{21}$ and $R_{22}$ each independently represent hydrogen; a $C_1$-$C_8$ alkyl, $C_2$-$C_8$ alkenyl, $C_2$-$C_8$ alkynyl, $C_1$-$C_8$ alkoxy, $C_1$-$C_8$ alkylthio, $C_1$-$C_8$ alkylsulfoxide, $C_1$-$C_8$ alkylsulfonyl, $C_1$-$C_8$ alkoxy-$C_1$-$C_8$ alkyl, $C_1$-$C_8$ alkylcarbonyl or $C_1$-$C_8$ alkoxycarbonyl, each of which contains or does not contain a halogen; a $C_3$-$C_8$ cycloalkyl, which is unsubstituted or substituted with at least one group selected from $C_1$-$C_8$ alkyl, cyano and halogen; aryl or heterocyclyl;

$R_{31}$ represents hydrogen; a $C_1$-$C_8$ alkyl, $C_2$-$C_8$ alkenyl or $C_2$-$C_8$ alkynyl, each of which contains or does not contain a halogen; a $C_3$-$C_8$ cycloalkyl, which is unsubstituted or substituted with at least one group selected from $C_1$-$C_8$ alkyl, cyano and halogen; aryl, heterocyclyl;

$R_{41}$, $R_{41}'$, $R_{42}$, $R_{42}'$, $R_{43}$ and $R_{43}'$ each independently represent hydrogen; a $C_1$-$C_8$ alkyl, $C_2$-$C_8$ alkenyl, $C_2$-$C_8$ alkynyl or $C_3$-$C_8$ cycloalkyl, each of which contains or does not contain a halogen; $C_1$-$C_8$ alkoxy; $C_1$-$C_8$ alkylthio; $C_1$-$C_8$ alkoxy-$C_1$-$C_8$ alkyl; $C_1$-$C_8$ alkylthio-$C_1$-$C_8$ alkyl; $C_1$-$C_8$ alkylcarbonyl; $C_1$-$C_8$ alkoxycarbonyl; aryl or heterocyclyl; or two of $R_{41}$, $R_{41}'$, $R_{42}$, $R_{42}'$, $R_{43}$ and $R_{43}'$ that are on different carbon atoms connect to form $CH_2$, $(CH_2)_2$, $(CH_2)_3$, $(CH_2)_4$, $(CH_2)_5$, $(CH_2)_6$, $O$, $O(CH_2)_2O$, $O(CH_2)_3O$, $O(CH_2)_4O$, $S(CH_2)_2S$ or $S(CH_2)_3S$, or two of $R_{41}$, $R_{41}'$, $R_{42}$, $R_{42}'$, $R_{43}$ and $R_{43}'$ that are the same carbon atoms connect to form $(CH_2)_2$, $(CH_2)_3$, $(CH_2)_4$, $(CH_2)_5$, $(CH_2)_6$, $O$, $O(CH_2)_2O$, $O(CH_2)_3O$, $O(CH_2)_4O$, $S(CH_2)_2S$ or $S(CH_2)_3S$;

$R_{44}$ is selected from $-OR_{45}$ or $-SR_{45}$;

$R_{51}$, $R_{51}'$, $R_{52}$, $R_{52}'$, $R_{53}$ and $R_{53}'$ each independently represent hydrogen; a $C_1$-$C_8$ alkyl, $C_2$-$C_8$ alkenyl, $C_2$-$C_8$ alkynyl or $C_3$-$C_8$ cycloalkyl, each of which contains or does not contain a halogen; $C_1$-$C_8$ alkoxy; $C_1$-$C_8$ alkylthio; $C_1$-$C_8$ alkoxy-$C_1$-$C_8$ alkyl; $C_1$-$C_8$ alkylthio-$C_1$-$C_8$ alkyl; $C_1$-$C_8$ alkylcarbonyl; $C_1$-$C_8$ alkoxycarbonyl; aryl or heterocyclyl; or two of $R_{51}$, $R_{51}'$, $R_{52}$, $R_{52}'$, $R_{53}$ and $R_{53}'$ that are on different carbon atoms connect to form $CH_2$, $(CH_2)_2$, $(CH_2)_3$, $(CH_2)_4$, $(CH_2)_5$, $(CH_2)_6$, $O$, $O(CH_2)_2O$, $O(CH_2)_3O$, $O(CH_2)_4O$, $S(CH_2)_2S$ or $S(CH_2)_3S$, or two of $R_{51}$, $R_{51}'$, $R_{52}$, $R_{52}'$, $R_{53}$ and $R_{53}'$ that are on the same carbon atoms connect to form $(CH_2)_2$, $(CH_2)_3$, $(CH_2)_4$, $(CH_2)_5$, $(CH_2)_6$, $O$, $O(CH_2)_2O$, $O(CH_2)_3O$, $O(CH_2)_4O$, $S(CH_2)_2S$ or $S(CH_2)_3S$;

$R_{13}$ and $R_{45}$ each independently represent hydrogen; $-R_{61}$, $-S(O)_nR_{62}$, $-CH_2R_{63}$, $-(C=O)R_{64}$, $-PO(OR_{65})_2$ or $-Si(OR_{66})_3$, wherein, $R_{61}$ represents alkali metal ion; ammonium ion; a $C_1$-$C_8$ alkyl, $C_2$-$C_8$ alkenyl or $C_2$-$C_8$ alkynyl, each of which contains or does not contain a halogen; aryl or heterocyclyl;

$R_{62}$ represents a $C_1$-$C_8$ alkyl, $C_2$-$C_8$ alkenyl or $C_2$-$C_8$ alkynyl, each of which contains or does not contain a halogen; aryl or heterocyclyl; n represents 1, 2 or 3;

$R_{63}$ represents halogen; nitro; cyano; a $C_1$-$C_8$ alkyl, $C_2$-$C_8$ alkenyl, $C_2$-$C_8$ alkynyl, $C_1$-$C_8$ alkoxy, $C_1$-$C_8$ alkoxycarbonyl or $C_1$-$C_8$ alkylthio, each of which contains or does not contain a halogen; a $C_3$-$C_8$ cycloalkyl, which is unsubstituted or substituted with at least one group selected from $C_1$-$C_8$ alkyl, cyano and halogen; an amino or aminocarbonyl, each of which is unsubstituted or substituted with one or two groups selected from $C_1$-$C_8$ alkyl, $C_1$-$C_8$ alkylcarbonyl and halogenated $C_1$-$C_8$ alkyl; aryl; heterocyclyl; arylcarbonyl or heterocyclylcarbonyl;

$R_{64}$ represents halogen; nitro; cyano; a $C_1$-$C_8$ alkyl, $C_2$-$C_8$ alkenyl, $C_2$-$C_8$ alkynyl, $C_1$-$C_8$ alkoxy, $C_1$-$C_8$ alkylthio, $C_1$-$C_8$ alkoxy-$C_1$-$C_8$ alkyl or $C_1$-$C_8$ alkylthio-$C_1$-$C_8$ alkyl, each of which contains or does not contain a halogen; an amino or amino-$C_1$-$C_8$ alkyl, each of which is unsubstituted or substituted with 1 or 2 groups selected from $C_1$-$C_8$ alkyl, $C_1$-$C_8$ alkylcarbonyl and halogenated $C_1$-$C_8$ alkyl; aryl; heterocyclyl; aryl-$C_1$-$C_8$ alkyl; heterocyclyl-$C_1$-$C_8$ alkyl; aryloxy; heterocyclyloxy; aryloxy-$C_1$-$C_8$ alkyl or heterocyclyloxy-$C_1$-$C_8$ alkyl;

$R_{65}$ and $R_{66}$ each independently represent hydrogen, $C_1$-$C_8$ alkyl, halogenated $C_1$-$C_8$ alkyl, $C_3$-$C_8$ cycloalkyl, aryl or heterocyclyl;

X and Z each independently represent hydrogen; halogen; cyano; nitro; $-NR_1R_2$; a $C_2$-$C_8$ alkenyl, $C_2$-$C_8$ alkynyl, $C_3$-$C_8$ cycloalkyl, $C_1$-$C_8$ alkoxy, $C_1$-$C_8$ alkylthio, $C_1$-$C_8$ alkylsulfoxide, $C_1$-$C_8$ alkylsulfonyl, $C_1$-$C_8$ alkoxy-$C_1$-$C_8$ alkyl, $C_1$-$C_8$ alkylthio-$C_1$-$C_8$ alkyl, $C_1$-$C_8$ alkylsulfoxide-$C_1$-$C_8$ alkyl or $C_1$-$C_8$ alkylsulfonyl-$C_1$-$C_8$ alkyl, each of which contains or does not contain a halogen;

$R_1$ and $R_2$ each independently represent hydrogen, $C_1$-$C_8$ alkyl or halogenated $C_1$-$C_8$ alkyl, or $-NR_1R_2$ represents a 5- to 8-membered lactam group;

Y represents hydrogen; halogen; formyl; cyano-$C_1$-$C_8$ alkyl; a $C_1$-$C_{18}$ alkyl, $C_2$-$C_8$ alkenyl or $C_2$-$C_8$ alkynyl, each of which contains or does not contain a halogen; $-OR_3$; $-OCOR_4$; $-COR_4$; $-SR_3$; $-SOR_4$; $-SO_2R_4$; $-(C_1$-$C_8$ alkyl)-$OR_3$; $-(C_1$-$C_8$ alkyl)-$OCOR_4$; $-(C_1$-$C_8$ alkyl)-$COR_4$; $-(C_1$-$C_8$ alkyl)-$SR_3$; $-(C_1$-$C_8$ alkyl)-$SOR_4$; $-(C_1$-$C_8$ alkyl)-$SO_2R_4$; an amino, amino-$C_1$-$C_8$ alkyl or aminoacyl, each of which is unsubstituted or substituted with 1 or 2 groups selected from $C_1$-$C_8$ alkyl, $C_2$-$C_8$ alkenyl, $C_2$-$C_8$ alkynyl, $C_1$-$C_8$ alkylacyl, halogenated $C_1$-$C_8$ alkyl, halogenated $C_2$-$C_8$ alkenyl, halogenated $C_2$-$C_8$ alkynyl, halogenated $C_1$-$C_8$ alkylacyl and aryl; a $C_3$-$C_8$ cycloalkyl, $C_3$-$C_8$ cycloalkyl-$C_1$-$C_8$ alkyl, $C_3$-$C_8$ cycloalkenyl or $C_3$-$C_8$ cycloalkenyl-$C_1$-$C_8$ alkyl, each of which is unsubstituted or substituted with at least one group selected from $C_1$-$C_8$ alkyl, cyano and halogen; aryl; heterocyclyl; aryl-$C_1$-$C_8$ alkyl or heterocyclyl-$C_1$-$C_8$ alkyl;

$R_3$ each independently represents hydrogen; alkali metal ion; a $C_1$-$C_8$ alkyl, $C_2$-$C_8$ alkenyl, $C_2$-$C_8$ alkynyl or $C_3$-$C_8$ cycloalkyl, each of which contains or does not contain a halogen;

$R_4$ each independently represents a $C_1$-$C_8$ alkyl group, $C_2$-$C_8$ alkenyl group, $C_2$-$C_8$ alkynyl group or $C_3$-$C_8$ cycloalkyl, each of which contains or does not contain a halogen;

the aryl or heterocyclyl is substituted or unsubstituted, respectively, and said "substituted" refers to being substituted with at least one group selected from halogen; nitro; cyano; thiocyano; cyano-$C_1$-$C_8$ alkyl; mercapto; hydroxyl; hydroxy-$C_1$-$C_8$ alkyl; carboxyl; formyl; azido; tri-$C_1$-$C_8$ alkylsilyl; di-$C_1$-$C_8$ alkylphosphono; a heterocyclyl, heterocyclyl-$C_1$-$C_8$ alkyl, aryl or aryl-$C_1$-$C_8$ alkyl, each of which is unsubstituted or substituted with at least one group selected from $C_1$-$C_8$ alkyl, halogenated $C_1$-$C_8$ alkyl, $C_1$-$C_8$ alkylsulfonyl, $C_1$-$C_8$ alkylacyl, $C_1$-$C_8$ alkylacyloxy, $C_1$-$C_8$ alkoxyacyl, halogen, $C_1$-$C_8$ alkoxy, $C_1$-$C_8$ alkylthio, cyano, amino and $C_1$-$C_8$ alkylamino; a $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, $C_3$-$C_8$ cycloalkyl-$C_1$-$C_8$ alkyl, $C_3$-$C_8$ cycloalkenyl-$C_1$-$C_8$ alkyl or $C_1$-$C_8$ alkyl-substituted $C_3$-$C_8$ cycloalkyl, OR", SR", —($C_1$-$C_8$)alkyl-OR", —O—($C_1$-$C_8$)alkyl-OR", —($C_1$-$C_8$)alkyl-SR", COR", —($C_1$-$C_8$)alkyl-COR", —O—($C_1$-$C_8$)alkyl-COR", COOR", —($C_1$-$C_8$)alkyl-COOR", —O—($C_1$-$C_8$)alkyl-COOR", COSR", SOR", SO$_2$R", —O—SO$_2$R", —($C_1$-$C_8$)alkyl-SO$_2$R", OCOR", —($C_1$-$C_8$)alkyl-OCOR" or SCOR", each of which contains or does not contain a halogen; an amino, aminocarbonyl, aminocarbonyl-$C_1$-$C_8$ alkyl or aminosulfonyl, each of which is unsubstituted or substituted with 1 or 2 groups selected from R", COR", COOR", SO$_2$R", —($C_1$-$C_8$)alkyl-SO$_2$R" or OR", wherein each of the group contains or does not contain a halogen; or forming a fused ring by connecting any two adjacent carbon atoms in the ring with the group —CH$_2$CH$_2$CH$_2$—, —OCH$_2$CH$_2$—, —OCH$_2$O—, —OCH$_2$CH$_2$O— or —CH═CH—CH═CH—;

R" each independently represents $C_1$-$C_8$ alkyl; $C_2$-$C_8$ alkenyl; $C_2$-$C_8$ alkynyl; $C_3$-$C_8$ cycloalkyl; $C_3$-$C_8$ cycloalkyl-$C_1$-$C_8$ alkyl; $C_3$-$C_8$ cycloalkenyl; $C_3$-$C_8$ cycloalkenyl-$C_1$-$C_8$ alkyl; or a heterocyclyl, heterocyclyl-$C_1$-$C_8$ alkyl, aryl or aryl-$C_1$-$C_8$ alkyl, each of which is unsubstituted or substituted with at least one group selected from halogen, $C_1$-$C_8$ alkyl, halogenated $C_1$-$C_8$ alkyl, $C_1$-$C_8$ alkoxy and amino.

More preferably, $R_{11}$ represents $C_1$-$C_6$ alkyl, halogenated $C_1$-$C_6$ alkyl or aryl;

$R_{12}$ represents hydrogen; a $C_1$-$C_6$ alkyl, $C_2$-$C_6$ alkenyl or $C_2$-$C_6$ alkynyl, each of which contains or does not contain a halogen; a $C_3$-$C_6$ cycloalkyl, which is unsubstituted or substituted with 1 to 2 groups selected from $C_1$-$C_6$ alkyl, cyano and halogen;

$R_{21}$ and $R_{22}$ each independently represent hydrogen; a $C_1$-$C_6$ alkyl, $C_2$-$C_6$ alkenyl, $C_2$-$C_6$ alkynyl, $C_1$-$C_6$ alkoxy, $C_1$-$C_6$ alkylthio, $C_1$-$C_6$ alkylsulfoxide, $C_1$-$C_6$ alkylsulfonyl, $C_1$-$C_6$ alkoxy-$C_1$-$C_6$ alkyl, $C_1$-$C_6$ alkylcarbonyl or $C_1$-$C_6$ alkoxycarbonyl, each of which contains or does not contain a halogen; a $C_3$-$C_6$ cycloalkyl, which is unsubstituted or substituted with 1 to 2 groups selected from $C_1$-$C_6$ alkyl, cyano and halogen; aryl or heterocyclyl;

$R_{31}$ represents hydrogen; a $C_1$-$C_6$ alkyl, $C_2$-$C_6$ alkenyl or $C_2$-$C_6$ alkynyl, each of which contains or does not contain a halogen; a $C_3$-$C_6$ cycloalkyl, which is unsubstituted or substituted with 1 to 2 groups selected from $C_1$-$C_6$ alkyl, cyano and halogen; aryl or heterocyclyl;

$R_{41}$, $R_{41}'$, $R_{42}$, $R_{42}'$, $R_{43}$ and $R_{43}'$ each independently represent hydrogen, $C_1$-$C_8$ alkyl, $C_2$-$C_8$ alkenyl, $C_2$-$C_8$ alkynyl, $C_3$-$C_8$ cycloalkyl, $C_1$-$C_6$ alkoxy, $C_1$-$C_6$ alkylthio, $C_1$-$C_6$ alkoxy-$C_1$-$C_6$ alkyl, $C_1$-$C_6$ alkylthio-$C_1$-$C_6$ alkyl, $C_1$-$C_6$ alkylcarbonyl, $C_1$-$C_6$ alkoxycarbonyl, aryl or heterocyclyl; or two of $R_{41}$, $R_{41}'$, $R_{42}$, $R_{42}'$, $R_{43}$ and $R_{43}'$ that are on different carbon atoms connect to form CH$_2$, (CH$_2$)$_2$, (CH$_2$)$_3$, (CH$_2$)$_4$, (CH$_2$)$_5$, (CH$_2$)$_6$, O, O(CH$_2$)$_2$O, O(CH$_2$)$_3$O, O(CH$_2$)$_4$O, S(CH$_2$)$_2$S or S(CH$_2$)$_3$S; or two of $R_{41}$, $R_{41}'$, $R_{42}$, $R_{42}'$, $R_{43}$ and $R_{43}'$ that are on the same carbon atoms connect to form (CH$_2$)$_2$, (CH$_2$)$_3$, (CH$_2$)$_4$, (CH$_2$)$_5$, (CH$_2$)$_6$, O, O(CH$_2$)$_2$O, O(CH$_2$)$_3$O, O(CH$_2$)$_4$O, S(CH$_2$)$_2$S or S(CH$_2$)$_3$S;

$R_{44}$ is selected from —OR$_{45}$ and —SR$_{45}$;

$R_{51}$, $R_{51}'$, $R_{52}$, $R_{52}'$, $R_{53}$ and $R_{53}'$ each independently represent hydrogen, $C_1$-$C_8$ alkyl, $C_2$-$C_8$ alkenyl, $C_2$-$C_8$ alkynyl, $C_3$-$C_8$ cycloalkyl, $C_1$-$C_6$ alkoxy, $C_1$-$C_6$ alkylthio, $C_1$-$C_6$ alkoxy-$C_1$-$C_6$ alkyl, $C_1$-$C_6$ alkylthio-$C_1$-$C_6$ alkyl, $C_1$-$C_6$ alkylcarbonyl, $C_1$-$C_6$ alkoxycarbonyl, aryl or heterocyclyl; or two of $R_{51}$, $R_{51}'$, $R_{52}$, $R_{52}'$, $R_{53}$ and $R_{53}'$ that are on different carbon atoms connect to form CH$_2$, (CH$_2$)$_2$, (CH$_2$)$_3$, (CH$_2$)$_4$, (CH$_2$)$_5$, (CH$_2$)$_6$, O, O(CH$_2$)$_2$O, O(CH$_2$)$_3$O, O(CH$_2$)$_4$O, S(CH$_2$)$_2$S or S(CH$_2$)$_3$S, or two of $R_{51}$, $R_{51}'$, $R_{52}$, $R_{52}'$, $R_{53}$ and $R_{53}'$ that are on the same carbon atoms connect to form (CH$_2$)$_2$, (CH$_2$)$_3$, (CH$_2$)$_4$, (CH$_2$)$_5$, (CH$_2$)$_6$, O, O(CH$_2$)$_2$O, O(CH$_2$)$_3$O, O(CH$_2$)$_4$O, S(CH$_2$)$_2$S or S(CH$_2$)$_3$S;

$R_{13}$ and $R_{45}$ each independently represent hydrogen, —R$_{61}$, —S(O)$_n$R$_{62}$, —CH$_2$R$_{63}$, —(C═O)R$_{64}$, —PO(OR$_{65}$)$_2$ or —Si(OR$_{66}$)$_3$, wherein, $R_{61}$ represents metal ion; ammonium ion; a $C_1$-$C_6$ alkyl, $C_2$-$C_6$ alkenyl or $C_2$-$C_6$ alkynyl, each of which contains or does not contain a halogen; aryl or heterocyclyl;

$R_{62}$ represents a $C_1$-$C_6$ alkyl, $C_2$-$C_6$ alkenyl or $C_2$-$C_6$ alkynyl, each of which contains or does not contain a halogen; aryl or heterocyclyl; n represents 1, 2 or 3;

$R_{63}$ represents halogen; nitro; cyano; a $C_1$-$C_6$ alkyl, $C_2$-$C_6$ alkenyl, $C_2$-$C_6$ alkynyl, $C_1$-$C_6$ alkoxy, $C_1$-$C_6$ alkoxycarbonyl or $C_1$-$C_6$ alkylthio, each of which contains or does not contain a halogen; a $C_3$-$C_6$ cycloalkyl, which is unsubstituted or substituted with 1 to 2 groups selected from $C_1$-$C_6$ alkyl, cyano or halogen; an amino or aminocarbonyl, each of which is unsubstituted or substituted with 1 to 2 groups selected from $C_1$-$C_6$ alkyl, $C_1$-$C_6$ alkylcarbonyl and halogenated $C_1$-$C_6$ alkyl; aryl; heterocyclyl; arylcarbonyl or heterocyclylcarbonyl;

$R_{64}$ represents halogen; nitro; cyano; a $C_1$-$C_6$ alkyl, $C_2$-$C_6$ alkenyl, $C_2$-$C_6$ alkynyl, $C_1$-$C_6$ alkoxy, $C_1$-$C_6$ alkylthio, $C_1$-$C_6$ alkoxy-$C_1$-$C_6$ alkyl or $C_1$-$C_6$ alkylthio-$C_1$-$C_6$ alkyl, each of which contains or does not contain a halogen; an amino or amino-$C_1$-$C_6$ alkyl, each of which is unsubstituted or substituted with 1 to 2 groups selected from $C_1$-$C_6$ alkyl, $C_1$-$C_6$ alkylcarbonyl and halogenated $C_1$-$C_6$ alkyl; aryl; heterocyclyl; aryl-$C_1$-$C_6$ alkyl; heterocyclyl-$C_1$-$C_6$ alkyl; aryloxy; heterocyclyloxy; aryloxy-$C_1$-$C_6$ alkyl or heterocyclyloxy-$C_1$-$C_6$ alkyl;

$R_{65}$ and $R_{66}$ each independently represent hydrogen, $C_1$-$C_6$ alkyl, halogenated $C_1$-$C_6$ alkyl, $C_3$-$C_6$ cycloalkyl, aryl or heterocyclyl;

X and Z each independently represent hydrogen; halogen; cyano; nitro; —NR$_1$R$_2$; a $C_2$-$C_6$ alkenyl, $C_2$-$C_6$ alkynyl, $C_3$-$C_6$ cycloalkyl, $C_1$-$C_6$ alkoxy, $C_1$-$C_6$ alkylthio, $C_1$-$C_6$ alkylsulfoxide, $C_1$-$C_6$ alkylsulfonyl, $C_1$-$C_6$ alkoxy-$C_1$-$C_6$ alkyl, $C_1$-$C_6$ alkylthio-$C_1$-$C_6$ alkyl, $C_1$-$C_6$ alkylsulfoxide-$C_1$-$C_6$ alkyl or $C_1$-$C_6$ alkylsulfonyl-$C_1$-$C_6$ alkyl, each of which contains or does not contain a halogen;

$R_1$ and $R_2$ each independently represent hydrogen, $C_1$-$C_6$ alkyl or halogenated $C_1$-$C_6$ alkyl, or —$NR_1R_2$ represents a 5- to 8-membered lactam group;

Y represents hydrogen; halogen; formyl; a $C_1$-$C_{12}$ alkyl, $C_2$-$C_6$ alkenyl, $C_2$-$C_6$ alkynyl, $C_1$-$C_6$ alkoxy, $C_1$-$C_6$ alkylthio, $C_1$-$C_6$ alkylsulfoxide, $C_1$-$C_6$ alkylsulfonyl, $C_1$-$C_6$ alkylacyl, cyano-$C_1$-$C_6$ alkyl, $C_1$-$C_6$ alkoxy-$C_1$-$C_6$ alkyl, $C_1$-$C_6$ alkylthio-$C_1$-$C_6$ alkyl, $C_1$-$C_6$ alkylsulfoxide-$C_1$-$C_6$ alkyl or $C_1$-$C_6$ alkylsulfonyl-$C_1$-$C_6$ alkyl, each of which contains or does not contain a halogen; an amino-$C_1$-$C_6$ alkyl or aminoacyl, each of which is unsubstituted or substituted with 1 to 2 groups selected from $C_1$-$C_6$ alkyl, $C_2$-$C_6$ alkenyl, $C_2$-$C_6$ alkynyl, $C_1$-$C_6$ alkylacyl, halogenated $C_1$-$C_6$ alkyl, halogenated $C_2$-$C_6$ alkenyl, halogenated $C_2$-$C_6$ alkynyl, halogenated $C_1$-$C_6$ alkylacyl and aryl; a $C_3$-$C_6$ cycloalkyl, $C_3$-$C_6$ cycloalkyl-$C_1$-$C_6$ alkyl, $C_3$-$C_6$ cycloalkenyl or $C_3$-$C_6$ cycloalkenyl-$C_1$-$C_6$ alkyl, each of which is unsubstituted or substituted with 1 to 2 groups selected from $C_1$-$C_6$ alkyl, cyano and halogen; aryl; heterocyclyl; aryl-$C_1$-$C_6$ alkyl or heterocyclyl-$C_1$-$C_6$ alkyl;

the aryl or heterocyclyl is substituted or unsubstituted, respectively, and said "substituted" refers to being substituted with 1 to 2 groups selected from halogen; nitro; cyano; thiocyano; cyano-$C_1$-$C_6$ alkyl; mercapto; hydroxyl; hydroxy-$C_1$-$C_6$ alkyl; carboxyl; formyl; azido; tri-$C_1$-$C_6$ alkylsilyl; di-$C_1$-$C_6$ alkylphosphono; a heterocyclyl, heterocyclyl-$C_1$-$C_6$ alkyl, aryl or aryl-$C_1$-$C_6$ alkyl, each of which is unsubstituted or substituted with 1 to 2 groups selected from $C_1$-$C_6$ alkyl, halogenated $C_1$-$C_6$ alkyl, $C_1$-$C_6$ alkylsulfonyl, $C_1$-$C_6$ alkylacyl, $C_1$-$C_6$ alkylacyloxy, $C_1$-$C_6$ alkoxyacyl, halogen, $C_1$-$C_6$ alkoxy, $C_1$-$C_6$ alkylthio, cyano, amino and $C_1$-$C_6$ alkylamino; a $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkenyl, $C_3$-$C_6$ cycloalkyl-$C_1$-$C_6$ alkyl, $C_3$-$C_6$ cycloalkenyl-$C_1$-$C_6$ alkyl, $C_1$-$C_6$ alkyl-substituted $C_3$-$C_6$ cycloalkyl, OR", SR", —($C_1$-$C_6$)alkyl-OR", —O—($C_1$-$C_6$)alkyl-OR", —($C_1$-$C_6$)alkyl-SR", COR", —($C_1$-$C_6$)alkyl-COR", —O—($C_1$-$C_6$)alkyl-COR", COOR", —($C_1$-$C_6$)alkyl-COOR", —O—($C_1$-$C_6$)alkyl-COOR", COSR", SOR", $SO_2R"$, —O—$SO_2R"$, —($C_1$-$C_6$)alkyl-$SO_2R"$, OCOR", —($C_1$-$C_6$)alkyl-OCOR" or SCOR", each of which contains or does not contain a halogen; an amino, aminocarbonyl, aminocarbonyl-$C_1$-$C_6$ alkyl or aminosulfonyl, each of which is unsubstituted or substituted with 1 to 2 groups selected from R", COR", COOR", $SO_2R"$, —($C_1$-$C_6$)alkyl-$SO_2R"$ or OR", wherein each of the group contains or does not contain a halogen; or forming a fused ring by connecting any two adjacent carbon atoms in the ring with the group —$CH_2CH_2CH_2$—, —$OCH_2CH_2$—, —$OCH_2O$—, —$OCH_2CH_2O$— or —CH=CH—CH=CH—;

R" each independently represents $C_1$-$C_6$ alkyl; $C_2$-$C_6$ alkenyl; $C_2$-$C_6$ alkynyl; $C_3$-$C_6$ cycloalkyl; $C_3$-$C_6$ cycloalkyl-$C_1$-$C_6$ alkyl; $C_3$-$C_6$ cycloalkenyl; $C_3$-$C_6$ cycloalkenyl-$C_1$-$C_6$ alkyl; or a heterocyclyl, heterocyclyl-$C_1$-$C_6$ alkyl, aryl or aryl-$C_1$-$C_6$ alkyl, each of which is unsubstituted or substituted with 1 to 3 groups selected from halogen, $C_1$-$C_6$ alkyl, halogenated $C_1$-$C_6$ alkyl, $C_1$-$C_6$ alkoxy and amino.

In another embodiment, $R_{11}$ represents $C_1$-$C_6$ alkyl, halogenated $C_1$-$C_6$ alkyl or aryl;

$R_{12}$ represents hydrogen; a $C_1$-$C_6$ alkyl, $C_2$-$C_6$ alkenyl or $C_2$-$C_6$ alkynyl, each of which contains or does not contain a halogen; a $C_3$-$C_6$ cycloalkyl, which is unsubstituted or substituted with 1 to 3 groups selected from $C_1$-$C_6$ alkyl, cyano and halogen;

$R_{21}$ and $R_{22}$ each independently represent hydrogen; a $C_1$-$C_6$ alkyl, $C_2$-$C_6$ alkenyl, $C_2$-$C_6$ alkynyl, $C_1$-$C_6$ alkoxy, $C_1$-$C_6$ alkylthio, $C_1$-$C_6$ alkylsulfoxide, $C_1$-$C_6$ alkylsulfonyl, $C_1$-$C_6$ alkoxy-$C_1$-$C_6$ alkyl, $C_1$-$C_6$ alkylcarbonyl or $C_1$-$C_6$ alkoxycarbonyl, each of which contains or does not contain a halogen; a $C_3$-$C_6$ cycloalkyl, which is unsubstituted or substituted with 1 to 3 groups selected from $C_1$-$C_6$ alkyl, cyano and halogen; aryl or heterocyclyl;

$R_{31}$ represents hydrogen; a $C_1$-$C_6$ alkyl, $C_2$-$C_6$ alkenyl or $C_2$-$C_6$ alkynyl, each of which contains or does not contain a halogen; a $C_3$-$C_6$ cycloalkyl, which is unsubstituted or substituted with 1 to 3 groups selected from $C_1$-$C_6$ alkyl, cyano and halogen; aryl or heterocyclyl;

$R_{41}$, $R_{41}'$, $R_{42}$, $R_{42}'$, $R_{43}$ and $R_{43}'$ each independently represent hydrogen; a $C_1$-$C_8$ alkyl, $C_2$-$C_8$ alkenyl, $C_2$-$C_8$ alkynyl or $C_3$-$C_8$ cycloalkyl, each of which contains or does not contain a halogen; $C_1$-$C_6$ alkoxy; $C_1$-$C_6$ alkylthio; $C_1$-$C_6$ alkoxy-$C_1$-$C_6$ alkyl; $C_1$-$C_6$ alkylthio-$C_1$-$C_6$ alkyl; $C_1$-$C_6$ alkylcarbonyl; $C_1$-$C_6$ alkoxycarbonyl; aryl or heterocyclyl; or two of $R_{41}$, $R_{41}'$, $R_{42}$, $R_{42}'$, $R_{43}$ and $R_{43}'$ that are on different carbon atoms connect to form $CH_2$, $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$; or two of $R_{41}$, $R_{41}'$, $R_{42}$, $R_{42}'$, $R_{43}$ and $R_{43}'$ that are on the same carbon atoms connect to form $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$;

$R_{44}$ is selected from —$OR_{45}$ and —$SR_{45}$;

$R_{51}$, $R_{51}'$, $R_{52}$, $R_{52}'$, $R_{53}$ and $R_{53}'$ each independently represent hydrogen; a $C_1$-$C_8$ alkyl, $C_2$-$C_8$ alkenyl, $C_2$-$C_8$ alkynyl or $C_3$-$C_8$ cycloalkyl, each of which contains or does not contain a halogen; $C_1$-$C_6$ alkoxy; $C_1$-$C_6$ alkylthio; $C_1$-$C_6$ alkoxy-$C_1$-$C_6$ alkyl; $C_1$-$C_6$ alkylthio-$C_1$-$C_6$ alkyl; $C_1$-$C_6$ alkylcarbonyl; $C_1$-$C_6$ alkoxycarbonyl; aryl or heterocyclyl; or two of $R_{51}$, $R_{51}'$, $R_{52}$, $R_{52}'$, $R_{53}$ and $R_{53}'$ that are on different carbon atoms connect to form $CH_2$, $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$, or two of $R_{51}$, $R_{51}'$, $R_{52}$, $R_{52}'$, $R_{53}$ and $R_{53}'$ that are on the same carbon atoms connect to form $(CH_2)_2$, $(CH_2)_3$, $(CH_2)_4$, $(CH_2)_5$, $(CH_2)_6$, O, $O(CH_2)_2O$, $O(CH_2)_3O$, $O(CH_2)_4O$, $S(CH_2)_2S$ or $S(CH_2)_3S$;

$R_{13}$ and $R_{45}$ each independently represent hydrogen, —$R_{61}$, —$S(O)_nR_{62}$, —$CH_2R_{63}$, —(C=O)$R_{64}$, —PO$(OR_{65})_2$ or —Si$(OR_{66})_3$, wherein, $R_{61}$ represents sodium ion, ammonium ion; a $C_1$-$C_6$ alkyl, $C_2$-$C_6$ alkenyl or $C_2$-$C_6$ alkynyl, each of which contains or does not contain a halogen; aryl or heterocyclyl;

$R_{62}$ represents a $C_1$-$C_6$ alkyl, $C_2$-$C_6$ alkenyl or $C_2$-$C_6$ alkynyl, each of which contains or does not contain a halogen; aryl or heterocyclyl; n represents 1, 2 or 3;

$R_{63}$ represents halogen; nitro; cyano; a $C_1$-$C_6$ alkyl, $C_2$-$C_6$ alkenyl, $C_2$-$C_6$ alkynyl, $C_1$-$C_6$ alkoxy, $C_1$-$C_6$ alkoxycarbonyl or $C_1$-$C_6$ alkylthio, each of which contains or does not contain a halogen; a $C_3$-$C_6$ cycloalkyl, which is unsubstituted or substituted with 1 to 3 groups selected from $C_1$-$C_6$ alkyl, cyano or halogen; an amino or aminocarbonyl, each of which is unsubstituted or substituted with 1 to 2 groups selected from $C_1$-$C_6$ alkyl, $C_1$-$C_6$ alkylcarbonyl and halogenated $C_1$-$C_6$ alkyl; aryl; heterocyclyl; arylcarbonyl or heterocyclylcarbonyl;

$R_{64}$ represents halogen; nitro; cyano; a $C_1$-$C_6$ alkyl, $C_2$-$C_6$ alkenyl, $C_2$-$C_6$ alkynyl, $C_1$-$C_6$ alkoxy, $C_1$-$C_6$ alkylthio, $C_1$-$C_6$ alkoxy-$C_1$-$C_6$ alkyl or $C_1$-$C_6$ alkylthio-$C_1$-$C_6$ alkyl, each of which contains or does not contain a halogen; an amino or amino-$C_1$-$C_6$ alkyl, each of which is unsubstituted or substituted with 1 to 2 groups selected from $C_1$-$C_6$ alkyl, $C_1$-$C_6$ alkylcarbonyl and halogenated $C_1$-$C_6$ alkyl; aryl; heterocyclyl; aryl-$C_1$-$C_6$ alkyl; heterocyclyl-$C_1$-$C_6$ alkyl; aryloxy; heterocyclyloxy; aryloxy-$C_1$-$C_6$ alkyl or heterocyclyloxy-$C_1$-$C_6$ alkyl;

$R_{65}$ and $R_{66}$ each independently represent hydrogen, $C_1$-$C_6$ alkyl, halogenated $C_1$-$C_6$ alkyl, $C_3$-$C_6$ cycloalkyl, aryl or heterocyclyl;

X and Z each independently represent hydrogen; halogen; cyano; nitro; —$NR_1R_2$; a $C_2$-$C_6$ alkenyl, $C_2$-$C_6$ alkynyl, $C_3$-$C_6$ cycloalkyl, $C_1$-$C_6$ alkoxy, $C_1$-$C_6$ alkylthio, $C_1$-$C_6$ alkylsulfoxide, $C_1$-$C_6$ alkylsulfonyl, $C_1$-$C_6$ alkoxy-$C_1$-$C_6$ alkyl, $C_1$-$C_6$ alkylthio-$C_1$-$C_6$ alkyl, $C_1$-$C_6$ alkylsulfoxide-$C_1$-$C_6$ alkyl or $C_1$-$C_6$ alkylsulfonyl-$C_1$-$C_6$ alkyl, each of which contains or does not contain a halogen;

$R_1$ and $R_2$ each independently represent hydrogen, $C_1$-$C_6$ alkyl or halogenated $C_1$-$C_6$ alkyl, or —$NR_1R_2$ represents a 5- to 8-membered lactam group;

Y represents hydrogen; halogen; formyl; cyano-$C_1$-$C_6$ alkyl; a $C_1$-$C_{12}$ alkyl, $C_2$-$C_6$ alkenyl or $C_2$-$C_6$ alkynyl, each of which contains or does not contain a halogen; —$OR_3$; —$OCOR_4$; —$COR_4$; —$SR_3$; —$SOR_4$; —$SO_2R_4$; —($C_1$-$C_6$ alkyl)-$OR_3$; —($C_1$-$C_6$ alkyl)-$OCOR_4$; —($C_1$-$C_6$ alkyl)-$COR_4$; —($C_1$-$C_6$ alkyl)-$SR_3$; —($C_1$-$C_6$ alkyl)-$SOR_4$; —($C_1$-$C_6$ alkyl)-$SO_2R_4$; an amino, amino-$C_1$-$C_6$ alkyl or aminoacyl, each of which is unsubstituted or substituted with 1 to 2 groups selected from $C_1$-$C_6$ alkyl, $C_2$-$C_6$ alkenyl, $C_2$-$C_6$ alkynyl, $C_1$-$C_6$ alkylacyl, halogenated $C_1$-$C_6$ alkyl, halogenated $C_2$-$C_6$ alkenyl, halogenated $C_2$-$C_6$ alkynyl, halogenated $C_1$-$C_6$ alkylacyl and aryl; a $C_3$-$C_6$ cycloalkyl, $C_3$-$C_6$ cycloalkyl-$C_1$-$C_6$ alkyl, $C_3$-$C_6$ cycloalkenyl or $C_3$-$C_6$ cycloalkenyl-$C_1$-$C_6$ alkyl, each of which is unsubstituted or substituted with 1 to 3 groups selected from $C_1$-$C_6$ alkyl, cyano and halogen; aryl; heterocyclyl; aryl-$C_1$-$C_6$ alkyl or heterocyclyl-$C_1$-$C_6$ alkyl;

$R_3$ each independently represents hydrogen; sodium ion; a $C_1$-$C_6$ alkyl, $C_2$-$C_6$ alkenyl, $C_2$-$C_6$ alkynyl or $C_3$-$C_6$ cycloalkyl, each of which contains or does not contain a halogen;

$R_4$ each independently represents a $C_1$-$C_6$ alkyl, $C_2$-$C_6$ alkenyl, $C_2$-$C_6$ alkynyl or $C_3$-$C_6$ cycloalkyl, each of which contains or does not contain a halogen;

the aryl or heterocyclyl is substituted or unsubstituted, respectively, and said "substituted" refers to being substituted with 1 to 3 groups selected from halogen; nitro; cyano; thiocyano; cyano-$C_1$-$C_6$ alkyl; mercapto; hydroxyl; hydroxy-$C_1$-$C_6$ alkyl; carboxyl; formyl; azido; tri-$C_1$-$C_6$ alkylsilyl; di-$C_1$-$C_6$ alkylphosphono; a heterocyclyl, heterocyclyl-$C_1$-$C_6$ alkyl, aryl or aryl-$C_1$-$C_6$ alkyl, each of which is unsubstituted or substituted with 1 to 3 groups selected from $C_1$-$C_6$ alkyl, halogenated $C_1$-$C_6$ alkyl, $C_1$-$C_6$ alkylsulfonyl, $C_1$-$C_6$ alkylacyl, $C_1$-$C_6$ alkylacyloxy, $C_1$-$C_6$ alkoxyacyl, halogen, $C_1$-$C_6$ alkoxy, $C_1$-$C_6$ alkylthio, cyano, amino and $C_1$-$C_6$ alkylamino; a $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkenyl, $C_3$-$C_6$ cycloalkyl-$C_1$-$C_6$ alkyl, $C_3$-$C_6$ cycloalkenyl-$C_1$-$C_6$ alkyl, $C_1$-$C_6$ alkyl-substituted $C_3$-$C_6$ cycloalkyl, OR", SR", —($C_1$-$C_6$)alkyl-OR", —O—($C_1$-$C_6$)alkyl-OR", —($C_1$-$C_6$)alkyl-SR", COR", —($C_1$-$C_6$)alkyl-COR", —O—($C_1$-$C_6$)alkyl-COR", COOR", —($C_1$-$C_6$)alkyl-COOR", —O—($C_1$-$C_6$)alkyl-COOR", COSR", SOR", $SO_2R''$, —O—$SO_2R''$, —($C_1$-$C_6$)alkyl-$SO_2R''$, OCOR", —($C_1$-$C_6$)alkyl-OCOR" or SCOR", each of which contains or does not contain a halogen; an amino, aminocarbonyl, aminocarbonyl-$C_1$-$C_6$ alkyl or aminosulfonyl, each of which is unsubstituted or substituted with 1 to 2 groups selected from R", COR", COOR", $SO_2R''$, —($C_1$-$C_6$)alkyl-$SO_2R''$ or OR", wherein each of the group contains or does not contain a halogen; or forming a fused ring by connecting any two adjacent carbon atoms in the ring with the group —$CH_2CH_2CH_2$—, —$OCH_2CH_2$—, —$OCH_2O$—, —$OCH_2CH_2O$— or —CH=CH—CH=CH—;

R" each independently represents $C_1$-$C_6$ alkyl; $C_2$-$C_6$ alkenyl; $C_2$-$C_6$ alkynyl; $C_3$-$C_6$ cycloalkyl; $C_3$-$C_6$ cycloalkyl-$C_1$-$C_6$ alkyl; $C_3$-$C_6$ cycloalkenyl; $C_3$-$C_6$ cycloalkenyl-$C_1$-$C_6$ alkyl; or a heterocyclyl, heterocyclyl-$C_1$-$C_6$ alkyl, aryl or aryl-$C_1$-$C_6$ alkyl, each of which is unsubstituted or substituted with 1 to 3 groups selected from halogen, $C_1$-$C_6$ alkyl, halogenated $C_1$-$C_6$ alkyl, $C_1$-$C_6$ alkoxy and amino.

More preferably, Q represents

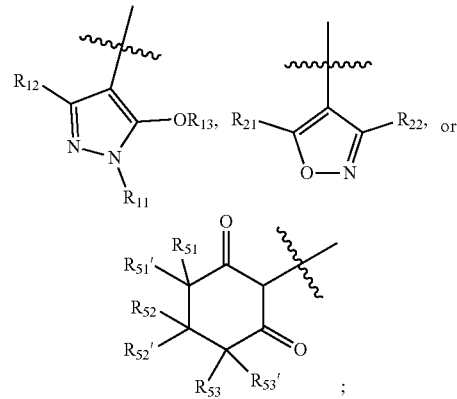

$R_{11}$ represents $C_1$-$C_6$ alkyl;

$R_{12}$ represents hydrogen, a $C_1$-$C_6$ alkyl which contains or does not contain a fluorine, or C3-C6 cycloalkyl;

$R_{13}$ represents hydrogen;

$R_{21}$ and $R_{22}$ each independently represent hydrogen or $C_3$-$C_6$ cycloalkyl;

$R_{51}$, $R_{51}'$, $R_{52}$, $R_{52}'$, $R_{53}$ and $R_{53}'$ each independently represent hydrogen or $C_1$-$C_6$ alkyl, or two of $R_{51}$, $R_{51}'$, $R_{52}$, $R_{52}'$, $R_{53}$ and $R_{53}'$ that are on different carbon atoms connect to form $CH_2$ or $(CH_2)_2$;

X represents hydrogen, fluorine, chlorine, bromine, iodine, cyano, nitro, —$NR_1R_2$, $C_2$-$C_6$ alkenyl, $C_2$-$C_6$ alkynyl, $C_3$-$C_6$ cycloalkyl, $C_1$-$C_6$ alkoxy, $C_1$-$C_6$ alkylthio, $C_1$-$C_6$ alkylsulfoxide, $C_1$-$C_6$ alkylsulfonyl or $C_1$-$C_6$ alkoxy-$C_1$-$C_6$ alkyl;

$R_1$ and $R_2$ each independently represent $C_1$-$C_6$ alkyl, or —$NR_1R_2$ represents butyrolactam group;

Y represents hydrogen; fluorine; chlorine; bromine; iodine; formyl; a $C_1$-$C_{10}$ alkyl, $C_2$-$C_6$ alkenyl or $C_2$-$C_6$ alkynyl, each of which contains or does not contain a fluorine or chlorine; $C_1$-$C_6$ alkoxy, $C_1$-$C_6$ alkylthio, $C_1$-$C_6$ alkylsulfoxide, $C_1$-$C_6$ alkylsulfonyl, $C_1$-$C_6$ alkylacyl, cyano-$C_1$-$C_6$ alkyl, $C_1$-$C_6$ alkoxy-$C_1$-$C_6$ alkyl, $C_1$-$C_6$ alkylthio-$C_1$-$C_6$ alkyl, $C_1$-$C_6$ alkylsulfoxide-$C_1$-$C_6$ alkyl, $C_1$-$C_6$ alkylsulfonyl-$C_1$-$C_6$ alkyl; an amino-$C_1$-$C_6$ alkyl or aminoacyl, each of which is unsubstituted or substituted with 1 to 2 groups selected from $C_1$-$C_6$ alkyl; a $C_3$-$C_6$ cycloalkyl, $C_3$-$C_6$ cycloalkyl-$C_1$-$C_6$ alkyl or $C_3$-$C_6$ cycloalkenyl, each of which is unsubstituted or substituted with 1 to 2 groups selected from $C_1$-$C_6$ alkyl, cyano and fluorine; aryl; heterocyclyl; aryl-$C_1$-$C_6$ alkyl or heterocyclyl-$C_1$-$C_6$ alkyl;

Z represents hydrogen, fluorine or chlorine;

the aryl or heterocyclyl is substituted or unsubstituted, respectively, and said "substituted" refers to being substituted with 1 to 2 groups selected from fluorine, chlorine, cyano, $C_1$-$C_6$ alkyl and phenyl;

the aryl is selected from phenyl and naphthyl; the heterocyclyl is selected from

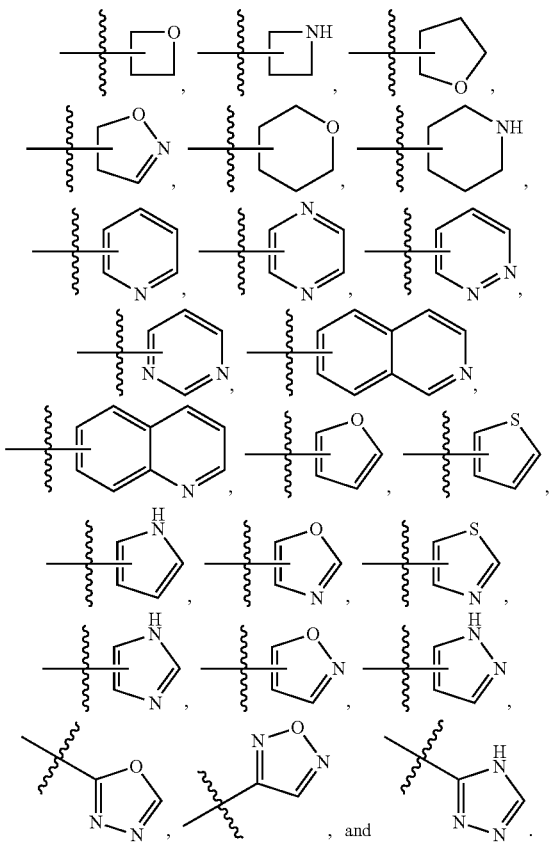

In another embodiment, Q represents

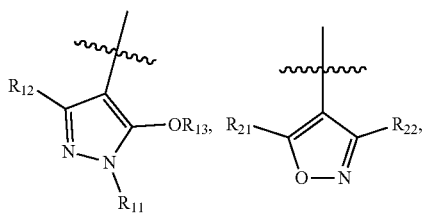

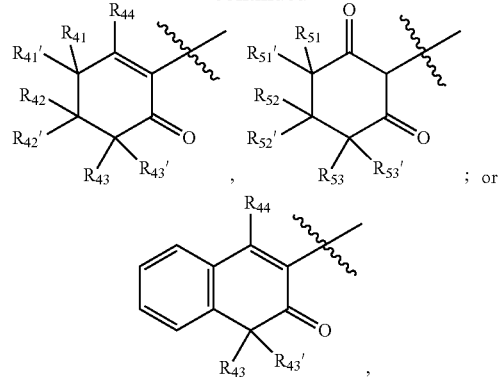

$R_{11}$ represents $C_1$-$C_6$ alkyl;

$R_{12}$ represents hydrogen, $C_1$-$C_6$ alkyl or $C_3$-$C_6$ cycloalkyl;

$R_{13}$ represents hydrogen, sodium ion or —(C=O)$R_{64}$;

$R_{21}$ and $R_{22}$ each independently represent hydrogen or $C_3$-$C_6$ cycloalkyl;

$R_{41}$, $R_{41}'$, $R_{42}$, $R_{42}'$, $R_{43}$ and $R_{43}'$ each independently represent hydrogen, $C_1$-$C_6$ alkyl or halogenated $C_1$-$C_6$ alkyl, or two of $R_{41}$, $R_{41}'$, $R_{42}$, $R_{42}'$, $R_{43}$ and $R_{43}'$ that are on different carbon atoms connect to form (CH$_2$)$_2$;

$R_{44}$ is selected from —ONa;

$R_{51}$, $R_{51}'$, $R_{52}$, $R_{52}'$, $R_{53}$ and $R_{53}'$ each independently represent hydrogen, $C_1$-$C_6$ alkyl or halogenated $C_1$-$C_6$ alkyl, or two of $R_{51}$, $R_{51}'$, $R_{52}$, $R_{52}'$, $R_{53}$ and $R_{53}'$ that are on different carbon atoms connect to form CH$_2$ or (CH$_2$)$_2$;

$R_{64}$ represents aryl or heterocyclyl;

X represents hydrogen, fluorine, chlorine, bromine, iodine, cyano, nitro, —NR$_1$R$_2$, $C_2$-$C_6$ alkenyl, $C_2$-$C_6$ alkynyl, $C_3$-$C_6$ cycloalkyl, $C_1$-$C_6$ alkoxy, $C_1$-$C_6$ alkylthio, $C_1$-$C_6$ alkylsulfoxide, $C_1$-$C_6$ alkylsulfonyl or $C_1$-$C_6$ alkoxy-$C_1$-$C_3$ alkyl;

$R_1$ and $R_2$ each independently represent $C_1$-$C_6$ alkyl, or —NR$_1$R$_2$ represents butyrolactam group;

Y represents hydrogen; fluorine; chlorine; bromine; iodine; formyl; cyano-$C_1$-$C_3$ alkyl; a $C_1$-$C_{10}$ alkyl, $C_2$-$C_6$ alkenyl or $C_2$-$C_6$ alkynyl, each of which contains or does not contain a fluorine or chlorine; —OR$_3$; —COR$_4$; —SR$_3$; —SOR$_4$; —SO$_2$R$_4$; —(C$_1$-$C_3$ alkyl)-OR$_3$; —(C$_1$-$C_6$ alkyl)-OCOR$_4$; —(C$_1$-$C_3$ alkyl)-SR$_3$; —(C$_1$-$C_3$ alkyl)-SOR$_4$; —(C$_1$-$C_3$ alkyl)-SO$_2$R$_4$; an amino, amino-$C_1$-$C_3$ alkyl or aminoacyl, each of which is unsubstituted or substituted with 1 to 2 groups selected from $C_1$-$C_6$ alkyl, $C_2$-$C_6$ alkenyl, $C_2$-$C_6$ alkynyl and $C_1$-$C_6$ alkylacyl; a $C_3$-$C_6$ cycloalkyl, $C_3$-$C_6$ cycloalkyl-$C_1$-$C_3$ alkyl or $C_3$-$C_6$ cycloalkenyl, each of which is unsubstituted or substituted with 1 to 2 groups selected from $C_1$-$C_6$ alkyl, cyano and fluorine; aryl; heterocyclyl; aryl-$C_1$-$C_3$ alkyl or heterocyclyl-$C_1$-$C_3$ alkyl;

$R_3$ each independently represents hydrogen, sodium ion, $C_1$-$C_6$ alkyl, $C_2$-$C_6$ alkenyl or $C_2$-$C_6$ alkynyl;

$R_4$ each independently represents $C_1$-$C_6$ alkyl;

Z represents hydrogen, fluorine or chlorine;

the aryl or heterocyclyl is substituted or unsubstituted, respectively, and said "substituted" refers to being substituted with 1 to 2 groups selected from fluorine, chlorine, cyano, $C_1$-$C_6$ alkyl and phenyl;

the aryl is selected from phenyl and naphthyl; the heterocyclyl is selected from

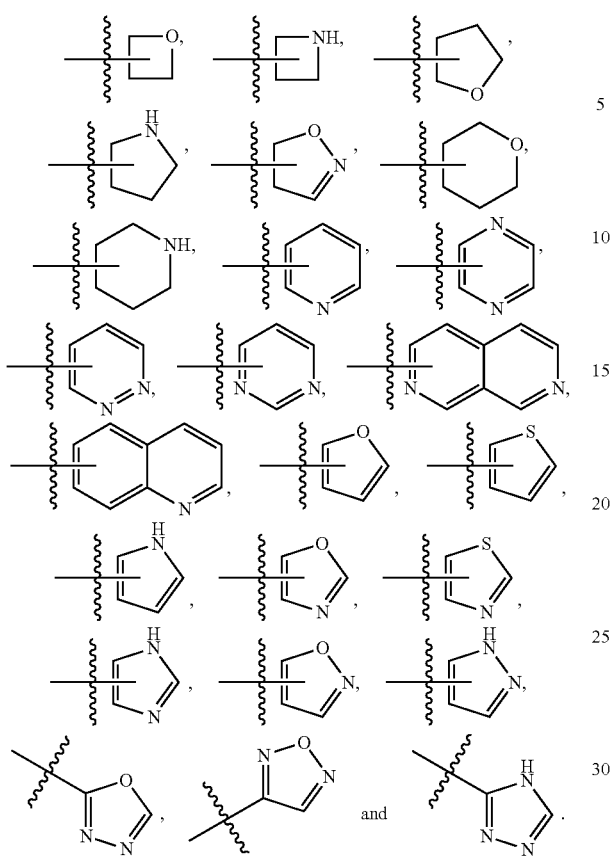

More preferably, Q represents

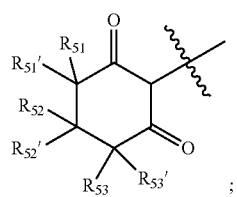

$R_{51}$, $R_{51}'$, $R_{52}$, $R_{52}'$, $R_{53}$ and $R_{53}'$ each independently represent hydrogen or $C_1$-$C_6$ alkyl, or two of $R_{51}$, $R_{51}'$, $R_{52}$, $R_{52}'$, $R_{53}$ and $R_{53}'$ that are on different carbon atoms connect to form $CH_2$ or $(CH_2)_2$;

X represents chlorine;

Y represents a $C_1$-$C_6$ alkyl which contains or does not contain a fluorine; $C_1$-$C_6$ alkoxy, $C_1$-$C_6$ alkylthio, $C_1$-$C_6$ alkoxy-$C_1$-$C_6$ alkyl; a $C_3$-$C_6$ cycloalkyl which is unsubstituted or substituted with 1 to 2 groups selected from $C_1$-$C_6$ alkyl and fluorine; or phenyl;

Z represents hydrogen.

In another embodiment, Q represents

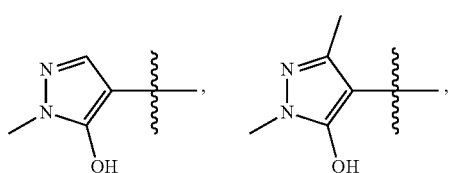

-continued

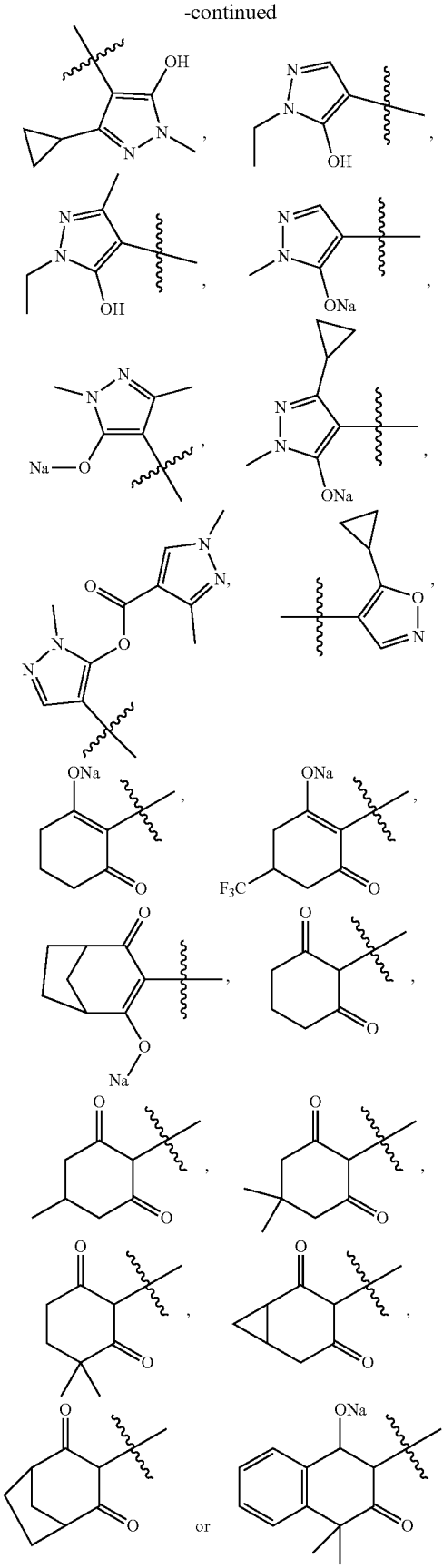

In the definition of the compound represented by the above Formula and all of the following structural formulas, the technical terms used, whether used alone or used in compound word, represent the following substituents: an alkyl having more than two carbon atoms may be linear or branched. For example, the alkyl in the compound word "-alkyl-OR"" may be —CH$_2$—, —CH$_2$CH$_2$—, —CH(CH$_3$)—, —C(CH$_3$)$_2$—, and the like. The alkyl is, for example, C$_1$ alkyl: methyl; C$_2$ alkyl: ethyl; C$_3$ alkyl: propyl such as n-propyl or isopropyl; C$_4$ alkyl: butyl such as n-butyl, isobutyl, tert-butyl or 2-butyl; C$_5$ alkyl: pentyl such as n-pentyl; C$_6$ alkyl: hexyl such as n-hexyl, isohexyl and 1,3-dimethylbutyl. Similarly, the alkenyl is, for example, allyl, 1-methylprop-2-en-1-yl, 2-methylprop-2-en-1-yl, but-2-en-1-yl, butyl-3-en-1-yl, 1-methylbut-3-en-1-yl and 1-methylbut-2-en-1-yl. The alkynyl is, for example, propargyl, but-2-yn-1-yl, but-3-yn-1-yl, 1-methylbut-3-yn-1-yl. At least one (for example, 1, 2 or 3) multiple bonds may be placed at any position of each unsaturated group. The cycloalkyl is a carbocyclic saturated ring system having, for example, three to six carbon atoms, such as cyclopropyl, cyclobutyl, cyclopentyl or cyclohexyl. Similarly, the cycloalkenyl is monocycloalkenyl having, for example, three to six carbon ring members, such as cyclopropenyl, cyclobutenyl, cyclopentenyl, and cyclohexenyl, wherein double bond can be at any position. Halogen is fluorine, chlorine, bromine or iodine.

Unless otherwise specified, the technical terms used, whether used alone or used in compound word, represent the following meanings: the "aryl" of the present invention includes, phenyl, naphthyl,

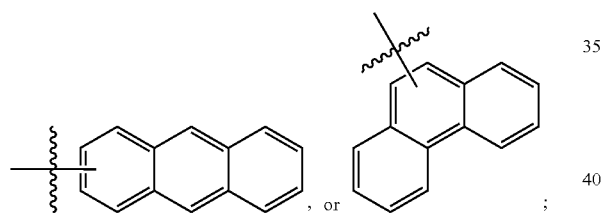
, or ;

the "heterocyclyl" not only includes,

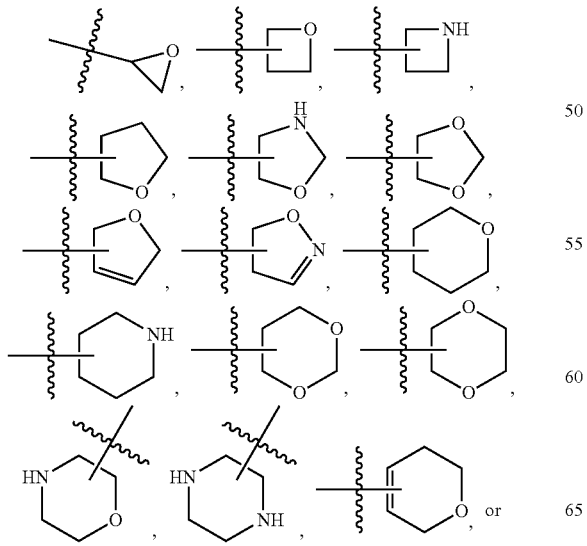

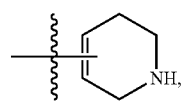

which has for example 0, 1 or 2 oxo groups; but also includes "heteroaryl" (also called "aromatic heterocyclic group", which is an aromatic cyclic group having, for example, 3 to 6 (for example, 3, 4, 5 or 6) ring atoms and which may also be fused with a benzo ring, and 1 to 4 (for example, 1, 2, 3 or 4) heteroatoms of the ring are selected from the group consisting of oxygen, nitrogen and sulfur. For example,

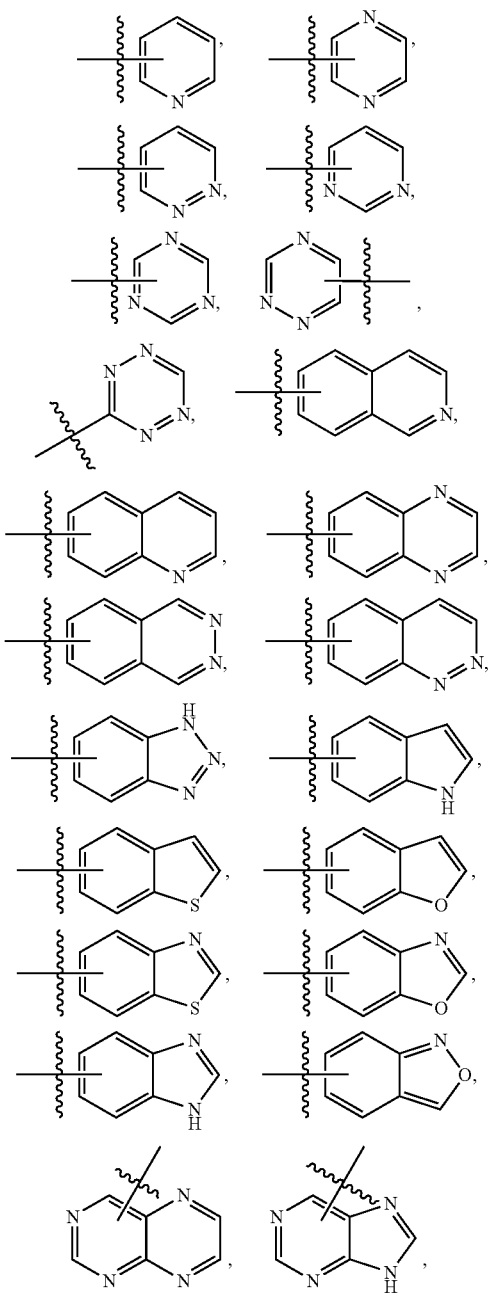

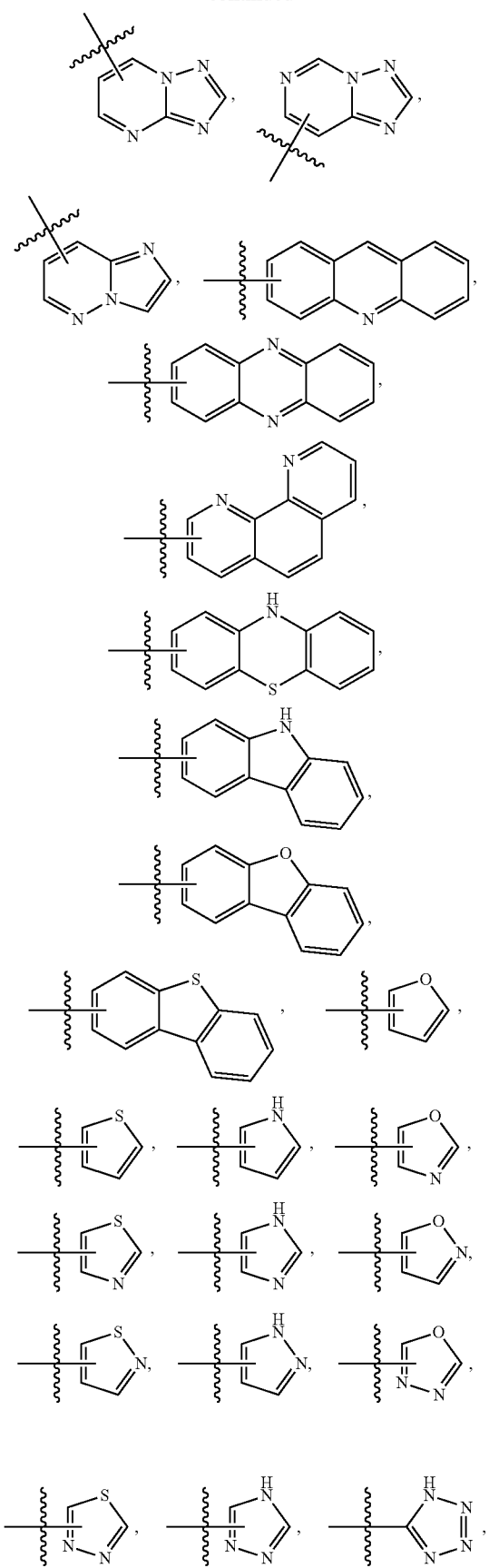

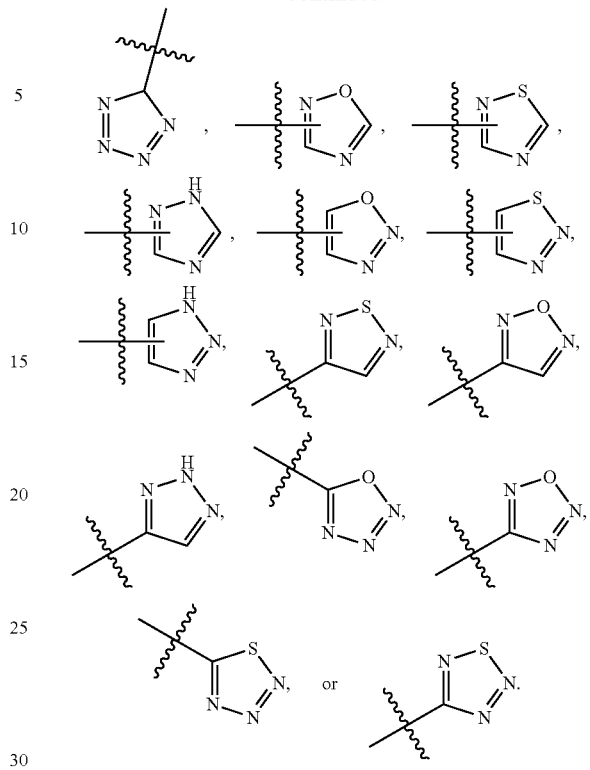

If a group is substituted by a group, which should be understood to mean that the group is substituted by one or more groups, which are same or different groups, selected from the mentioned groups. In addition, the same or different substitution characters contained in the same or different substituents are independently selected, and may be the same or different. This is also applicable to ring systems formed with different atoms and units. Meanwhile, the scope of the claims will exclude those compounds chemically unstable under standard conditions known to those skilled in the art.

In addition, unless specifically defined, the term occurring before or after multiple juxtaposed substituents (separated by "," or "or") in the present invention has a limiting effect on each of the substituents, such as the term "with or without halogen" in "alkyl, alkenyl, or alkynyl with or without halogen" has a limiting effect on each of the following groups "alkyl", "alkenyl", and "alkynyl"; "alkylamino" refers to an amino group that is mono- or di-substituted by an alkyl group, and other substituted amino groups have similar definitions; a group (including heterocyclyl, aryl, heteroaryl, etc.) without being specified a linking site may be attached at any site, including a C or N site; if it is substituted, the substituent may be substituted at any site as long as it comply with the valence bond theory. For example, if the heteroaryl

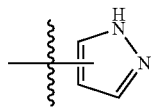

is substituted with one methyl, it can be

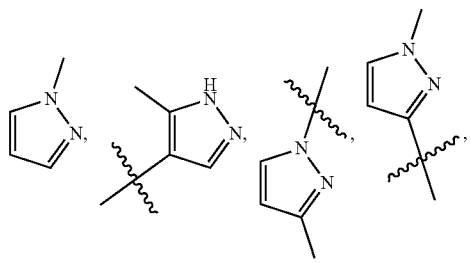

etc. . . .

Depending on the property of substituents and the linkage manner thereof, the compound of Formula I and its derivatives may exist as a stereoisomer. For example, if a compound has one or more asymmetric carbon atoms, it may has enantiomers and diastereomers. The stereoisomer can be obtained from the mixtures obtained in the preparation by conventional separation methods, for example by chromatographic separation. The stereoisomer may also be prepared selectively by using stereoselective reactions and using optically active starting materials and/or auxiliaries. The present invention also relates to all stereoisomers and mixtures thereof which are included in the general Formula I but are not specifically defined.

A method for preparing the substituted 1,2,4-triazolo[4,3-a]pyridine derivatives comprises the following steps:

Reacting with compound

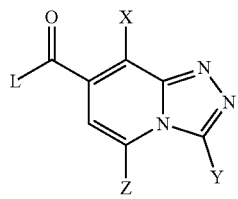

as an intermediate, wherein, L represents a leaving group, such as halogen (F, or Cl), p-nitrophenoxy, or cyano, etc. . . .

For example, when the target product is a compound of formula I, wherein Q represents

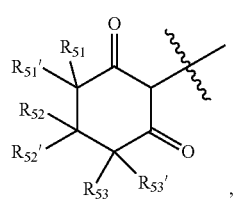

its preparation method comprises the following steps:

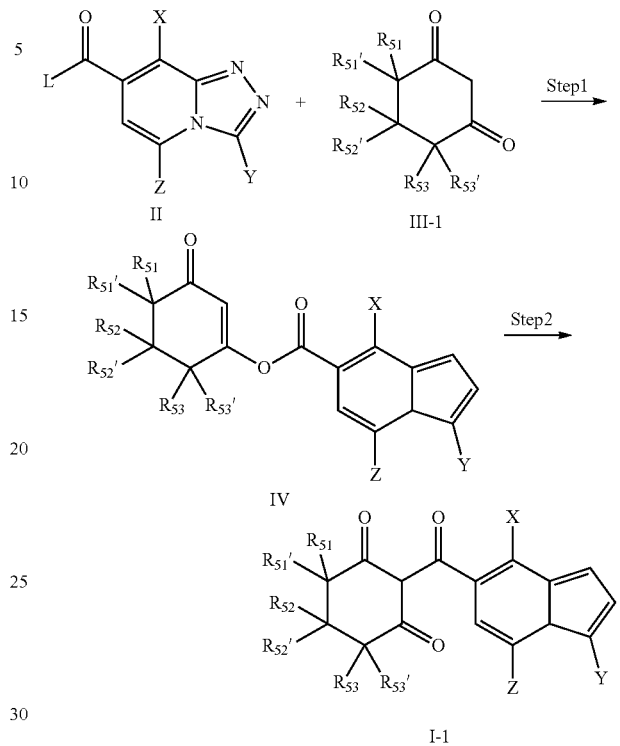

When the target product is a compound of formula I, wherein Q represents

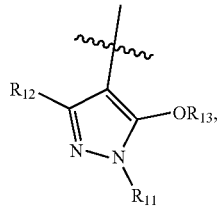

its preparation method comprises the following steps:

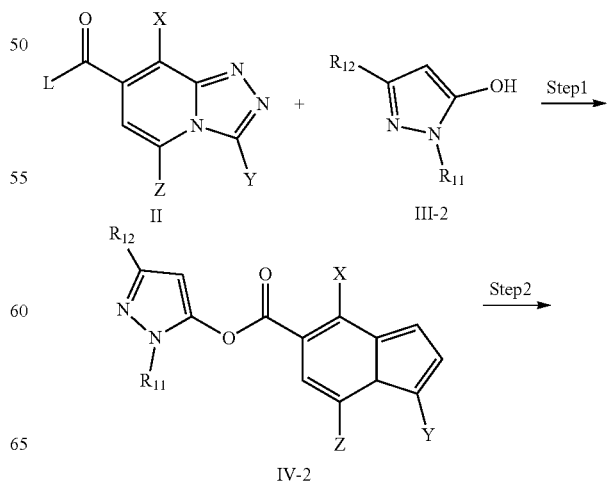

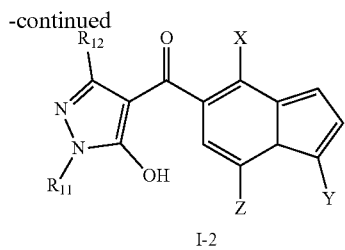

I-2

Wherein, the Step 1 is a condensation reaction carried out in the presence of a base (such as triethylamine) and a solvent (such as dichloromethane); the reaction temperature is 0-25° C.

The Step 2 is a rearrangement reaction carried out in the presence of a catalyst (such as acetone cyanohydrin), a base (such as triethylamine) and a solvent (such as acetonitrile); the reaction temperature is 20-70° C.

The compound of the present invention can be prepared by referring to the relevant method described in patent WO2008006540A1.

A herbicidal composition comprising (i) the substituted 1,2,4-triazolo[4,3-a]pyridine derivatives; preferably, further comprising (ii) one or more further herbicides and/or safeners; more preferably, further comprising (iii) agrochemically acceptable formulation auxiliaries.

A method for controlling a weed which comprises applying a herbicidally effective amount of at least one of the substituted 1,2,4-triazolo[4,3-a]pyridine derivatives or the herbicidal composition to a plant or a weed area.

Use of at least one of the substituted 1,2,4-triazolo[4,3-a]pyridine derivatives or the herbicidal composition as above-described for controlling a weed, preferably, wherein the substituted 1,2,4-triazolo[4,3-a]pyridine derivatives is used for preventing and/or controlling a weed in a useful crop, wherein the useful crop is a transgenic crop or a crop treated by gene editing technique.

The compounds of the formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium purpureum, Polygonum convulvulus, Stellaria media, Veronica hederifolia, Veronica persica, Viola tricolor* and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of:

genetically engineered changes in crop plants in order to modify the starch synthesized in the plants (for example WO 92/11376, WO 92/14827, WO 91/19806), transgenic crop plants which are resistant to certain herbicides of the glufosinate- (cf., for example, EP-A 0 242 236, EP-A 0 242 246) or glyphosate-type (WO 92/00377), or of the sulfonylurea-type (EP-A 0 257 993, U.S. Pat. No. 5,013,659A), transgenic crop plants, for example cotton, having the ability to produce *Bacillus thuringiensis* toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the above-mentioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I. The compounds of the formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil dispersions (OD), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflüchenaktive Äthylenoxidaddkte" [Surface-active ethylene oxide adducts], Wiss. Verlagagesell. Stuttgart 1976; Winnacker-Küchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula I. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example World Herbicide New Product Technology Handbook, China Agricultural Science and Farming Techniques Press, 2010.9 and in the literature cited therein. For example the following active compounds may be mentioned as herbicides which can be combined with the compounds of the formula I (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, EL-177, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethylamine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiapropethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWCO535, DK-8910, V-53482, PP-600, MBH-001, KIH-9201, ET-751, KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 250 g/ha.

Specific Mode for Carrying Out the Invention

The following embodiments are used to illustrate the present invention in detail and should not be taken as any limit to the present invention. The scope of the invention would be explained through the Claims.

In view of economics and variety of a compound, we preferably synthesized several compounds, part of which are listed in the following Table 1. The structure and information of a certain compound are shown in Table 1. The compounds in Table 1 are listed for further explication of the present invention, other than any limit therefor. The subject of the present invention should not be interpreted by those skilled in the art as being limited to the following compounds.

TABLE 1

Structures and ¹H NMR data of compounds

[Structure: triazolopyridine core with substituents X, Y, Z and C(=O)Q group]

| NO. | Q | X | Y | Z | ¹HNMR |
|---|---|---|---|---|---|
| 1 | [2-substituted cyclohexane-1,3-dione] | F | [cyclopropyl] | H | ¹H NMR (500 MHz, Chloroform-d) δ 8.72 (d, J = 7.0 Hz, 1H), 7.14 (dd, J = 7.0, 5.5 Hz, 1H), 4.64 (s, 1H), 2.67-2.52 (m, 5H), 1.81-1.67 (m, 4H), 1.59-1.55 (m, 2H). |
| 2 | [2-substituted cyclohexane-1,3-dione] | Cl | [cyclopropyl] | H | ¹H NMR (500 MHz, Chloroform-d) δ 8.94 (d, J = 7.0 Hz, 1H), 7.80 (d, J = 7.0 Hz, 1H), 4.39 (s, 1H), 2.95 (p, J = 5.5 Hz, 1H), 2.63-2.51(m, 4H), 1.79-1.55 (m, 6H). |
| 3 | [2-substituted cyclohexane-1,3-dione] | Br | [cyclopropyl] | H | ¹H NMR (500 MHz, Chloroform-d) δ 9.01 (d, J = 7.0 Hz, 1H), 7.39 (d, J = 7.0 Hz, 1H), 4.48 (s, 1H), 2.95 (p, J = 5.5 Hz, 1H), 2.63-2.54(m, 4H), 1.81-1.67 (m, 4H), 1.59-1.53 (m, 2H). |
| 4 | [2-substituted cyclohexane-1,3-dione] | I | [cyclopropyl] | H | ¹H NMR (500 MHz, Chloroform-d) δ 8.87 (d, J = 7.0 Hz, 1H), 7.05 (d, J = 7.0 Hz, 1H), 4.47 (s, 1H), 2.95 (p, J = 5.5 Hz, 1H), 2.63-2.52(m, 4H), 1.80-1.65 (m, 4H), 1.58-1.53 (m, 2H). |

TABLE 1-continued

Structures and ¹H NMR data of compounds

| NO. | Q | X | Y | Z | ¹HNMR |
|---|---|---|---|---|---|
| 5 | cyclohexane-1,3-dione | allyl | cyclopropyl | H | ¹H NMR (500 MHz, Chloroform-d) δ 8.79 (d, J = 7.5 Hz, 1H), 7.17 (d, J = 7.5 Hz, 1H), 6.95-6.86 (m, 1H), 5.75 (d, J = 14.0 Hz, 2H), 4.54 (s, 1H), 2.70-2.52 (m, 5H), 1.81-1.67 (m, 4H), 1.59 (p, J = 6.6 Hz, 2H). |
| 6 | cyclohexane-1,3-dione | ethynyl | cyclopropyl | H | ¹H NMR (500 MHz, Chloroform-d) δ 8.85 (d, J = 6.5 Hz, 1H), 7.08 (d, J = 6.5 Hz, 1H), 4.60 (s, 1H), 4.40 (s, 1H), 2.95-2.91 (m, 1H), 2.63-2.57 (m, 4H), 1.82-1.66 (m, 4H), 1.59-1.55(m, 2H). |
| 7 | cyclohexane-1,3-dione | cyclopropyl | cyclopropyl | H | ¹H NMR (500 MHz, Chloroform-d) δ 8.81 (d, J = 7.0 Hz, 1H), 7.16 (d, J = 7.0 Hz, 1H), 4.54 (s, 1H), 3.05-3.01 (m, 1H), 2.97-2.91 (m, 1H), 2.63-2.55(m, 4H), 1.80-1.65 (m, 4H), 1.59 (p, J = 6.5 Hz, 2H), 1.46-1.32 (m, 4H). |
| 8 | cyclohexane-1,3-dione | CN | cyclopropyl | H | ¹H NMR (500 MHz, Chloroform-d) δ 9.26 (d, J = 7.0 Hz, 1H), 7.47 (d, J = 7.0 Hz, 1H), 4.51 (s, 1H), 2.95 (p, J = 5.5 Hz, 1H), 2.63-2.58(m, 4H), 1.79-1.62 (m, 4H), 1.59 (p, J = 6.5 Hz, 2H). |
| 9 | cyclohexane-1,3-dione | NO₂ | cyclopropyl | H | ¹H NMR (500 MHz, Chloroform-d) δ 9.17 (d, J = 7.0 Hz, 1H), 7.38 (d, J =7.0 Hz, 1H), 4.45 (s, 1H), 2.95 (p, J = 5.5 Hz, 1H), 2.67-2.60 (m, 4H), 1.80-1.55 (m, 6H). |

TABLE 1-continued

Structures and $^1$H NMR data of compounds

| NO. | Q | X | Y | Z | $^1$HNMR |
|---|---|---|---|---|---|
| 10 | 2,6-dioxocyclohexyl | CH$_2$OCH$_3$ | cyclopropyl | H | $^1$H NMR (500 MHz, Chloroform-d) δ 8.85 (d, J = 7.0 Hz, 1H), 7.26 (d, J = 7.0 Hz, 1H), 4.78 (s, 2H), 4.51 (s, 1H), 3.36 (s, 3H), 2.63-2.57(m, 4H), 2.63-2.51 (m, 1H), 1.78-1.55 (m, 6H). |
| 11 | 2,6-dioxocyclohexyl | SCH$_3$ | cyclopropyl | H | $^1$H NMR (500 MHz, Chloroform-d) δ 8.71 (d, J = 7.0 Hz, 1H), 7.15 (d, J = 1.0 Hz, 1H), 4.52 (s, 1H), 2.95 (p, J = 5.5 Hz, 1H), 2.69-2.54 (m, 4H), 2.48 (s, 3H), 1.80-1.65 (m, 4H), 1.59 (p, J = 6.5 Hz, 2H). |
| 12 | 2,6-dioxocyclohexyl | S(O)CH$_3$ | cyclopropyl | H | $^1$H NMR (500 MHz, Chloroform-d) δ 9.00 (d, J = 7.0 Hz, 1H), 7.34 (d, J = 7.0 Hz, 1H), 4.37 (s, 1H), 3.05 (s, 3H), 2.95 (p, J = 5.5 Hz, 1H), 2.63-2.55(m, 4H), 1.78-1.68 (m, 2H), 1.67-1.55 (m, 4H). |
| 13 | 2,6-dioxocyclohexyl | S(O)$_2$CH$_3$ | cyclopropyl | H | $^1$H NMR (500 MHz, Chloroform-d) δ 9.16 (d, J = 7.0 Hz, 1H), 7.44 (d, J = 7.0 Hz, 1H), 4.45 (s, 1H), 3.20 (s, 3H), 2.95 (p, J = 5.5 Hz, 1H), 2.70-2.59 (m, 4H), 1.81-1.67 (m, 4H), 1.59 (p, J = 6.5 Hz, 2H). |

TABLE 1-continued

Structures and $^1$H NMR data of compounds

| NO. | Q | X | Y | Z | $^1$HNMR |
|---|---|---|---|---|---|
| 14 | cyclohexane-1,3-dione | methoxy-tert | cyclopropyl | H | $^1$H NMR (500 MHz, Chloroform-d) δ 8.70 (d, J = 7.0 Hz, 1H), 7.26 (d, J = 7.0 Hz, 1H), 4.58 (s, 1H), 3.97 (s, 3H), 2.70-2.50 (m, 5H), 1.79-1.67 (m, 4H), 1.59 (p, J = 6.5 Hz, 2H). |
| 15 | cyclohexane-1,3-dione | NH$_2$ | cyclopropyl | H | |
| 16 | cyclohexane-1,3-dione | N(CH$_3$)$_2$ | cyclopropyl | H | $^1$H NMR (500 MHz, Chloroform-d) δ 8.59 (d, J = 7.5 Hz, 1H), 7.15 (d, J = 7.5 Hz, 1H), 4.71 (s, 1H), 3.10 (s, 6H), 2.70-2.51 (m, 5H), 1.79-1.55 (m, 6H). |
| 17 | cyclohexane-1,3-dione | 2-oxopyrrolidin-1-yl | cyclopropyl | H | $^1$H NMR (500 MHz, Chloroform-d) δ 8.77 (d, J = 7.0 Hz, 1H), 7.18 (d, J = 7.0 Hz, 1H), 4.35 (s, 1H), 3.93 (t, J = 5.0 Hz, 2H), 2.95 (p, J = 5.5 Hz, 1H), 2.66-2.52 (m, 6H), 2.10-2.00 (m, 2H), 1.79-1.66 (m, 4H), 1.60 (p, J = 6.5 Hz, 2H). |

TABLE 1-continued

Structures and ¹H NMR data of compounds

| NO. | Q | X | Y | Z | ¹HNMR |
|---|---|---|---|---|---|
| 18 | cyclohexane-1,3-dione | H | CH₃ | H | ¹H NMR (500 MHz, Chloroform-d) δ 8.86 (d, J = 6.5 Hz, 1H), 7.82 (d, J = 1.5 Hz, 1H), 7.71 (dd, J = 6.5, 1.5 Hz 1H), 4.50 (s, 1H), 2.78 (s, 3H), 2.67-2.52 (m, 4H), 1.59-1.55(m, 2H). |
| 19 | cyclohexane-1,3-dione | F | CH₃ | H | |
| 20 | cyclohexane-1,3-dione | Cl | CH₃ | H | ¹H NMR (500 MHz, Chloroform-d) δ 8.92 (d, J = 7.0 Hz, 1H), 7.26 (d, J = 7.0 Hz, 1H), 4.51 (s, 1H), 2.84 (s, 3H), 2.67-2.52 (m, 4H), 1.59 (p, J = 6.5 Hz, 2H). |
| 21 | cyclohexane-1,3-dione | Br | CH₃ | H | |

TABLE 1-continued
Structures and ¹H NMR data of compounds
| NO. | Q | X | Y | Z | ¹HNMR |
|---|---|---|---|---|---|
| 22 | 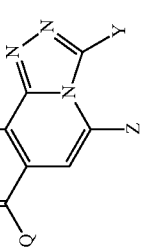 | I | CH₃ | H | |
| 23 | 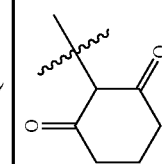 | vinyl | CH₃ | H | |
| 24 | 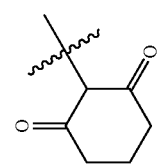 | ethynyl | CH₃ | H | |
| 25 | 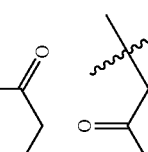 | cyclopropyl | CH₃ | H | |

TABLE 1-continued

Structures and ¹H NMR data of compounds

| NO. | Q | X | Y | Z | ¹HNMR |
|---|---|---|---|---|---|
| 26 | 2,6-dioxocyclohexyl | CN | CH₃ | H | |
| 27 | 2,6-dioxocyclohexyl | NO₂ | CH₃ | H | |
| 28 | 2,6-dioxocyclohexyl | CH₂OCH₃ | CH₃ | H | |
| 29 | 2,6-dioxocyclohexyl | SCH₃ | CH₃ | H | |

TABLE 1-continued

Structures and ¹H NMR data of compounds

| NO. | Q | X | Y | Z | ¹HNMR |
|---|---|---|---|---|---|
| 30 | 2-(1,3-dioxocyclohexyl) | S(=O)CH₃ (tert) | CH₃ | H | |
| 31 | 2-(1,3-dioxocyclohexyl) | S(=O)₂CH₃ (tert) | CH₃ | H | |
| 32 | 2-(1,3-dioxocyclohexyl) | OCH₃ (tert) | CH₃ | H | |
| 33 | 2-(1,3-dioxocyclohexyl) | NH₂ | CH₃ | H | |

TABLE 1-continued

Structures and $^1$H NMR data of compounds

| NO. | Q | X | Y | Z | $^1$HNMR |
|---|---|---|---|---|---|
| 34 | 2-oxocyclohexyl | N,N-dimethylamino (tert-butyl-like) | CH$_3$ | H | |
| 35 | 2-oxocyclohexyl | 2-oxopyrrolidin-1-yl | CH$_3$ | H | |
| 36 | 2-oxocyclohexyl | Cl | H | H | $^1$H NMR (500 MHz, Chloroform-d) δ 8.95 (d, J = 7.0 Hz, 1H), 8.50 (s, 1H), 7.39 (d, J = 7.0 Hz, 1H), 4.50 (s, 1H), 2.67-2.52 (m, 4H), 1.59 (p, J = 6.5 Hz, 2H). |
| 37 | 2-oxocyclohexyl | Cl | F | H | $^1$H NMR (500 MHz, Chloroform-d) δ 8.97 (d, J = 7.0 Hz, 1H), 7.30 (d, J = 7.0 Hz, 1H), 4.51 (s, 1H), 2.67-2.54 (m, 4H), 1.59 (p, J = 6.5 Hz, 2H). |

TABLE 1-continued

Structures and ¹H NMR data of compounds

| NO. | Q | X | Y | Z | ¹HNMR |
|---|---|---|---|---|---|
| 38 | (2-oxocyclohexyl) | Cl | Cl | H | ¹H NMR (500 MHz, Chloroform-d) δ 8.96 (d, J = 7.0 Hz, 1H), 7.29 (d, J = 7.0 Hz, 1H), 4.50 (s, 1H), 2.67-2.54 (m, 4H), 1.59 (p, J = 6.5 Hz, 2H). |
| 39 | (2-oxocyclohexyl) | Cl | Br | H | ¹H NMR (500 MHz, Chloroform-d) δ 8.93 (d, J = 7.0 Hz, 1H), 7.29 (d, J = 7.0 Hz, 1H), 4.51 (s, 1H), 2.67-2.54 (m, 4H), 1.59 (p, J = 6.5 Hz, 2H). |
| 40 | (2-oxocyclohexyl) | Cl | I | H | ¹H NMR (500 MHz, Chloroform-d) δ 8.93 (d, J = 7.0 Hz, 1H), 7.34 (d, J = 7.0 Hz, 1H), 4.51 (s, 1H), 2.67-2.54 (m, 4H), 1.59 (p, J = 6.5 Hz, 2H). |
| 41 | (2-oxocyclohexyl) | Cl | CH$_2$CH$_3$ | H | ¹H NMR (500 MHz, Chloroform-d) δ 8.93 (d, J = 7.0 Hz, 1H), 7.27 (d, J = 7.0 Hz, 1H), 4.52 (s, 1H), 3.11 (q, J = 7.5 Hz, 2H), 2.67-2.52 (m, 4H), 1.59 (p, J = 6.5 Hz, 2H), 1.45 (t, J = 7.5 Hz, 3H). |

TABLE 1-continued

Structures and ¹H NMR data of compounds

| NO. | Q | X | Y | Z | ¹HNMR |
|---|---|---|---|---|---|
| 42 | 2-oxocyclohexyl | Cl | n-butyl | H | |
| 43 | 2-oxocyclohexyl | Cl | isopropyl | H | ¹H NMR (500 MHz, Chloroform-d) δ 8.94 (d, J = 7.0 Hz, 1H), 7.30 (d, J = 7.0 Hz, 1H), 4.52 (s, 1H), 3.45-3.38 (m, 1H), 2.69-2.52 (m, 4H), 1.59 (p, J = 6.5 Hz, 2H), 1.32 (d, J = 6.5 Hz, 6H). |
| 44 | 2-oxocyclohexyl | Cl | n-pentyl | H | |
| 45 | 2-oxocyclohexyl | Cl | tert-butyl | H | ¹H NMR (500 MHz, Chloroform-d) δ 8.75 (d, J = 7.0 Hz, 1H), 7.31 (d, J = 7.0 Hz, 1H), 4.51 (s, 1H), 2.68-2.53 (m, 4H), 1.59 (p, J = 6.5 Hz, 2H), 1.44 (s, 9H). |

TABLE 1-continued

Structures and ¹H NMR data of compounds

| NO. | Q | X | Y | Z | ¹HNMR |
|---|---|---|---|---|---|
| 46 | 2-oxocyclohexyl | Cl | sec-pentyl (CH(Et)(CH2CH3)) | H | ¹H NMR (500 MHz, Chloroform-d) δ 8.94 (d, J = 6.5 Hz, 1H), 7.28 (d, J = 6.5 Hz, 1H), 4.51 (s, 1H), 3.65-3.62 (m, 1H), 2.68-2.52 (m, 4H), 1.83-1.80 (m, 2H), 1.59 (p, J = 6.5 Hz, 2H), 1.46 (d, J = 6.5 Hz, 3H), 0.95 (t, J = 7.5 Hz, 3H). |
| 47 | 2-oxocyclohexyl | Cl | isobutyl | H | ¹H NMR (500 MHz, Chloroform-d) δ 9.14 (d, J = 7.0 Hz, 1H), 7.88 (d, J = 7.0 Hz, 1H), 4.56 (s, 1H), 3.65-3.62 (m, 2H), 2.84-2.75 (m, 2H), 2.47 (d, J = 7.0 Hz, 2H), 2.30-2.28 (m, 1H), 1.85-181 (m, 2H), 1.03 (d, J = 6.5 Hz, 6H). |
| 48 | 2-oxocyclohexyl | Cl | tert-alkyl | H | ¹H NMR (500 MHz, Chloroform-d) δ 8.93 (d, J = 6.5 Hz, 1H), 7.28 (d, J = 6.5 Hz, 1H), 4.51 (s, 1H), 2.88 (t, J = 6.5 Hz, 2H), 2.68-2.52 (m, 4H), 1.88-1.85(m, 2H), 1.59-1.55 (m, 2H), 1.44-1.27 (m, 4H), 0.89 (t, J = 6.5 Hz, 3H). |
| 49 | 2-oxocyclohexyl | Cl | sec-hexyl | H | ¹H NMR (500 MHz, Chloroform-d) δ 9.12 (d, J = 7.0 Hz, 1H), 7.89 (d, J = 7.0 Hz, 1H), 4.56 (s, 1H), 3.35-3.23 (m, 2H), 3.07-3.04(m, 1H), 2.84-2.75 (m, 2H), 2.15-2.13 (m, 1H), 1.94-1.93(m, 1H), 1.85-1.82 (m, 2H), 1.70-1.56 (m, 1H), 1.55-1.48 (m, 1H), 1.42 (d, J = 6.5 Hz, 3H), 0.91 (t, J = 8.0 Hz, 3H). |

TABLE 1-continued

Structures and ¹H NMR data of compounds

| NO. | Q | X | Y | Z | ¹HNMR |
|---|---|---|---|---|---|
| 50 | cyclohexane-1,3-dione | Cl | sec-butyl branched alkyl | H | ¹H NMR (500 MHz, Chloroform-d) δ 9.13 (d, J = 6.5 Hz, 1H), 7.86 (d, J = 6.5 Hz, 1H), 4.56 (s, 1H), 3.29-3.25 (m, 2H), 3.08 (d, J = 6.5 Hz, 2H), 2.84-2.72 (m, 2H), 2.08-2.05 (m, 1H), 1.85-1.81 (m, 2H), 1.73-1.70 (m, 1H), 1.61-1.49 (m, 1H), 1.08 (d, J = 7.0 Hz, 3H), 0.95 (t, J = 8.0 Hz, 3H). |
| 51 | cyclohexane-1,3-dione | Cl | isopentyl branched alkyl | H | ¹H NMR (500 MHz, Chloroform-d) δ 9.13 (d, J = 6.5 Hz, 1H), 7.86 (d, J = 6.5 Hz, 1H), 4.56 (s, 1H), 3.35-3.23 (m, 2H), 2.84-2.75 (m, 2H), 2.53 (t, J = 8.0 Hz, 2H), 1.85-1.81 (m, 2H), 1.67-1.63(m, 1H), 1.58-1.50 (m, 2H), 0.97 (d, J = 7.0 Hz, 6H). |
| 52 | cyclohexane-1,3-dione | Cl | 3-pentyl branched alkyl | H | ¹H NMR (500 MHz, Chloroform-d) δ 9.12 (d, J = 6.5 Hz, 1H), 7.87 (d, J = 6.5 Hz, 1H), 4.56 (s, 1H), 3.29-3.25(m, 2H), 2.99-2.91 (m, 1H), 2.84-2.75 (m, 2H), 2.26-2.22 (m, 2H), 1.95-1.92 (m, 2H), 1.89-1.81 (m, 2H), 0.97 (t, J = 8.0 Hz, 6H). |
| 53 | cyclohexane-1,3-dione | Cl | tert-pentyl branched alkyl | H | ¹H NMR (500 MHz, Chloroform-d) δ 9.09 (d, J = 6.5 Hz, 1H), 7.64 (d, J = 6.5 Hz, 1H), 4.67 (s, 1H), 2.98-2.88 (m, 2H), 2.66-2.62(m, 2H), 1.89-1.80 (m, 2H), 1.75 (q, J = 8.0 Hz, 2H), 1.53 (s, 6H), 0.97 (t, J = 8.0 Hz, 3H). |

TABLE 1-continued

Structures and $^1$H NMR data of compounds

| NO. | Q | X | Y | Z | $^1$HNMR |
|---|---|---|---|---|---|
| 54 | 2-cyclohexane-1,3-dione | Cl | neopentyl | H | $^1$H NMR (500 MHz, Chloroform-d) δ 9.12 (d, J = 6.5 Hz, 1H), 7.87 (d, J = 6.5 Hz, 1H), 4.57 (s, 1H), 5.34-3.22 (m, 2H), 2.84-2.75 (m, 2H), 2.41 (s, 2H), 1.85-1.81 (m, 2H), 1.05 (s, 9H). |
| 55 | 2-cyclohexane-1,3-dione | Cl | n-heptyl | H | $^1$H NMR (500 MHz, Chloroform-d) δ 8.92 (d, J = 6.5 Hz, 1H), 7.28 (d, J = 6.5 Hz, 1H), 4.52 (s, 1H), 2.85 (t, J = 6.5 Hz, 2H), 2.68-2.52 (m, 4H), 1.89-1.85(m, 2H), 1.59-1.55( m, 2H), 1.45-1.38(m, 2H), 1.37-1.25 (m, 4H), 0.93-0.84 (m, 3H). |
| 56 | 2-cyclohexane-1,3-dione | Cl | isohexyl | H | |
| 57 | 2-cyclohexane-1,3-dione | Cl | 3-methylpentyl | H | |

TABLE 1-continued

Structures and ¹H NMR data of compounds

| NO. | Q | X | Y | Z | ¹HNMR |
|---|---|---|---|---|---|
| 58 | cyclohexane-1,3-dione | Cl | 2-methylpentyl | H | |
| 59 | cyclohexane-1,3-dione | Cl | 2-methylpentyl | H | |
| 60 | cyclohexane-1,3-dione | Cl | 3-ethylhexyl | H | |
| 61 | cyclohexane-1,3-dione | Cl | 3-ethyl-3-methylpentyl | H | |

TABLE 1-continued
Structures and ¹H NMR data of compounds

| NO. | Q | X | Y | Z | ¹HNMR |
|---|---|---|---|---|---|
| 62 |  | Cl | 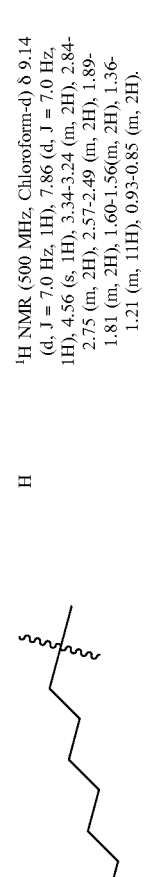 | H | ¹H NMR (500 MHz, Chloroform-d) δ 8.93 (d, J = 6.5 Hz, 1H), 7.28 (d, J = 6.5 Hz, 1H), 4.52 (s, 1H), 2.89 (t, J = 6.5 Hz, 2H), 2.68-2.52 (m, 4H), 1.89-1.85(m, 2H), 1.59-1.55( m, 2H), , 1.51-1.38(m, 4H), 1.32-1.22 (m, 4H), 0.92-0.85 (m, 3H). |
| 63 |  | Cl |  | H | ¹H NMR (500 MHz, Chloroform-d) δ 9.14 (d, J = 6.5 Hz, 1H), 7.86 (d, J = 6.5 Hz, 1H), 4.56 (s, 1H), 3.34-3.24 (m, 2H), 2.84-2.75 (m, 2H), 2.53 (t, J = 8.0 Hz, 2H), 1.85-1.82 (m, 2H), 1.67-1.55 (m, 3H), 1.36-1.26 (m, 2H), 1.23-1.15 (m, 2H), 0.93 (d, J = 6.5 Hz, 6H). |
| 64 | 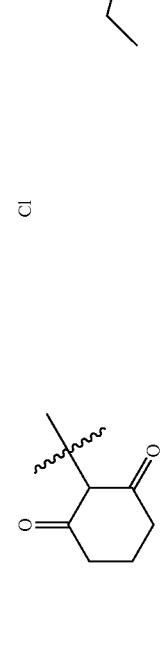 | Cl |  | H | ¹H NMR (500 MHz, Chloroform-d) δ 9.12 (d, J = 6.5 Hz, 1H), 7.88 (d, J = 6.5 Hz, 1H), 4.56 (s, 1H), 3.27-3.24 (m, 2H), 2.84-2.72 (m, 3H), 2.26-2.10 (m, 2H), 1.94-1.77 (m, 4H), 1.58-1.31 (m, 4H), 0.91-0.85(m, 6H). |
| 65 |  | Cl | 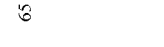 | H | ¹H NMR (500 MHz, Chloroform-d) δ 9.14 (d, J = 7.0 Hz, 1H), 7.86 (d, J = 7.0 Hz, 1H), 4.56 (s, 1H), 3.34-3.24 (m, 2H), 2.84-2.75 (m, 2H), 2.57-2.49 (m, 2H), 1.89-1.81 (m, 2H), 1.60-1.56(m, 2H), 1.36-1.21 (m, 11H), 0.93-0.85 (m, 2H). |

TABLE 1-continued

Structures and ¹H NMR data of compounds

| NO. | Q | X | Y | Z | ¹HNMR |
|---|---|---|---|---|---|
| 66 | cyclohexane-1,3-dione | Cl | n-alkyl chain | H | ¹H NMR (500 MHz, Chloroform-d) δ 9.14 (d, J = 6.5 Hz, 1H), 7.89 (d, J = 6.5 Hz, 1H), 4.56 (s, 1H), 3.34-3.24 (m, 2H), 2.84-2.75 (m, 2H), 2.57-2.49 (m, 2H), 1.86-1.82(m, 2H), 1.60-1.54 (m, 2H), 1.38-1.21 (m, 13H), 0.93-0.85 (m, 2H). |
| 67 | cyclohexane-1,3-dione | Cl | n-alkyl chain | H | ¹H NMR (500 MHz, Chloroform-d) δ 9.14 (d, J = 6.5 Hz, 1H), 7.86 (d, J = 6.5 Hz, 1H), 4.56 (s, 1H), 3.34-3.24 (m, 2H), 2.84-2.75 (m, 2H), 2.53 (t, J = 8.0 Hz, 2H), 1.85-1.80(m, 2H), 1.60-1.54(m, 2H), 1.36-1.20 (m, 15H), 0.93-0.85 (m, 2H). |
| 68 | cyclohexane-1,3-dione | Cl | CHF₂ | H | ¹H NMR (500 MHz, Chloroform-d) δ 8.96 (d, J = 7.0 Hz, 1H), 7.30 (d, J =7.0 Hz, 1H), 7.17-6.94 (m, 1H), 4.50(s, 1H), 2.68-2.54 (m, 4H), 1.59 (p, J = 6.5 Hz, 2H). |
| 69 | cyclohexane-1,3-dione | Cl | CF₃ | H | ¹H NMR (500 MHz, Chloroform-d) δ 8.85 (d, J = 7.0 Hz, 1H), 7.33 (d, J = 7.0 Hz, 1H), 4.50 (s, 1H), 2.68-2.54 (m, 4H), 1.59 (p, J = 6.5 Hz, 2H). |

TABLE 1-continued
Structures and ¹H NMR data of compounds
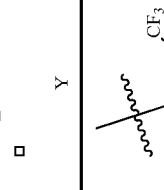
| NO. | Q | X | Y | Z | ¹HNMR |
|---|---|---|---|---|---|
| 70 | 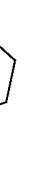 | Cl | 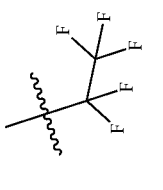 | H | ¹H NMR (500 MHz, Chloroform-d) δ 9.14 (d, J = 6.5 Hz, 1H), 7.88 (d, J = 6.5 Hz, 1H), 4.56 (s, 1H), 3.35-3.23 (m, 2H), 2.85-2.75 (m, 2H), 2.53 (t, J = 8.5 Hz, 2H), 2.14-2.11 (m, 2H), 1.85-1.81(m, 2H). |
| 71 | 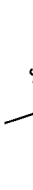 | Cl | 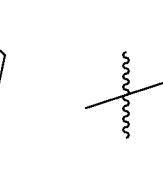 | H | ¹H NMR (500 MHz, Chloroform-d) δ 9.26 (d, J = 6.5 Hz, 1H), 7.93 (d, J = 6.5 Hz, 1H), 4.57 (s, 1H), 3.33-3.23 (m, 2H), 2.80-2.76(m, 2H), 1.85-1.81 (m, 2H). |
| 72 | 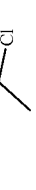 | Cl | 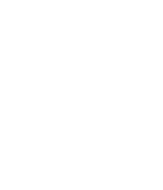 | H | ¹H NMR (500 MHz, Chloroform-d) δ 9.16 (d, J = 6.5 Hz, 1H), 7.87 (d, J = 6.5 Hz, 1H), 4.57 (s, 1H), 3.92-3.88 (m, 2H), 3.33-3.20 (m, 2H), 2.87-2.78 (m, 4H), 1.89-1.81 (m, 2H). |
| 73 | 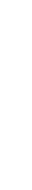 | Cl | (Cl) | H | ¹H NMR (500 MHz, Chloroform-d) δ 9.26 (d, J = 6.5 Hz, 1H), 7.90 (d, J = 6.5 Hz, 1H), 5.40-5.38(m, 1H), 4.56 (s, 1H), 3.36-3.23 (m, 2H), 2.84-2.75 (m, 2H), 2.06-2.03(m, 3H), 1.85-1.82 (m, 2H). |

TABLE 1-continued

Structures and $^1$H NMR data of compounds

| NO. | Q | X | Y | Z | $^1$HNMR |
|---|---|---|---|---|---|
| 74 | (2-oxocyclohexyl) | Cl | (chlorobutyl) | H | $^1$H NMR (500 MHz, Chloroform-d) δ 9.19 (d, J = 6.5 Hz, 1H), 7.88 (d, J = 6.5 Hz, 1H), 4.57 (s, 1H), 3.52-3.48 (m, 2H), 3.35-3.23 (m, 2H), 2.84-2.75 (m, 2H), 2.53-2.50 (m, 2H), 1.95-1.81 (m, 4H). |
| 75 | (2-oxocyclohexyl) | Cl | (allyl) | H | $^1$H NMR (500 MHz, Chloroform-d) δ 8.93 (d, J = 6.5 Hz, 1H), 7.57-7.47 (m, 1H), 7.28 (d, J = 6.5 Hz, 1H), 5.67 (d, J = 13.0 Hz, 1H), 4.51 (s, 1H), 2.67-2.53 (m, 4H), 1.59-1.55(m, 2H). |
| 76 | (2-oxocyclohexyl) | Cl | (butenyl) | H | |
| 77 | (2-oxocyclohexyl) | Cl | (methylbutenyl) | H | $^1$H NMR (500 MHz, Chloroform-d) δ 9.16 (d, J = 6.5 Hz, 1H), 7.86 (d, J = 6.5 Hz, 1H), 5.35-5.32 (m, 2H), 4.51 (s, 1H), 2.88-2.85 (m, 2H), 2.79-2.70 (m, 2H), 2.19 (s, 3H), 1.89-1.81 (m, 2H). |

TABLE 1-continued

Structures and ¹H NMR data of compounds

| NO. | Q | X | Y | Z | ¹HNMR |
|---|---|---|---|---|---|
| 78 | 2-oxocyclohexyl | Cl | (E)-propenyl | H | ¹H NMR (500 MHz, Chloroform-d) δ 9.42 (d, J = 6.5 Hz, 1H), 7.90 (d, J = 6.5 Hz, 1H), 6.99 (d, J = 15.0 Hz, 1H), 6.26-6.23 (m, 1H), 4.57 (s, 1H), 3.29-3.24(m, 2H), 2.85-2.75 (m, 2H), 1.85-1.81 (m, 2H), 1.79-1.74 (m, 3H). |
| 79 | 2-oxocyclohexyl | Cl | 1,2-difluorovinyl-methyl | H | ¹H NMR (500 MHz, Chloroform-d) δ 9.08 (d, J = 7.0 Hz, 1H), 8.01 (d, J = 7.0 Hz, 1H), 4.08 (s, 1H), 2.49-2.44(m, 2H), 2.37-2.34 (m, 2H), 1.85-1.82(m, 2H). |
| 80 | 2-oxocyclohexyl | Cl | propynyl | H | ¹H NMR (500 MHz, Chloroform-d) δ 9.28 (d, J = 6.5 Hz, 1H), 7.92 (d, J = 6.5 Hz, 1H), 4.56 (s, 1H), 3.34-3.22 (m, 2H), 2.84-2.74 (m, 2H), 1.92-1.81 (m, 5H). |
| 81 | 2-oxocyclohexyl | Cl | but-2-ynyl | H | |

TABLE 1-continued

Structures and ¹H NMR data of compounds

| NO. | Q | X | Y | Z | ¹HNMR |
|---|---|---|---|---|---|
| 82 | cyclohexane-1,3-dione attached | Cl | 1-methylcyclopropyl | H | ¹H NMR (500 MHz, Chloroform-d) δ 8.87 (d, J = 7.0 Hz, 1H), 7.31 (d, J = 7.0 Hz, 1H), 4.51 (s, 1H), 2.69-2.53 (m, 4H), 2.05-1.92 (m, 4H), 1.59 (p, J = 6.5 Hz, 2H), 1.39 (s, 3H). |
| 83 | cyclohexane-1,3-dione attached | Cl | 1-methyl-cyclopropyl (ethyl variant) | H | ¹H NMR (500 MHz, Chloroform-d) δ 8.94 (d, J = 7.0 Hz, 1H), 7.28 (d, J = 7.0 Hz, 1H), 4.52 (s, 1H), 2.69-2.53 (m, 5H), 1.88-1.77 (m, 2H), 1.62-1.58 (m, 3H), 1.05 (d, J = 6.5 Hz, 3H). |
| 84 | cyclohexane-1,3-dione attached | Cl | 1-fluoro-cyclopropyl-methyl | H | ¹H NMR (500 MHz, Chloroform-d) δ 8.93 (d, J = 7.0 Hz, 1H), 7.27 (d, J = 7.0 Hz, 1H), 5.11-5.02 (m, 1H), 4.52 (s, 1H), 3.01-2.98 (m, 1H), 2.68-2.53 (m, 4H), 2.34-2.21 (m,, 2H), 1.59 (p, J = 6.5 Hz, 2H). |
| 85 | cyclohexane-1,3-dione attached | Cl | 1-cyano-cyclopropyl-methyl | H | ¹H NMR (500 MHz, Chloroform-d) δ 8.86 (d, J = 7.0 Hz, 1H), 7.29 (d, J = 7.0 Hz, 1H), 4.50 (s, 1H), 2.69-2.53 (m, 4H), 2.46-2.33 (m, 4H), 1.59 (p, J = 6.5 Hz, 2H). |

TABLE 1-continued

Structures and ¹H NMR data of compounds

| NO. | Q | X | Y | Z | ¹HNMR |
|---|---|---|---|---|---|
| 86 | (2-oxocyclohexyl) | Cl | (2,2-dimethylcyclopropyl) | H | ¹H NMR (500 MHz, Chloroform-d) δ 8.94 (d, J = 7.0 Hz, 1H), 7.27 (d, J = 7.0 Hz, 1H), 4.51 (s, 1H), 2.85 (t, J = 6.5 Hz, 1H), 2.68-2.53 (m, 4H), 1.66-1.55 (m, 4H), 1.06 (s, 3H), 1.01 (s, 3H). |
| 87 | (2-oxocyclohexyl) | Cl | (2,2-difluorocyclopropyl) | H | ¹H NMR (500 MHz, Chloroform-d) δ 8.93 (d, J = 7.0 Hz, 1H), 7.25 (d, J = 7.0 Hz, 1H), 4.52 (s, 1H), 3.85-3.79 (m, 1H), 2.68-2.45 (m, 6H), 1.59 (p, J = 6.5 Hz, 2H). |
| 88 | (2-oxocyclohexyl) | Cl | (cyclobutyl) | H | ¹H NMR (500 MHz, Chloroform-d) δ 8.94 (d, J = 7.0 Hz, 1H), 7.28 (d, J = 7.0 Hz, 1H), 4.51 (s, 1H), 3.41 (p, J = 5.5 Hz, 1H), 2.69-2.53 (m, 4H), 2.34-2.17 (m, 4H), 2.00-1.84 (m, 2H), 1.59 (p, J = 6.5 Hz, 2H). |
| 89 | (2-oxocyclohexyl) | Cl | (cyclopentyl) | H | ¹H NMR (500 MHz, Chloroform-d) δ 9.12 (d, J = 6.5 Hz, 1H), 7.89 (d, J = 6.5 Hz, 1H), 4.56 (s, 1H), 3.37-3.34 (m, 1H), 3.28-3.24 (m, 2H), 2.84-2.74 (m, 2H), 2.19-2.07 (m, 2H), 1.89-1.73 (m, 6H), 1.61-1.58 (m, 2H). |

TABLE 1-continued

Structures and ¹H NMR data of compounds

| NO. | Q | X | Y | Z | ¹HNMR |
|---|---|---|---|---|---|
| 90 | cyclohexane-1,3-dione | Cl | cyclohexyl | H | ¹H NMR (500 MHz, Chloroform-d) δ 9.12 (d, J = 6.5 Hz, 1H), 7.89 (d, J = 6.5 Hz, 1H), 4.56 (s, 1H), 3.35-3.23 (m, 2H), 3.10-3.08 (m, 1H), 2.80-2.76 (m, 2H), 2.48-2.44(m, 2H), 2.01-1.98(m, 2H), 1.90-1.81 (m, 4H), 1.79-1.75 (m, 2H), 1.44-1.41 (m, 2H). |
| 91 | cyclohexane-1,3-dione | Cl | cyclopentenyl | H | ¹H NMR (500 MHz, Chloroform-d) δ 9.28 (d, J = 6.5 Hz, 1H), 7.91 (d, J = 6.5 Hz, 1H), 6.14 (t, J = 6.5 Hz, 1H), 4.58 (s, 1H), 3.27-3.23(m, 2H), 2.84-2.74 (m, 2H). 2.30-2.22(m, 4H), 1.89-1.77 (m, 4H). |
| 92 | cyclohexane-1,3-dione | Cl | cyclohexenyl | H | |
| 93 | cyclohexane-1,3-dione | Cl | cyclopropylmethyl | H | ¹H NMR (500 MHz, Chloroform-d) δ 9.09 (d, J = 6.5 Hz, 1H), 7.85 (d, J = 6.5 Hz, 1H), 4.57 (s, 1H), 3.27-3.23 (m, 2H), 2.84-2.74 (m, 2H), 2.47 (d, J = 6.5 Hz, 2H), 1.85-1.81 (m, 2H), 1.00-0.98(m, 1H), 0.56-0.52(m, 2H), 0.42-0.39 (m, 2H). |

TABLE 1-continued

Structures and ¹H NMR data of compounds

| NO. | Q | X | Y | Z | ¹HNMR |
|---|---|---|---|---|---|
| 94 | 2-(1,3-dioxocyclohexyl) | Cl | cyclopentylmethyl (with methyl branch) | H | |
| 95 | 2-(1,3-dioxocyclohexyl) | Cl | cyclohexylmethyl (with methyl branch) | H | |
| 96 | 2-(1,3-dioxocyclohexyl) | Cl | oxiranyl (with methyl branch) | H | |
| 97 | 2-(1,3-dioxocyclohexyl) | Cl | 3-methyloxetan-3-yl (with methyl branch) | H | ¹H NMR (500 MHz, Chloroform-d) δ 9.08 (d, J = 6.5 Hz, 1H), 8.01 (d, J = 6.5 Hz, 1H), 5.09 (s, 2H), 4.84 (s, 2H), 4.08 (s, 1H), 2.49 (t, J = 7.0 Hz, 2H), 2.37 (t, J = 7.0 Hz, 2H), 1.85-1.81(m, 2H), 1.37 (s, 3H). |

TABLE 1-continued

Structures and $^1$H NMR data of compounds

| NO. | Q | X | Y | Z | $^1$HNMR |
|---|---|---|---|---|---|
| 98 | 2-oxocyclohexyl | Cl | 1-methylazetidin-3-yl | H | $^1$H NMR (500 MHz, Chloroform-d) δ 9.08 (d, J = 6.5 Hz, 1H), 8.01 (d, J = 6.5 Hz, 1H), 4.08 (s, 1H), 3.75-3.72 (m, 2H), 3.56-3.46 (m, 3H), 2.49 (t, J = 7.0 Hz, 2H), 2.37 (t, J = 7.0 Hz, 2H), 2.30 (s, 3H), 1.85-1.81 (m, 2H). |
| 99 | 2-oxocyclohexyl | Cl | tetrahydrofuran-2-yl | H | $^1$H NMR (500 MHz, Chloroform-d) δ 9.22 (d, J = 6.5 Hz, 1H), 7.89 (d, J = 6.5 Hz, 1H), 5.39 (t, J = 7.0 Hz, 1H), 4.57 (s, 1H), 4.06-4.03 (m, 1H), 3.93-3.91(m, 1H), 3.30-3.25 (m, 2H), 2.84-2.74 (m, 2H), 2.55-2.53 (m, 1H), 2.24-2.21 (m, 1H), 2.07-2.05 (m, 1H), 1.85-1.81 (m, 2H), 1.67-1.65 (m, 1H). |
| 100 | 2-oxocyclohexyl | Cl | tetrahydrofuran-3-yl | H | $^1$H NMR (500 MHz, Chloroform-d) δ 9.14 (d, J = 6.5 Hz, 1H), 7.89 (d, J = 6.5 Hz, 1H), 4.56 (s, 1H), 4.50-4.48 (m, 1H), 4.26-4.24 (m, 1H), 4.01-3.98 (m, 1H), 3.89-3.86(m, 1H), 3.51-3.48 (m, 1H), 3.28-3.25 (m, 2H), 2.84-2.75 (m, 2H), 2.58-2.55 (m, 1H), 2.19-2.17 (m, 2H), 1.85-1.82 (m, 2H). |
| 101 | 2-oxocyclohexyl | Cl | pyrrolidin-3-yl | H | |

TABLE 1-continued

Structures and ¹H NMR data of compounds

| NO. | Q | X | Y | Z | ¹HNMR |
|---|---|---|---|---|---|
| 102 | 2-(cyclohexane-1,3-dione) | Cl | 1,3-dioxolan-2-yl methyl | H | |
| 103 | 2-(cyclohexane-1,3-dione) | Cl | 2,5-dihydrofuran-2-yl (dimethyl) | H | |
| 104 | 2-(cyclohexane-1,3-dione) | Cl | 5,5-diphenyl-4,5-dihydroisoxazol-3-yl | H | ¹H NMR (500 MHz, Chloroform-d) δ 9.27 (d, J = 6.5 Hz, 1H), 7.84 (d, J = 6.5 Hz, 1H), 7.67-7.02 (m, 4H), 7.39-7.32 (m, 4H), 7.34-7.26 (m, 2H), 4.57 (s, 1H), 2.90 (s, 2H), 2.83-2.72 (m, 2H), 2.62-2.53 (m, 2H), 1.89-1.80 (m, 2H). |
| 105 | 2-(cyclohexane-1,3-dione) | Cl | tetrahydro-2H-pyran-4-yl (dimethyl) | H | ¹H NMR (500 MHz, Chloroform-d) δ 9.13 (d, J = 6.5 Hz, 1H), 7.87 (d, J = 6.5 Hz, 1H), 4.56 (s, 1H), 3.99-3.96 (m, 2H), 3.77-3.74 (m, 2H), 3.35-3.23 (m, 2H), 3.12-3.09 (m, 1H), 2.84-2.75 (m, 2H), 2.23-2.20(m, 2H), 2.05-2.02 (m, 2H), 1.85-1.81 (m, 2H). |

TABLE 1-continued

Structures and ¹H NMR data of compounds

| NO. | Q | X | Y | Z | ¹HNMR |
|---|---|---|---|---|---|
| 106 | 2-(cyclohexane-1,3-dione) | Cl | 1-methylpiperidin-4-yl | H | ¹H NMR (500 MHz, Chloroform-d) δ 9.14 (d, J = 6.5 Hz, 1H), 7.87 (d, J = 6.5 Hz, 1H), 4.56 (s, 1H), 3.35-3.23 (m, 2H), 3.05-3.02 (m, 2H), 2.95-2.91 (m, 1H), 2.84-2.75 (m, 2H), 2.37 (s, 3H), 2.31-2.29 (m, 2H), 2.18-2.15 (m, 2H), 1.93-1.81 (m, 4H). |
| 107 | 2-(cyclohexane-1,3-dione) | Cl | 1,3-dioxan-5-yl | H | |
| 108 | 2-(cyclohexane-1,3-dione) | Cl | 1,4-dioxan-2-yl | H | |
| 109 | 2-(cyclohexane-1,3-dione) | Cl | morpholin-2-yl | H | |

TABLE 1-continued

Structures and ¹H NMR data of compounds

| NO. | Q | X | Y | Z | ¹HNMR |
|---|---|---|---|---|---|
| 110 | 2,6-dioxocyclohexyl | Cl | piperazin-2-yl (NH, NH) | H | |
| 111 | 2,6-dioxocyclohexyl | Cl | 3,4-dihydro-2H-pyran-2-yl | H | |
| 112 | 2,6-dioxocyclohexyl | Cl | 1,2,3,6-tetrahydropyridin-4-yl (NH) | H | |
| 113 | 2,6-dioxocyclohexyl | Cl | -C(CH₃)₂CN | H | ¹H NMR (500 MHz, Chloroform-d) δ 8.65 (d, J = 7.0 Hz, 1H), 7.27 (d, J = 7.0 Hz, 1H), 4.51 (s, 1H), 4.06 (s, 2H), 2.69-2.53 (m, 4H), 1.59-1.55(m, 2H). |

TABLE 1-continued
Structures and ¹H NMR data of compounds
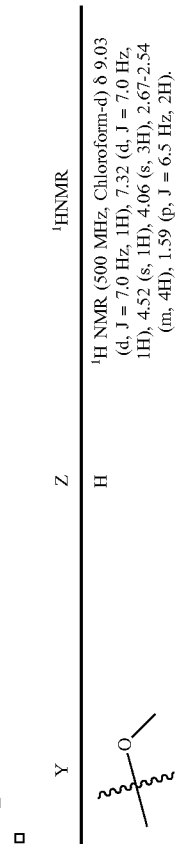
| NO. | Q | X | Y | Z | ¹HNMR |
|---|---|---|---|---|---|
| 114 | 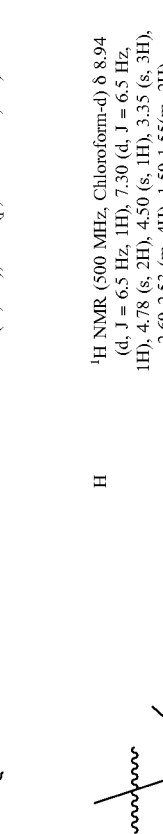 | Cl | 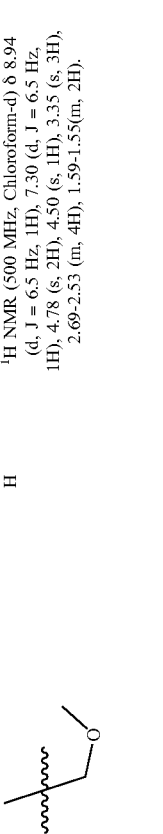 | H | ¹H NMR (500 MHz, Chloroform-d) δ 9.03 (d, J = 7.0 Hz, 1H), 7.32 (d, J = 7.0 Hz, 1H), 4.52 (s, 1H), 4.06 (s, 3H), 2.67-2.54 (m, 4H), 1.59 (p, J = 6.5 Hz, 2H). |
| 115 | 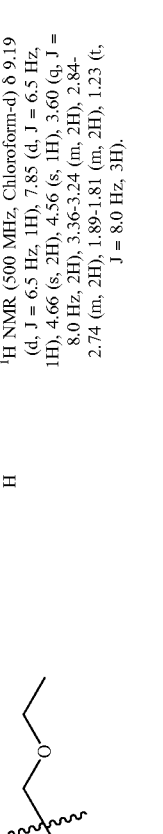 | Cl | 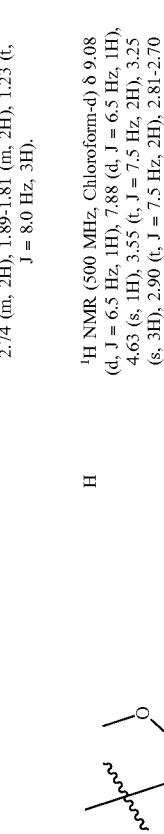 | H | ¹H NMR (500 MHz, Chloroform-d) δ 8.94 (d, J = 6.5 Hz, 1H), 7.30 (d, J = 6.5 Hz, 1H), 4.78 (s, 2H), 4.50 (s, 1H), 3.35 (s, 3H), 2.69-2.53 (m, 4H), 1.59-1.55(m, 2H). |
| 116 |  | Cl | 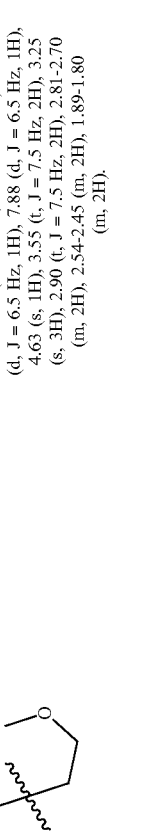 | H | ¹H NMR (500 MHz, Chloroform-d) δ 9.19 (d, J = 6.5 Hz, 1H), 7.85 (d, J = 6.5 Hz, 1H), 4.66 (s, 2H), 4.56 (s, 1H), 3.60 (q, J = 8.0 Hz, 2H), 3.36-3.24 (m, 2H), 2.84-2.74 (m, 2H), 1.89-1.81 (m, 2H), 1.23 (t, J = 8.0 Hz, 3H). |
| 117 |  | Cl |  | H | ¹H NMR (500 MHz, Chloroform-d) δ 9.08 (d, J = 6.5 Hz, 1H), 7.88 (d, J = 6.5 Hz, 1H), 4.63 (s, 1H), 3.55 (t, J = 7.5 Hz, 2H), 3.25 (s, 3H), 2.90 (t, J = 7.5 Hz, 2H), 2.81-2.70 (m, 2H), 2.54-2.45 (m, 2H), 1.89-1.80 (m, 2H). |

TABLE 1-continued

Structures and ¹H NMR data of compounds

| NO. | Q | X | Y | Z | ¹HNMR |
|---|---|---|---|---|---|
| 118 | 2-oxocyclohexyl | Cl | S-tBu | H | ¹H NMR (500 MHz, Chloroform-d) δ 8.86 (d, J = 7.0 Hz, 1H), 7.29 (d, J = 7.0 Hz, 1H), 4.51 (s, 1H), 2.71 (s, 3H), 2.68-2.54 (m, 4H), 1.59 (p, J = 6.5 Hz, 2H). |
| 119 | 2-oxocyclohexyl | Cl | S(O)-tBu | H | ¹H NMR (500 MHz, Chloroform-d) δ 9.01 (d, J = 7.0 Hz, 1H), 7.25 (d, J = 7.0 Hz, 1H), 4.50 (s, 1H), 3.01 (s, 3H), 2.68-2.54 (m, 4H), 1.59 (p, J = 6.5 Hz, 2H). |
| 120 | 2-oxocyclohexyl | Cl | S(O)₂-tBu | H | ¹H NMR (500 MHz, Chloroform-d) δ 9.03 (d, J = 7.0 Hz, 1H), 7.34 (d, J = 7.0 Hz, 1H), 4.49 (s, 1H), 3.18 (s, 3H), 2.68-2.54 (m, 4H), 1.59 (p, J = 6.5 Hz, 2H). |
| 121 | 2-oxocyclohexyl | Cl | CH₂-S-tBu | H | ¹H NMR (500 MHz, Chloroform-d) δ 9.24 (d, J = 6.5 Hz, 1H), 7.89 (d, J = 6.5 Hz, 1H), 4.57 (s, 1H), 3.70 (s, 2H), 3.34-3.21 (m, 2H), 2.84-2.74 (m, 2H), 2.27 (s, 3H), 1.85-1.81 (m, 2H). |

TABLE 1-continued

Structures and ¹H NMR data of compounds

| NO. | Q | X | Y | Z | ¹HNMR |
|---|---|---|---|---|---|
| 122 | 2-oxocyclohexan-1-yl (attached via C) | Cl | isobutylthio (–SCH₂CH(CH₃)₂) | H | ¹H NMR (500 MHz, Chloroform-d) δ 8.93 (d, J = 7.0 Hz, 1H), 7.25 (d, J = 7.0 Hz, 1H), 4.51 (s, 1H), 4.12 (s, 2H), 3.10 (hept, J = 6.5 Hz, 1H), 2.68-2.53 (m, 4H), 1.60 (p, J = 6.5 Hz, 2H), 1.30 (d, J = 6.5 Hz, 6H). |
| 123 | 2-oxocyclohexan-1-yl | Cl | isobutylsulfinyl | H | ¹H NMR (500 MHz, Chloroform-d) δ 8.65 (d, J = 7.0 Hz, 1H), 7.29 (d, J = 7.0 Hz, 1H), 4.53 (s, 1H), 4.28 (s, 2H), 3.06-3.01 (m, 1H), 2.68-2.53 (m, 4H), 1.59 (p, J = 6.5 Hz, 2H), 1.37 (d, J = 6.0 Hz, 6H). |
| 124 | 2-oxocyclohexan-1-yl | Cl | isobutylsulfonyl | H | ¹H NMR (500 MHz, Chloroform-d) δ 8.91 (d, J = 7.0 Hz, 1H), 7.36 (d, J = 7.0 Hz, 1H), 4.56 (s, 2H), 4.51 (s, 1H), 3.62 (hept, J = 6.0 Hz, 1H), 2.69-2.53 (m, 4H), 1.59 (p, J = 6.5 Hz, 2H), 1.39 (d, J = 6.0 Hz, 6H). |
| 125 | 2-oxocyclohexan-1-yl | Cl | (dimethylamino)methyl | H | ¹H NMR (500 MHz, Chloroform-d) δ 8.93 (d, J = 6.5 Hz, 1H), 7.27 (d, J = 6.5 Hz, 1H), 4.51 (s, 1H), 4.27 (s, 2H), 2.69-2.53 (m, 4H), 2.41 (s, 6H), 1.59-1.55 (m, 2H). |

TABLE 1-continued

Structures and ¹H NMR data of compounds

| NO. | Q | X | Y | Z | ¹HNMR |
|---|---|---|---|---|---|
| 126 | 2-oxocyclohexyl | Cl | CHO | H | ¹H NMR (500 MHz, Chloroform-d) δ 10.41 (s, 1H), 9.21 (d, J = 7.0 Hz, 1H), 7.84 (d, J = 7.0 Hz, 1H), 4.54 (s, 1H), 2.49-2.44(m, 2H), 2.37-2.34 (m, 2H), 1.85-1.82(m, 2H). |
| 127 | 2-oxocyclohexyl | Cl | C(O)CH₃ | H | ¹H NMR (500 MHz, Chloroform-d) δ 9.60 (d, J = 6.5 Hz, 1H), 7.92 (d, J = 6.5 Hz, 1H), 4.62 (s, 1H), 2.80-2.70 (m, 2H), 2.67 (s, 3H), 2.51-2.48 (m, 2H), 1.89-1.80 (m, 2H). |
| 128 | 2-oxocyclohexyl | Cl | C(O)N(CH₃)₂ | H | ¹H NMR (500 MHz, Chloroform-d) δ 9.76 (d, J = 6.5 Hz, 1H), 7.95 (d, J = 6.5 Hz, 1H), 4.59 (s, 1H), 3.33-3.24 (m, 2H), 3.15 (s, 6H), 2.85-2.73 (m, 2H), 1.85-1.82 (m, 2H). |
| 129 | 2-oxocyclohexyl | Cl | CH₂Ph | H | ¹H NMR (500 MHz, Chloroform-d) δ 9.15 (d, J = 6.5 Hz, 1H), 7.84 (d, J = 6.5 Hz, 1H), 7.50-7.45 (m, 2H), 7.29-7.25 (m, 2H), 7.15-7.13(m, 1H), 4.56 (s, 1H), 3.81 (s, 2H), 3.31-3.22 (m, 2H), 2.85-2.73 (m, 2H), 1.85-1.82 (m, 2H). |

TABLE 1-continued

Structures and ¹H NMR data of compounds

| NO. | Q | X | Y | Z | ¹HNMR |
|---|---|---|---|---|---|
| 130 | 2-(cyclohexane-1,3-dione) | Cl | -CH2-(pyridin-3-yl) | H | ¹H NMR (500 MHz, Chloroform-d) δ 9.13 (d, J = 7.0 Hz, 1H), 8.72 (s, 1H), 8.39-8.36(m, 1H), 7.86-7.83 (m, 2H), 7.41-7.38 (m, 1H), 4.55 (s, 1H), 3.81 (s, 2H), 3.34-3.22 (m, 2H), 2.83-2.74 (m, 2H), 1.85-1.82 (m, 2H). |
| 131 | 2-(cyclohexane-1,3-dione) | Cl | -CH2-(thiophen-2-yl) | H | ¹H NMR (500 MHz, Chloroform-d) δ 9.38 (d, J = 6.5 Hz, 1H), 7.94 (d, J = 6.5 Hz, 1H), 7.19-7.17 (m, 1H), 6.98-6.96(m, 1H), 6.90-6.88 (m, 1H), 4.58 (s, 1H), 4.08 (s, 2H), 3.36-3.24 (m, 2H), 2.85-2.76 (m, 2H), 1.85-1.82 (m, 2H). |
| 132 | 2-(cyclohexane-1,3-dione) | Cl | -CH2-(thiophen-3-yl) | H | ¹H NMR (500 MHz, Chloroform-d) δ 9.30 (d, J = 6.5 Hz, 1H), 7.90 (d, J = 6.5 Hz, 1H), 7.28 (d, J = 7.0 Hz, 1H), 7.12 (s, 1H), 7.06 (d, J = 7.0 Hz, 1H), 4.57 (s, 1H), 3.86 (s, 2H), 3.36-3.23 (m, 2H), 2.85-2.75 (m, 2H), 1.85-1.82 (m, 2H). |
| 133 | 2-(cyclohexane-1,3-dione) | Cl | phenyl | H | ¹H NMR (500 MHz, Chloroform-d) δ 8.87 (d, J = 7.0 Hz, 1H), 8.17-8.13 (m, 2H), 7.51-7.46 (m, 3H), 7.30 (d, J = 7.0 Hz, 1H), 4.53 (s, 1H), 2.68-2.53 (m, 4H), 1.59 (p, J = 6.5 Hz, 2H). |

TABLE 1-continued

Structures and ¹H NMR data of compounds

| NO. | Q | X | Y | Z | ¹HNMR |
|---|---|---|---|---|---|
| 134 | 2-(cyclohexane-1,3-dione) | Cl | 4-fluorophenyl | H | ¹H NMR (500 MHz, Chloroform-d) δ 9.22 (d, J = 6.5 Hz, 1H), 7.91 (d, J = 6.5 Hz, 1H), 7.76-7.69 (m, 2H), 7.29-7.21 (m, 2H), 4.64 (s, 1H), 2.82-2.72 (m, 2H), 2.50-2.46 (m, 2H), 1.91-1.80 (m, 2H). |
| 135 | 2-(cyclohexane-1,3-dione) | Cl | 3-fluorophenyl | H | ¹H NMR (500 MHz, Chloroform-d) δ 9.31 (d, J = 6.5 Hz, 1H), 7.91 (d, J = 6.5 Hz, 1H), 7.84-7.82 (m, 1H), 7.60-7.57 (m, 1H), 7.52-7.49 (m, 1H), 7.297.25 (m, 1H), 4.58 (s, 1H), 3.35-3.25 (m, 2H), 2.86-2.74 (m, 2H), 1.89-1.81 (m, 2H). |
| 136 | 2-(cyclohexane-1,3-dione) | Cl | 2-fluorophenyl | H | ¹H NMR (500 MHz, Chloroform-d) δ 9.29 (d, J = 6.5 Hz, 1H), 7.90 (d, J = 6.5 Hz, 1H), 7.70-7.66 (m, 1H), 7.43-7.40 (m, 1H), 7.34-7.30 (m, 1H), 7.26-7.23(m, 1H), 4.58 (s, 1H), 3.36-3.26 (m, 2H), 2.80-2.76 (m, 2H), 1.89-1.81 (m, 2H). |

TABLE 1-continued

Structures and ¹H NMR data of compounds

| NO. | Q | X | Y | Z | ¹HNMR |
|---|---|---|---|---|---|
| 137 | 2-oxocyclohexan-1-one (attached at 2-position) | Cl | 4-cyanophenyl | H | ¹H NMR (500 MHz, Chloroform-d) δ 9.22 (d, J = 6.5 Hz, 1H), 7.91-7.86 (m, 3H), 7.88-7.82 (m, 2H), 4.64 (s, 1H), 2.82-2.73 (m, 2H), 2.50-2.46 (m, 2H), 1.89-1.80 (m, 2H). |
| 138 | 2-oxocyclohexan-1-one (attached at 2-position) | Cl | 3-cyanophenyl | H | ¹H NMR (500 MHz, Chloroform-d) δ 9.30 (d, J = 6.5 Hz, 1H), 8.37-8.35 (m, 1H), 8.06 (s, 1H), 7.90 (d, J = 6.5 Hz, 1H), 7.71-7.64 (m, 2H), 4.58 (s, 1H), 3.33-3.24 (m, 2H), 2.80-2.75 (m, 2H), 1.85-1.81 (m, 2H). |
| 139 | 2-oxocyclohexan-1-one (attached at 2-position) | Cl | 2-cyanophenyl | H | ¹H NMR (500 MHz, Chloroform-d) δ 9.14 (d, J = 6.5 Hz, 1H), 7.92 (d, J = 6.5 Hz, 1H), 7.86-7.82(m, 2H), 7.71-7.67 (m, 1H), 7.64-7.60(m, 1H), 4.60 (s, 1H), 3.34-3.24 (m, 2H), 2.80-2.77 (m, 2H), 1.85-1.82 (m, 2H). |

TABLE 1-continued

Structures and ¹H NMR data of compounds

| NO. | Q | X | Y | Z | ¹HNMR |
|---|---|---|---|---|---|
| 140 | 2-(cyclohexane-1,3-dione) | Cl | 4-chlorophenyl | H | ¹H NMR (500 MHz, Chloroform-d) δ 9.30 (d, J = 6.5 Hz, 1H), 7.88 (d, J = 6.5 Hz, 1H), 7.73-7.67 (m, 2H), 7.58-7.51 (m, 2H), 4.58 (s, 1H), 3.32-3.23 (m, 2H), 2.80-2.76 (m, 2H), 1.89-1.81 (m, 2H). |
| 141 | 2-(cyclohexane-1,3-dione) | Cl | 3-chlorophenyl | H | ¹H NMR (500 MHz, Chloroform-d) δ 9.30 (d, J = 6.5 Hz, 1H), 8.00-7.96 (m, 1H), 7.89 (d, J = 6.5 Hz, 1H), 7.71 (s, 1H), 7.57-7.54 (m, 1H), 7.50-7.47 (m, 1H), 4.59 (s, 1H), 3.32-3.23 (m, 2H), 2.80-2.76(m, 2H), 1.85-1.82 (m, 2H). |
| 142 | 2-(cyclohexane-1,3-dione) | Cl | 2-chlorophenyl | H | ¹H NMR (500 MHz, Chloroform-d) δ 9.25 (d, J = 6.5 Hz, 1H), 7.89 (d, J = 6.5 Hz, 1H), 7.66-7.62 (m, 2H), 7.45-7.34 (m, 2H), 4.58 (s, 1H), 3.35-3.26 (m, 2H), 2.80-2.76 (m, 2H), 1.89-1.81 (m, 2H). |
| 143 | 2-(cyclohexane-1,3-dione) | Cl | 2-bromophenyl | H | |

TABLE 1-continued

Structures and ¹H NMR data of compounds

| NO. | Q | X | Y | Z | ¹HNMR |
|---|---|---|---|---|---|
| 144 | 2-(cyclohexane-1,3-dione) | Cl | 3-methylphenyl | H | |
| 145 | 2-(cyclohexane-1,3-dione) | Cl | 4-(prop-1-en-1-yl)phenyl | H | |
| 146 | 2-(cyclohexane-1,3-dione) | Cl | 4-(2-chlorovinyl)phenyl | H | |
| 147 | 2-(cyclohexane-1,3-dione) | Cl | 3-ethynylphenyl | H | |

TABLE 1-continued

Structures and ¹H NMR data of compounds

| NO. | Q | X | Y | Z | ¹HNMR |
|---|---|---|---|---|---|
| 148 | 2-oxocyclohexan-1-yl | Cl | 4-(CF₃)phenyl | H | |
| 149 | 2-oxocyclohexan-1-yl | Cl | 3-(OH)phenyl | H | |
| 150 | 2-oxocyclohexan-1-yl | Cl | 3-(OMe)phenyl | H | |
| 151 | 2-oxocyclohexan-1-yl | Cl | 3-(SO₂Me)phenyl | H | |

TABLE 1-continued
Structures and ¹H NMR data of compounds
| NO. | Q | X | Y | Z | ¹HNMR |
|---|---|---|---|---|---|
| 152 | 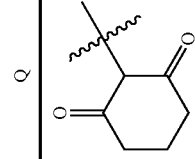 | Cl | 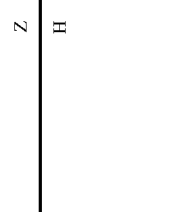 | H | |
| 153 | 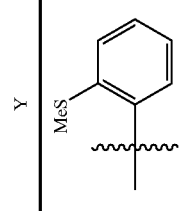 | Cl | 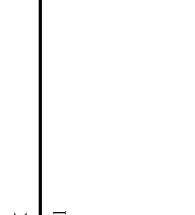 | H | |
| 154 | 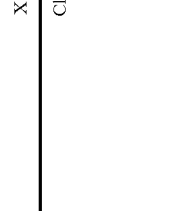 | Cl | 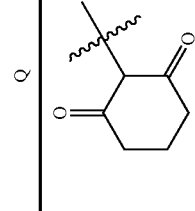 | H | |
| 155 | 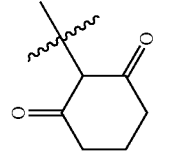 | Cl |  | H | |

TABLE 1-continued

Structures and ¹H NMR data of compounds

| NO. | Q | X | Y | Z | ¹HNMR |
|-----|---|---|---|---|-------|
| 156 | 2,6-dioxocyclohexyl | Cl | 2-acetoxyphenyl | H | |
| 157 | 2,6-dioxocyclohexyl | Cl | 4-formylphenyl | H | |
| 158 | 2,6-dioxocyclohexyl | Cl | 3-acetylphenyl | H | |
| 159 | 2,6-dioxocyclohexyl | Cl | 3-(dimethylamino)phenyl | H | |

TABLE 1-continued

Structures and ¹H NMR data of compounds

| NO. | Q | X | Y | Z | ¹HNMR |
|---|---|---|---|---|---|
| 160 | 2-(1,3-dioxocyclohexyl) | Cl | 4-(NHC(O)CH₃)phenyl | H | |
| 161 | 2-(1,3-dioxocyclohexyl) | Cl | 4-(S(O)CH₃)phenyl | H | |
| 162 | 2-(1,3-dioxocyclohexyl) | Cl | 3-(CH₂CN)phenyl | H | |
| 163 | 2-(1,3-dioxocyclohexyl) | Cl | 4-(CH₂OH)phenyl | H | |

TABLE 1-continued

Structures and ¹H NMR data of compounds

| NO. | Q | X | Y | Z | ¹HNMR |
|---|---|---|---|---|---|
| 164 | cyclohexane-1,3-dione (2-substituted) | Cl | 4-(methoxymethyl)phenyl | H | |
| 165 | cyclohexane-1,3-dione (2-substituted) | Cl | 3-amino-5-methylphenyl | H | ¹H NMR (500 MHz, Chloroform-d) δ 9.57 (d, J = 6.5 Hz, 1H), 8.87 (d, J = 5.0 Hz, 1H), 8.09 (d, J = 8.0 Hz, 1H), 7.96 (d, J = 6.5 Hz, 1H), 7.76 (t, J = 8.0, 1H), 7.29-7.26(m, 1H), 4.60 (s, 1H), 3.36-3.26 (m, 2H), 2.80-2.76 (m, 2H), 1.85-1.82 (m, 2H). |
| 166 | cyclohexane-1,3-dione (2-substituted) | Cl | pyridin-2-yl | H | |
| 167 | cyclohexane-1,3-dione (2-substituted) | Cl | 3,6-dichloropyridin-2-yl | H | ¹H NMR (500 MHz, Chloroform-d) δ 9.40 (d, J = 6.5 Hz, 1H), 7.93 (d, J = 6.5 Hz, 1H), 7.56-7.52 (m, 2H), 4.60 (s, 1H), 3.34-3.25 (m, 2H), 2.80-2.76(m, 2H), 1.85-1.81 (m, 2H). |

TABLE 1-continued

Structures and ¹H NMR data of compounds

| NO. | Q | X | Y | Z | ¹HNMR |
|---|---|---|---|---|---|
| 168 | 2-oxocyclohexyl | Cl | 4,6-dichloropyridin-2-yl | H | ¹H NMR (500 MHz, Chloroform-d) δ 9.60 (d, J = 6.5 Hz, 1H), 8.04 (s, 1H), 7.97 (d, J = 6.5 Hz, 1H), 7.77 (s, 1H), 4.60 (s, 1H), 3.35-3.26 (m, 2H), 2.80-2.76 (m, 2H), 1.85-1.81 (m, 2H). |
| 169 | 2-oxocyclohexyl | Cl | 3,5-dichloropyridin-2-yl | H | ¹H NMR (500 MHz, Chloroform-d) δ 9.36 (d, J = 6.5 Hz, 1H), 8.84 (s, 1H), 8.15 (s, 1H), 7.93 (d, J = 6.5 Hz, 1H), 4.59 (s, 1H), 3.35-3.26 (m, 2H), 2.80-2.76 (m, 2H), 1.85-1.82 (m, 2H). |
| 170 | 2-oxocyclohexyl | Cl | pyridin-3-yl | H | ¹H NMR (500 MHz, Chloroform-d) δ 9.31 (d, J = 6.5 Hz, 1H), 9.12 (s, 1H), 8.65 (d, J = 5.0, 1H), 8.22 (d, J = 8.0, 1H), 7.94 (d, J = 6.5 Hz, 1H), 7.59 (dd, J = 8.0, 5.0 Hz, 1H), 4.58 (s, 1H), 3.34-3.25 (m, 2H), 2.80-2.75 (m, 2H), 1.85-1.82 (m, 2H). |
| 171 | 2-oxocyclohexyl | Cl | 2,4-dichloropyridin-3-yl | H | ¹H NMR (500 MHz, Chloroform-d) δ 9.15 (d, J = 6.5 Hz, 1H), 8.58 (d, J = 5.0 Hz, 1H), 7.91 (d, J = 6.5 Hz, 1H), 7.74 (d, J = 5.0 Hz, 1H), 4.58 (s, 1H), 3.33-3.24 (m, 2H), 2.80-2.76 (m, 2H), 1.85-1.81(m, 2H). |

TABLE 1-continued

Structures and ¹H NMR data of compounds

| NO. | Q | X | Y | Z | ¹HNMR |
|---|---|---|---|---|---|
| 172 | cyclohexane-1,3-dione (2-yl) | Cl | 2,5-dichloropyridin-3-yl | H | ¹H NMR (500 MHz, Chloroform-d) δ 9.25 (d, J = 6.5 Hz, 1H), 8.65 (s, 1H), 8.37 (s, 1H), 7.90 (d, J = 6.5 Hz, 1H), 4.57 (s, 1H), 3.35-3.25 (m, 2H), 2.80-2.76 (m, 2H), 1.85-1.81 (m, 2H). |
| 173 | cyclohexane-1,3-dione (2-yl) | Cl | 2,3-dichloropyridin-... | H | ¹H NMR (500 MHz, Chloroform-d) δ 9.26 (d, J = 6.5 Hz, 1H), 8.41 (d, J = 8.0 Hz, 1H), 7.90 (d, J = 6.5 Hz, 1H), 7.63 (d, J = 8.0 Hz, 1H), 4.57 (s, 1H), 3.35-3.25 (m, 2H), 2.86-2.74 (m, 2H), 1.89-1.81 (m, 2H). |
| 174 | cyclohexane-1,3-dione (2-yl) | Cl | 4,6-dichloropyridin-3-yl | H | ¹H NMR (500 MHz, Chloroform-d) δ 9.23 (d, J = 6.5 Hz, 1H), 7.92 (d, J = 6.5 Hz, 1H), 7.84 (s, 1H), 4.58 (s, 1H), 3.33-3.24 (m, 2H), 2.87-2.74 (m, 2H), 1.89-1.81 (m, 2H). |

TABLE 1-continued

Structures and ¹H NMR data of compounds

| NO. | Q | X | Y | Z | ¹HNMR |
|---|---|---|---|---|---|
| 175 | cyclohexane-1,3-dione | Cl | 5,6-dichloropyridin-3-yl | H | ¹H NMR (500 MHz, Chloroform-d) δ 9.30 (d, J = 6.5 Hz, 1H), 9.04 (s, 1H), 8.49 (s, 1H), 7.94 (d, J = 6.5 Hz, 1H), 4.58 (s, 1H), 3.34-3.24 (m, 2H), 2.81-2.78 (m, 2H), 1.85-1.81 (m, 2H). |
| 176 | cyclohexane-1,3-dione | Cl | pyridin-4-yl | H | ¹H NMR (500 MHz, Chloroform-d) δ 8.87 (d, J = 7.0 Hz, 1H), 8.81-8.76 (m, 2H), 8.02-7.97 (m, 2H), 7.32 (d, J = 7.0 Hz, 1H), 4.53 (s, 1H), 2.68-2.53 (m, 4H), 1.59 (p, J = 6.5 Hz, 2H). |
| 177 | cyclohexane-1,3-dione | Cl | 2,3-dichloropyridin-4-yl | H | ¹H NMR (500 MHz, Chloroform-d) δ 9.25 (d, J = 6.5 Hz, 1H), 8.58 (d, J = 5.0 Hz, 1H), 8.00 (d, J = 5.0 Hz, 1H), 7.90 (d, J = 6.5 Hz, 1H), 4.57 (s, 1H), 3.35-3.25 (m, 2H), 2.80-2.76 (m, 2H), 1.85-1.82(m, 2H). |
| 178 | cyclohexane-1,3-dione | Cl | 2-chloro-3-fluoropyridin-4-yl | H | ¹H NMR (500 MHz, Chloroform-d) δ 9.28 (d, J = 6.5 Hz, 1H), 8.36 (d, J = 5.0 Hz, 1H), 7.94-7.88 (m, 2H), 4.58 (s, 1H), 3.35-3.26 (m, 2H), 2.80-2.76 (m, 2H), 1.89-1.81 (m, 2H). |

TABLE 1-continued

Structures and ¹H NMR data of compounds

| NO. | Q | X | Y | Z | ¹HNMR |
|---|---|---|---|---|---|
| 179 | cyclohexane-1,3-dione | Cl | 2,6-dichloropyridin-4-yl | H | ¹H NMR (500 MHz, Chloroform-d) δ 9.30 (d, J = 6.5 Hz, 1H), 8.14 (s, 2H), 7.93 (d, J = 6.5 Hz, 1H), 4.58 (s, 1H), 3.35-3.23 (m, 2H), 2.86-2.76 (m, 2H), 1.89-1.81 (m, 2H). |
| 180 | cyclohexane-1,3-dione | Cl | 3,5-dichloropyridin-4-yl | H | ¹H NMR (500 MHz, Chloroform-d) δ 9.14 (d, J = 6.5 Hz, 1H), 8.66 (s, 2H), 7.91 (d, J = 6.5 Hz, 1H), 4.57 (s, 1H), 3.34-3.24 (m, 2H), 2.86-2.74 (m, 2H), 1.89-1.81 (m, 2H). |
| 181 | cyclohexane-1,3-dione | Cl | 2,5-dichloropyridin-4-yl | H | ¹H NMR (500 MHz, Chloroform-d) δ 9.24 (d, J = 7.5 Hz, 1H), 8.72 (s, 1H), 8.10 (s, 1H), 7.93 (d, J = 7.5 Hz, 1H), 4.58 (s, 1H), 3.33-3.24 (m, 2H), 2.87-2.74 (m, 2H), 1.89-1.81 (m, 2H). |
| 182 | cyclohexane-1,3-dione | Cl | pyrimidin-2-yl | H | ¹H NMR (500 MHz, Chloroform-d) δ 9.46 (d, J = 6.5 Hz, 1H), 9.04 (d, J = 5.0 Hz, 2H), 7.91 (d, J = 6.5 Hz, 1H), 7.47 (t, J = 5.0 Hz, 1H), 4.59 (s, 1H), 3.35-3.25 (m, 2H), 2.86-2.74 (m, 2H), 1.89-1.81 (m, 2H). |

TABLE 1-continued

Structures and $^1$H NMR data of compounds

| NO. | Q | X | Y | Z | $^1$HNMR |
|---|---|---|---|---|---|
| 183 | 2-(1,3-dioxocyclohexyl) | Cl | pyrimidin-2-yl | H | $^1$H NMR (500 MHz, Chloroform-d) δ 9.58-9.50 (m, 2H), 9.12 (d, J = 5.0 Hz, 1H), 7.97-7.89 (m, 2H), 4.59 (s, 1H), 3.30-3.26 (m, 2H), 2.85-2.76 (m, 2H), 1.85-1.82 (m, 2H). |
| 184 | 2-(1,3-dioxocyclohexyl) | Cl | pyrazin-2-yl | H | $^1$H NMR (500 MHz, Chloroform-d) δ 9.30 (d, J = 6.5 Hz, 1H), 9.16-9.12 (m, 3H), 7.85 (d, J = 6.5 Hz, 1H), 4.60 (s, 1H), 3.32-3.23 (m, 2H), 2.81-2.78 (m, 2H), 1.85-1.81 (m, 2H). |
| 185 | 2-(1,3-dioxocyclohexyl) | Cl | pyridazin-3-yl | H | $^1$H NMR (500 MHz, Chloroform-d) δ 9.56-9.49 (m, 2H), 8.18 (d, J = 7.0 Hz, 1H), 7.97 (d, J = 6.5 Hz, 1H), 7.87 (t, J = 7.0 Hz, 1H), 4.60 (s, 1H), 3.35-3.26 (m, 2H), 2.80-2.76 (m, 2H), 1.85-1.82 (m, 2H). |
| 186 | 2-(1,3-dioxocyclohexyl) | Cl | pyridazin-4-yl | H | $^1$H NMR (500 MHz, Chloroform-d) δ 9.80 (s, 1H), 9.48 (d, J = 6.0 Hz, 1H), 9.31 (d, J = 6.5 Hz, 1H), 8.10 (d, J = 6.0 Hz, 1H), 7.94 (d, J = 6.5 Hz, 1H), 4.58 (s, 1H), 3.32-3.23 (m, 2H), 2.80-2.76 (m, 2H), 1.85-1.81 (m, 2H). |

TABLE 1-continued

Structures and ¹H NMR data of compounds

| NO. | Q | X | Y | Z | ¹HNMR |
|---|---|---|---|---|---|
| 187 | 2,6-dioxocyclohexyl | Cl | 2-pyrazinyl | H | ¹H NMR (500 MHz, Chloroform-d) δ 9.51 (d, J = 6.5 Hz, 1H), 9.39 (s, 1H), 8.91 (d, J = 6.0 Hz, 1H), 8.76 (d, J = 6.0 Hz, 1H), 7.96 (d, J = 6.5 Hz, 1H), 4.59 (s, 1H), 3.35-3.26 (m, 2H), 2.86-2.74 (m, 2H), 1.85-1.82 (m, 2H). |
| 188 | 2,6-dioxocyclohexyl | Cl | 2-pyrimidinyl | H | |
| 189 | 2,6-dioxocyclohexyl | Cl | 5-pyrimidinyl | H | |
| 190 | 2,6-dioxocyclohexyl | Cl | 1,2,4-triazinyl | H | |

TABLE 1-continued
Structures and ¹H NMR data of compounds
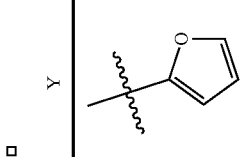
| NO. | Q | X | Y | Z | ¹HNMR |
|---|---|---|---|---|---|
| 191 | 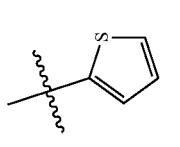 | Cl | 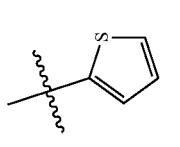 | H | ¹H NMR (500 MHz, Chloroform-d) δ 9.50 (d, J = 6.5 Hz, 1H), 7.89 (dd, J = 7.0, 1.5 Hz, 1H), 7.71 (d, J = 6.5 Hz, 1H), 7.06 (dd, J = 7.0, 1.5 Hz, 1H), 6.70 (t, J = 7.0 Hz, 1H), 4.68 (s, 1H), 2.99-2.89 (m, 2H), 2.67-2.64(m, 2H), 1.85-1.81 (m, 2H). |
| 192 | 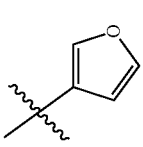 | Cl | 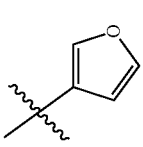 | H | ¹H NMR (500 MHz, Chloroform-d) δ 9.41 (d, J = 6.5 Hz, 1H), 7.86 (d, J = 6.5 Hz, 1H), 7.70 (dd, J = 7.0, 1.5 Hz, 1H), 7.62 (dd, J = 7.0, 1.5 Hz, 1H), 7.29 (t, J =1.0 Hz, 1H), 4.62 (s, 1H), 3.17-3.14(m, 2H), 2.80-2.71 (m, 2H), 1.85-1.82(m, 2H). |
| 193 | 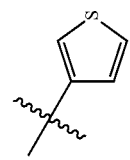 | Cl | 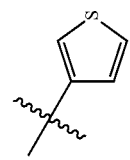 | H | ¹H NMR (500 MHz, Chloroform-d) δ 9.51 (d, J = 6.5 Hz, 1H), 7.97-7.92 (m, 2H), 7.63-7.60 (m, 2H), 4.59 (s, 1H), 3.28-3.25 (m, 2H), 2.85-2.75 (m, 2H), 1.85-1.82 (m, 2H). |
| 194 |  | Cl |  | H | ¹H NMR (500 MHz, Chloroform-d) δ 9.54 (d, J = 6.5 Hz, 1H), 7.95 (d, J = 6.5 Hz, 1H), 7.85 (d, J = 7.0, 1H), 7.63 (s 1H), 7.52 (d, J = 7.0 Hz, 1H), 4.59 (s, 1H), 3.28-3.25 (m, 2H), 2.85-2.76 (m, 2H), 1.85-1.82 (m, 2H). |

TABLE 1-continued

Structures and ¹H NMR data of compounds

| NO. | Q | X | Y | Z | ¹HNMR |
|---|---|---|---|---|---|
| 195 | 2-(cyclohexane-1,3-dione) | Cl | 1-methyl-pyrrol-2-yl | H | ¹H NMR (500 MHz, Chloroform-d) δ 9.43 (d, J = 6.5 Hz, 1H), 7.94 (d, J = 6.5 Hz, 1H), 6.84-6.80 (m, 2H), 6.32 (t, J = 6.5 Hz, 1H), 4.59 (s, 1H), 3.85 (s, 3H), 3.29-3.25 (m, 2H), 2.85-2.75 (m, 2H), 1.85-1.82 (m, 2H). |
| 196 | 2-(cyclohexane-1,3-dione) | Cl | 1-methyl-pyrrol-3-yl | H | |
| 197 | 2-(cyclohexane-1,3-dione) | Cl | 1-methyl-pyrazol-4-yl | H | ¹H NMR (500 MHz, Chloroform-d) δ 9.44 (d, J = 6.5 Hz, 1H), 8.15 (s, 1H), 7.92 (d, J = 6.5 Hz, 1H), 7.45 (s, 1H), 4.58 (s, 1H), 4.00 (s, 3H), 3.36-3.24 (m, 2H), 2.85-2.76 (m, 2H), 1.89-1.81 (m, 2H). |
| 198 | 2-(cyclohexane-1,3-dione) | Cl | 1,3-dimethyl-pyrazol-4-yl | H | ¹H NMR (500 MHz, Chloroform-d) δ 8.97 (d, J = 7.0 Hz, 1H), 7.87 (s, 1H), 7.32 (d, J = 7.0 Hz, 1H), 4.54 (s, 1H), 3.91 (s, 3H), 2.68-2.53 (m, 7H), 1.60 (p, J = 6.5 Hz, 2H). |

TABLE 1-continued

Structures and $^1$H NMR data of compounds

| NO. | Q | X | Y | Z | $^1$HNMR |
|---|---|---|---|---|---|
| 199 | 2,6-dioxocyclohexyl | Cl | 1-methyl-1H-pyrazol-3-yl | H | $^1$H NMR (500 MHz, Chloroform-d) δ 9.50 (d, J = 6.5 Hz, 1H), 7.71 (d, J = 6.5 Hz, 1H), 7.33 (d, J = 6.5 Hz, 1H), 6.67 (d, J = 6.5 Hz, 1H), 4.67 (s, 1H), 3.94 (s, 3H), 2.99-2.90 (m, 2H), 2.67-2.64 (m, 2H), 1.89-1.80 (m, 2H). |
| 200 | 2,6-dioxocyclohexyl | Cl | 1-methyl-1H-pyrazol-5-yl | H | $^1$H NMR (500 MHz, Chloroform-d) δ 9.41 (d, J = 6.5 Hz, 1H), 7.95 (d, J = 6.5 Hz, 1H), 7.69 (d, J = 6.5 Hz, 1H), 6.71 (d, J = 6.5 Hz, 1H), 4.58 (s, 1H), 4.14 (s, 3H), 3.35-3.22 (m, 2H), 2.85-2.76 (m, 2H), 1.85-1.82 (m, 2H). |
| 201 | 2,6-dioxocyclohexyl | Cl | isoxazol-4-yl | H | $^1$H NMR (500 MHz, Chloroform-d) δ 9.44 (d, J = 6.5 Hz, 1H), 8.91 (s, 1H), 8.42 (s, 1H), 7.96 (d, J = 6.5 Hz, 1H), 4.58 (s, 1H), 3.29-3.25 (m, 2H), 2.86-2.76 (m, 2H), 1.85-1.81 (m, 2H). |
| 202 | 2,6-dioxocyclohexyl | Cl | isoxazol-5-yl | H | $^1$H NMR (500 MHz, Chloroform-d) δ 9.51 (d, J = 7.0 Hz, 1H), 8.24 (d, J = 7.0 Hz, 1H), 7.98 (d, J = 7.0 Hz, 1H), 7.28 (d, J = 7.0 Hz, 1H), 4.59 (s, 1H), 3.29-3.26 (m, 2H), 2.85-2.76 (m, 2H), 1.85-1.82(m, 2H). |

TABLE 1-continued

Structures and ¹H NMR data of compounds

| NO. | Q | X | Y | Z | ¹HNMR |
|---|---|---|---|---|---|
| 203 | (2-substituted cyclohexane-1,3-dione) | Cl | (3-isoxazolyl) | H | ¹H NMR (500 MHz, Chloroform-d) δ 9.52 (d, J = 6.5 Hz, 1H), 8.74 (d, J = 7.0 Hz, 1H), 7.96 (d, J = 6.5 Hz, 1H), 7.51 (d, J = 7.0 Hz, 1H), 4.60 (s, 1H), 3.30-3.25 (m, 2H), 2.85-2.76 (m, 2H), 1.85-1.82 (m, 2H). |
| 204 | (2-substituted cyclohexane-1,3-dione) | Cl | (5-isothiazolyl) | H | |
| 205 | (2-substituted cyclohexane-1,3-dione) | Cl | (4-isothiazolyl) | H | |
| 206 | (2-substituted cyclohexane-1,3-dione) | Cl | (3-isothiazolyl) | H | |

TABLE 1-continued

Structures and ¹H NMR data of compounds

| NO. | Q | X | Y | Z | ¹HNMR |
|---|---|---|---|---|---|
| 207 | 2-oxocyclohexyl | Cl | oxazol-4-yl | H | ¹H NMR (500 MHz, Chloroform-d) δ 9.55 (d, J = 7.0 Hz, 1H), 8.34-8.30 (m, 2H), 7.95 (d, J = 7.0 Hz, 1H), 4.60 (s, 1H), 3.35-3.23 (m, 2H), 2.84-2.74 (m, 2H), 1.85-1.82(m, 2H). |
| 208 | 2-oxocyclohexyl | Cl | oxazol-5-yl | H | ¹H NMR (500 MHz, Chloroform-d) δ 9.47 (d, J = 7.0 Hz, 1H), 8.03 (s, 1H), 7.97 (d, J = 7.0 Hz, 1H), 7.43 (s, 1H), 4.59 (s, 1H), 3.30-3.26 (m, 2H), 2.86-2.76 (m, 2H), 1.89-1.81 (m, 2H). |
| 209 | 2-oxocyclohexyl | Cl | thiazol-4-yl | H | ¹H NMR (500 MHz, Chloroform-d) δ 9.43 (d, J = 6.5 Hz, 1H), 9.08 (s, 1H), 8.61 (s, 1H), 7.96 (d, J = 6.5 Hz, 1H), 4.58 (s, 1H), 3.36-3.24 (m, 2H), 2.85-2.76 (m, 2H), 1.85-1.81 (m, 2H). |
| 210 | 2-oxocyclohexyl | Cl | thiazol-5-yl | H | ¹H NMR (500 MHz, Chloroform-d) δ 9.58 (d, J = 6.5 Hz, 1H), 9.19 (s, 1H), 7.95 (d, J = 6.5 Hz, 1H), 7.71 (s, 1H), 4.60 (s, 1H), 3.29-3.25(m, 2H), 2.84-2.75 (m, 2H), 1.85-1.81 (m, 2H). |

TABLE 1-continued

Structures and $^1$H NMR data of compounds

| NO. | Q | X | Y | Z | $^1$HNMR |
|---|---|---|---|---|---|
| 211 | 2-(1,3-dioxocyclohexyl) | Cl | 2-thiazolyl | H | $^1$H NMR (500 MHz, Chloroform-d) δ 9.58 (d, J = 6.5 Hz, 1H), 8.11 (d, J = 7.0 Hz, 1H), 7.96 (d, J = 6.5 Hz, 1H), 7.46 (d, J = 7.0 Hz, 1H), 4.60 (s, 1H), 3.29-3.25 (m, 2H), 2.84-2.75 (m, 2H), 1.89-1.81 (m, 2H). |
| 212 | 2-(1,3-dioxocyclohexyl) | Cl | 1-methyl-imidazol-5-yl | H | $^1$H NMR (500 MHz, Chloroform-d) δ 9.44 (d, J = 6.5 Hz, 1H), 7.96 (d, J = 6.5 Hz, 1H), 7.83 (s, 1H), 7.73 (s, 1H), 4.59 (s, 1H), 4.08 (s, 3H), 3.35-3.23 (m, 2H), 2.85-2.76 (m, 2H), 1.85-1.82 (m, 2H). |
| 213 | 2-(1,3-dioxocyclohexyl) | Cl | 1-methyl-imidazol-4-yl | H | $^1$H NMR (500 MHz, Chloroform-d) δ 9.57 (d, J = 6.5 Hz, 1H), 7.94 (d, J = 6.5 Hz, 1H), 7.80 (s, 1H), 7.52 (s, 1H), 4.60 (s, 1H), 3.69 (s, 3H), 3.31-3.28 (m, 2H), 2.85-2.75 (m, 2H), 1.85-1.81 (m, 2H). |
| 214 | 2-(1,3-dioxocyclohexyl) | Cl | 1-methyl-imidazol-2-yl | H | $^1$H NMR (500 MHz, Chloroform-d) δ 9.56 (d, J = 6.5 Hz, 1H), 7.95 (d, J = 6.5 Hz, 1H), 7.47 (d, J = 6.0 Hz, 1H), 7.16 (d, J = 6.0 Hz, 1H), 4.60 (s, 1H), 3.89 (s, 3H), 3.35-3.23 (m, 2H), 2.84-2.74 (m, 2H), 1.85-1.82 (m, 2H). |

TABLE 1-continued

Structures and ¹H NMR data of compounds

| NO. | Q | X | Y | Z | ¹HNMR |
|---|---|---|---|---|---|
| 215 | 2,6-dioxocyclohexyl | Cl | isoxazol-4-yl | H | ¹H NMR (500 MHz, Chloroform-d) δ 9.28 (d, J = 6.5 Hz, 1H), 7.92 (d, J = 6.5 Hz, 1H), 7.74 (s, 1H), 4.58 (s, 1H), 3.31-3.22 (m, 2H), 2.85-2.73 (m, 2H), 1.85-1.82 (m, 2H). |
| 216 | 2,6-dioxocyclohexyl | Cl | isothiazol-4-yl | H | |
| 217 | 2,6-dioxocyclohexyl | Cl | 1H-pyrazol-4-yl | H | |
| 218 | 2,6-dioxocyclohexyl | Cl | 5-methyl-1,3,4-oxadiazol-2-yl | H | ¹H NMR (500 MHz, Chloroform-d) δ 9.31 (d, J = 6.5 Hz, 1H), 7.93 (d, J = 6.5 Hz, 1H), 4.58 (s, 1H), 3.33-3.21 (m, 2H), 2.83-2.74 (m, 2H), 2.51 (s, 3H), 1.85-1.82 (m, 2H). |

TABLE 1-continued

Structures and ¹H NMR data of compounds

| NO. | Q | X | Y | Z | ¹HNMR |
|---|---|---|---|---|---|
| 219 | 2-cyclohexane-1,3-dione | Cl | 1,3,4-thiadiazol-2-yl | H | ¹H NMR (500 MHz, Chloroform-d) δ 11.00(s, 1H), 9.93 (s, 1H), 9.53 (d, J = 6.5 Hz, 1H), 7.97 (d, J = 6.5 Hz, 1H), 4.61 (s, 1H), 3.33-3.21 (m, 2H), 2.83-2.74 (m, 2H), 1.85-1.82 (m, 2H). |
| 220 | 2-cyclohexane-1,3-dione | Cl | 1H-imidazol-2-yl | H | |
| 221 | 2-cyclohexane-1,3-dione | Cl | 1,2,4-oxadiazol-3-yl | H | |
| 222 | 2-cyclohexane-1,3-dione | Cl | 1,3,4-thiadiazol-2-yl | H | |

TABLE 1-continued

Structures and $^1$H NMR data of compounds

| NO. | Q | X | Y | Z | $^1$HNMR |
|---|---|---|---|---|---|
| 223 | 2,6-dioxocyclohexyl | Cl | 1H-imidazol-2-yl | H | |
| 224 | 2,6-dioxocyclohexyl | Cl | isoxazol-4-yl | H | |
| 225 | 2,6-dioxocyclohexyl | Cl | 1,2,3-thiadiazol-5-yl | H | |
| 226 | 2,6-dioxocyclohexyl | Cl | 1H-1,2,3-triazol-4-yl | H | |

TABLE 1-continued

Structures and ¹H NMR data of compounds

| NO. | Q | X | Y | Z | ¹HNMR |
|---|---|---|---|---|---|
| 227 | cyclohexane-1,3-dione-2-yl | Cl | 1,2,5-oxadiazole | H | |
| 228 | cyclohexane-1,3-dione-2-yl | Cl | 1,2,5-thiadiazole | H | |
| 229 | cyclohexane-1,3-dione-2-yl | Cl | 1,2,3-oxadiazole | H | |
| 230 | cyclohexane-1,3-dione-2-yl | Cl | 1,2,3-thiadiazole | H | |

TABLE 1-continued

Structures and ¹H NMR data of compounds

| NO. | Q | X | Y | Z | ¹HNMR |
|---|---|---|---|---|---|
| 231 | 2,6-dioxocyclohexyl | Cl | 1H-tetrazol-5-yl | H | |
| 232 | 2,6-dioxocyclohexyl | Cl | 4H-1,2,4-triazol-3-yl (methyl) | H | |
| 233 | 2,6-dioxocyclohexyl | Cl | naphthalen-1-yl | H | ¹H NMR (500 MHz, Chloroform-d) δ 9.17 (d, J = 6.5 Hz, 1H), 8.27 (d, J = 7.5, 1H), 8.11 (t, J = 7.5 Hz, 1H), 8.03 (d, J = 7.5, 1H), 7.95-7.91 (m, 2H), 7.89 (d, J = 6.5 Hz, 1H), 7.53-7.50(m, 2H), 4.58 (s, 1H), 3.35-3.25 (m, 2H), 2.80-2.77 (m, 2H), 1.85-1.81 (m, 2H). |
| 234 | 2,6-dioxocyclohexyl | Cl | naphthalen-2-yl | H | ¹H NMR (500 MHz, Chloroform-d) δ 9.35 (d, J = 6.5 Hz, 1H), 8.78 (s, 1H), 8.16 (d, J = 7.5, 1H), 8.09-8.05 (m, 2H), 7.95-7.91 (m, 2H), 7.55-7.51(m, 2H), 4.59 (s, 1H), 3.34-3.25 (m, 2H), 2.81-2.78(m, 2H), 1.85-1.82 (m, 2H). |

TABLE 1-continued

Structures and $^1$H NMR data of compounds

| NO. | Q | X | Y | Z | $^1$HNMR |
|---|---|---|---|---|---|
| 235 | 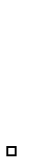 | Cl | 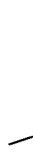 | H | $^1$H NMR (500 MHz, Chloroform-d) δ 9.27 (d, J = 6.5 Hz, 1H), 9.05 (d, J = 5.0, 1H), 8.33 (d, J = 7.5, 1H), 8.20 (d, J = 7.5 Hz 1H), 8.00 (d, J = 7.5 Hz, 1H), 7.89 (d, J = 6.5 Hz, 1H), 7.77 (t, J = 7.5 Hz, 1H), 7.52-7.49 (m, 1H), 4.60 (s, 1H), 3.37-3.28 (m, 2H), 2.80-2.76 (m, 2H), 1.85-1.81 (m, 2H). |
| 236 | 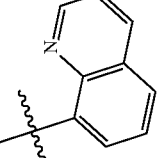 | Cl |  | H | $^1$H NMR (500 MHz, Chloroform-d) δ 9.18 (d, J = 6.5 Hz, 1H), 8.90 (d, J = 7.5, 1H), 8.38 (d, J = 7.5, 1H), 8.30 (d, J = 7.5, 1H), 8.06-7.96 (m, 2H), 7.87 (d, J = 6.5 Hz, 1H), 7.57-7.54 (m, 1H), 4.59 (s, 1H), 3.33-3.24 (m, 2H), 2.80-2.76 (m, 2H), 1.85-1.81 (m, 2H). |
| 237 | 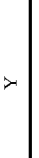 | Cl | 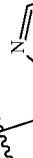 | H | $^1$H NMR (500 MHz, Chloroform-d) δ 9.13-9.09 (m, 2H), 8.21-8.19 (m, 1H), 8.03-8.00 (m, 1H), 7.88-7.85 (m, 2H), 7.72 (t, J = 7.5, , 1H), 7.58 (t, J = 7.5 Hz, 1H), 4.64 (s, 1H), 2.81-2.71 (m, 2H), 2.48-2.44 (m, 2H), 1.89-1.80 (m, 2H). |
| 238 | 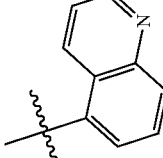 | Cl | 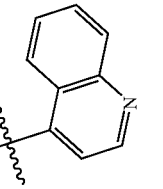 | H | $^1$H NMR (500 MHz, Chloroform-d) δ 9.44 (d, J = 6.5 Hz, 1H), 8.87 (d, J = 6.5 Hz, 1H), 8.32 (d, J = 7.0 Hz, 1H), 7.97-7.92 (m, 3H), 7.72-7.61 (m, 2H), 4.60 (s, 1H), 3.37-3.28 (m, 2H), 2.80-2.76 (m, 2H), 1.85-1.82 (m, 2H). |

TABLE 1-continued

Structures and ¹H NMR data of compounds

| NO. | Q | X | Y | Z | ¹HNMR |
|---|---|---|---|---|---|
| 239 | 2,6-dioxocyclohexyl | Cl | 3,7-dichloroquinolin-8-yl | H | ¹H NMR (500 MHz, Chloroform-d) δ 9.16 (d, J = 6.5 Hz, 1H), 8.98 (s, 1H), 8.20 (d, J = 7.5, 1H), 8.09 (s, 1H), 7.88 (d, J = 7.5 Hz, 1H), 7.78 (d, J = 6.5 Hz, 1H), 4.59 (s, 1H), 3.31-3.22 (m, 2H), 2.85-2.73 (m, 2H), 1.85-1.82 (m, 2H). |
| 240 | 2,6-dioxocyclohexyl | Cl | quinoxalin-5-yl | H | |
| 241 | 2,6-dioxocyclohexyl | Cl | phthalazin-5-yl | H | |
| 242 | 2,6-dioxocyclohexyl | Cl | cinnolin-5-yl | H | |

TABLE 1-continued

Structures and ¹H NMR data of compounds

| NO. | Q | X | Y | Z | ¹HNMR |
|---|---|---|---|---|---|
| 243 | 2,6-dioxocyclohexyl | Cl | pyrido-pyrazine | H | |
| 244 | 2,6-dioxocyclohexyl | Cl | benzofuran | H | |
| 245 | 2,6-dioxocyclohexyl | Cl | benzothiophene | H | |
| 246 | 2,6-dioxocyclohexyl | Cl | indole | H | |

TABLE 1-continued

Structures and ¹H NMR data of compounds

| NO. | Q | X | Y | Z | ¹HNMR |
|---|---|---|---|---|---|
| 247 | 2,6-dioxocyclohexyl | Cl | benzoxazol-2-yl | H | |
| 248 | 2,6-dioxocyclohexyl | Cl | benzothiazol-5-yl | H | |
| 249 | 2,6-dioxocyclohexyl | Cl | 1H-benzimidazol-5-yl | H | |
| 250 | 2,6-dioxocyclohexyl | Cl | benzo[c]isoxazol-5-yl | H | |

TABLE 1-continued

Structures and ¹H NMR data of compounds

| NO. | Q | X | Y | Z | ¹HNMR |
|---|---|---|---|---|---|
| 251 | cyclohexane-1,3-dione | Cl | imidazo[1,2-a]pyridine | H | |
| 252 | cyclohexane-1,3-dione | Cl | benzotriazole | H | |
| 253 | cyclohexane-1,3-dione | Cl | imidazo[4,5-b]pyridine | H | |
| 254 | cyclohexane-1,3-dione | Cl | imidazo[1,2-a]pyrimidine | H | |

TABLE 1-continued

Structures and ¹H NMR data of compounds

| NO. | Q | X | Y | Z | ¹HNMR |
|---|---|---|---|---|---|
| 255 | 2,6-dioxocyclohexyl | Cl | imidazo[1,2-a]pyrazinyl | H | |
| 256 | 2,6-dioxocyclohexyl | Cl | anthracenyl | H | |
| 257 | 2,6-dioxocyclohexyl | Cl | phenanthrenyl | H | |
| 258 | 2,6-dioxocyclohexyl | Cl | acridinyl | H | |

TABLE 1-continued

Structures and ¹H NMR data of compounds

| NO. | Q | X | Y | Z | ¹HNMR |
|---|---|---|---|---|---|
| 259 | 2-oxocyclohexanone linked | Cl | dibenzo[a,c]phenazine-type (acridine) group | H | |
| 260 | 2-oxocyclohexanone linked | Cl | 1,10-phenanthrolin-5-yl | H | |
| 261 | 2-oxocyclohexanone linked | Cl | cyclopropyl | F | ¹H NMR (500 MHz, Chloroform-d) δ 7.89 (d, J = 11.0 Hz, 1H), 4.55 (s, 1H), 3.12-3.09 (m, 1H), 2.63-2.58 (m, 4H), 1.82-1.66 (m, 4H), 1.59-1.55(m, 2H). |
| 262 | 2-oxocyclohexanone linked | Cl | cyclopropyl | Cl | ¹H NMR (500 MHz, Chloroform-d) δ 7.97 (s, 1H), 4.57 (s, 1H), 3.17-3.14(m, 1H), 2.63-2.58 (m, 4H), 1.82-1.66 (m, 4H), 1.59-1.55(m, 2H). |

TABLE 1-continued

Structures and ¹H NMR data of compounds

| NO. | Q | X | Y | Z | ¹HNMR |
|---|---|---|---|---|---|
| 263 | 5-methyl-2,6-dioxocyclohexyl | Cl | cyclopropyl | H | ¹H NMR (500 MHz, Chloroform-d) δ 8.92 (d, J = 7.0 Hz, 1H), 7.25 (d, J = 7.0 Hz, 1H), 4.51 (s, 1H), 2.95 (p, J = 5.5 Hz, 1H), 2.51-2.43 (m, 4H), 2.31-2.17 (m, 1H), 1.79-1.62 (m, 4H), 1.09 (d, J = 1.0 Hz, 3H). |
| 264 | 5,5-dimethyl-2,6-dioxocyclohexyl | Cl | cyclopropyl | H | ¹H NMR (500 MHz, Chloroform-d) δ 8.92 (d, J = 7.0 Hz, 1H), 7.28 (d, J = 7.0 Hz, 1H), 4.50 (s, 1H), 2.95 (p, J = 5.5 Hz, 1H), 2.29 (s, 4H), 1.79-1.62 (m, 4H), 1.03 (s, 6H). |
| 265 | 3,3-dimethyl-2,6-dioxocyclohexyl | Cl | cyclopropyl | H | ¹H NMR (500 MHz, Chloroform-d) δ 8.93 (d, J = 7.0 Hz, 1H), 7.29 (d, J = 7.0 Hz, 1H), 4.62 (s, 1H), 2.95 (p, J = 5.5 Hz, 1H), 2.65-2.04 (m, 4H), 1.79-1.62 (m, 4H), 1.19 (s, 3H), 1.14 (s, 3H). |
| 266 | 3,3,5,5-tetramethyl-2,6-dioxocyclohexyl | Cl | cyclopropyl | H | |

TABLE 1-continued
Structures and ¹H NMR data of compounds
| NO. | Q | X | Y | Z | ¹HNMR |
|-----|---|---|---|---|-------|
| 267 | 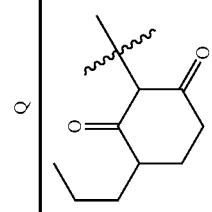 | Cl | 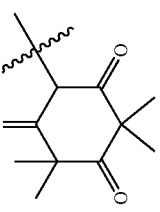 | H | |
| 268 | 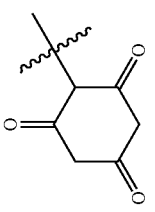 | Cl | 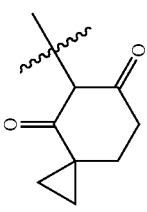 | H | |
| 269 | 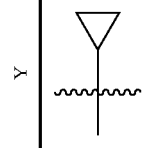 | Cl | 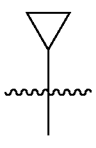 | H | |
| 270 | | Cl | | H | |

TABLE 1-continued

Structures and ¹H NMR data of compounds

| NO. | Q | X | Y | Z | ¹HNMR |
|---|---|---|---|---|---|
| 271 | | Cl | cyclopropyl | H | ¹H NMR (500 MHz, Chloroform-d) δ 8.94 (d, J = 7.0 Hz, 1H), 7.30 (d, J = 7.0 Hz, 1H), 4.67 (s, 1H), 2.95 (p, J = 5.5 Hz, 1H), 2.61-2.38 (m, 3H), 1.88-1.55 (m, 7H). |
| 272 | | Cl | cyclopropyl | H | |
| 273 | | F | cyclopropyl | H | |
| 274 | | Cl | cyclopropyl | H | ¹H NMR (500 MHz, Chloroform-d) δ 8.94 (d, J = 7.0 Hz, 1H), 7.27 (d, J = 7.0 Hz, 1H), 4.42 (s, 1H), 3.06-2.91 (m, 3H), 2.20-2.11 (m, 2H), 2.00-1.88 (m, 2H), 1.88-1.62 (m, 6H). |

TABLE 1-continued

Structures and ¹H NMR data of compounds

| NO. | Q | X | Y | Z | ¹HNMR |
|---|---|---|---|---|---|
| 275 | (bicyclic diketone) | Br | cyclopropyl | H | |
| 276 | (bicyclic diketone) | I | cyclopropyl | H | |
| 277 | (bicyclic diketone) | vinyl | cyclopropyl | H | |
| 278 | (bicyclic diketone) | ethynyl | cyclopropyl | H | |

TABLE 1-continued

Structures and ¹H NMR data of compounds

| NO. | Q | X | Y | Z | ¹HNMR |
|---|---|---|---|---|---|
| 279 | | cyclopropyl | cyclopropyl | H | |
| 280 | | CN | cyclopropyl | H | |
| 281 | | NO₂ | cyclopropyl | H | |
| 282 | | CH₂OCH₃ | cyclopropyl | H | |

TABLE 1-continued

Structures and ¹H NMR data of compounds

| NO. | Q | X | Y | Z | ¹HNMR |
|---|---|---|---|---|---|
| 283 | bicyclic diketone | S-methyl | cyclopropyl | H | |
| 284 | bicyclic diketone | S(=O)-methyl | cyclopropyl | H | |
| 285 | bicyclic diketone | S(=O)₂-methyl | cyclopropyl | H | |
| 286 | bicyclic diketone | O-methyl | cyclopropyl | H | |

TABLE 1-continued

Structures and ¹H NMR data of compounds

| NO. | Q | X | Y | Z | ¹HNMR |
|---|---|---|---|---|---|
| 287 | bicyclic diketone | NH₂ | cyclopropyl | H | |
| 288 | bicyclic diketone | N(CH₃)₂ | cyclopropyl | H | |
| 289 | bicyclic diketone | 2-oxopyrrolidinyl | cyclopropyl | H | |
| 290 | bicyclic diketone | H | CH₃ | H | ¹H NMR (500 MHz, Chloroform-d) δ 8.86 (d, J = 6.5 Hz, 1H), 7.82 (d, J = 1.5 Hz, 1H), 7.68 (dd, J = 6.5, 1.5 Hz, 1H), 4.45 (s, 1H), 3.06-2.95 (m, 2H), 2.82 (s, 3H), 2.14-2.11 (m, 1H), 1.98-1.89 (m, 2H), 1.92-1.80 (m, 2H), 1.82-1.74 (m, 1H). |

TABLE 1-continued

Structures and ¹H NMR data of compounds

| NO. | Q | X | Y | Z | ¹HNMR |
|---|---|---|---|---|---|
| 291 | | CN | CH₃ | H | |
| 292 | | Cl | | H | |
| 293 | | Cl | | H | ¹H NMR (500 MHz, Deuterium Oxide) δ 8.25 (d, J = 7.0 Hz, 1H), 6.88 (d, J = 7.0 Hz, 1H), 2.61-2.55 (m, 1H), 2.30 (t, J = 6.5 Hz, 4H), 1.86-1.78 (m, 2H), 1.66-1.14 (m, 8H), 0.90 (t, J = 8.0 Hz, 3H), 0.84 (t, J = 8.0 Hz, 3H). |
| 294 | | Cl | | H | ¹H NMR (500 MHz, DMSO-d₆) δ 8.33 (d, J = 7.5 Hz, 1H), 6.98(d, J = 7.5 Hz, 1H), 2.97-2.92 (m, 2H), 2.34-2.28 (m, 4H), 1.61-1.53 (m, 4H), 1.30-1.24 (m, 10H), 0.97-0.75 (m, 3H). |

TABLE 1-continued

Structures and $^1$H NMR data of compounds

| NO. | X | Y | Z | $^1$HNMR |
|-----|---|---|---|----------|
| 295 | Cl | n-nonyl chain | H | $^1$H NMR (500 MHz, DMSO) δ 8.24 (d, J = 7.0 Hz, 1H), 6.60 (d, J = 7.0 Hz, 1H), 3.06 (t, J = 7.5 Hz, 2H), 2.23-2.15 (m, 4H), 1.76-1.72 (m, 3H), 1.37-1.20 (m, 13H), 0.86 (d, J = 6.5 Hz, 3H). |
| 296 | Cl | n-nonyl chain | H | $^1$H NMR (500 MHz, DMSO) δ 8.12 (d, J = 7.0 Hz, 1H), 6.87 (d, J = 7.0 Hz, 1H), 2.97-2.92 (m, 2H), 2.34-2.28 (m, 4H), 1.61-1.53 (m, 4H), 1.30-1.24 (m, 14H), 0.97 (t, J = 7.0 Hz, 3H). |
| 297 | Cl | isobutenyl | H | |
| 298 | Cl | perfluoropropenyl | H | $^1$H NMR (500 MHz, DMSO-d$_6$) δ 8.26 (d, J = 7.5 Hz, 1H), 6.95 (d, J = 7.5 Hz, 1H), 5.33 (d, J = 2.0, 1H), 4.96 (d, J = 2.0, 1H), 242-2.35 (m, 4H), 2.13 (s, 3H), 1.79-1.71 (m, 2H) |

Q for all entries: sodium enolate of cyclohexane-1,3-dione

TABLE 1-continued

Structures and ¹H NMR data of compounds

| NO. | Q | X | Y | Z | ¹HNMR |
|---|---|---|---|---|---|
| 299 | ONa-cyclohexenone | Cl | -CH₂CH₂Cl | H | |
| 300 | ONa-cyclohexenone | Cl | -CH(Cl)CH₃ | H | |
| 301 | ONa-cyclohexenone | Cl | -CH₂CH₂CH₂Cl | H | ¹H NMR (500 MHz, Deuterium Oxide) δ 8.15 (d, J = 7.0 Hz, 1H), 6.83 (d, J = 7.0 Hz, 1H), 3.63 (t, J = 6.0 Hz, 2H), 3.24-3.20 (m, 2H), 2.38-2.25 (m, 6H), 1.86-1.82 (m, 2H). |
| 302 | ONa-cyclohexenone | Cl | -CH(CHO)CH₃ | H | |

TABLE 1-continued

Structures and $^1$H NMR data of compounds

| NO. | Q | X | Y | Z | $^1$HNMR |
|---|---|---|---|---|---|
| 303 | ONa-cyclohexanone | Cl | acetyl | H | |
| 304 | ONa-cyclohexanone | Cl | N-methylamide | H | |
| 305 | ONa-cyclohexanone | Cl | tetrahydrofuran-2-yl | H | $^1$H NMR (500 MHz, DMSO) δ 8.28 (d, J = 7.0 Hz, 1H), 6.66 (d, J = 7.0 Hz, 1H), 5.47 (t, J = 6.5 Hz, 1H), 3.96-3.73 (m, 4H), 2.74-2.62 (m, 1H), 2.40-2.30 (m, 1H), 2.14-1.94 (m, 4H), 1.81-1.69 (m, 2H). |
| 306 | ONa-cyclohexanone | Cl | tetrahydrofuran-3-yl | H | $^1$H NMR (500 MHz, DMSO) δ 8.28 (d, J = 7.0 Hz, 1H), 6.66 (d, J = 7.0 Hz, 1H), 5.47-5.43 (m, 1H), 3.96-3.73 (m, 2H), 2.56-2.54 (m, 2H), 2.41-2.38 (m, 2H), 2.04-1.94 (m, 4H), 1.80-1.75(m, 2H). |

TABLE 1-continued

Structures and ¹H NMR data of compounds

| NO. | Q | X | Y | Z | ¹HNMR |
|---|---|---|---|---|---|
| 307 | | Cl | | H | ¹H NMR (500 MHz, DMSO) δ 8.25 (d, J = 7.0 Hz, 1H), 7.46-7.44(m, 4H), 7.33-7.29 (m, 4H), 7.23-7.20 (m, 2H), 6.68 (d, J = 7.0 Hz, 1H), 2.90 (s, 2H), 2.37-2.35 (m, 4H), 1.81-1.79 (m, 2H). |
| 308 | | Cl | | H | ¹H NMR (500 MHz, Deuterium Oxide) δ 8.02 (d, J = 7.0 Hz, 1H), 7.35-7.30 (m, 2H), 7.29-7.23 (m, 3H), 6.75 (d, J = 7.0 Hz, 1H), 4.50 (s, 2H), 2.34 (t, J = 6.5 Hz, 4H), 1.88-1.80 (m, 2H). |
| 309 | | Cl | | H | |
| 310 | | Cl | | H | ¹H NMR (500 MHz, Deuterium Oxide) δ 8.07 (d, J = 7.0 Hz, 1H), 7.27-7.24 (m, 6.93-6.92 (m, 2H), 6.77 (d, J = 7.0 Hz, 2.32-2.44 (m, 6H), 1.82-1.76 (m, 2H). |

TABLE 1-continued

Structures and ¹H NMR data of compounds

| NO. | Q | X | Y | Z | ¹HNMR |
|---|---|---|---|---|---|
| 311 | (3-ONa cyclohexenone, 2-position attachment) | Cl | (methylene-thiophen-3-yl with gem-dimethyl) | H | ¹H NMR (500 MHz, DMSO-d₆) δ 8.63 (d, J = 7.0 Hz, 1H), 8.38 (s, 1H), 7.85 (d, J = 2.0 Hz, 1H), 7.73 (d, J = 2.0 Hz, 1H), 6.99 (d, J = 7.0 Hz, 1H), 2.56-2.48 (m, 6H), 1.98-1.88 (m. 2H). |
| 312 | (3-phenoxy cyclohexenone) | Cl | (cyclopropyl with methyl) | H | |
| 313 | (3-phenylthio cyclohexenone) | Cl | (cyclopropyl with methyl) | H | |

TABLE 1-continued

Structures and ¹H NMR data of compounds

| NO. | Q | X | Y | Z | ¹HNMR |
|---|---|---|---|---|---|
| 314 | | Cl | cyclopropyl | H | |
| 315 | | Cl | cyclopropyl | H | |
| 316 | | F | cyclopropyl | H | |
| 317 | | Cl | cyclopropyl | H | ¹H NMR (500 MHz, Chloroform-d) δ 8.99 (d, J = 7.0 Hz, 1H), 7.89 (s, 1H), 7.33 (d, J = 7.0 Hz, 1H), 5.23 (s, 1H), 3.75 (s, 3H), 2.95 (p, J = 5.5 Hz, 1H), 1.81-1.67 (m, 4H). |
| 318 | | Br | cyclopropyl | H | |

TABLE 1-continued
Structures and ¹H NMR data of compounds
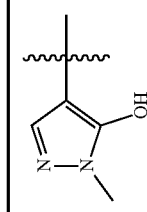
| NO. | Q | X | Y | Z | ¹HNMR |
|---|---|---|---|---|---|
| 319 | 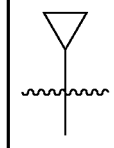 | I | 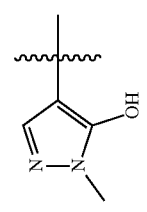 | H | |
| 320 | 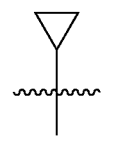 | 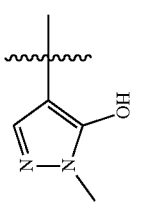 | 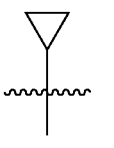 | H | |
| 321 | 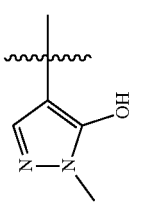 | 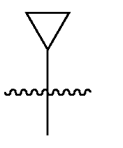 | 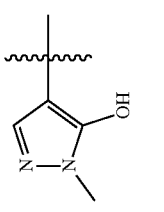 | H | |
| 322 | | | | H | |
| 323 | | CN | | H | |

TABLE 1-continued

Structures and ¹H NMR data of compounds

| NO. | Q | X | Y | Z | ¹HNMR |
|---|---|---|---|---|---|
| 324 | 4-hydroxy-1-methyl-pyrazol-3-yl | NO₂ | cyclopropyl | H | |
| 325 | 4-hydroxy-1-methyl-pyrazol-3-yl | CH₂OCH₃ (neopentyl-like) | cyclopropyl | H | |
| 326 | 4-hydroxy-1-methyl-pyrazol-3-yl | SCH₃ | cyclopropyl | H | |
| 327 | 4-hydroxy-1-methyl-pyrazol-3-yl | S(O)CH₃ | cyclopropyl | H | |
| 328 | 4-hydroxy-1-methyl-pyrazol-3-yl | SO₂CH₃ | cyclopropyl | H | |

TABLE 1-continued

Structures and ¹H NMR data of compounds

| NO. | Q | X | Y | Z | ¹HNMR |
|---|---|---|---|---|---|
| 329 | pyrazole-OH | OMe | cyclopropyl | H | |
| 330 | pyrazole-OH | NH₂ | cyclopropyl | H | |
| 331 | pyrazole-OH | N(CH₃)₂ | cyclopropyl | H | |
| 332 | pyrazole-OH | 2-oxopyrrolidin-1-yl | cyclopropyl | H | |
| 333 | pyrazole-OH | H | CH₃ | H | ¹H NMR (500 MHz, Chloroform-d) δ 8.92 (d, J = 6.5 Hz, 1H), 8.02 (d, J = 1.5 Hz, 1H), 7.81 (s, 1H), 7.75 (dd, J = 6.5, 1.5 Hz, 1H), 5.25 (s, 1H), 3.76 (s, 3H), 2.85 (s, 3H). |

TABLE 1-continued

Structures and ¹H NMR data of compounds

| NO. | Q | X | Y | Z | ¹HNMR |
|---|---|---|---|---|---|
| 334 | | F | CH₃ | H | |
| 335 | | Cl | CH₃ | H | |
| 336 | | Br | CH₃ | H | |
| 337 | | I | CH₃ | H | |
| 338 | | (allyl) | CH₃ | H | |

TABLE 1-continued

Structures and ¹H NMR data of compounds

| NO. | Q | X | | Y | Z | ¹HNMR |
|---|---|---|---|---|---|---|
| 339 | pyrazol-OH (N-Me) | ethynyl | | CH₃ | H | |
| 340 | pyrazol-OH (N-Me) | cyclopropyl | | CH₃ | H | |
| 341 | pyrazol-OH (N-Me) | CN | | CH₃ | H | |
| 342 | pyrazol-OH (N-Me) | NO₂ | | CH₃ | H | |
| 343 | pyrazol-OH (N-Me) | CH₂OCH₃ | | CH₃ | H | |

TABLE 1-continued

Structures and ¹H NMR data of compounds

| NO. | Q | X | Y | Z | ¹HNMR |
|---|---|---|---|---|---|
| 344 | 4-hydroxy-1-methyl-pyrazole | -S-C(CH₃)₂- | CH₃ | H | |
| 345 | 4-hydroxy-1-methyl-pyrazole | -S(=O)-C(CH₃)₂- | CH₃ | H | |
| 346 | 4-hydroxy-1-methyl-pyrazole | -S(=O)₂-C(CH₃)₂- | CH₃ | H | |
| 347 | 4-hydroxy-1-methyl-pyrazole | -O-C(CH₃)₂- | CH₃ | H | |
| 348 | 4-hydroxy-1-methyl-pyrazole | NH₂ | CH₃ | H | |

TABLE 1-continued

Structures and ¹H NMR data of compounds

| NO. | Q | X | Y | Z | ¹HNMR |
|---|---|---|---|---|---|
| 349 | 4-(1-methyl-5-hydroxy-pyrazolyl) | N,N-dimethylamino-tert-butyl | CH₃ | H | |
| 350 | 4-(1-methyl-5-hydroxy-pyrazolyl) | 1-(2-oxopyrrolidinyl)-tert-butyl | CH₃ | H | |
| 351 | 4-(1-methyl-5-hydroxy-pyrazolyl) | Cl | H | H | |
| 352 | 4-(1-methyl-5-hydroxy-pyrazolyl) | Cl | F | H | |
| 353 | 4-(1-methyl-5-hydroxy-pyrazolyl) | Cl | Cl | H | |

TABLE 1-continued
Structures and ¹H NMR data of compounds
| NO. | Q | X | Y | Z | ¹HNMR |
|---|---|---|---|---|---|
| 354 |  | Cl | Br | H | |
| 355 | 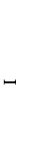 | Cl | I | H | |
| 356 | 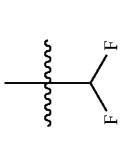 | Cl | CHF₂ | H | |
| 357 |  | Cl | CF₃ | H | |
| 358 |  | Cl |  | H | |

TABLE 1-continued
Structures and ¹H NMR data of compounds
| NO. | Q | X | Y | Z | ¹HNMR |
|---|---|---|---|---|---|
| 359 | 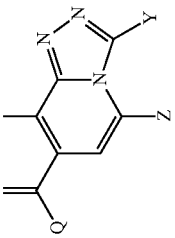 | Cl | CH₂CH₃ | H | |
| 360 | 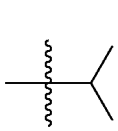 | Cl | 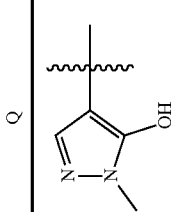 | H | |
| 361 | 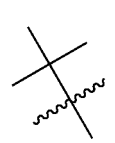 | Cl | 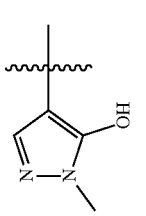 | H | |
| 362 |  | Cl | 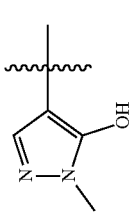 | H | |
| 363 | 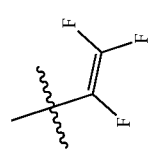 | Cl | 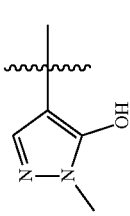 | H | |

TABLE 1-continued

Structures and ¹H NMR data of compounds

| NO. | Q | X | Y | Z | ¹HNMR |
|-----|---|---|---|---|-------|
| 364 | 4-hydroxy-1-methyl-pyrazol-3-yl | Cl | ethynyl-dimethyl | H | |
| 365 | 4-hydroxy-1-methyl-pyrazol-3-yl | Cl | 1-methylcyclopropyl | H | |
| 366 | 4-hydroxy-1-methyl-pyrazol-3-yl | Cl | 1-methyl-cyclopropyl | H | |
| 367 | 4-hydroxy-1-methyl-pyrazol-3-yl | Cl | 2-fluorocyclopropyl-methyl | H | |
| 368 | 4-hydroxy-1-methyl-pyrazol-3-yl | Cl | 1-cyano-cyclopropyl-methyl | H | |

TABLE 1-continued
Structures and ¹H NMR data of compounds
| NO. | Q | X | Y | Z | ¹HNMR |
|---|---|---|---|---|---|
| 369 | 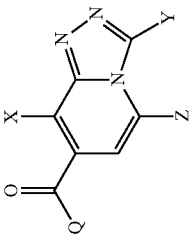 | Cl | 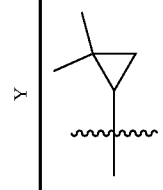 | H | |
| 370 | 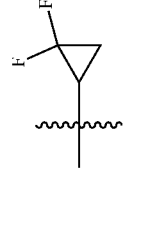 | Cl | 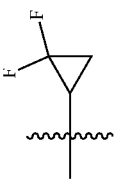 | H | |
| 371 |  | Cl | 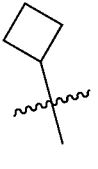 | H | |
| 372 | 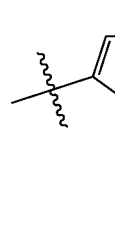 | Cl | 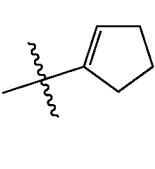 | H | |
| 373 | 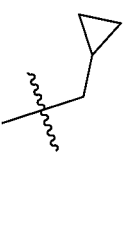 | Cl | 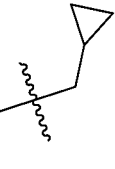 | H | |

TABLE 1-continued
Structures and ¹H NMR data of compounds
| NO. | Q | X | Y | Z | ¹HNMR |
|---|---|---|---|---|---|
| 374 | 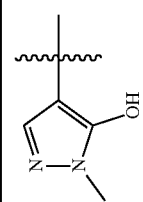 | Cl | 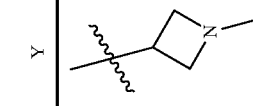 | H | |
| 375 | 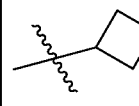 | Cl | 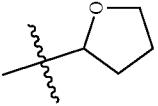 | H | |
| 376 | 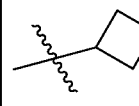 | Cl | 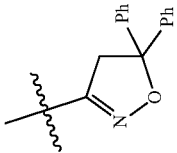 | H | |
| 377 | 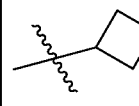 | Cl | 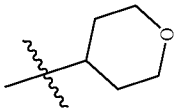 | H | |

TABLE 1-continued
Structures and ¹H NMR data of compounds
| NO. | Q | X | Y | Z | ¹HNMR |
|---|---|---|---|---|---|
| 378 | 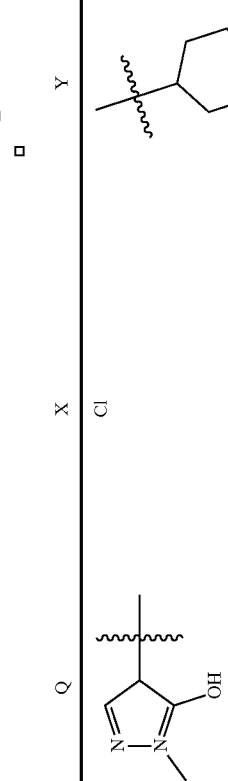 | Cl | 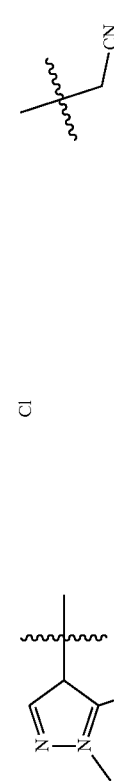 | H | |
| 379 | 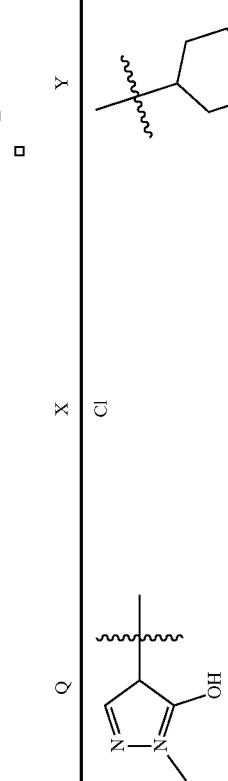 | Cl | 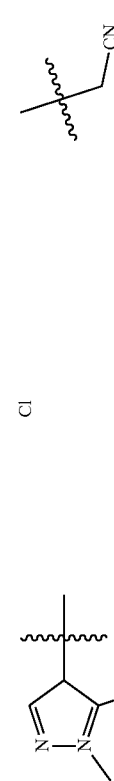 | H | |
| 380 | 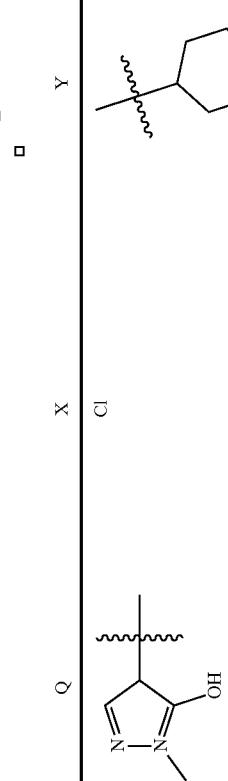 | Cl | 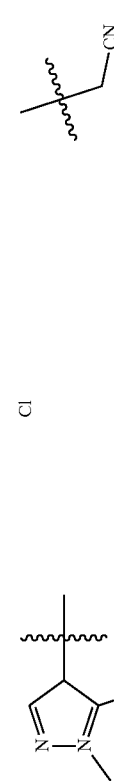 | H | |
| 381 | 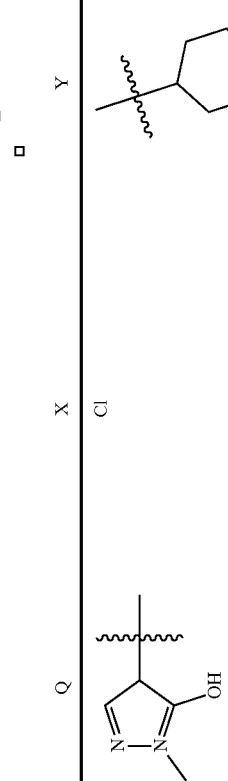 | Cl | 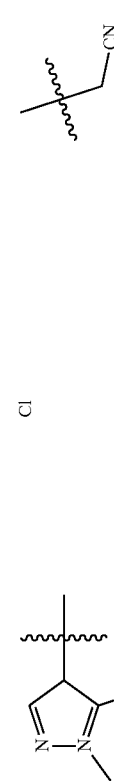 | H | |

TABLE 1-continued

Structures and $^1$H NMR data of compounds

| NO. | Q | X | Y | Z | $^1$HNMR |
|---|---|---|---|---|---|
| 382 | pyrazole-OH | Cl | SMe (t-Bu) | H | |
| 383 | pyrazole-OH | Cl | S(=O)Me (t-Bu) | H | |
| 384 | pyrazole-OH | Cl | S(=O)$_2$Me (t-Bu) | H | |
| 385 | pyrazole-OH | Cl | CH$_2$-S-iPr | H | |
| 386 | pyrazole-OH | Cl | CH$_2$-S(=O)-iPr | H | |

TABLE 1-continued

Structures and ¹H NMR data of compounds

| NO. | Q | X | Y | Z | ¹HNMR |
|---|---|---|---|---|---|
| 387 | pyrazol-OH | Cl | isopropyl sulfonyl-CH2- | H | |
| 388 | pyrazol-OH | Cl | -CH2-N(CH3)2 | H | |
| 389 | pyrazol-OH | Cl | -C(CH3)2-CHO | H | |
| 390 | pyrazol-OH | Cl | -C(CH3)2-C(O)CH3 | H | |
| 391 | pyrazol-OH | Cl | -C(CH3)2-C(O)N(CH3)2 | H | |

TABLE 1-continued

Structures and ¹H NMR data of compounds

| NO. | Q | X | Y | Z | ¹HNMR |
|---|---|---|---|---|---|
| 392 | pyrazol-OH | Cl | benzyl | H | |
| 393 | pyrazol-OH | Cl | (pyridin-3-yl)methyl | H | |
| 394 | pyrazol-OH | Cl | (thiophen-2-yl)methyl | H | |
| 395 | pyrazol-OH | Cl | phenyl | H | |

TABLE 1-continued

Structures and ¹H NMR data of compounds

| NO. | Q | X | Y | Z | ¹HNMR |
|---|---|---|---|---|---|
| 396 | pyrazol-OH, N-methyl | Cl | 4-fluorophenyl | H | |
| 397 | pyrazol-OH, N-methyl | Cl | 2-cyanophenyl | H | |
| 398 | pyrazol-OH, N-methyl | Cl | pyridin-4-yl | H | |
| 399 | pyrazol-OH, N-methyl | Cl | 3,6-dichloropyridin-2-yl | H | |

TABLE 1-continued
Structures and ¹H NMR data of compounds
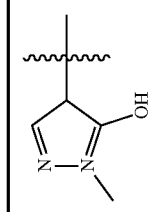
| NO. | Q | X | Y | Z | ¹HNMR |
|---|---|---|---|---|---|
| 400 | 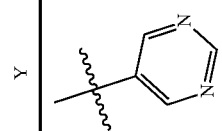 | Cl | 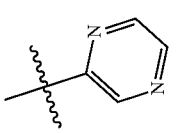 | H | |
| 401 | 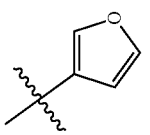 | Cl | 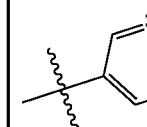 | H | |
| 402 | 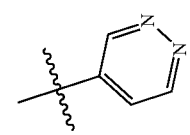 | Cl | 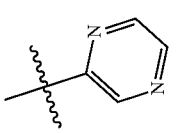 | H | |
| 403 | 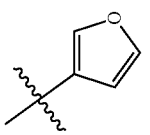 | Cl | 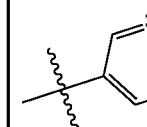 | H | |

TABLE 1-continued

Structures and ¹H NMR data of compounds

| NO. | Q | X | Y | Z | ¹HNMR |
|---|---|---|---|---|---|
| 404 | (4-hydroxy-1-methyl-pyrazol-3-yl) | Cl | (thiophen-3-yl) | H | |
| 405 | (4-hydroxy-1-methyl-pyrazol-3-yl) | Cl | (1-methyl-pyrrol-2-yl) | H | |
| 406 | (4-hydroxy-1-methyl-pyrazol-3-yl) | Cl | (1,3-dimethyl-pyrazol-4-yl) | H | |
| 407 | (4-hydroxy-1-methyl-pyrazol-3-yl) | Cl | (isoxazol-3-yl) | H | |

TABLE 1-continued

Structures and $^1$H NMR data of compounds

| NO. | Q | X | Y | Z | $^1$HNMR |
|---|---|---|---|---|---|
| 408 | 1-methyl-5-hydroxy-pyrazol-4-yl | Cl | oxazol-5-yl | H | |
| 409 | 1-methyl-5-hydroxy-pyrazol-4-yl | Cl | thiazol-5-yl | H | |
| 410 | 1-methyl-5-hydroxy-pyrazol-4-yl | Cl | 1-methyl-imidazol-2-yl | H | |
| 411 | 1-methyl-5-hydroxy-pyrazol-4-yl | Cl | isoxazol-3-yl | H | |

TABLE 1-continued
Structures and ¹H NMR data of compounds
| NO. | Q | X | Y | Z | ¹HNMR |
|---|---|---|---|---|---|
| 412 | 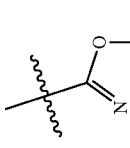 | Cl | 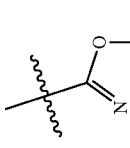 | H | |
| 413 |  | Cl |  | H | |
| 414 | 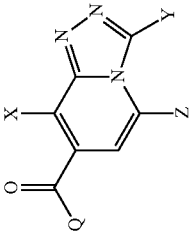 | Cl | 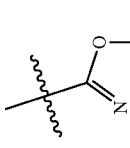 | H | |
| 415 |  | Cl |  | H | |

TABLE 1-continued

Structures and ¹H NMR data of compounds

| NO. | Q | X | Y | Z | ¹HNMR |
|---|---|---|---|---|---|
| 416 | 4-hydroxy-1-methyl-1H-pyrazol-3-yl | Cl | isoquinolin-1-yl | H | |
| 417 | 3-methyl-4-hydroxy-1-methyl-1H-pyrazol-5-yl | Cl | cyclopropyl | H | ¹H NMR (500 MHz, Chloroform-d) δ 8.99 (d, J = 7.0 Hz, 1H), 7.33 (d, J = 7.0 Hz, 1H), 5.25 (s, 1H), 3.72 (s, 3H), 2.95 (p, J = 5.5 Hz, 1H), 2.66 (s, 3H), 1.79-1.62 (m, 4H). |
| 418 | 3-methyl-4-hydroxy-1-methyl-1H-pyrazol-5-yl | Cl | isobutylthiomethyl | H | ¹H NMR (500 MHz, Chloroform-d) δ 8.99 (d, J = 7.0 Hz, 1H), 7.33 (d, J = 7.0 Hz, 1H), 5.25 (s, 1H), 3.72 (s, 3H), 4.12 (s, 2H), 3.10 (hept, J = 6.5 Hz, 1H), 2.66 (s, 3H), 1.30 (d, J = 6.5 Hz, 6H). |
| 419 | 5-cyclopropyl-4-hydroxy-1-methyl-1H-pyrazol-3-yl | Cl | cyclopropyl | H | ¹H NMR (500 MHz, Chloroform-d) δ 8.99 (d, J = 7.0 Hz, 1H), 7.33 (d, J = 7.0 Hz, 1H), 5.25 (s, 1H), 3.74 (s, 3H), 2.95 (p, J = 5.5 Hz, 1H), 2.61 (p, J = 5.5 Hz, 1H), 1.79-1.62 (m, 4H), 1.03-0.87 (m, 4H). |

TABLE 1-continued

Structures and ¹H NMR data of compounds

| NO. | Q | X | Y | Z | ¹HNMR |
|---|---|---|---|---|---|
| 420 | pyrazole with CF₃, OH, N-methyl | Cl | cyclopropyl | H | |
| 421 | pyrazole with OH, N-ethyl | Cl | cyclopropyl | H | ¹H NMR (500 MHz, Chloroform-d) δ 8.99 (d, J = 7.0 Hz, 1H), 7.97 (s, 1H), 7.31 (d, J = 7.0 Hz, 1H), 5.24 (s, 1H), 4.13 (q, J = 7.0 Hz, 2H), 2.95 (p, J = 5.5 Hz, 1H), 1.79-1.62 (m, 4H), 1.34 (t, J = 7.0 Hz, 3H). |
| 422 | pyrazole with CH₃, OH, N-ethyl | Cl | cyclopropyl | H | ¹H NMR (500 MHz, Chloroform-d) δ 8.99 (d, J = 7.0 Hz, 1H), 7.33 (d, J = 7.0 Hz, 1H), 5.25 (s, 1H), 4.11 (q, J = 7.0 Hz, 2H), 2.95 (p, J = 5.5 Hz, 1H), 2.64 (s, 3H), 1.79-1.62 (m, 4H), 1.36 (t, J = 7.0 Hz, 3H). |
| 423 | pyrazole with OH, N-CHF₂ | Cl | cyclopropyl | H | |

TABLE 1-continued

Structures and ¹H NMR data of compounds

| NO. | Q | X | Y | Z | ¹HNMR |
|---|---|---|---|---|---|
| 424 | (CF₃-pyrazole-OH with N-phenyl) | Cl | cyclopropyl | H | |
| 425 | (isoxazole) | Cl | cyclopropyl | H | |
| 426 | (5-methylisoxazole) | Cl | cyclopropyl | H | |
| 427 | (5-tert-butylisoxazole) | Cl | cyclopropyl | H | |
| 428 | (5-CF₃-isoxazole) | Cl | cyclopropyl | H | |

TABLE 1-continued

Structures and $^1$H NMR data of compounds

| NO. | Q | X | Y | Z | $^1$HNMR |
|---|---|---|---|---|---|
| 429 | 5-cyclopropyl-isoxazol-4-yl | F | cyclopropyl | H | $^1$H NMR (500 MHz, Chloroform-d) δ 8.99 (d, J = 7.0 Hz, 1H), 8.64 (s, 1H), 7.29 (d, J = 7.0 Hz, 1H), 2.95 (p, J = 5.5 Hz, 1H), 2.74 (p, J = 5.5 Hz, 1H), 1.79-1.70 (m, 4H), 1.72-1.58 (m, 4H). |
| 430 | 5-cyclopropyl-isoxazol-4-yl | Cl | cyclopropyl | H | |
| 431 | 5-cyclopropyl-isoxazol-4-yl | Br | cyclopropyl | H | |
| 432 | 5-cyclopropyl-isoxazol-4-yl | I | cyclopropyl | H | |

TABLE 1-continued

Structures and ¹H NMR data of compounds

| NO. | Q | X | Y | Z | ¹HNMR |
|---|---|---|---|---|---|
| 433 | 5-cyclopropylisoxazol-4-yl | vinyl | cyclopropyl | H | |
| 434 | 5-cyclopropylisoxazol-4-yl | ethynyl | cyclopropyl | H | |
| 435 | 5-cyclopropylisoxazol-4-yl | cyclopropyl | cyclopropyl | H | |
| 436 | 5-cyclopropylisoxazol-4-yl | CN | cyclopropyl | H | |

TABLE 1-continued

Structures and $^1$H NMR data of compounds

| NO. | Q | X | Y | Z | $^1$HNMR |
|---|---|---|---|---|---|
| 437 | 5-cyclopropylisoxazol-4-yl | NO$_2$ | cyclopropyl | H | |
| 438 | 5-cyclopropylisoxazol-4-yl | CH$_2$OCH$_3$ (methoxymethyl, tert) | cyclopropyl | H | |
| 439 | 5-cyclopropylisoxazol-4-yl | SCH$_3$ | cyclopropyl | H | |
| 440 | 5-cyclopropylisoxazol-4-yl | S(O)CH$_3$ | cyclopropyl | H | |

TABLE 1-continued

Structures and ¹H NMR data of compounds

| NO. | Q | X | Y | Z | ¹HNMR |
|---|---|---|---|---|---|
| 441 | 5-cyclopropylisoxazol-4-yl | methylsulfonyl | cyclopropyl | H | |
| 442 | 5-cyclopropylisoxazol-4-yl | methoxy | cyclopropyl | H | |
| 443 | 5-cyclopropylisoxazol-4-yl | NH₂ | cyclopropyl | H | |
| 444 | 5-cyclopropylisoxazol-4-yl | N,N-dimethylamino | cyclopropyl | H | |

TABLE 1-continued

Structures and ¹H NMR data of compounds

| NO. | Q | X | Y | Z | ¹HNMR |
|---|---|---|---|---|---|
| 445 | 5-cyclopropylisoxazol-4-yl | pyrrolidin-2-one-1-yl | cyclopropyl | H | |
| 446 | 5-cyclopropylisoxazol-4-yl | F | CH₃ | H | ¹H NMR (500 MHz, Chloroform-d) δ 8.90 (d, J = 6.5 Hz, 1H), 8.57 (s, 1H), 7.79-7.71 (m, 1H), 2.84 (s, 3H), 2.74 (p, J = 5.5 Hz, 1H), 1.70-1.61 (m, 4H). |
| 447 | 5-cyclopropylisoxazol-4-yl | F | CH₃ | H | |
| 448 | 5-cyclopropylisoxazol-4-yl | Cl | CH₃ | H | |

TABLE 1-continued

Structures and ¹H NMR data of compounds

| NO. | Q | X | Y | Z | ¹HNMR |
|---|---|---|---|---|---|
| 449 | 5-cyclopropylisoxazol-4-yl | Br | CH₃ | H | |
| 450 | 5-cyclopropylisoxazol-4-yl | I | CH₃ | H | |
| 451 | 5-cyclopropylisoxazol-4-yl | vinyl | CH₃ | H | |
| 452 | 5-cyclopropylisoxazol-4-yl | ethynyl | CH₃ | H | |

TABLE 1-continued

Structures and ¹H NMR data of compounds

| NO. | Q | X | Y | Z | ¹HNMR |
|---|---|---|---|---|---|
| 453 | 5-cyclopropyl-isoxazol-4-yl | cyclopropyl | CH₃ | H | |
| 454 | 5-cyclopropyl-isoxazol-4-yl | CN | CH₃ | H | |
| 455 | 5-cyclopropyl-isoxazol-4-yl | NO₂ | CH₃ | H | |
| 456 | 5-cyclopropyl-isoxazol-4-yl | CH₂OCH₃ | CH₃ | H | |

TABLE 1-continued

Structures and ¹H NMR data of compounds

| NO. | Q | X | Y | Z | ¹HNMR |
|-----|---|---|---|---|-------|
| 457 | 5-cyclopropylisoxazol-4-yl | SMe (t-Bu) | CH₃ | H | |
| 458 | 5-cyclopropylisoxazol-4-yl | S(O)Me (t-Bu) | CH₃ | H | |
| 459 | 5-cyclopropylisoxazol-4-yl | SO₂Me (t-Bu) | CH₃ | H | |
| 460 | 5-cyclopropylisoxazol-4-yl | OMe (t-Bu) | CH₃ | H | |

TABLE 1-continued

Structures and ¹H NMR data of compounds

| NO. | Q | X | Y | Z | ¹HNMR |
|---|---|---|---|---|---|
| 461 | 5-cyclopropylisoxazol-4-yl | NH₂ | CH₃ | H | |
| 462 | 5-cyclopropylisoxazol-4-yl | N(CH₃)₂ | CH₃ | H | |
| 463 | 5-cyclopropylisoxazol-4-yl | 2-oxopyrrolidin-1-yl | CH₃ | H | |
| 464 | 5-cyclopropylisoxazol-4-yl | Cl | H | H | |

TABLE 1-continued

Structures and ¹H NMR data of compounds

| NO. | Q | X | | Y | Z | ¹HNMR |
|---|---|---|---|---|---|---|
| 465 | 5-cyclopropyl-isoxazol-4-yl | Cl | | F | H | |
| 466 | 5-cyclopropyl-isoxazol-4-yl | Cl | | Cl | H | |
| 467 | 5-cyclopropyl-isoxazol-4-yl | Cl | | Br | H | |
| 468 | 5-cyclopropyl-isoxazol-4-yl | Cl | | I | H | |

TABLE 1-continued

Structures and ¹H NMR data of compounds

| NO. | Q | X | Y | Z | ¹HNMR |
|-----|---|---|---|---|-------|
| 469 | 5-cyclopropyl-isoxazol-4-yl | Cl | CHF₂ | H | |
| 470 | 5-cyclopropyl-isoxazol-4-yl | Cl | CF₃ | H | |
| 471 | 5-cyclopropyl-isoxazol-4-yl | Cl | C(CH₃)₂CH₂Cl | H | |
| 472 | 5-cyclopropyl-isoxazol-4-yl | Cl | CH₂CH₃ | H | |

TABLE 1-continued
Structures and $^1$H NMR data of compounds
| NO. | Q | X | Y | Z | $^1$HNMR |
|---|---|---|---|---|---|
| 473 | 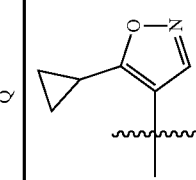 | Cl | 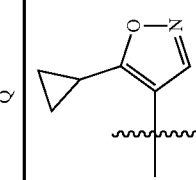 | H | |
| 474 | 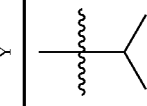 | Cl | 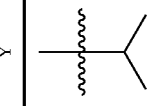 | H | |
| 475 | 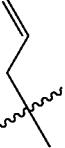 | Cl | 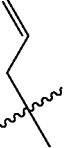 | H | |
| 476 | 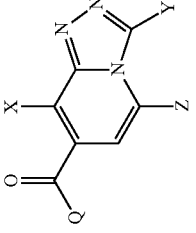 | Cl | 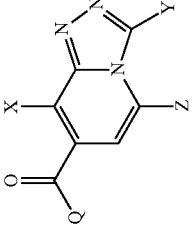 | H | |

TABLE 1-continued

Structures and ¹H NMR data of compounds

| NO. | Q | X | Y | Z | ¹HNMR |
|---|---|---|---|---|---|
| 477 | 5-cyclopropyl-isoxazol-4-yl | Cl | ethynyl-dimethyl | H | |
| 478 | 5-cyclopropyl-isoxazol-4-yl | Cl | cyclopropyl-dimethyl | H | |
| 479 | 5-cyclopropyl-isoxazol-4-yl | Cl | dimethyl-cyclopropyl-methylcyclopropyl | H | |
| 480 | 5-cyclopropyl-isoxazol-4-yl | Cl | fluorocyclopropyl-methyl | H | |

TABLE 1-continued

Structures and ¹H NMR data of compounds

| NO. | Q | X | Y | Z | ¹HNMR |
|---|---|---|---|---|---|
| 481 | 5-cyclopropyl-isoxazol-4-yl | Cl | 1-cyano-cyclopropyl (with methyl) | H | |
| 482 | 5-cyclopropyl-isoxazol-4-yl | Cl | 2,2-dimethylcyclopropyl | H | |
| 483 | 5-cyclopropyl-isoxazol-4-yl | Cl | 2,2-difluorocyclopropyl | H | |
| 484 | 5-cyclopropyl-isoxazol-4-yl | Cl | cyclobutyl (with methyl) | H | |

TABLE 1-continued

Structures and ¹H NMR data of compounds

| NO. | Q | X | Y | Z | ¹HNMR |
|---|---|---|---|---|---|
| 485 | 5-cyclopropyl-isoxazol-4-yl | Cl | cyclopentenyl | H | |
| 486 | 5-cyclopropyl-isoxazol-4-yl | Cl | cyclopropylmethyl | H | |
| 487 | 5-cyclopropyl-isoxazol-4-yl | Cl | 1-methylazetidin-3-yl | H | |
| 488 | 5-cyclopropyl-isoxazol-4-yl | Cl | tetrahydrofuran-2-yl | H | |

TABLE 1-continued

Structures and $^1$H NMR data of compounds

| NO. | Q | X | Y | Z | $^1$HNMR |
|---|---|---|---|---|---|
| 489 | 5-cyclopropyl-isoxazol-4-yl | Cl | 3-(4,4-diphenyl)-isoxazolin-5-yl | H | |
| 490 | 5-cyclopropyl-isoxazol-4-yl | Cl | tetrahydropyran-4-yl | H | |
| 491 | 5-cyclopropyl-isoxazol-4-yl | Cl | 1-methylpiperidin-4-yl | H | |
| 492 | 5-cyclopropyl-isoxazol-4-yl | Cl | CH$_2$CN | H | |

TABLE 1-continued

Structures and ¹H NMR data of compounds

| NO. | Q | X | Y | Z | ¹HNMR |
|---|---|---|---|---|---|
| 493 | 5-cyclopropylisoxazol-4-yl | Cl | methoxy-methyl | H | |
| 494 | 5-cyclopropylisoxazol-4-yl | Cl | ethoxy-methyl | H | |
| 495 | 5-cyclopropylisoxazol-4-yl | Cl | methylthio-methyl | H | |
| 496 | 5-cyclopropylisoxazol-4-yl | Cl | methylsulfinyl-methyl | H | |

TABLE 1-continued

Structures and ¹H NMR data of compounds

| NO. | Q | X | Y | Z | ¹HNMR |
|---|---|---|---|---|---|
| 497 | 5-cyclopropyl-isoxazol-4-yl | Cl | isopropylsulfonyl-methyl | H | |
| 498 | 5-cyclopropyl-isoxazol-4-yl | Cl | isopropylthio-methyl | H | |
| 499 | 5-cyclopropyl-isoxazol-4-yl | Cl | isopropylsulfinyl-methyl | H | |
| 500 | 5-cyclopropyl-isoxazol-4-yl | Cl | isopropylsulfonyl-methyl | H | |

TABLE 1-continued
Structures and ¹H NMR data of compounds
| NO. | Q | X | Y | Z | ¹HNMR |
|---|---|---|---|---|---|
| 501 | 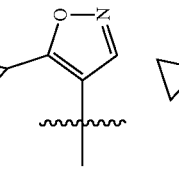 | Cl | 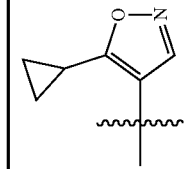 | H | |
| 502 | 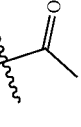 | Cl | 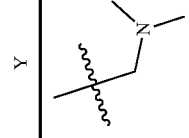 | H | |
| 503 | 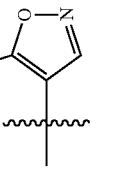 | Cl | 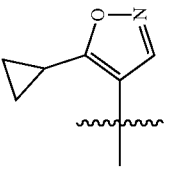 | H | |
| 504 | 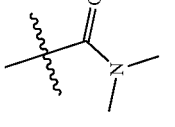 | Cl | 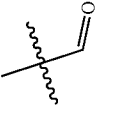 | H | |

TABLE 1-continued

Structures and ¹H NMR data of compounds

| NO. | Q | X | Y | Z | ¹HNMR |
|---|---|---|---|---|---|
| 505 | 5-cyclopropylisoxazol-4-yl | Cl | benzyl | H | |
| 506 | 5-cyclopropylisoxazol-4-yl | Cl | (pyridin-3-yl)methyl | H | |
| 507 | 5-cyclopropylisoxazol-4-yl | Cl | (thiophen-2-yl)methyl | H | |
| 508 | 5-cyclopropylisoxazol-4-yl | Cl | phenyl | H | |

TABLE 1-continued
Structures and ¹H NMR data of compounds
| NO. | Q | X | Y | Z | ¹HNMR |
|---|---|---|---|---|---|
| 509 | 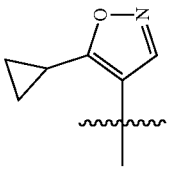 | Cl | 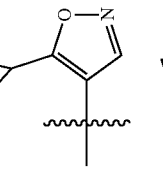 | H | |
| 510 | 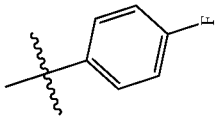 | Cl | 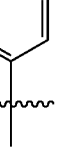 | H | |
| 511 | 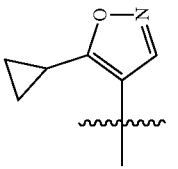 | Cl | 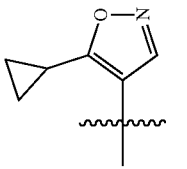 | H | |
| 512 | 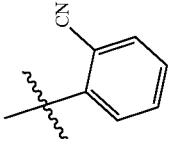 | Cl | 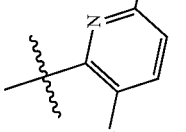 | H | |

TABLE 1-continued

Structures and ¹H NMR data of compounds

| NO. | Q | X | Y | Z | ¹HNMR |
|---|---|---|---|---|---|
| 513 | cyclopropyl-isoxazole | Cl | pyrimidine | H | |
| 514 | cyclopropyl-isoxazole | Cl | pyridazine | H | |
| 515 | cyclopropyl-isoxazole | Cl | pyrazine | H | |
| 516 | cyclopropyl-isoxazole | Cl | furan | H | |

TABLE 1-continued

Structures and ¹H NMR data of compounds

| NO. | Q | X | Y | Z | ¹HNMR |
|---|---|---|---|---|---|
| 517 | 5-cyclopropylisoxazol-4-yl | Cl | 3-thienyl (gem-dimethyl linker) | H | |
| 518 | 5-cyclopropylisoxazol-4-yl | Cl | 1-methyl-1H-pyrrol-2-yl (gem-dimethyl linker) | H | |
| 519 | 5-cyclopropylisoxazol-4-yl | Cl | 1,3-dimethyl-1H-pyrazol-4-yl (gem-dimethyl linker) | H | |
| 520 | 5-cyclopropylisoxazol-4-yl | Cl | isoxazol-3-yl (gem-dimethyl linker) | H | |

TABLE 1-continued

Structures and ¹H NMR data of compounds

| NO. | Q | X | Y | Z | ¹HNMR |
|---|---|---|---|---|---|
| 521 | 5-cyclopropyl-isoxazol-4-yl | Cl | oxazol-5-yl | H | |
| 522 | 5-cyclopropyl-isoxazol-4-yl | Cl | thiazol-4-yl | H | |
| 523 | 5-cyclopropyl-isoxazol-4-yl | Cl | 1-methyl-imidazol-2-yl | H | |
| 524 | 5-cyclopropyl-isoxazol-4-yl | Cl | isoxazol-4-yl | H | |

TABLE 1-continued

Structures and ¹H NMR data of compounds

| NO. | Q | X | Y | Z | ¹HNMR |
|---|---|---|---|---|---|
| 525 | 5-cyclopropyl-isoxazol-4-yl | Cl | 2-methyl-1,3,4-oxadiazol-5-yl | H | |
| 526 | 5-cyclopropyl-isoxazol-4-yl | Cl | 1H-1,2,4-triazol-3-yl | H | |
| 527 | 5-cyclopropyl-isoxazol-4-yl | Cl | naphthalen-2-yl | H | |
| 528 | 5-cyclopropyl-isoxazol-4-yl | Cl | 3,6-dichloroquinolin-8-yl | H | |

TABLE 1-continued

Structures and ¹H NMR data of compounds

| NO. | Q | X | Y | Z | ¹HNMR |
|---|---|---|---|---|---|
| 529 | 5-cyclopropyl-isoxazol-4-yl | Cl | isoquinolin-8-yl | H | |
| 530 | 5-cyclopropyl-3-(methylthio)-isoxazol-4-yl | Cl | cyclopropyl | H | |
| 531 | 5-cyclopropyl-3-(methylsulfinyl)-isoxazol-4-yl | Cl | cyclopropyl | H | |

TABLE 1-continued

Structures and ¹H NMR data of compounds

| NO. | Q | X | Y | Z | ¹HNMR |
|---|---|---|---|---|---|
| 532 | 5-cyclopropyl-4-(methoxycarbonyl)isoxazol-3-yl | Cl | cyclopropyl | H | |
| 533 | 5-cyclopropyl-4-(ethoxycarbonyl)isoxazol-3-yl | Cl | cyclopropyl | H | |
| 534 | 1-cyano-3,3-dimethyl-2-oxobutyl | Cl | cyclopropyl | H | |
| 535 | 1-cyano-2-cyclopropyl-2-oxoethyl | Cl | cyclopropyl | H | |

TABLE 1-continued

Structures and ¹H NMR data of compounds

| NO. | Q | X | Y | Z | ¹HNMR |
|---|---|---|---|---|---|
| 536 | | F | | H | |
| 537 | | Cl | | H | |
| 538 | | Br | | H | |
| 539 | | I | | H | |
| 540 | | | | H | |

TABLE 1-continued

Structures and ¹H NMR data of compounds

| NO. | Q | X | Y | Z | ¹HNMR |
|---|---|---|---|---|---|
| 541 | cyclopropyl-C(O)-CH(CN)- | ethynyl | cyclopropyl | H | |
| 542 | cyclopropyl-C(O)-CH(CN)- | cyclopropyl | cyclopropyl | H | |
| 543 | cyclopropyl-C(O)-CH(CN)- | CN | cyclopropyl | H | |
| 544 | cyclopropyl-C(O)-CH(CN)- | NO₂ | cyclopropyl | H | |
| 545 | cyclopropyl-C(O)-CH(CN)- | CH₂OCH₃ | cyclopropyl | H | |

TABLE 1-continued

Structures and ¹H NMR data of compounds

| NO. | Q | X | Y | Z | ¹HNMR |
|---|---|---|---|---|---|
| 546 | -C(=O)-CH(CN)-cyclopropyl | -S-CH₃ | cyclopropyl | H | |
| 547 | -C(=O)-CH(CN)-cyclopropyl | -S(=O)-CH₃ | cyclopropyl | H | |
| 548 | -C(=O)-CH(CN)-cyclopropyl | -S(=O)₂-CH₃ | cyclopropyl | H | |
| 549 | -C(=O)-CH(CN)-cyclopropyl | -O-CH₃ | cyclopropyl | H | |
| 550 | -C(=O)-CH(CN)-cyclopropyl | NH₂ | cyclopropyl | H | |

TABLE 1-continued

Structures and ¹H NMR data of compounds

| NO. | Q | X | Y | Z | ¹HNMR |
|---|---|---|---|---|---|
| 551 | (cyclopropyl ketone with CN) | N(CH₃)– | cyclopropyl | H | |
| 552 | (cyclopropyl ketone with CN) | 2-oxopyrrolidin-1-yl | cyclopropyl | H | |
| 553 | (cyclopropyl ketone with CN) | Cl | H | H | |
| 554 | (cyclopropyl ketone with CN) | Cl | F | H | |
| 555 | (cyclopropyl ketone with CN) | Cl | Cl | H | |

TABLE 1-continued

Structures and ¹H NMR data of compounds

| NO. | Q | X | Y | Z | ¹HNMR |
|---|---|---|---|---|---|
| 556 | ![Q group: C(=O)-CH(CN)-cyclopropyl] | Cl | Br | H | |
| 557 | ![Q group: C(=O)-CH(CN)-cyclopropyl] | Cl | I | H | |
| 558 | ![Q group: C(=O)-CH(CN)-cyclopropyl] | Cl | CHF₂ | H | |
| 559 | ![Q group: C(=O)-CH(CN)-cyclopropyl] | Cl | CF₃ | H | |
| 560 | ![Q group: C(=O)-CH(CN)-cyclopropyl] | Cl | C(CH₃)(CH₂CH₂Cl) | H | |

TABLE 1-continued

Structures and ¹H NMR data of compounds

| NO. | Q | X | | Y | Z | ¹HNMR |
|---|---|---|---|---|---|---|
| 561 | ![Q structure] | Cl | | CH₃ | H | |
| 562 | ![Q structure] | Cl | | CH₂CH₃ | H | |
| 563 | ![Q structure] | Cl | | isopropyl | H | |
| 564 | ![Q structure] | Cl | | tert-butyl | H | |
| 565 | ![Q structure] | Cl | | but-3-en-2-yl | H | |

TABLE 1-continued

Structures and ¹H NMR data of compounds

| NO. | Q | X | Y | Z | ¹HNMR |
|---|---|---|---|---|---|
| 566 | cyclopropyl-C(O)-CH(CN)- | Cl | 1,2,2-trifluorovinyl-C(CH₃)- | H | |
| 567 | cyclopropyl-C(O)-CH(CN)- | Cl | ethynyl-C(CH₃)- | H | |
| 568 | cyclopropyl-C(O)-CH(CN)- | Cl | cyclopropyl-C(CH₃)- | H | |
| 569 | cyclopropyl-C(O)-CH(CN)- | Cl | (2-methylcyclopropyl)- | H | |
| 570 | cyclopropyl-C(O)-CH(CN)- | Cl | (2-fluorocyclopropyl)-C(CH₃)- | H | |

TABLE 1-continued

Structures and ¹H NMR data of compounds

| NO. | Q | X | Y | Z | ¹HNMR |
|---|---|---|---|---|---|
| 571 | (cyclopropyl-C(O)-CH(CN)-) | Cl | 1-methylcyclopropyl | H | |
| 572 | (cyclopropyl-C(O)-CH(CN)-) | Cl | 2,2-dimethylcyclopropyl | H | |
| 573 | (cyclopropyl-C(O)-CH(CN)-) | Cl | 2,2-difluorocyclopropyl | H | |
| 574 | (cyclopropyl-C(O)-CH(CN)-) | Cl | cyclobutyl | H | |
| 575 | (cyclopropyl-C(O)-CH(CN)-) | Cl | 1-(cyclopent-1-en-1-yl)ethyl | H | |

TABLE 1-continued

Structures and ¹H NMR data of compounds

| NO. | Q | X | Y | Z | ¹HNMR |
|---|---|---|---|---|---|
| 576 | ![Q structure with cyclopropyl ketone and CN] | Cl | ![cyclopropylmethyl] | H | |
| 577 | ![Q structure with cyclopropyl ketone and CN] | Cl | ![N-methyl azetidinyl] | H | |
| 578 | ![Q structure with cyclopropyl ketone and CN] | Cl | ![tetrahydrofuranyl] | H | |
| 579 | ![Q structure with cyclopropyl ketone and CN] | Cl | ![5,5-diphenyl isoxazoline] | H | |

TABLE 1-continued

Structures and ¹H NMR data of compounds

| NO. | Q | X | Y | Z | ¹HNMR |
|-----|---|---|---|---|-------|
| 580 | cyclopropyl-C(O)-CH(CN)- | Cl | tetrahydropyran-4-yl (quaternary) | H | |
| 581 | cyclopropyl-C(O)-CH(CN)- | Cl | 1-methylpiperidin-4-yl (quaternary) | H | |
| 582 | cyclopropyl-C(O)-CH(CN)- | Cl | -C(CH₃)₂-CH₂-CN | H | |
| 583 | cyclopropyl-C(O)-CH(CN)- | Cl | -C(CH₃)₂-OCH₃ | H | |

TABLE 1-continued

Structures and ¹H NMR data of compounds

| NO. | Q | X | Y | Z | ¹HNMR |
|---|---|---|---|---|---|
| 584 | cyclopropyl-C(O)-CH(CN)- | Cl | -CH(CH₃)CH₂OEt | H | |
| 585 | cyclopropyl-C(O)-CH(CN)- | Cl | -C(CH₃)₂SMe | H | |
| 586 | cyclopropyl-C(O)-CH(CN)- | Cl | -C(CH₃)₂S(O)Me | H | |
| 587 | cyclopropyl-C(O)-CH(CN)- | Cl | -C(CH₃)₂S(O)₂Me | H | |
| 588 | cyclopropyl-C(O)-CH(CN)- | Cl | -C(CH₃)₂CH₂S-iPr | H | |

TABLE 1-continued
Structures and ¹H NMR data of compounds
| NO. | Q | X | Y | Z | ¹HNMR |
|---|---|---|---|---|---|
| 589 | 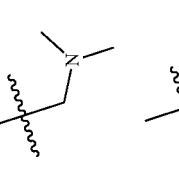 | Cl | 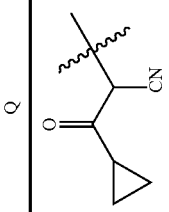 | H | |
| 590 | 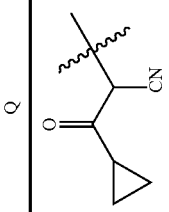 | Cl | 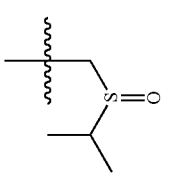 | H | |
| 591 | 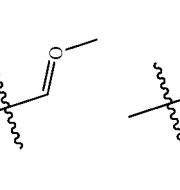 | Cl | 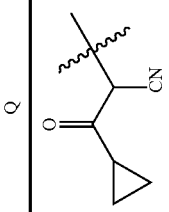 | H | |
| 592 | 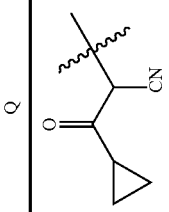 | Cl | 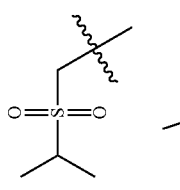 | H | |
| 593 | 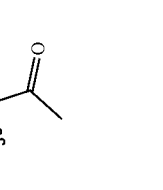 | Cl | 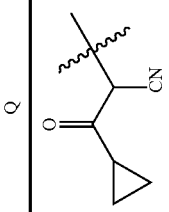 | H | |

TABLE 1-continued

Structures and ¹H NMR data of compounds

| NO. | Q | X | Y | Z | ¹HNMR |
|-----|---|---|---|---|-------|
| 594 | cyclopropyl-C(O)-CH(CN)- | Cl | -C(CH₃)₂-C(O)-N(CH₃)₂ | H | |
| 595 | cyclopropyl-C(O)-CH(CN)- | Cl | -C(CH₃)₂-CH₂-phenyl | H | |
| 596 | cyclopropyl-C(O)-CH(CN)- | Cl | -C(CH₃)₂-CH₂-(3-pyridyl) | H | |
| 597 | cyclopropyl-C(O)-CH(CN)- | Cl | -C(CH₃)₂-CH₂-(2-thienyl) | H | |

TABLE 1-continued
Structures and ¹H NMR data of compounds
| NO. | Q | X | Y | Z | ¹HNMR |
|---|---|---|---|---|---|
| 598 | 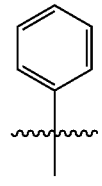 | Cl | 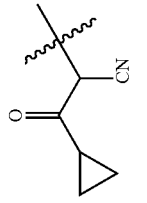 | H | |
| 599 | 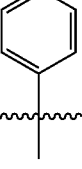 | Cl | 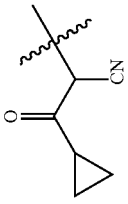 | H | |
| 600 | 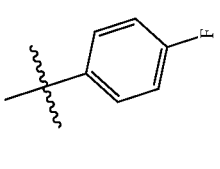 | Cl | 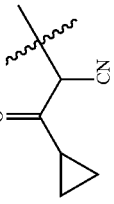 | H | |
| 601 | 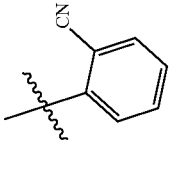 | Cl | 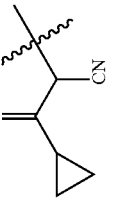 | H | |

TABLE 1-continued
Structures and ¹H NMR data of compounds
| NO. | Q | X | Y | Z | ¹HNMR |
|---|---|---|---|---|---|
| 602 | 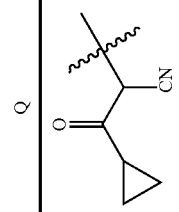 | Cl | 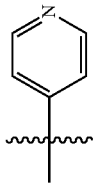 | H | |
| 603 | 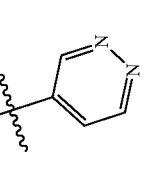 | Cl | 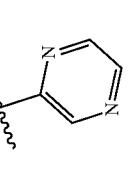 | H | |
| 604 | 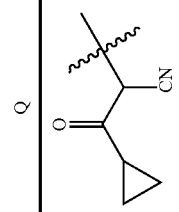 | Cl | 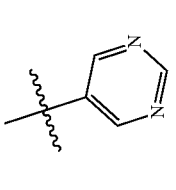 | H | |
| 605 | 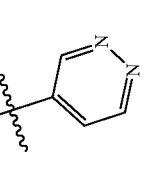 | Cl | 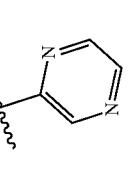 | H | |

TABLE 1-continued
Structures and ¹H NMR data of compounds
| NO. | Q | X | Y | Z | ¹HNMR |
|---|---|---|---|---|---|
| 606 | 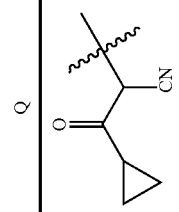 | Cl | 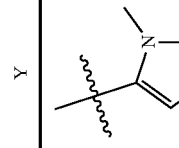 | H | |
| 607 | 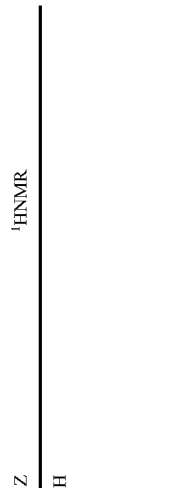 | Cl | 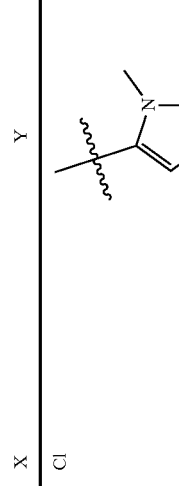 | H | |
| 608 | 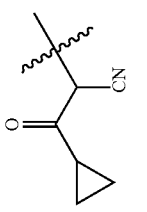 | Cl | 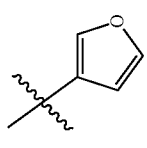 | H | |
| 609 |  | Cl | 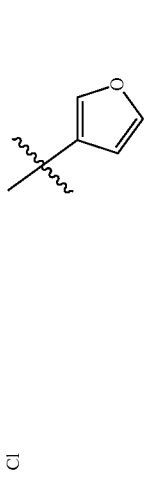 | H | |
| 610 | 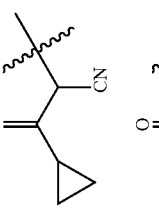 | Cl | 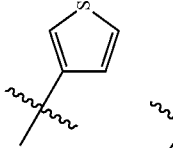 | H | |

TABLE 1-continued

Structures and ¹H NMR data of compounds

| NO. | Q | X | Y | Z | ¹HNMR |
|---|---|---|---|---|---|
| 611 | cyclopropyl-C(O)-CH(CN)- | Cl | oxazol-5-yl | H | |
| 612 | cyclopropyl-C(O)-CH(CN)- | Cl | thiazol-4-yl | H | |
| 613 | cyclopropyl-C(O)-CH(CN)- | Cl | 1-methylimidazol-2-yl | H | |
| 614 | cyclopropyl-C(O)-CH(CN)- | Cl | isoxazol-3-yl | H | |

TABLE 1-continued

Structures and ¹H NMR data of compounds

| NO. | Q | X | Y | Z | ¹HNMR |
|---|---|---|---|---|---|
| 615 | cyclopropyl-C(O)-CH(CN)- | Cl | 2-methyl-oxadiazol-5-yl | H | |
| 616 | cyclopropyl-C(O)-CH(CN)- | Cl | 1H-triazol-3-yl | H | |
| 617 | cyclopropyl-C(O)-CH(CN)- | Cl | naphthalen-2-yl | H | |
| 618 | cyclopropyl-C(O)-CH(CN)- | Cl | 3,7-dichloroquinolin-8-yl | H | |

TABLE 1-continued

Structures and $^1$H NMR data of compounds

| NO. | Q | X | Y | Z | $^1$HNMR |
|---|---|---|---|---|---|
| 619 | (2-oxo-1-cyanocyclopropyl group) | Cl | (isoquinolin-1-yl) | H | |
| 620 | (cyclohexane-1,3-dione-2-yl) | (but-3-en-2-yl) | (cyclopropyl) | H | |
| 621 | (cyclohexane-1,3-dione-2-yl) | (methoxy-methyl) | $CH_2CH_3$ | H | $^1$H NMR (500 MHz, DMSO-d$_6$) δ 8.37 (d, J = 7.0 Hz, 1H), 7.30 (d, J = 7.0 Hz, 1H), 4.71 (s, 1H), 3.35 (s, 3H), 3.20-3.08 (m, 4H), 2.56-2.51 (m, 2H), 2.14-2.08 (m, 2H), 1.40 (t, J = 7.5 Hz, 3H). |
| 622 | (cyclohexane-1,3-dione-2-yl) | (methylthio-methyl) | $CH_2CH_3$ | H | $^1$H NMR (500 MHz, DMSO-d$_6$) δ 8.21 (d, J = 7.0 Hz, 1H), 7.04 (d, J = 7.0 Hz, 1H), 2.86 (q, J = 7.5 Hz, 2H), 2.56 (s, 3H), 2.36-2.32 (m, 4H), 1.86-1.79 (m, 2H), 1.46 (t, J = 7.5 Hz, 3H) |

TABLE 1-continued

Structures and ¹H NMR data of compounds

| NO. | Q | X | Y | Z | ¹HNMR |
|---|---|---|---|---|---|
| 623 | 2-yl-cyclohexane-1,3-dione | S-iPr | n-butyl (sec) | H | ¹H NMR (500 MHz, DMSO-d₆) δ 8.23 (d, J = 7.0 Hz, 1H), 7.03 (d, J = 7.0 Hz, 1H), 2.86-2.76 (m, 5H), 2.36-2.33 (m, 4H), 1.84-1.78 (m, 2H), 1.42-1.33 (m, 2H), 0.95 (t, J = 1.5 Hz, 3H). |
| 624 | 2-yl-cyclohexane-1,3-dione | S(O)-iPr | CH₂CH₃ | H | ¹H NMR (500 MHz, DMSO-d₆) δ 8.17 (d, J = 7.0 Hz, 1H), 7.02 (d, J = 7.0 Hz, 1H), 2.86-2.76 (m, 5H), 2.36-2.32 (m, 4H), 1.83-1.78 (m, 2H), 1.46 (t, J = 1.5 Hz, 3H). |
| 625 | 2-yl-cyclohexane-1,3-dione | S(O)-iPr | n-butyl (sec) | H | ¹H NMR (500 MHz, DMSO-d₆) δ 8.19 (d, J = 7.0 Hz, 1H), 6.98 (d, J = 7.0 Hz, 1H), 2.86-2.76 (m, 5H), 2.36-2.32 (m, 4H), 1.83-1.78 (m, 2H), 1.42-1.33 (m, 2H), 0.95 (t, J = 7.5 Hz, 3H). |
| 626 | ONa-cyclohexenone | Cl | Cl | H | ¹H NMR (500 MHz, Deuterium Oxide) δ 8.16 (d, J = 7.0 Hz, 1H), 6.95 (d, J = 7.0 Hz, 1H), 2.37-2.35 (m, 4H), 1.88-1.85 (m, 2H). |

TABLE 1-continued

Structures and ¹H NMR data of compounds

| NO. | Q | X | Y | Z | ¹HNMR |
|---|---|---|---|---|---|
| 627 | ONa-cyclohexanedione | Cl | Br | H | ¹H NMR (500 MHz, DMSO) δ 8.23 (d, J = 7.0 Hz, 1H), 6.67 (d, J = 7.0 Hz, 1H), 2.36-2.34(m, 4H), 1.80-1.78 (m, 2H). |
| 628 | ONa-cyclohexanedione | Cl | sec-butyl-methyl | H | ¹H NMR (500 MHz, Deuterium Oxide) δ 8.29 (d, J = 7.0 Hz, 1H), 6.84 (d, J = 7.0 Hz, 1H), 3.16-3.12 (m, 1H), 2.22 (t, J = 6.5 Hz, 4H), 1.88-1.83 (m, 4H), 0.98(d, J = 7.5 Hz, 3H), 0.74 (t, J = 7.5 Hz, 3H). |
| 629 | ONa-cyclohexanedione | Cl | 3-pentyl | H | ¹H NMR (500 MHz, Deuterium Oxide) δ 8.35 (d, J = 7.0 Hz, 1H), 6.96 (d, J = 7.0 Hz, 1H), 2.61-2.55 (m, 1H), 2.31 (t, J = 6.5 Hz, 4H), 2.00-1.92 (m, 2H), 1.85-1.79 (m, 2H), 1.50-1.40 (m, 2H), 0.84 (t, J = 8.0 Hz, 6H). |
| 630 | ONa-cyclohexanedione | Cl | neopentyl | H | ¹H NMR (500 MHz, Deuterium Oxide) δ 8.25 (d, J = 7.0 Hz, 1H), 6.82 (d, J = 7.0 Hz, 1H), 3.01 (s, 2H), 2.36-2.29 (m, 4H), 1.88-1.84 (m, 2H), 0.94 (s, 9H). |

TABLE 1-continued

Structures and ¹H NMR data of compounds

| NO. | Q | X | Y | Z | ¹HNMR |
|---|---|---|---|---|---|
| 631 | ONa, cyclohexanone-enolate | Cl | cyclohexyl-methyl | H | ¹H NMR (500 MHz, Deuterium Oxide) δ 8.13 (d, J = 7.0 Hz, 1H), 6.82 (d, J = 7.0 Hz, 1H), 3.06 (t, J = 7.5 Hz, 2H), 2.35 (t, J = 6.5 Hz, 4H), 1.87-1.84 (m, 2H), 1.79-1.71 (m, 2H), 1.24-1.18 (m, 6H), 0.75 (t, J = 7.0 Hz, 3H). |
| 632 | ONa, cyclohexanone-enolate | Cl | isobutyl | H | ¹H NMR (500 MHz, Deuterium Oxide) δ 8.37 (d, J = 6.5 Hz, 1H), 6.98 (d, J = 6.5 Hz, 1H), 2.64-2.58 (m, 4H), 1.90 (t, J = 7.0 Hz, 2H), 1.64-1.49 (m, 5H), 0.89 (d, J = 6.5 Hz, 6H). |
| 633 | ONa, cyclohexanone-enolate | Cl | long alkyl chain | H | ¹H NMR (500 MHz, Deuterium Oxide) δ 8.18 (d, J = 7.0 Hz, 1H), 6.85(d, J = 7.0 Hz, 1H), 3.06 (t, J = 7.5 Hz, 2H), 2.35 (t, J = 6.5 Hz, 4H), 1.87-1.84 (m, 2H), 1.79-1.71 (m, 2H), 1.24-1.18 (m, 8H), 0.75 (t, J = 7.0 Hz, 3H). |
| 634 | ONa, cyclohexanone-enolate | Cl | alkenyl | H | ¹H NMR (500 MHz, Deuterium Oxide) δ 8.19 (d, J = 7.0 Hz, 1H), 6.93-6.88 (m, 1H), 6.83 (d, J = 7.0 Hz, 1H), 6.63 (d, J = 16.0 Hz, 1H), 2.35 (t, J = 6.5 Hz, 4H), 1.99-1.92 (m, 3H), 1.86 (t, J = 6.5 Hz, 2H). |

TABLE 1-continued

Structures and ¹H NMR data of compounds

| NO. | Q | X | Y | Z | ¹HNMR |
|---|---|---|---|---|---|
| 635 | ONa, cyclohexenone | Cl | ethynyl | H | ¹H NMR (500 MHz, Deuterium Oxide) δ 8.25 (d, J = 7.0 Hz, 1H), 6.91 (d, J = 7.0 Hz, 1H), 2.39-2.35 (m, 4H), 2.18 (s, 3H), 1.92-1.86 (m, 2H). |
| 636 | ONa, cyclohexenone | Cl | CH2Cl | H | |
| 637 | ONa, cyclohexenone | Cl | (CH2)4Cl | H | ¹H NMR (500 MHz, Deuterium Oxide) δ 8.17 (d, J = 7.0 Hz, 1H), 6.84 (d, J = 7.0 Hz, 1H), 3.60 (t, J = 7.0 Hz, 2H), 3.13 (t, J = 7.5 Hz, 2H), 2.37 (t, J = 6.5 Hz, 4H), 1.99-1.90 (m, 2H), 1.89-1.81 (m, 4H). |
| 638 | ONa, cyclohexenone | Cl | CH2CF3 | H | ¹H NMR (500 MHz, DMSO) δ 8.54 (d, J = 7.0 Hz, 1H), 6.92 (d, J = 7.0 Hz, 1H), 3.35 (s, 2H), 2.38-2.32 (m, 4H) 1.87-1.84 (m, 2H). |

TABLE 1-continued

Structures and $^1$H NMR data of compounds

| NO. | Q | X | Y | Z | $^1$HNMR |
|-----|---|---|---|---|----------|
| 639 | ONa, cyclohexanone | Cl | CF$_2$-ethyl | H | $^1$H NMR (500 MHz, Deuterium Oxide) δ 8.42 (d, J = 7.0 Hz, 1H), 6.94 (d, J = 7.0 Hz, 1H), 2.57-2.44 (m, 2H), 2.35 (t, J = 6.5 Hz, 4H), 1.92-1.81 (m, 2H), 1.06 (t, J = 7.5 Hz, 3H). |
| 640 | ONa, cyclohexanone | Cl | C(CH$_3$)$_2$CF$_3$ | H | $^1$H NMR (500 MHz, Deuterium Oxide) δ 8.23 (d, J = 7.0 Hz, 1H), 6.92 (d, J = 7.0 Hz, 1H), 2.39 (t, J = 6.5 Hz, 4H), 1.88-1.84 (m, 2H), 1.19(s, 6H). |
| 641 | ONa, cyclohexanone | Cl | CH=CHCl | H | $^1$H NMR (500 MHz, Deuterium Oxide) δ 8.19 (d, J = 7.0 Hz, 1H), 7.36 (d, J = 13.5 Hz, 1H), 7.14 (d, J = 13.5 Hz, 1H), 6.86 (d, J = 7.0 Hz, 1H), 2.37-2.35 (m, 4H), 1.86-1.85 (m, 2H). |
| 642 | ONa, cyclohexanone | Cl | cyclopropyl-methyl | H | |

TABLE 1-continued

Structures and ¹H NMR data of compounds

| NO. | Q | X | Y | Z | ¹HNMR |
|---|---|---|---|---|---|
| 643 | ONa, cyclohexanone substituent | Cl | cyclopentyl | H | ¹H NMR (500 MHz, Deuterium Oxide) δ 8.12 (d, J = 6.5 Hz, 1H), 6.76 (d, J = 6.5 Hz, 1H), 2.43-2.01 (m, 6H), 1.91-1.58 (m, 9H). |
| 644 | ONa, cyclohexanone substituent | Cl | cyclopentenyl | H | ¹H NMR (500 MHz, DMSO-d₆) δ 8.12 (d, J = 7.0 Hz, 1H), 6.93 (d, J = 7.0 Hz, 1H), 5.96-5.92 (m, 1H), 2.37-2.18 (m, 8H), 1.87-1.74 (m, 4H). |
| 645 | ONa, cyclohexanone substituent | Cl | cyclohexenyl | H | ¹H NMR (500 MHz, Deuterium Oxide) δ 8.37 (d, J = 7.0 Hz, 1H), 6.87 (d, J = 7.0 Hz, 1H), 6.52-6.50 (m, 1H), 2.52-2.50 (m, 2H), 2.43 (t, J = 6.5 Hz, 4H), 2.34-2.32 (m, 2H), 1.96-1.91 (m, 2H), 1.88-1.79 (m, 2H), 1.79-1.70 (m, 2H). |
| 646 | ONa, cyclohexanone substituent | Cl | CH₂ONa | H | ¹H NMR (500 MHz, DMSO) δ 8.24 (d, J = 7.0 Hz, 1H), 6.65 (d, J = 7.0 Hz, 1H), 4.79 (s, 2H), 2.37-2.35(m, 4H), 1.81-1.78 (m, 2H). |

TABLE 1-continued

Structures and ¹H NMR data of compounds

| NO. | Q | X | Y | Z | ¹HNMR |
|---|---|---|---|---|---|
| 647 | ONa, cyclohexanone enolate | Cl | CH(CH₃)OCH₃ | H | ¹H NMR (500 MHz, Deuterium Oxide) δ 8.21 (d, J = 7.0 Hz, 1H), 6.89 (d, J = 7.0 Hz, 1H), 4.70-4.66 (m, 1H), 3.33 (s, 3H), 2.30 (t, J = 6.5 Hz, 4H), 1.86-1.81 (m, 2H), 1.51 (d, J = 7.0 Hz, 3H). |
| 648 | ONa, cyclohexanone enolate | Cl | S-ethyl, methyl branched | H | ¹H NMR (500 MHz, Deuterium Oxide) δ 8.27 (d, J = 7.0 Hz, 1H), 6.89 (d, J = 7.0 Hz, 1H), 2.99-2.95 (m, 2H), 2.33-2.31 (m, 4H), 1.85-1.81 (m, 2H), 1.14 (t, J = 7.5 Hz, 3H). |
| 649 | ONa, cyclohexanone enolate | Cl | S-propyl, methyl branched | H | ¹H NMR (500 MHz, DMSO) δ 8.25 (d, J = 7.0 Hz, 1H), 6.66 (d, J = 7.0 Hz, 1H), 3.09 (t, J = 7.0 Hz, 2H), 2.35-2.32(m, 4H), 1.81-1.77 (m, 2H), 1.75-1.68 (m, 2H), 1.03 (t, J = 8.0 Hz, 3H). |
| 650 | ONa, cyclohexanone enolate | Cl | S-allyl, methyl branched | H | ¹H NMR (500 MHz, DMSO) δ 8.26 (d, J = 7.0 Hz, 1H), 6.70 (d, J = 6.9 Hz, 1H), 5.92-5.80 (m, 1H), 4.99-4.95 (m, 1H), 4.95-4.90 (m, 1H), 3.90-3.87 (m, 2H), 2.73-2.70 (m, 2H), 2.19-2.06 (m, 2H), 1.77-1.71 (m, 2H). |

TABLE 1-continued

Structures and ¹H NMR data of compounds

| NO. | Q | X | Y | Z | ¹HNMR |
|---|---|---|---|---|---|
| 651 | ONa, cyclohexanone enolate | Cl | propargylthio | H | ¹H NMR (500 MHz, Deuterium Oxide) δ 8.37 (d, J = 7.0 Hz, 1H), 6.99 (d, J = 7.0 Hz, 1H), 4.91-4.86 (m, 1H), 3.18 (s, 2H), 2.39 (t, J = 6.5 Hz, 4H), 1.93-1.85 (m, 2H). |
| 652 | ONa, cyclohexanone enolate | Cl | tert-butyl sulfoxide | H | ¹H NMR (500 MHz, Deuterium Oxide) δ 8.62 (d, J = 7.0 Hz, 1H), 7.06 (d, J = 7.0 Hz, 1H), 3.31 (s, 3H), 2.39-2.37 (m, 4H), 1.93-1.88 (m, 2H). |
| 653 | ONa, cyclohexanone enolate | Cl | NH₂ | H | ¹H NMR (500 MHz, DMSO) δ 8.35 (d, J = 7.0 Hz, 1H), 6.69 (d, J = 7.0 Hz, 1H), 5.91 (s, 2H), 2.55-2.49 (m, 4H), 2.14-2.10(m, 2H). |
| 654 | ONa, cyclohexanone enolate | Cl | N,N-dimethylamino | H | ¹H NMR (500 MHz, DMSO) δ 8.75 (d, J = 7.0 Hz, 1H), 6.91 (d, J = 7.0 Hz, 1H), 2.29-2.17 (m, 4H), 1.79-1.65 (m, 8H). |

TABLE 1-continued

Structures and ¹H NMR data of compounds

| NO. | Q | X | Y | Z | ¹HNMR |
|---|---|---|---|---|---|
| 655 | ONa-cyclohexanedione | Cl | N(allyl)₂ | H | ¹H NMR (500 MHz, DMSO-d₆) δ 8.75 (d, J = 7.0 Hz, 1H), 6.91 (d, J = 7.0 Hz, 1H), 5.86-5.85(m, 2H), 5.18-5.02 (m, 4H), 3.73-3.72 (m, 4H), 2.64-2.58 (m, 4H), 1.84-1.79 (m, 2H). |
| 656 | ONa-cyclohexanedione | Cl | N(propargyl)₂ | H | ¹H NMR (500 MHz, Deuterium Oxide) δ 8.09 (d, J = 7.0 Hz, 1H), 6.84 (d, J = 7.0 Hz, 1H), 4.18 (s, 4H), 4.14 (s, 2H), 2.38 (t, J = 6.5 Hz, 4H), 1.91-1.85 (m, 2H). |
| 657 | ONa-cyclohexanedione | Cl | NHAc | H | ¹H NMR (500 MHz, DMSO) δ 8.45 (d, J = 7.0 Hz, 1H), 6.61 (d, J = 7.0 Hz, 1H), 5.91 (s, 1H), 2.15-2.06 (m, 7H), 1.98-1.93 (m, 2H). |
| 658 | ONa-cyclohexanedione | Cl | CH(CH₃)OH | H | ¹H NMR (500 MHz, Deuterium Oxide) δ 8.32 (d, J = 7.0 Hz, 1H), 6.81 (d, J = 7.0 Hz, 1H), 5.35 (q, J = 6.5 Hz, 1H), 2.31-2.29 (m, 4H), 1.83-1.78 (m, 2H), 1.67 (d, J = 7.0 Hz, 3H). |

TABLE 1-continued

Structures and $^1$H NMR data of compounds

| NO. | Q | X | Y | Z | $^1$HNMR |
|---|---|---|---|---|---|
| 659 | (ONa-cyclohexenone) | Cl | -CH$_2$-S-CH$_3$ | H | $^1$H NMR (500 MHz, Deuterium Oxide) δ 8.29 (d, J = 7.0 Hz, 1H), 6.89 (d, J = 7.0 Hz, 1H), 4.22 (s, 2H), 2.37 (t, J = 6.5 Hz, 4H), 1.96 (s, 3H), 1.88-1.83 (m, 2H). |
| 660 | (ONa-cyclohexenone) | Cl | -C(CH$_3$)$_2$-CH$_2$-N(CH$_3$)$_2$ | H | $^1$H NMR (500 MHz, DMSO) δ 8.25 (d, J = 7.0 Hz, 1H), 6.61 (d, J = 7.0 Hz, 1H), 3.91 (s, 2H), 2.22-2.07 (m, 10H), 1.78-1.66 (m, 2H) |
| 661 | (ONa-cyclohexenone) | Cl | -CH$_2$-O-C(O)CH$_3$ | H | |
| 662 | (ONa-cyclohexenone) | Cl | -pyrrolidine | H | $^1$H NMR (500 MHz, Deuterium Oxide) δ 8.09 (d, J = 7.0 Hz, 1H), 6.63 (d, J = 7.0 Hz, 1H), 3.45-3.40 (m, 4H), 2.36-2.32 (m, 4H), 2.02-1.94 (m, 4H), 1.86-1.82 (m, 2H). |

TABLE 1-continued

Structures and $^1$H NMR data of compounds

| NO. | Q | X | Y | Z | $^1$HNMR |
|---|---|---|---|---|---|
| 663 | ONa, cyclohexanone enolate | Cl | 1-methylpiperidin-4-yl | H | $^1$H NMR (500 MHz, DMSO) δ 8.26 (d, J = 7.0 Hz, 1H), 6.67 (d, J = 7.0 Hz, 1H), 2.68-2.63 (m, 1H), 2.58-2.53 (m, 4H), 2.36-2.33 (m, 4H), 2.25 (s, 3H), 1.82-1.78 (m, 2H), 1.57-1.50 (m, 4H). |
| 664 | ONa, cyclohexanone enolate | Cl | 3-fluorophenyl | H | $^1$H NMR (500 MHz, DMSO) δ 7.79-7.57 (m, 3H), 7.46-7.43 (m, 1H), 7.41-6.83 (m, 1H), 6.69 (d, J = 7.5 Hz, 1H), 2.26-2.15 (m, 4H), 1.86-1.73 (m, 2H). |
| 665 | ONa, cyclohexanone enolate | Cl | 2-chlorophenyl | H | $^1$H NMR (500 MHz, DMSO-d$_6$) δ 8.30 (d, J = 7.5 Hz, 1H), 7.72 (s, 1H), 7.64 (m, 2H), 7.44-7.35 (m, 2H), 6.95 (d, J = 7.5 Hz, 1H), 2.35 (t, J = 6.5 Hz, 4H), 1.89-1.83 (m, 2H). |
| 666 | ONa, cyclohexanone enolate | Cl | 3-chlorophenyl | H | $^1$H NMR (500 MHz, Deuterium Oxide) δ 8.27-8.21 (m, 1H), 7.72 (s, 1H), 7.61 (d, J = 7.5 Hz, 1H), 7.52-7.48 (m, 2H), 6.86-6.82 (m, 1H), 2.38-2.32 (m, 4H), 1.87-1.79 (m, 2H). |

TABLE 1-continued

Structures and ¹H NMR data of compounds

| NO. | Q | X | Y | Z | ¹HNMR |
|---|---|---|---|---|---|
| 667 | ONa, cyclohexenone | Cl | 4-chlorophenyl | H | ¹H NMR (500 MHz, Deuterium Oxide) δ 8.28 (d, J = 7.0 Hz, 1H), 7.72 (d, J = 8.5 Hz, 2H), 7.60 (d, J = 8.5 Hz, 2H), 6.86 (d, J = 7.0 Hz, 1H), 2.35 (t, J = 6.5 Hz, 4H), 1.92-1.81 (m, 2H). |
| 668 | ONa, cyclohexenone | Cl | furan-3-yl | H | ¹H NMR (500 MHz, DMSO-d₆) δ 8.19-8.15 (m, 2H), 7.56 (d, J = 5.0 Hz, 1H), 7.16-6.98 (m, 2H), 2.37-2.32 (m, 4H), 1.83-1.79 (m, 2H). |
| 669 | ONa, cyclohexenone | Cl | thiophen-3-yl | H | MHz, DMSO-d₆) δ 8.38 (d, J = 7.0 Hz, 1H), 8.18 (s, 1H), 7.65 (d, J = 2.0 Hz, 1H), 7.23 (d, J = 2.0 Hz, 1H), 6.85 (d, J = 7.0 Hz, 1H), 2.56-2.48 (m, 4H), 1.94-1.88 (m, 2H). |
| 670 | ONa, cyclohexenone | Cl | isoxazol-3-yl | H | ¹H NMR (500 MHz, DMSO-d₆) δ 8.34 (d, J = 5.0 Hz, 1H), 8.14 (d, J = 7.0 Hz, 1H), 7.78 (d, J = 5.0 Hz, 1H), 6.89 (d, J = 7.0 Hz, 1H), 2.38-2.33 (m, 4H), 1.85-1.79 (m, 2H). |

TABLE 1-continued

Structures and ¹H NMR data of compounds

| NO. | Q | X | Y | Z | ¹HNMR |
|---|---|---|---|---|---|
| 671 | ONa-cyclohexanone | Cl | oxazole | H | ¹H NMR (500 MHz, DMSO-d₆) δ 8.12 (d, J = 7.0 Hz, 1H), 7.94 (s, 1H), 7.48 (s, 1H), 6.94 (d, J = 7.0 Hz, 1H), 2.36-2.31 (m, 4H), 1.85-1.79 (m, 2H). |
| 672 | ONa-cyclohexanone | Cl | thiazol-2-yl | H | ¹H NMR (500 MHz, DMSO-d₆) δ 9.26 (d, J = 7.0 Hz, 1H), 8.19 (s, 1H), 8.04 (s, 1H), 6.95 (d, J = 7.0 Hz, 1H), 2.22 (t, J = 6.5 Hz, 4H), 1.83-1.78 (m, 2H). |
| 673 | ONa-cyclohexanone | Cl | thiazol-5-yl | H | ¹H NMR (500 MHz, DMSO-d₆) δ 8.93 (s, 1H), 8.14 (d, J = 7.0 Hz, 1H), 7.94 (s, 1H), 6.99 (d, J = 7.0 Hz, 1H), 2.38-2.34 (m, 4H), 1.88-1.81 (m, 2H). |
| 674 | ONa-cyclohexanone | Cl | thiazol-4-yl | H | ¹H NMR (500 MHz, DMSO-d₆) δ 8.73 (s, 1H), 8.14 (d, J = 7.0 Hz, 1H), 7.82 (s, 1H), 6.99 (d, J = 7.0 Hz, 1H), 2.37-2.31 (m, 4H), 1.84-1.77 (m, 2H). |

TABLE 1-continued

Structures and ¹H NMR data of compounds

| NO. | Q | X | Y | Z | ¹HNMR |
|---|---|---|---|---|---|
| 675 | ONa-cyclohexenone | Cl | 1-methylimidazol-5-yl | H | ¹H NMR (500 MHz, DMSO-d₆) 8.16 (d, J = 7.0 Hz, 1H), 7.88 (s, 1H), 7.36 (s, 1H), 6.92 (d, J = 7.0 Hz, 1H), 3.92 (s, 3H), 2.34-2.30 (m, 4H), 1.82-1.77 (m, 2H). |
| 676 | ONa-cyclohexenone | Cl | 1-methylimidazol-4-yl | H | ¹H NMR (500 MHz, DMSO-d₆) 8.16 (d, J = 7.0 Hz, 1H), 7.81(s, 1H), 7.26 (s, 1H), 6.99 (d, J = 7.0 Hz, 1H), 3.96 (s, 3H), 2.36-2.32 (m, 4H), 1.83-1.78 (m, 2H). |
| 677 | ONa-cyclohexenone | Cl | 1-methylimidazol-2-yl | H | ¹H NMR (500 MHz, DMSO-d₆) δ 8.15 (d, J = 7.5 Hz, 1H), 7.18 (d, J = 4.5 Hz, 1H), 7.15 (d, J = 4.5 Hz, 1H), 6.90(d, J = 7.5 Hz, 1H), 3.88 (s, 3H), 2.33-2.29 (m, 4H), 1.84-1.77? (m, 2H). |
| 678 | ONa-cyclohexenone | Cl | pyridin-4-yl | H | ¹H NMR (500 MHz, DMSO-d₆) δ 8.39 (d, J = 7.5 Hz, 2H), 8.21 (d, J = 7 Hz, 1H), 7.68 (d, J = 7.5 Hz, 2H), 6.89 (d, J = 7.0 Hz, 1H), 2.33-2.28 (m, 4H), 1.86-1.80 (m, 2H). |

TABLE 1-continued

Structures and ¹H NMR data of compounds

| NO. | Q | X | Y | Z | ¹HNMR |
|---|---|---|---|---|---|
| 679 | ONa, cyclohexanone-enolate | Cl | 2-pyridyl | H | ¹H NMR (500 MHz, Deuterium Oxide) δ 9.11 (d, J = 7.0 Hz, 1H), 8.60-8.57(m, 1H), 7.98-7.90 (m, 2H), 7.46-7.43(m, 1H), 6.89 (d, J = 7.0 Hz, 1H), 2.34 (t, J = 6.5 Hz, 4H), 1.92-1.77 (m, 2H). |
| 680 | ONa, cyclohexanone-enolate | Cl | 3-pyridyl | H | ¹H NMR (500 MHz, Deuterium Oxide) δ 9.20-8.70 (m, 2H), 8.40-8.30 (m, 3H), 6.92 (d, J = 7.0 Hz, 1H), 2.45-2.40 (m, 4H), 1.96-1.91(m, 2H). |
| 681 | ONa, cyclohexanone-enolate | Cl | 2,6-dichloropyridin-4-yl | H | ¹H NMR (500 MHz, DMSO) δ 9.20 (d, J = 7.0 Hz, 1H), 8.39 (s, 1H), 7.95 (s, 1H), 6.93 (d, J = 7.0 Hz, 1H), 2.16 (t, J = 6.0 Hz, 4H), 1.78-1.68 (m, 2H). |
| 682 | ONa, cyclohexanone-enolate | Cl | 3,5-dichloropyridin-2-yl | H | ¹H NMR (500 MHz, Deuterium Oxide) δ8.95 (s, 1H), 8.36 (d, J = 7.5 Hz, 1H), 8.15 (s, 1H), 6.88 (d, J = 7.5 Hz, 1H), 2.46-2.38 (m, 4H), 1.89-1.85 (m, 2H) |

TABLE 1-continued

Structures and $^1$H NMR data of compounds

| NO. | Q | X | Y | Z | $^1$HNMR |
|---|---|---|---|---|---|
| 683 | ONa-cyclohexanedione enol | Cl | 3,6-dichloropyridin-2-yl | H | $^1$H NMR (500 MHz, Deuterium Oxide) δ 8.49 (d, J = 7.0 Hz, 1H), 8.08 (d, J = 5.0 Hz, 1H), 7.60 (d, J = 5.0 Hz, 1H), 6.91 (d, J = 7.0 Hz, 1H), 2.34-2.29 (m, 4H), 1.86-1.80 (m, 2H). |
| 684 | ONa-cyclohexanedione enol | Cl | 2,5-dichloropyridin-3-yl | H | $^1$H NMR (500 MHz, Deuterium Oxide) δ 8.81 (s, 1H), 8.38 (d, J = 7.0 Hz, 1H), 7.90 (s, 1H), 6.89 (d, J = 7.0 Hz, 1H), 2.35-2.29 (m, 4H), 1.88-1.81 (m, 2H). |
| 685 | ONa-cyclohexanedione enol | Cl | 2,4-dichloropyridin-3-yl | H | $^1$H NMR (500 MHz, Deuterium Oxide) δ 8.51 (d, J = 4.5 Hz, 1H), 8.32 (d, J = 7.5 Hz, 1H), 7.80 (d, J = 4.5 Hz, 1H), 6.85 (d, J = 7.5 Hz, 1H), 2.34 (t, J = 6.5 Hz, 4H), 1.92-1.77 (m, 2H). |

TABLE 1-continued

Structures and ¹H NMR data of compounds

| NO. | Q | X | Y | Z | ¹HNMR |
|---|---|---|---|---|---|
| 686 | ONa, cyclohexanone enolate | Cl | 2,3-dichloropyridin-5-yl | H | ¹H NMR (500 MHz, DMSO) δ 8.92 (s, 1H), 8.70 (s, 1H), 8.52 (d, J = 7.0 Hz, 1H), 6.76-6.69 (m, 1H), 2.19 (m, 4H), 1.83-1.73 (m, 2H). |
| 687 | ONa, cyclohexanone enolate | Cl | 2,6-dichloropyridin-3-yl | H | ¹H NMR (500 MHz, DMSO) δ 8.34-8.30 (m, 2H), 7.91 (d, J = 8.0 Hz, 1H), 7.41 (d, J = 7.0 Hz, 1H), 2.55-2.54 (m, 4H), 2.14-2.13 (m, 2H). |
| 688 | ONa, cyclohexanone enolate | Cl | 2,4-dichloropyridin-5-yl | H | ¹H NMR (500 MHz, DMSO) δ 8.75 (d, J = 7.0 Hz, 1H), 8.19-8.07 (m, 2H), 6.70 (d, J = 7.0 Hz, 1H), 2.20-2.19 (m, 4H), 1.83-1.70 (m, 2H). |

TABLE 1-continued

Structures and $^1$H NMR data of compounds

| NO. | Q | X | Y | Z | $^1$HNMR |
|---|---|---|---|---|---|
| 689 | ONa-cyclohexanone | Cl | 2-chloro-3-fluoropyridin-4-yl | H | $^1$H NMR (500 MHz, DMSO-d$_6$) δ 8.49 (d, J = 5.0 Hz, 1H), 8.22 (d, J = 7.0 Hz, 1H), 7.75-7.66 (m, 1H), 6.95 (d, J = 7.0 Hz, 1H), 2.39-2.33 (m, 4H), 1.84-1.76 (m, 2H). |
| 690 | ONa-cyclohexanone | Cl | pyridazin-4-yl | H | $^1$H NMR (500 MHz, DMSO-d$_6$) δ 9.58 (s, 1H), 9.43 (d, J = 5.5 Hz, 1H), 8.15 (d, J = 7.5 Hz, 1H), 7.89 (d, J = 5.5 Hz, 1H), 6.90 (d, J = 7.5 Hz, 1H), 2.35-2.31 (m, 4H), 1.86-1.80 (m, 2H). |
| 691 | ONa-cyclohexanone | Cl | pyrazin-2-yl | H | $^1$H NMR (500 MHz, DMSO-d$_6$) δ 9.36 (s, 1H), 9.12 (s, 2H), 8.15 (d, J = 7.5 Hz, 1H), 6.90 (d, J = 7.5 Hz, 1H), 2.36-2.32 (m, 4H), 1.83-1.78 (m, 2H). |
| 692 | ONa-cyclohexanone | Cl | quinolin-8-yl | H | $^1$H NMR (500 MHz, DMSO-d$_6$) δ 8.74 (d, J = 7.0 Hz, 1H), 8.31-8.22 (m, 4H), 7.77-7.62 (m, 2H), 7.04 (d, J = 7.0 Hz, 1H), 2.39-2.34 (m, 4H), 1.81-1.76 (m, 2H), |

TABLE 1-continued
Structures and $^1$H NMR data of compounds
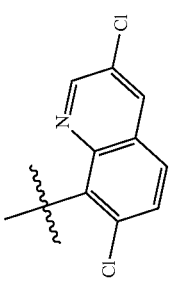
| NO. | Q | X | Y | Z | $^1$HNMR |
|---|---|---|---|---|---|
| 693 | 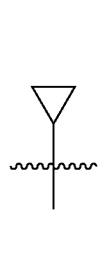 | Cl | 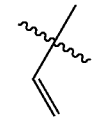 | H | $^1$H NMR (500 MHz, DMSO-d$_6$) δ 8.68 (d, J = 7.0 Hz, 1H), 8.21-7.92 (m, 4H), 7.04 (d, J = 7.0 Hz, 1H), 2.35-2.30 (m, 4H), 1.82-1.77? (m, 2H), |
| 694 | | H | | H | $^1$H NMR (500 MHz, Deuterium Oxide) δ 8.28 (d, J = 6.5 Hz, 1H), 7.83 (s, 1H), 7.13 (d, J = 6.5 Hz, 1H), 2.35 (t, J = 6.5 Hz, 4H), 1.98-1.89(m, 3H), 1.19-1.10 (m, 2H), 0.96-0.92 (m, 2H). |
| 695 | | | CH$_3$ | H | |
| 696 | | | | H | |

TABLE 1-continued

Structures and $^1$H NMR data of compounds

| NO. | Q | X | Y | Z | $^1$HNMR |
|---|---|---|---|---|---|
| 697 | ONa, cyclohexanone-enolate | -O-Me | cyclopropyl | H | $^1$H NMR (500 MHz, Deuterium Oxide) δ 8.29 (d, J = 6.5 Hz, 1H), 6.88 (d, J = 6.5 Hz, 1H), 3.60 (s, 3H), 2.33 (t, J = 6.5 Hz, 4H), 2.19-2.16 (m, 1H), 1.87-1.84 (m, 2H), 1.21-1.11 (m, 2H), 1.00-0.95 (m, 2H). |
| 698 | ONa, cyclohexanone-enolate | -O-Me | -S-Me | H | $^1$H NMR (500 MHz, DMSO) δ 8.24 (d, J = 7.0 Hz, 1H), 6.65 (d, J = 7.0 Hz, 1H), 3.81 (s, 3H), 2.55 (s, 3H), 2.36-2.33 (m, 4H), 1.82-1.78 (m, 2H). |
| 699 | ONa, cyclohexanone-enolate | -S-Me | cyclopropyl | H | $^1$H NMR (500 MHz, Deuterium Oxide) δ 8.22 (d, J = 6.0 Hz, 1H), 6.95 (d, J = 6.0 Hz, 1H), 2.45 (t, J = 7.0 Hz, 4H), 2.46 (s, 3H), 2.18-2.13 (m, 1H), 1.54-1.50 (m, 2H), 1.13-1.10 (m, 2H), 0.91-0.88 (m, 2H). |
| 700 | ONa, cyclohexanone-enolate | -S-Me | -O-Me | H | $^1$H NMR (500 MHz, Deuterium Oxide) δ 7.70 (d, J = 7.0 Hz, 1H), 6.46 (d, J = 7.0 Hz, 1H), 3.58 (s, 3H), 2.32-2.30 (m, 4H), 2.24 (s, 3H), 1.84-1.80 (m, 2H). |

TABLE 1-continued

Structures and $^1$H NMR data of compounds

| NO. | Q | X | Y | Z | $^1$HNMR |
|---|---|---|---|---|---|
| 701 | ONa, cyclohexenone | S-methyl | S-methyl | H | $^1$H NMR (500 MHz, DMSO) δ 8.26 (d, J = 7.0 Hz, 1H), 6.67 (d, J = 7.0 Hz, 1H), 2.55 (s, 3H), 2.46 (s, 3H), 2.37-2.35 (m, 4H),1.83-1.79 (m, 2H). |
| 702 | ONa, cyclohexenone | S-ethyl | cyclopropyl | H | $^1$H NMR (500 MHz, Deuterium Oxide) δ 8.43 (d, J = 7.0 Hz, 1H), 6.91 (d, J = 7.0 Hz, 1H), 3.79-3.70 (m, 2H), 2.34 (t, J = 6.5 Hz, 4H), 2.20-2.16 (m, 1H), 1.89-1.84 (m, 4H), 1.23-1.13 (m, 2H), 1.07 (t, J = 6.5 Hz, 3H), 1.03-0.95 (m, 2H). |
| 703 | ONa, cyclohexenone | S-isopropyl | cyclopropyl | H | $^1$H NMR (500 MHz, Deuterium Oxide) δ 8.33 (d, J = 7.0 Hz, 1H), 6.81 (d, J = 7.0 Hz, 1H), 3.72-3.67 (m, 1H), 2.34 (t, J = 6.5 Hz, 4H), 2.20-2.16 (m, 1H), 1.89-1.84 (m, 2H), 1.23-1.13 (m, 2H), 1.07 (d, J = 6.5 Hz, 6H), 1.03-0.95 (m, 2H). |
| 704 | ONa, cyclohexenone | S(=O)-methyl | cyclopropyl | H | $^1$H NMR (500 MHz, Deuterium Oxide) δ 8.30 (d, J = 7.0 Hz, 1H), 6.88 (d, J = 7.0 Hz, 1H), 3.62 (s, 3H), 2.32 (t, J = 6.5 Hz, 4H), 2.21-2.17 (m, 1H), 1.88-1.83 (m, 2H), 1.22-1.12 (m, 2H), 1.01-0.95 (m, 2H). |

TABLE 1-continued

Structures and $^1$H NMR data of compounds

| NO. | Q | X | Y | Z | $^1$HNMR |
|---|---|---|---|---|---|
| 705 | ONa-cyclohexenone (gem-dimethyl) | methylsulfinyl (S(=O)CH₃) | OCH(CH₃)₂ (isopropoxy) | H | $^1$H NMR (500 MHz, Deuterium Oxide) δ 7.87 (d, J = 7.0 Hz, 1H), 7.70 (d, J = 7.0 Hz, 1H), 3.64 (s, 3H), 3.11 (s, 3H), 2.38-2.35 (m, 4H), 1.88-1.85 (m, 2H). |
| 706 | ONa-cyclohexenone (gem-dimethyl) | N(CH₃)₂ | cyclopropyl | H | $^1$H NMR (500 MHz, Deuterium Oxide) δ 8.19 (d, J = 7.0 Hz, 1H), 7.26-7.23 (m, 1H), 3.26 (s, 6H), 2.35-2.30 (m, 4H), 1.95-1.88 (m, 3H), 1.12-0.96 (m, 2H),0.95-0.90 (m, 2H) |
| 707 | ONa-cyclohexenone with CF₃ | Cl | cyclopropyl | H | $^1$H NMR (500 MHz, DMSO-d₆) δ 8.38 (d, J = 7.0 Hz, 1H), 6.68 (d, J = 7.0 Hz, 1H), 2.85-2.83(m, 1H), 2.39-2.29 (m, 5H), 1.14-1.08 (m, 2H), 1.05-0.98 (m, 2H). |
| 708 | bicyclic enol ether ONa ketone | Cl | CH₃ | H | $^1$H NMR (500 MHz, Deuterium Oxide) δ 8.12 (d, J = 7.0 Hz, 1H), 6.81 (d, J = 7.0 Hz, 1H), 2.70 (s, 3H), 2.10-2.03 (m, 4H), 1.72-1.69 (m, 2H), 1.59-1.56 (m, 2H). |

TABLE 1-continued

Structures and ¹H NMR data of compounds

| NO. | X | Q | Y | Z | ¹HNMR |
|---|---|---|---|---|---|
| 709 | Cl | | | H | ¹H NMR (500 MHz, Deuterium Oxide) δ 8.12 (d, J = 7.0 Hz, 1H), 6.74 (d, J = 7.0 Hz, 1H), 3.03-3.00 (m, 2H), 2.69-2.65 (m, 2H), 2.03-1.97 (m, 4H), 1.81-1.75 (m, 2H), 1.66-1.63-1.59 (m, 2H), 0.88 (t, J = 7.5 Hz, 3H). |
| 710 | Cl | | | H | ¹H NMR (500 MHz, Deuterium Oxide) δ 8.19 (d, J = 7.0 Hz, 1H), 6.75 (d, J = 7.0 Hz, 1H), 3.09-3.05 (m, 2H), 2.68-2.65 (m, 2H), 2.04-1.98 (m, 4H), 1.83-1.47 (m, 4H), 1.37-0.97 (m, 2H), 0.76 (t, J = 6.5 Hz, 3H) |
| 711 | Cl | | | H | ¹H NMR (500 MHz, Deuterium Oxide) δ 8.15 (d, J = 7.0 Hz, 1H), 6.77 (d, J = 7.0 Hz, 1H), 3.06 (t, J = 7.5 Hz, 2H), 2.69-2.64 (m, 2H), 2.02-2.00 (m, 4H), 1.79-1.76 (m, 2H), 1.68-1.66 (m, 2H), 1.33-1.26 (m, 4H), 0.78 (t, J = 7.0 Hz, 3H). |

TABLE 1-continued

Structures and $^1$H NMR data of compounds

| NO. | Q | X | Y | Z | $^1$HNMR |
|---|---|---|---|---|---|
| 712 | | Cl | | H | $^1$H NMR (500 MHz, Deuterium Oxide) δ 8.10 (d, J = 7.0 Hz, 1H), 6.75 (d, J = 7.0 Hz, 1H), 3.06-2.98 (m, 1H), 2.20-2.14 (m, 2H), 2.09-2.03 (m, 4H), 1.73-1.69 (m, 2H), 1.59-1.55 (m, 2H), 1.37-1.33 (m, 3H), 0.85 (t, J = 8.0 Hz, 3H) |
| 713 | | Cl | | H | $^1$H NMR (500 MHz, Deuterium Oxide) δ 8.22 (d, J = 7.0 Hz, 1H), 6.74 (d, J = 7.0 Hz, 1H), 2.98 (s, 2H), 2.67-2.66 (m, 2H), 2.01-1.99 (m, 4H), 1.65-1.63 (m, 2H), 0.91 (s, 9H). |
| 714 | | Cl | | H | $^1$H NMR (500 MHz, Deuterium Oxide) δ 8.10 (d, J = 7.0 Hz, 1H), 6.74 (d, J = 7.0 Hz, 1H), 3.04 (t, J = 8.0 Hz, 2H), 2.72-2.64 (m, 2H), 2.08-1.94 (m, 3H), 1.72-1.59 (m, 4H), 1.57-1.48 (m, 2H), 0.84 (d, J = 7.0 Hz, 6H). |

TABLE 1-continued

Structures and ¹H NMR data of compounds

| NO. | Q | X | Y | Z | ¹HNMR |
|---|---|---|---|---|---|
| 715 | | Cl | | H | ¹H NMR (500 MHz, Deuterium Oxide) δ 8.13 (d, J = 7.0 Hz, 1H), 6.74 (d, J = 7.0 Hz, 1H), 3.06-3.02 (m, 1H), 2.88-2.84 (m, 1H), 2.67 (s, 2H), 2.09-1.85 (m, 4H), 1.65 (d, J = 8.5 Hz, 2H), 1.53-1.49 (m, 1H), 1.37-1.13 (m. 2H), 0.82-0.72 (m, 6H). |
| 716 | | Cl | | H | ¹H NMR (500 MHz, Deuterium Oxide) δ 8.18 (d, J = 7.0 Hz, 1H), 6.79 (d, J = 7.0 Hz, 1H), 3.08-3.05 (m, 2H), 2.70-2.66 (m, 2H), 2.04-1.98 (m, 3H), 1.83-1.47 (m, 4H), 1.37-0.97 (m, 7H), 0.74 (t, J = 6.5 Hz, 3H) |
| 717 | | Cl | | H | ¹H NMR (500 MHz, Deuterium Oxide) δ 8.14 (d, J = 7.0 Hz, 1H), 6.77 (d, J = 7.0 Hz, 1H), 3.08-3.05 (m, 2H), 2.70-2.67 (m, 2H), 2.05-1.98 (m, 3H), 1.83-1.47 (m, 4H), 1.36-0.97 (m, 11H), 0.75 (t, J = 6.5 Hz, 3H). |

TABLE 1-continued

Structures and ¹H NMR data of compounds

| NO. | Q | X | Y | Z | ¹HNMR |
|---|---|---|---|---|---|
| 718 | (bicyclic enone with ONa) | Cl | long alkyl chain | H | ¹H NMR (500 MHz, DMSO-d₆) δ 8.69(d, J = 7.5 Hz, 1H), 6.93 (d, J = 7.5 Hz, 1H), 3.46-3.35 (m, 2H), 2.15-2.13 (m, 4H), 1.90-1.85 (m, 2H), 1.62-1.39 (m, 5H), 1.38-1.12 (m, 11H), 0.92-0.82 (m, 3H). |
| 719 | (bicyclic enone with ONa) | Cl | isopropenyl-isopropyl | H | ¹H NMR (500 MHz, DMSO-d₆) δ 8.45 (d, J = 7.0 Hz, 1H), 6.67 (d, J = 7.0 Hz, 1H), 5.73-5.68(m, 2H), 2.85-2.64 (m, 2H), 2.33 (s, 3H), 2.08-1.83 (m, 4H), 1.67-1.63(m, 2H). |
| 720 | (bicyclic enone with ONa) | Cl | cyclopentyl | H | ¹H NMR (500 MHz, DMSO-d₆) δ 8.31 (d, J = 7.0 Hz, 1H), 6.88 (d, J = 7.0 Hz, 1H), 3.31-3.27 (m, 1H), 2.89-2.83 (m, 2H), 2.71-2.65 (m, 2H), 2.21-2.09 (m, 2H), 1.99-1.84 (m, 4H), 1.83-1.58 (m, 7H). |

TABLE 1-continued

Structures and ¹H NMR data of compounds

| NO. | Q | X | Y | Z | ¹HNMR |
|---|---|---|---|---|---|
| 721 | (bicyclic ketone-ONa substituent) | Cl | CF₂-C(CH₃)-CH₂CH₃ | H | ¹H NMR (500 MHz, Deuterium Oxide) δ 8.41 (d, J = 7.0 Hz, 1H), 6.88 (d, J = 7.0 Hz, 1H), 2.70-2.68 (m, 1H), 2.60-2.37 (m, 2H), 2.03-1.99 (m, 3H), 1.91-1.89(m, 1H), 1.72-1.41 (m, 3H), 1.06 (t, J = 7.0 Hz, 3H). |
| 722 | (bicyclic ketone-ONa substituent) | Cl | CH₂CH₂CF₃ | H | ¹H NMR (500 MHz, Deuterium Oxide) δ 8.16 (d, J = 7.0 Hz, 1H), 6.81 (d, J = 7.0 Hz, 1H), 3.38 (t, J = 8.0 Hz, 2H), 2.84-2.75 (m, 2H), 2.74-2.65 (m, 2H), 2.05-1.98 (m, 4H), 1.68-1.53 (m, 2H). |
| 723 | (bicyclic ketone-ONa substituent) | Cl | CH₂C(F)₂CF₃ | H | ¹H NMR (500 MHz, DMSO-d₆) δ 8.56 (d, J = 7.0 Hz, 1H), 6.99 (d, J = 7.0 Hz, 1H), 4.71 (s, 1H), 2.62-2.57 (m, 2H), 2.11-2.08 (m, 2H), 2.06-1.92 (m, 2H), 1.71-1.67 (m, 2H), 1.54-1.49 (m, 2H). |

TABLE 1-continued

Structures and ¹H NMR data of compounds

| NO. | Q | X | Y | Z | ¹HNMR |
|---|---|---|---|---|---|
| 724 | (bicyclic ketone-ONa group) | Cl | (chlorocyclopentyl with methyl) | H | ¹H NMR (500 MHz, Deuterium Oxide) δ 8.14 (d, J = 7.0 Hz, 1H), 6.77 (d, J = 7.0 Hz, 1H), 3.62 (t, J = 6.0 Hz, 2H), 3.23 (t, J = 7.0 Hz, 2H), 2.72-2.65 (m, 2H), 2.34-2.24 (m, 2H), 2.05-1.97 (m, 4H), 1.69-1.65 (m, 2H). |
| 725 | (bicyclic ketone-ONa group) | Cl | (methoxy-methyl group) | H | ¹H NMR (500 MHz, Deuterium Oxide) δ 7.75 (d, J = 7.0 Hz, 1H), 6.50 (d, J = 7.0 Hz, 1H), 3.61 (s, 3H), 2.75-2.63 (m, 2H), 2.05-1.98 (m, 4H), 1.71-1.65 (m, 2H). |
| 726 | (bicyclic ketone-ONa group) | Cl | (ethoxymethyl-methyl group) | H | ¹H NMR (500 MHz, Deuterium Oxide) δ 8.29 (d, J = 7.0 Hz, 1H), 6.86 (d, J = 7.0 Hz, 1H), 5.05 (s, 2H), 3.60 (q, J = 7.0 Hz, 2H), 2.75-2.70 (m, 2H), 2.06-2.01 (m, 4H), 1.72-1.67 (m, 2H), 1.15 (t, J = 7.0 Hz, 3H). |

TABLE 1-continued

Structures and $^1$H NMR data of compounds

| NO. | Q | X | Y | Z | $^1$HNMR |
|---|---|---|---|---|---|
| 727 | (bicyclic enone-O-Na structure) | Cl | (methoxy isopropyl) | H | $^1$H NMR (500 MHz, DMSO-$d_6$) δ 8.40 (d, J = 7.0 Hz, 1H), 6.77 (d, J = 7.0 Hz, 1H), 5.12 (q, J = 6.7 Hz, 1H), 3.29 (s, 3H), 2.85-2.64 (m, 2H), 2.08-1.83 (m, 4H), 1.67-1.63 (m, 2H), 1.55 (d, J = 7.0 Hz, 3H). |
| 728 | (bicyclic enone-O-Na structure) | Cl | (methylthioethyl) | H | $^1$H NMR (500 MHz, Deuterium Oxide) δ 8.25 (d, J = 7.0 Hz, 1H), 6.80 (d, J = 7.0 Hz, 1H), 4.18 (s, 2H), 2.67 (s, 3H), 2.03-1.99 (m, 4H), 1.91-1.88 (m, 4H). |
| 729 | (bicyclic enone-O-Na structure) | Cl | (tetrahydrofuranyl methyl) | H | $^1$H NMR (500 MHz, DMSO-$d_6$) δ 8.24 (d, J = 7.0 Hz, 1H), 6.61 (d, J = 7.0 Hz, 1H), 5.45 (t, J = 6.5 Hz, 1H), 3.89-3.71 (m, 2H), 2.72-2.59 (m, 2H), 2.39-2.22 (m, 2H), 2.13-1.76 (m, 4H), 1.63-1.58 (m, 2H), 1.51-1.33 (m, 2H). |

TABLE 1-continued

Structures and ¹H NMR data of compounds

| NO. | Q | X | Y | Z | ¹HNMR |
|---|---|---|---|---|---|
| 730 | (bicyclic enone-ONa) | Cl | tetrahydropyran-4-yl | H | ¹H NMR (500 MHz, Deuterium Oxide) δ 8.32 (d, J = 7.0 Hz, 1H), 6.76 (d, J = 7.0 Hz, 1H), 3.86-3.70 (m, 4H), 3.24-3.21 (m, 2H), 2.91-2.85 (m, 1H), 2.69-2.67 (m, 2H), 1.81-1.75 (m, 4H), 1.72-1.59 (m, 4H). |
| 731 | (bicyclic enone-ONa) | Cl | oxazol-4-yl | H | ¹H NMR (500 MHz, DMSO-$d_6$) δ 9.04 (s, 1H), 8.88 (d, J = 7.0 Hz, 1H), 8.81 (s, 1H), 6.78 (d, J = 7.0 Hz, 1H), 2.00-1.84 (m, 4H), 1.68-1.62 (m, 2H), 1.48-1.42 (m, 2H). |
| 732 | (bicyclic enone-ONa) | Cl | thiazol-4-yl | H | ¹H NMR (500 MHz, DMSO-$d_6$) δ 8.73 (s, 1H), 8.19 (d, J = 7.0 Hz, 1H), 7.82 (s, 1H), 6.98 (d, J = 7.0 Hz, 1H), 2.02-1.86 (m, 4H), 1.67-1.63 (m, 2H), 1.45-1.40 (m, 2H). |
| 733 | (pyrazole-ONa) | Cl | sec-butyl | H | ¹H NMR (500 MHz, DMSO-$d_6$) δ 8.22 (d, J = 7.0 Hz, 1H), 6.79 (d, J = 7.0 Hz, 1H), 3.10-3.06 (m, 1H), 3.19 (s, 3H), 1.80 (s, 3H), 1.62-1.58 (m, 2H), 1.39-1.35 (m, 3H), 0.87 (t, J = 8.0 Hz, 3H). |

TABLE 1-continued

Structures and $^1$H NMR data of compounds

| NO. | Q | X | Y | Z | $^1$HNMR |
|---|---|---|---|---|---|
| 734 | | Cl | | H | $^1$H NMR (500 MHz, Deuterium Oxide) δ 8.29 (d, J = 7.0 Hz, 1H), 6.84 (d, J = 7.0 Hz, 1H), 3.18 (s, 3H), 3.16-3.12 (m, 1H), 2.17 (s, 3H), 1.87-1.82 (m, 4H), 0.74 (t, J = 7.5 Hz, 6H). |
| 735 | | Cl | | H | $^1$H NMR (500 MHz, Deuterium Oxide) δ 8.23 (d, 7.0 Hz, 1H), 6.83 (d, J = 7.0 Hz, 1H), 3.17 (s, 3H), 2.30-2.15 (m, 1H), 2.08-2.03 (m, 2H), 1.76-1.69 (m, 3H), 1.39-1.34 (m, 3H), 1.25-1.17 (m, 2H), 0.79-0.75 (m, 3H). |
| 736 | | Cl | | H | $^1$H NMR (500 MHz, Deuterium Oxide) δ 8.15 (d, J = 7.0 Hz, 1H), 6.88 (d, J = 7.0 Hz, 1H), 3.15 (s, 3H), 3.08-3.01 (m, 2H), 2.14 (s, 3H), 1.78-1.71 (m, 2H), 1.27-1.17 (m, 6H), 0.77-0.68 (m, 3H). |
| 737 | | Cl | | H | $^1$H NMR (500 MHz, Deuterium Oxide) δ 8.35 (d, J = 7.0 Hz, 1H), 8.15 (s, 1H), 8.06 (d, J = 8.0 Hz, 1H), 7.94 (d, J = 8.0 Hz, 1H), 7.79-7.68 (m, 1H), 6.89 (d, J = 7.0 Hz, 1H), 3.14 (s, 3H), 2.16 (s, 3H). |

TABLE 1-continued

Structures and $^1$H NMR data of compounds

| NO. | Q | X | Y | Z | $^1$HNMR |
|---|---|---|---|---|---|
| 738 | pyrazole-ONa structure | Cl | thiophene | H | $^1$H NMR (500 MHz, DMSO-d$_6$) δ 8.88 (d, J = 7.0 Hz, 1H), 7.75-7.63 (m, 2H), 7.24-7.21(m, 1H), 6.78 (d, J = 7.0 Hz, 1H), 3.18(s, 3H), 2.18(s, 3H) |
| 739 | ONa-naphthalenone structure | Cl | pyrrolidine | H | $^1$H NMR (500 MHz, Deuterium Oxide) δ 8.35 (d, J = 7.0 Hz, 1H), 7.94 (d, J = 8.0 Hz, 1H), 7.57-7.51(m, 2H), 7.38-7.35 (m, 1H), 6.94-6.90 (m, 1H), 3.45-3.40 (m, 4H), 1.41 (s, 6H), 1.22-1.11 (m, 4H). |
| 740 | ONa-cyclohexenone structure | H | CH$_3$ | H | $^1$H NMR (500 MHz, Deuterium Oxide) δ 8.09 (d, J = 7.0 Hz, 1H), 7.86 (s, 1H), 7.13 (d, J = 7.0 Hz, 1H), 2.66 (s, 3H), 2.36 (t, J = 6.5 Hz, 4H), 1.98-1.89 (m, 2H). |
| 741 | ONa-cyclohexenone structure | cyclopropyl | cyclopropyl | H | $^1$H NMR (500 MHz, DMSO-d$_6$) δ 8.13 (d, J = 7.0 Hz, 1H), 6.92 (d, J = 7.0 Hz, 1H), 2.36-2.32 (m, 4H), 2.23-2.08 (m, 2H) 1.83-1.78 (m, 2H), 1.29-1.12 (m, 4H), 1.02-0.83 (m, 4H). |

TABLE 1-continued

Structures and ¹H NMR data of compounds

| NO. | Q | X | Y | Z | ¹HNMR |
|---|---|---|---|---|---|
| 742 | ONa-cyclohexanedione | Cl | H | H | ¹H NMR (500 MHz, Deuterium Oxide) δ 9.10 (s, 1H), 8.29 (d, J = 7.0 Hz, 1H), 6.81 (d, J = 7.0 Hz, 1H), 2.35-2.30 (m, 4H), 1.87-1.81 (m, 2H). |
| 743 | ONa-cyclohexanedione | Cl | CF₃ | H | ¹H NMR (500 MHz, Deuterium Oxide) δ 8.29 (d, J = 7.0 Hz, 1H), 6.99 (d, J = 7.0 Hz, 1H), 2.38 (t, J = 6.5 Hz, 4H), 1.98-1.89 (m, 2H). |
| 744 | ONa-cyclohexanedione | Cl | CF₂CH₃ | H | ¹H NMR (500 MHz, Deuterium Oxide) δ 8.15 (d, J = 7.0 Hz, 1H), 6.80 (d, J = 7.0 Hz, 1H), 2.35, (t, J = 6.5 Hz, 4H), 1.87-1.81 (m, 2H), 1.60 (t, J = 7.5 Hz, 3H). |
| 745 | ONa-cyclohexanedione | Cl | C₂F₅ | H | ¹H NMR (500 MHz, Deuterium Oxide) δ 8.41 (d, J = 7.0 Hz, 1H), 7.01 (d, J = 7.0 Hz, 1H), 2.33 (t, J = 6.5 Hz, 4H), 1.87-1.79 (m, 2H). |

TABLE 1-continued

Structures and $^1$H NMR data of compounds

| NO. | Q | X | Y | Z | $^1$HNMR |
|---|---|---|---|---|---|
| 746 | ONa, cyclohexanone | Cl | CH$_2$CH$_2$CF$_3$ branched | H | $^1$H NMR (500 MHz, Deuterium Oxide) δ 8.14 (d, J = 7.0 Hz, 1H), 6.84 (d, J = 7.0 Hz, 1H), 3.37 (t, J = 7.0 Hz, 2H), 2.78-2.74 (m, 2H), 2.40-2.24 (m, 4H), 1.91-1.80 (m, 2H). |
| 747 | ONa, cyclohexanone | Cl | CH(CH$_2$Cl)CH$_2$CH$_2$Cl | H | $^1$H NMR (500 MHz, DMSO-d$_6$) δ 8.60 (d, J = 7.0 Hz, 1H), 6.66 (d, J = 7.0 Hz, 1H), 4.22-4.16 (m, 2H), 3.34 (m, 2H), 3.16-3.12 (m, 1H), 2.35-2.15 (m, 6H), 1.76-7.71(m, 2H) |
| 748 | ONa, cyclohexanone | Cl | C(=CH$_2$)CH$_2$CH$_2$Cl | H | $^1$H NMR (500 MHz, DMSO-d$_6$) δ 8.41 (d, J = 7.0 Hz, 1H), 6.87 (d, J = 7.0 Hz, 1H), 5.78-5.66 (m, 2H), 3.84-3.80 (m, 2H), 3.11-3.06 (m, 4H), 2.16-2.10 (m, 2H), 1.78-1.73(m, 2H). |
| 749 | ONa, cyclohexanone | Cl | fluorocyclopropyl-methyl | H | $^1$H NMR (500 MHz, DMSO-d$_6$) δ 8.38 (d, J = 7.0 Hz, 1H), 6.75 (d, J = 7.0 Hz, 1H), 2.16-2.14(m, 4H), 1.76-1.72 (m, 2H), 1.23-1.20(m, 4H). |

TABLE 1-continued

Structures and $^1$H NMR data of compounds

| NO. | Q | X | Y | Z | $^1$HNMR |
|---|---|---|---|---|---|
| 750 | ONa-cyclohexanone enolate | Cl | CH$_3$ | H | $^1$H NMR (500 MHz, Deuterium Oxide) δ 8.15 (d, J = 7.0 Hz, 1H), 7.01(d, J = 7.0 Hz, 1H), 2.66 (s, 3H), 2.36 (t, J = 6.5 Hz, 4H), 1.98-1.89 (m, 2H). |
| 751 | ONa-cyclohexanone enolate | Cl | CH$_2$CH$_3$ | H | $^1$H NMR (500 MHz, Deuterium Oxide) δ 8.23 (d, J = 7.0 Hz, 1H), 6.85 (d, J = 7.0 Hz, 1H), 3.25(q, J = 8.0 Hz, 2H), 2.36 (t, J = 6.5 Hz, 4H), 1.98-1.89 (m, 2H), 1.46 (t, J = 8.0 Hz, 3H). |
| 752 | ONa-cyclohexanone enolate | Cl | n-butyl | H | $^1$H NMR (500 MHz, Deuterium Oxide) δ 8.12 (d, J = 7.0 Hz, 1H), 6.80 (d, J = 7.0 Hz, 1H), 3.01 (t, J = 7.5 Hz, 2H), 2.38-2.30 (m, 4H), 1.88-1.75 (m, 4H), 0.88 (t, J = 8.0 Hz, 3H). |
| 753 | ONa-cyclohexanone enolate | Cl | isobutyl | H | $^1$H NMR (500 MHz, Deuterium Oxide) δ 8.14 (d, J = 7.0 Hz, 1H), 6.78 (d, J = 7.0 Hz, 1H), 3.45-3.38 (m, 1H), 2.33-2.28 (m, 4H), 1.85-1.79 (m, 2H), 1.34 (d, J = 7.0 Hz, 6H). |

TABLE 1-continued

Structures and ¹H NMR data of compounds

| NO. | Q | X | Y | Z | ¹HNMR |
|---|---|---|---|---|---|
| 754 | ONa, cyclohexanone enolate | Cl | n-pentyl with gem-dimethyl | H | ¹H NMR (500 MHz, Deuterium Oxide) δ 8.13 (d, J = 7.0 Hz, 1H), 6.81 (d, J = 7.0 Hz, 1H), 3.06 (t, J = 7.5 Hz, 2H), 2.34 (t, J = 6.5 Hz, 4H), 1.86-1.82 (m, 2H), 1.77-1.74 (m, 2H), 1.21-1.18 (m, 2H), 0.84 (t, J = 7.5 Hz, 3H). |
| 755 | ONa, cyclohexanone enolate | Cl | isobutyl branched | H | ¹H NMR (500 MHz, Deuterium Oxide) δ 8.16 (d, J = 7.0 Hz, 1H), 6.81 (d, J = 7.5 Hz, 2H), 2.96 (d, J = 7.5 Hz, 2H), 2.35-2.33 (m, 4H), 2.18-2.11 (m, 1H), 1.87-1.82 (m, 2H), 0.90 (d, J = 6.5 Hz, 6H). |
| 756 | ONa, cyclohexanone enolate | Cl | tert-butyl | H | ¹H NMR (500 MHz, Deuterium Oxide) δ 8.11 (d, J = 7.0 Hz, 1H), 7.05 (d, J = 7.0 Hz, 1H), 2.36 (t, J = 6.5 Hz, 4H), 1.98-1.89 (m, 2H), 1.48(s, 9H). |
| 757 | ONa, cyclohexanone enolate | Cl | gem-dimethyl hexyl | H | ¹H NMR (500 MHz, Deuterium Oxide) δ 8.14 (d, J = 7.0 Hz, 1H), 6.82 (d, J = 7.0 Hz, 1H), 3.06 (t, J = 7.5 Hz, 2H), 2.36-2.33 (m, 4H), 1.86-1.84 (m, 2H), 1.27-1.25 (m, 6H), 0.79 (t, J = 7.0 Hz, 3H). |

TABLE 1-continued

Structures and ¹H NMR data of compounds

| NO. | Q | X | Y | Z | ¹HNMR |
|---|---|---|---|---|---|
| 758 | ONa-cyclohexanone | Cl | neopentyl-like | H | ¹H NMR (500 MHz, Deuterium Oxide) δ 8.09 (d, J = 7.0 Hz, 1H), 6.92 (d, J = 7.0 Hz, 1H), 2.36 (t, J = 6.5 Hz, 4H), 1.98-1.89 (m, 2H), 1.65 (q, J = 8.0 Hz, 2H), 1.49(s, 6H), 0.86 (t, J = 8.0 Hz, 3H). |
| 759 | ONa-cyclohexanone | Cl | sec-butyl branched | H | ¹H NMR (500 MHz, Deuterium Oxide) δ 8.15 (d, J = 7.0 Hz, 1H), 6.81 (d, J = 7.0 Hz, 1H), 3.10-3.05 (m, 1H), 2.92-2.88 (m, 1H), 2.35 (t, J = 6.5 Hz, 4H), 1.97-1.82 (m, 3H), 1.40-1.18(m, 2H), 0.88-0.80 (m, 6H). |
| 760 | ONa-cyclohexanone | Cl | dimethylcyclopropyl | H | ¹H NMR (500 MHz, Deuterium Oxide) δ 8.21 (d, J = 7.0 Hz, 1H), 6.78 (d, J = 7.0 Hz, 1H), 3.53 (q, J = 7.0 Hz, 1H), 2.31 (t, J = 6.5 Hz, 4H), 1.89-1.78 (m, 2H), 1.36-1.31 (m, 1H), 1.17 (d, J = 6.0 Hz, 3H), 1.08-0.91 (m, 2H). |
| 761 | ONa-cyclohexanone | Cl | cyclopropylmethyl branched | H | ¹H NMR (500 MHz, Deuterium Oxide) δ 8.15 (d, J = 7.0 Hz, 1H), 6.83 (d, J = 7.0 Hz, 1H), 2.75 (d, J = 7.0 Hz, 2H), 2.37-2.35 (m, 4H), 1.85-1.83 (m, 2H), 1.02-0.98(m, 1H), 0.44-0.41 (m, 4H). |

TABLE 1-continued

Structures and ¹H NMR data of compounds

| NO. | Q | X | Y | Z | ¹HNMR |
|---|---|---|---|---|---|
| 762 | ONa, cyclohexenone-O-Na | Cl | cyclohexyl | H | ¹H NMR (500 MHz, Deuterium Oxide) δ 8.17 (d, J = 7.0 Hz, 1H), 6.79 (d, J = 7.0 Hz, 1H), 3.15-3.09 (m, 1H), 2.34 (t, J = 6.5 Hz, 4H), 1.99-1.93(m, 3H), 1.88-1.75 (m, 4H), 1.62-1.50 (m, 2H), 1.40-1.35(m, 2H), 1.26-1.21(m, 1H). |
| 763 | ONa, cyclohexenone-O-Na | Cl | tetrahydropyran-4-yl | H | ¹H NMR (500 MHz, Deuterium Oxide) δ 8.13 (d, J = 7.0 Hz, 1H), 6.81(d, J = 7.0 Hz, 1H), 3.92-3.74 (m, 4H), 3.12-3.06 (m, 1H), 2.34 (t, J = 6.5 Hz, 4H), 1.98-1.93(m, 2H), 1.88-1.75 (m, 4H). |
| 764 | ONa, cyclohexenone-O-Na | Cl | 2-methoxypropan-2-yl | H | ¹H NMR (500 MHz, Deuterium Oxide) δ 8.16 (d, J = 7.0 Hz, 1H), 6.85 (d, J = 7.0 Hz, 1H), 3.85 (s, 3H), 2.36-2.34 (m, 4H), 1.84-1.82 (m, 2H). |
| 765 | ONa, cyclohexenone-O-Na | Cl | methoxymethyl-t-Bu | H | ¹H NMR (500 MHz, DMSO-d6) δ 8.22 (d, J = 7.0 Hz, 1H), 6.72 (d, J = 7.0 Hz, 1H), 4.94 (s, 2H), 3.32 (s, 3H), 2.36 (t, J = 6.5 Hz, 4H), 1.98-1.89(m, 2H). |

TABLE 1-continued

Structures and $^1$H NMR data of compounds

| NO. | Q | X | Y | Z | $^1$HNMR |
|---|---|---|---|---|---|
| 766 | ONa, cyclohexanone | Cl | ethoxy-dimethyl | H | $^1$H NMR (500 MHz, Deuterium Oxide) δ 8.27 (d, J = 7.0 Hz, 1H), 6.89 (d, J = 7.0 Hz, 1H), 5.03 (s, 2H), 3.58 (d, J = 7.0 Hz, 2H), 2.36-2.34 (m, 4H), 1.92-1.80 (m, 2H), 1.12 (t, J = 7.0 Hz, 3H). |
| 767 | ONa, cyclohexanone | Cl | methoxyethyl-methyl | H | $^1$H NMR (500 MHz, Deuterium Oxide) δ 8.18 (d, J = 7.0 Hz, 1H), 6.84 (d, J = 7.0 Hz, 1H), 3.90 (t, J = 6.0 Hz, 2H), 3.36 (t, J = 6.0 Hz, 2H), 3.29 (s, 3H), 2.35 (t, J = 6.5 Hz, 4H), 1.88-1.83 (m, 2H). |
| 768 | ONa, cyclohexanone | Cl | methylthio-dimethyl | H | $^1$H NMR (500 MHz, Deuterium Oxide) δ 8.18 (d, J = 7.0 Hz, 1H), 6.88 (d, J = 7.0 Hz, 1H), 2.56 (s, 3H), 2.34 (t, J = 6.5 Hz, 4H), 1.87-1.82 (m, 2H). |
| 769 | ONa, cyclohexanone | Cl | methylthiomethyl-methyl | H | $^1$H NMR (500 MHz, Deuterium Oxide) δ 8.18 (d, J = 7.0 Hz, 1H), 6.88 (d, J = 7.0 Hz, 1H), 3.70 (s, 2H), 2.56 (s, 3H), 2.34 (t, J = 6.5 Hz, 4H), 1.87-1.82 (m, 2H). |

TABLE 1-continued

Structures and ¹H NMR data of compounds

| NO. | Q | X | Y | Z | ¹HNMR |
|---|---|---|---|---|---|
| 770 | ONa, cyclohexanone enolate | Cl | 2-fluorophenyl | H | ¹H NMR (500 MHz, Deuterium Oxide) δ 8.08 (d, J = 7.0 Hz, 1H), 7.68-7.61 (m, 2H), 7.40-7.33 (m, 2H), 6.86 (d, J = 7.0 Hz, 1H), 2.36-2.33 (m, 4H), 1.86-1.82 (m, 2H). |
| 771 | ONa, cyclohexanone enolate | Cl | 4-fluorophenyl | H | ¹H NMR (500 MHz, Deuterium Oxide) δ 8.22 (d, J = 7.0 Hz, 1H), 7.82-7.62 (m, 2H), 7.32-7.21 (m, 2H), 6.81 (d, J = 7.0 Hz, 1H), 2.33 (t, J = 6.5 Hz, 4H), 1.84-1.82 (m, 2H). |
| 772 | ONa, cyclohexanone enolate | Cl | 3-cyanophenyl | H | ¹H NMR (500 MHz, Deuterium Oxide) δ 8.30 (d, J = 7.0 Hz, 1H), 8.15 (s, 1H), 8.05-7.94 (m, 2H), 7.78-7.72 (m, 1H), 6.89 (d, J = 7.0 Hz, 1H), 2.41-2.27 (m, 4H), 1.89-1.80 (m, 2H). |

TABLE 1-continued
Structures and $^1$H NMR data of compounds
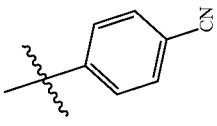
| NO. | Q | X | Y | Z | $^1$HNMR |
|---|---|---|---|---|---|
| 773 | 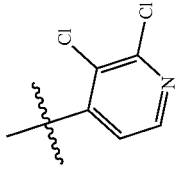 | Cl | 4-cyanophenyl | H | $^1$H NMR (500 MHz, Deuterium Oxide) δ 8.41 (d, J = 7.0 Hz, 1H), 7.96-7.90 (m, 4H), 6.91 (d, J = 7.0 Hz, 1H), 2.32-2.28 (m, 4H), 1.86-1.81 (m, 2H). |
| 774 | | Cl | 2,3-dichloropyridin-4-yl | H | $^1$H NMR (500 MHz, DMSO-$d_6$) δ 8.49 (d, J = 5.0 Hz, 1H), 8.19 (d, J = 7.0 Hz, 1H), 7.72 (d, J = 5.0 Hz, 1H), 6.95 (d, J = 7.0 Hz, 1H), 2.35-2.32 (m, 4H), 1.83-1.77 (m, 2H). |
| 775 | | Cl | pyrazin-2-yl | H | $^1$H NMR (500 MHz, DMSO-$d_6$) δ 9.02 (s, 1H), 8.79-8.72 (m, 2H), 8.08 (d, J = 7.0 Hz, 1H), 6.90 (d, J = 7.0 Hz, 1H), 2.36-2.32 (m, 4H), 1.82-1.78 (m, 2H). |
| 776 | | Cl | furan-2-yl | H | $^1$H NMR (500 MHz, DMSO-$d_6$) δ 8.19-8.15 (m, 2H), 7.10-6.92 (m, 2H), 6.71 (d, J = 5.0 Hz, 1H), 2.39-2.36 (m, 4H), 1.79-1.76 (m, 2H). |

TABLE 1-continued

Structures and ¹H NMR data of compounds

| NO. | Q | X | Y | Z | ¹HNMR |
|---|---|---|---|---|---|
| 777 | ONa, cyclohexenone | Cl | thiophen-2-yl | H | ¹H NMR (500 MHz, DMSO-d₆) δ 8.21 (d, J = 7.0 Hz, 1H), 7.75-7.63 (m, 2H), 7.24 (m, 1H), 6.93 (d, J = 7.0 Hz, 1H), 2.36-2.32 (m, 4H), 1.88-1.85 (m, 2H). |
| 778 | ONa, cyclohexenone | Cl | 1-methyl-1H-pyrazol-4-yl | H | ¹H NMR (500 MHz, DMSO-d₆) δ 8.22 (d, J = 7.0 Hz, 1H), 7.75-7.63 (m, 2H), 6.99 (d, J = 7.0 Hz, 1H), 3.96 (s, 3H), 2.37-2.33 (m, 4H), 1.83-1.78 (m, 2H). |
| 779 | ONa, cyclohexenone | Cl | 1-methyl-1H-pyrazol-5-yl | H | ¹H NMR (500 MHz, DMSO-d₆) δ 8.12 (d, J = 7.0 Hz, 1H), 7.24-7.21 (m, 1H), 6.89 (d, J = 7.0 Hz, 1H), 6.65 (d, J = 5.0 Hz, 1H), 3.92 (s, 3H), 2.33-2.30 (m, 4H), 1.83-1.77 (m, 2H). |
| 780 | ONa, cyclohexenone | Cl | 1-methyl-1H-pyrazol-3-yl | H | ¹H NMR (500 MHz, DMSO-d₆) δ 8.14 (d, J = 7.0 Hz, 1H), 7.64-7.62 (m, 1H), 6.92 (d, J = 7.0 Hz, 1H), 6.61 (d, J = 5.0 Hz, 1H), 3.94 (s, 3H), 2.34-2.30 (m, 4H), 1.79-1.76 (m, 2H). |

TABLE 1-continued

Structures and $^1$H NMR data of compounds

| NO. | Q | X | Y | Z | $^1$HNMR |
|---|---|---|---|---|---|
| 781 | ONa-cyclohexenone | Cl | 1H-triazolyl | H | $^1$H NMR (500 MHz, DMSO-d$_6$) δ 8.29 (s, 1H), 8.14 (d, J = 7.0 Hz, 1H), 6.91 (d, J = 7.0 Hz, 1H), 2.38-2.34(m, 4H), 1.87-1.82 (m, 2H). |
| 782 | ONa-cyclohexenone | Cl | naphthyl | H | $^1$H NMR (500 MHz, DMSO-d$_6$) δ 8.39 (s, 1H), 8.29-8.02 (m, 5H), 7.78-7.65 (m, 2H), 6.91 (d, J = 7.0 Hz, 1H), 2.36-2.32 (m, 4H), 1.86-1.81 (m, 2H). |
| 783 | ONa-cyclohexenone | Cl | isoquinolinyl | H | $^1$H NMR (500 MHz, DMSO-d$_6$) δ 8.86-8.74 (m, 2H), 8.17 (d, J = 7.0 Hz, 1H), 7.98-7.75 (m, 4H), 6.95 (d, J = 7.0 Hz, 1H), 2.38-2.34 (m, 4H), 1.82-1.78 (m, 2H). |
| 784 | ONa-cyclohexenone | S-iPr | isobutyl | H | $^1$H NMR (500 MHz, DMSO-d$_6$) δ 8.18 (d, J = 7.0 Hz, 1H), 7.01 (d, J = 7.0 Hz, 1H), 2.92-2.86 (m, 4H), 2.36-2.32 (m, 4H), 1.87-1.82 (m, 2H), 1.26 (d, J = 7.5 Hz, 6H) |

TABLE 1-continued

Structures and ¹H NMR data of compounds

| NO. | Q | X | Y | Z | ¹HNMR |
|---|---|---|---|---|---|
| 785 | ONa, cyclohexanone-enolate | S(=O)CH₃ | isobutyl | H | ¹H NMR (500 MHz, DMSO-d₆) δ 8.21 (d, J = 7.0 Hz, 1H), 7.02 (d, J = 7.0 Hz, 1H), 3.12-2.99 (m, 4H), 2.35-2.31 (m, 4H), 1.85-1.80 (m, 2H), 1.26 (d, J = 7.5 Hz, 6H) |
| 786 | ONa, cyclohexanone-enolate | Cl | CH₂OC(=O)CH₃ | H | ¹H NMR (500 MHz, DMSO) δ 8.16 (d, J = 7.0 Hz, 1H), 6.93(d, J = 7.0 Hz, 1H), 5.75 (s, 2H), 2.71-2.63 (m, 4H), 2.10 (s, 3H), 1.67-1.54 (m, 2H). |
| 787 | ONa, cyclohexanone-enolate | Cl | CH₂Cl | H | ¹H NMR (500 MHz, Deuterium Oxide) δ 8.13 (d, J = 7.0 Hz, 1H), 6.82 (d, J = 7.0 Hz, 1H), 4.26 (s, 2H), 3.38(s, 1H) 2.37-2.35 (m, 4H), 1.85-1.83 (m, 2H). |
| 788 | ONa, bicyclic diketone | H | CH₃ | H | ¹H NMR (500 MHz, Deuterium Oxide) δ 8.12 (d, J = 7.0 Hz, 1H), 7.86 (s, 1H), 6.81 (d, J = 7.0 Hz, 1H), 2.70 (s, 3H), 2.10-2.03 (m, 4H), 1.72-1.69 (m, 2H), 1.59-1.56 (m, 2H). |

TABLE 1-continued

Structures and $^1$H NMR data of compounds

| NO. | Q | X | Y | Z | $^1$HNMR |
|---|---|---|---|---|---|
| 789 | (ONa-substituted bicyclic ketone) | Cl | (sec-butyl-methyl branched) | H | $^1$H NMR (500 MHz, Deuterium Oxide) δ 8.12 (d, J = 7.0 Hz, 1H), 6.81 (d, J = 7.0 Hz, 1H), 3.06-2.99 (m, 1H), 2.20-2.14 (m, 2H), 2.10-2.03 (m, 4H), 1.72-1.69 (m, 2H), 1.59-1.56 (m, 2H), 1.50-1.40 (m, 2H), 1.37-1.35 (m, 3H), 0.87 (t, J = 8.0 Hz, 3H). |
| 790 | (ONa-substituted bicyclic ketone) | Cl | (tert-butyl-methyl branched) | H | $^1$H NMR (500 MHz, Deuterium Oxide) δ 8.39 (d, J = 7.0 Hz, 1H), 6.72 (d, J = 7.0 Hz, 1H), 2.06-2.01 (m, 4H), 1.82-1.77 (m, 2H), 1.65-1.59 (m, 2H), 1.58-1.55 (m, 2H), 1.20 (s, 6H), 0.85 (t, J = 7.0 Hz, 3H). |
| 791 | (ONa-substituted bicyclic ketone) | Cl | (cyclopropyl) | H | $^1$H NMR (500 MHz, Deuterium Oxide) δ 8.28 (d, J = 6.5 Hz, 1H), 6.92 (d, J = 6.5 Hz, 1H), 2.22-2.16 (m, 3H), 2.10-2.03 (m, 4H), 1.72-1.69 (m, 2H), 1.19-1.10 (m, 2H), 0.96-0.92 (m, 2H). |
| 792 | (ONa-substituted bicyclic ketone) | Cl | (dimethylcyclopropyl) | H | $^1$H NMR (500 MHz, Deuterium Oxide) δ 8.12 (d, J = 7.0 Hz, 1H), 6.78 (d, J = 7.0 Hz, 1H), 3.01-2.98 (m, 2H), 2.64-2.62 (m, 1H), 2.03-1.98 (m, 4H), 1.83-1.78 (m, 2H), 1.22-1.16 (m, 1H), 1.02-0.98 (m, 1H), 0.89 (s, 6H). |

TABLE 1-continued

Structures and $^1$H NMR data of compounds

| NO. | Q | X | Y | Z | $^1$HNMR |
|---|---|---|---|---|---|
| 793 | | Cl | cyclohexyl | H | $^1$H NMR (500 MHz, Deuterium Oxide) δ 8.17 (d, J = 7.0 Hz, 1H), 6.73 (d, J = 7.0 Hz, 1H), 2.59-2.49 (m, 1H), 2.06-2.01 (m, 4H), 1.80-1.72 (m, 2H), 1.65-1.59 (m, 2H), 1.20-1.08 (m, 10H). |
| 794 | | Cl | cyclopentenyl | H | $^1$H NMR (500 MHz, DMSO-d$_6$) δ 8.22 (d, 7.0 Hz, 1H), 6.98 (d, 7.0 Hz, 1H), 5.96-5.92 (m, 1H), 2.36-2.22 (m, 4H), 1.96-1.84 (m, 6H), 1.68-1.62 (m, 2H), 1.48-1.42 (m, 2H). |
| 795 | | Cl | 3-thienyl | H | $^1$H NMR (500 MHz, DMSO-d$_6$) δ 8.88 (d, J = 7.0 Hz, 1H), 7.98 (s, 1H), 7.90 (d, J = 5.0 Hz, 1H), 7.89 (d, J = 5.0 Hz, 1H), 6.81 (d, J = 7.0 Hz, 1H), 2.00-1.84 (m, 4H), 1.67-1.62 (m, 2H), 1.45-1.41 (m, 2H). |
| 796 | | Cl | 2-thienyl | H | $^1$H NMR (500 MHz, DMSO-d6) δ 8.88 (d, J = 7.0 Hz, 1H), 7.75-7.63 (m, 2H), 7.24 (m, 1H), 6.88 (d, J = 7.0 Hz, 1H), 2.00-1.85 (m, 4H), 1.68-1.62 (m, 2H), 1.47-1.42 (m, 2H). |

TABLE 1-continued

Structures and ¹H NMR data of compounds

| NO. | Q | X | Y | Z | ¹HNMR |
|---|---|---|---|---|---|
| 797 | (cyclohexanone with ONa substituent) | Cl | (isoxazole) | H | ¹H NMR (500 MHz, DMSO-d₆) δ 8.88 (d, J = 7.0 Hz, 1H), 8.34 (d, J = 5.0 Hz, 1H), 7.78 (d, J = 5.0 Hz, 1H), 6.78 (d, J = 7.0 Hz, 1H), 2.00-1.84 (m, 4H), 1.66-1.61 (m, 2H), 1.47-1.42 (m, 2H). |
| 798 | (pyrazole-ONa) | Cl | (CH₂CH₂CF₃) | H | ¹H NMR (500 MHz, Deuterium Oxide) δ 8.23 (d, J = 7.0 Hz, 1H), 6.88 (d, J = 7.0 Hz, 1H), 3.40 (t, J = 7.5 Hz, 2H), 3.17 (s, 3H), 2.86 (t, J = 1.5 Hz, 2H), 2.17 (s, 3H). |
| 799 | (pyrazole-ONa) | Cl | (butyl) | H | ¹H NMR (500 MHz, Deuterium Oxide) δ 8.24 (d, J = 7.0 Hz, 1H), 6.88 (d, J = 7.0 Hz, 1H), 3.26-2.79 (m, 5H), 2.15 (s, 3H), 1.74-1.66 (m, 2H), 0.90 (t, J = 8.0 Hz, 3H). |
| 800 | (pyrazole-ONa) | Cl | (methylpentyl) | H | ¹H NMR (500 MHz, Deuterium Oxide) δ 8.13 (d, J = 7.0 Hz, 1H), 6.74 (d, J = 7.0 Hz, 1H), 3.19 (s, 3H), 3.06-3.02 (m, 2H), 2.88-2.84 (m, 1H), 2.18 (s, 3H), 1.37-1.13 (m, 2H), 0.82-0.72 (m, 6H). |

TABLE 1-continued

Structures and $^1$H NMR data of compounds

| NO. | Q | X | Y | Z | $^1$HNMR |
|---|---|---|---|---|---|
| 801 | pyrazole-ONa | Cl | tert-pentyl | H | $^1$H NMR (500 MHz, Deuterium Oxide) δ 8.23 (d, J = 7.0 Hz, 1H), 6.83 (d, J = 7.0 Hz, 1H), 3.17 (s, 3H), 1.76 (s, 3H), 1.39 (s, 6H), 1.25-1.17 (m, 2H), 0.79-0.75 (m, 3H). |
| 802 | pyrazole-ONa | Cl | long alkyl | H | $^1$H NMR (500 MHz, Deuterium Oxide) δ 8.15 (d, J = 7.0 Hz, 1H), 6.88 (d, J = 7.0 Hz, 1H), 3.15 (s, 3H), 3.08-3.01 (m, 2H), 1.88 (s, 3H), 1.78-1.71 (m, 2H), 1.27-1.17 (m, 8H), 0.77-0.68 (m, 3H). |
| 803 | pyrazole-ONa | Cl | CH(CH$_3$)OCH$_3$ | H | $^1$H NMR (500 MHz, Deuterium Oxide) δ 7.81 (d, J = 7.0 Hz, 1H), 6.57 (d, J = 7.0 Hz, 1H), 3.62 (s, 3H), 3.18 (s, 3H), 2.17 (s, 3H). |
| 804 | pyrazole-ONa | Cl | CH(CH$_3$)OCH$_2$CH$_3$ | H | $^1$H NMR (500 MHz, Deuterium Oxide) δ 8.35 (d, J = 7.0 Hz, 1H), 6.92 (d, J = 7.0 Hz, 1H), 5.06 (s, 2H), 3.59 (q, J = 7.0 Hz, 2H), 3.17 (s, 3H), 2.18 (s, 3H), 1.20-1.05 (t, J = 7.0 Hz, 3H). |

TABLE 1-continued

Structures and ¹H NMR data of compounds

| NO. | Q | X | Y | Z | ¹HNMR |
|---|---|---|---|---|---|
| 805 | pyrazole-ONa | Cl | 4-cyanophenyl | H | ¹H NMR (500 MHz, Deuterium Oxide) δ 8.40 (d, J = 7.0 Hz, 1H), 7.94-7.90 (m, 4H), 6.90 (t, J = 7.0 Hz, 1H), 3.16 (s, 3H), 2.18 (s, 3H). |
| 806 | pyrazole-ONa | Cl | pyrazinyl | H | ¹H NMR (500 MHz, Deuterium Oxide) δ 9.02 (s, 1H), 8.79-8.72 (m, 2H), 8.25 (d, J = 7.0 Hz, 1H), 6.85 (d, J = 7.0 Hz, 1H), 3.18 (s, 3H), 2.17 (s, 3H). |
| 807 | pyrazole-ONa | Cl | 2-furyl | H | ¹H NMR (500 MHz, DMSO-d₆) δ 8.19-8.15 (m, 2H), 7.10-6.92 (m, 2H), 6.71 (d, 5.0 Hz, 1H), 3.18 (s, 3H), 2.17 (s, 3H). |
| 808 | pyrazole-ONa | Cl | 3-thienyl | H | ¹H NMR (500 MHz, DMSO-d₆) δ 8.21 (d, J = 7.0 Hz, 1H), 7.75-7.63 (m, 2H), 7.24 (m, 1H), 6.78 (d, J = 7.0 Hz, 1H), 3.18 (s, 3H), 2.17 (s, 3H). |

TABLE 1-continued

Structures and $^1$H NMR data of compounds

| NO. | Q | X | Y | Z | $^1$HNMR |
|---|---|---|---|---|---|
| 809 | 3,5-dimethyl-1H-pyrazol-4-yl with ONa | Cl | 1-methyl-1H-pyrazol-4-yl | H | $^1$H NMR (500 MHz, DMSO-d$_6$) δ 8.10(d, J = 7.0 Hz, 1H), 7.75-7.63 (m, 2H), 6.92 (d, J = 7.0 Hz, 1H), 3.96 (s, 3H), 3.18 (s, 3H), 2.17 (s, 3H). |
| 810 | 3,5-dimethyl-1H-pyrazol-4-yl with ONa | Cl | 1-methyl-1H-pyrazol-3-yl | H | $^1$H NMR (500 MHz, DMSO-d$_6$) δ 8.15(d, J = 7.0 Hz, 1H), 7.24 (m, 1H), 6.94 (d, J = 7.0 Hz, 1H), 6.65 (d, J = 5.0 Hz, 1H), 3.92 (s, 3H), 3.18 (s, 3H), 2.17 (s, 3H). |
| 811 | 3,5-dimethyl-1H-pyrazol-4-yl with ONa | Cl | 1-methyl-1H-pyrazol-5-yl | H | $^1$H NMR (500 MHz, DMSO-d$_6$) δ 8.20 (d, J = 7.0 Hz, 1H), 7.24-7.21 (m, 1H), 6.94 (d, J = 7.0 Hz, 1H), 3.92 (s, 3H), 3.18 (s, 3H), 2.17 (s, 3H). |
| 812 | 3,5-dimethyl-1H-pyrazol-4-yl with ONa | Cl | 2,3-dichloropyridin-4-yl | H | $^1$H NMR (500 MHz, DMSO-d$_6$) δ 8.49 (d, J = 5.0 Hz, 1H), 8.19 (d, J = 7.0 Hz, 1H), 7.72 (d, J = 5.0 Hz, 1H), 6.93 (d, J = 7.0 Hz, 1H), 3.18 (s, 3H), 2.17 (s, 3H). |

TABLE 1-continued

Structures and ¹H NMR data of compounds

| NO. | Q | X | Y | Z | ¹HNMR |
|---|---|---|---|---|---|
| 813 | (1-methyl-4-methyl-pyrazol-3-yl ONa) | H | CH₃ | H | ¹H NMR (500 MHz, Deuterium Oxide) δ 8.06 (d, J = 7.0 Hz, 1H), 7.71 (s, 1H),7.36 (s, 1H), 7.03 (d, J = 7.0 Hz, 1H), 3.25 (s, 3H), 2.61 (s, 3H). |
| 814 | (1-methyl-4-methyl-3-cyclopropyl-pyrazol-ONa) | Cl | cyclopropyl | H | ¹H NMR (500 MHz, Deuterium Oxide) δ 8.30 (d, J = 7.0 Hz, 1H), 6.95 (d, J = 7.0 Hz, 1H), 3.63 (s, 3H), 2.67-2.64 (m, 1H), 2.18-2.15 (m, 1H), 1.13-1.08 (m, 2H), 1.04-0.93 (m, 2H), 0.90-0.82 (m, 4H). |
| 815 | (1,3-dimethylpyrazole-4-carboxylate ester of 1,4-dimethylpyrazol-5-yl) | Cl | cyclopropyl | H | ¹H NMR (500 MHz, DMSO-d₆) δ 8.46 (d, J = 7.0 Hz, 1H), 8.05 (s, 1H), 7.95 (s, 1H), 6.89 (d, J = 7.0 Hz, 1H), 3.67 (s, 3H), 3.63 (s, 3H), 2.25-2.21 (m, 1H), 2.15 (s, 3H), 1.12-1.08 (m, 2H), 1.02-0.99 (m, 2H). |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Examples of representative compounds are as follows, the synthesis methods of other compounds are similar, and will not be described in detail here.

1. Synthesis of Compound 2

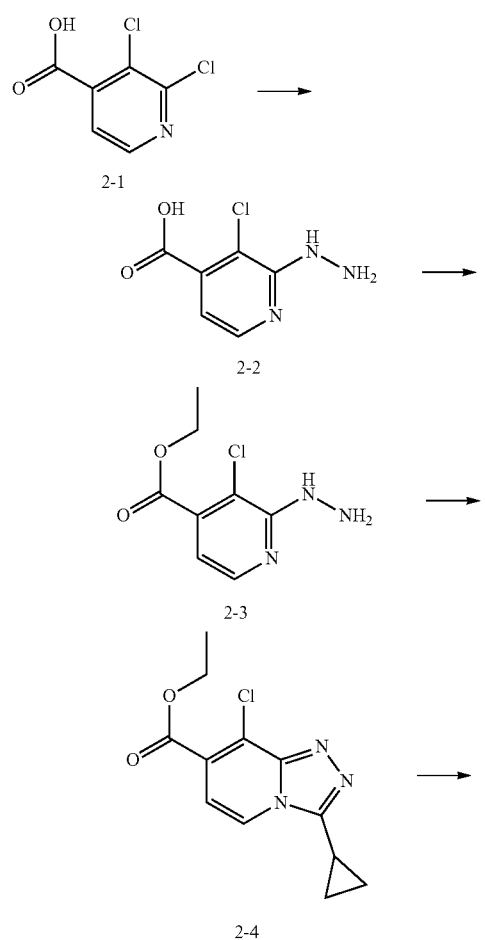

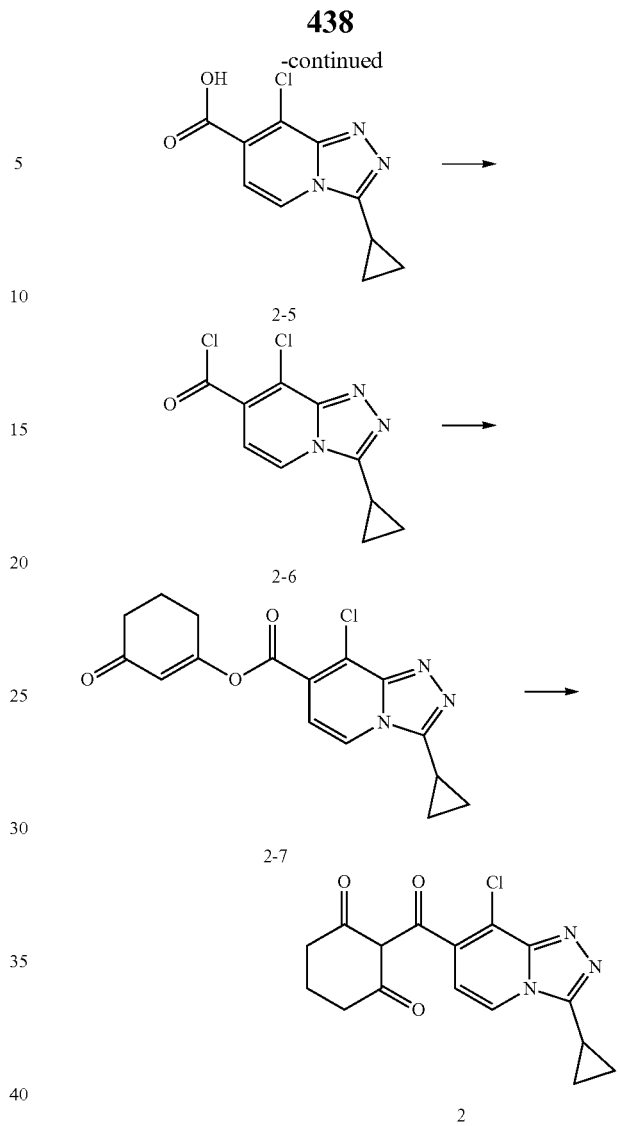

A reactor was charged with 100 g (1.0 eq) of compound 2-1, 1 L of hydrazine hydrate (80%, 10V) was added, and then heated to 100° C. and allowed to react for 20 hours. Upon completion of the reaction, the hydrazine hydrate was removed under vacuum to obtain a solid, the solid was purified by beating with ethanol to obtain the product 2-2 with yield of 98%.

To 1 L of ethanol was added the obtained product 2-2, followed by the addition of a catalytic amount of concentrated sulfuric acid, and then heated to 80° C. and allowed to react for 18 hours. Upon the completion of the reaction, the insoluble matter was removed by filtration, the filter cake was washed with ethanol, and the ethanol phase was collected. After the ethanol was removed under vacuum, 1 L of ethyl acetate and 1 L of water were added to perform extraction and liquid separation, the aqueous phase was extracted once with 1 L of ethyl acetate, the organic phases were combined and washed once with sodium bicarbonate solution, and then washed once with saturated brine, and the organic phase was subjected to rotatory evaporation to remove ethyl acetate. After drying, product 2-3 was obtained with yield of 95%.

To a reactor were added the obtained product 2-3, then 10V of toluene as solvent, and

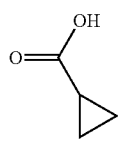

(1.1 eq). The reaction system was heated to 80° C. and added with phosphorus oxychloride (2.5 eq), and allowed to react for 10 hours, then heated to 100° C. and allowed to react for 1 hour. Upon the completion of the reaction, the reaction system was controlled to 20° C. and added into water; extraction and separation were performed, the toluene phase was collected, the aqueous phase was extracted twice with ethyl acetate (5V), and the organic phase was collected. After being washed with sodium bicarbonate solution (10V), the organic phase was removed under vacuum to obtain a solid product, then the product was purified by beating with isopropyl ether and filtered to obtain product 2-4 with yield of 92%.

The resultant product 2-4 was dissolved in 5V of dioxane and controlled to 20° C., followed by the addition of the prepared sodium hydroxide aqueous solution (1.2 eq of sodium hydroxide dissolved in 5V of water) in a dropwise manner, and then was allowed to react for 2 hours. Upon the completion of the reaction, dioxane was removed. pH was adjusted to 1 to 2 with 1M aqueous hydrochloric acid solution. The stirring was continued for 2 hours after the precipitation of the solid, then filtration was performed, the filter cake was washed once with water, and the solid was dried to obtain product 2-5 with yield of 92%.

To a reactor were added the obtained product 2-5 and 10V of dichloromethane, and 2.5 eq of thionyl chloride was added in a dropwise manner with stirring at a controlled temperature of 20° C., then allowed to react for 1 hour. Upon the completion of the reaction, dichloromethane and thionyl chloride were removed under vacuum, and then the residue was dissolved in 3V of dichloromethane for later use.

To a reactor were added 1,3-cyclohexanedione, 10V of dichloromethane, and 2.5 eq of triethylamine, and then the above obtained acyl chloride in dichloromethane solution was added in a dropwise manner at controlled temperature of 20° C., and allowed to react for 4 hours. Upon the completion of the reaction, dichloromethane and triethylamine were removed under vacuum to obtain crude product 2-7.

The crude product 2-7 was dissolved into 10V of acetonitrile, added with 3.0 eq of triethylamine, then a catalytic amount of acetone cyanohydrin was added under nitrogen protection, and allowed to react at 50° C. for 15 hours. Upon the completion of the reaction, the product was mixed with silica gel and purified by column chromatography to obtain the target product 2 with yield of 54%.

2. Synthesis of Compound 5

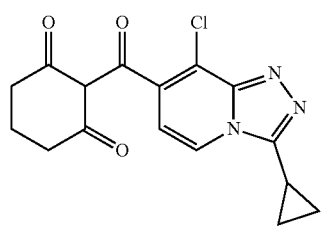

2

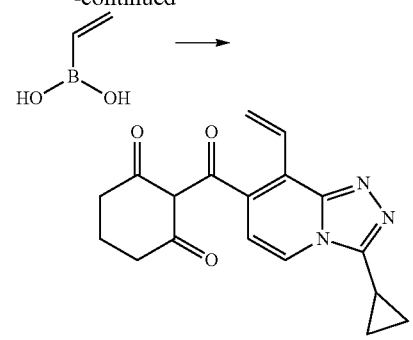

5

1 gram of compound 2 was dissolved in dioxane/water (10:1), added with 1.2 eq of vinyl boric acid, and 3.0 eq of potassium carbonate, followed by 1,1'-bis(diphenylphosphino)ferrocene palladium(II) dichloride dichloromethane complex as catalyst under the protection of nitrogen, then heated to 80° C. and reacted for 15 hours with stirring. Upon the completion of the reaction, the product was mixed with silica gel and purified by column chromatography to obtain product 5 with a yield of 78%.

3. Synthesis of Compounds 11 and 12

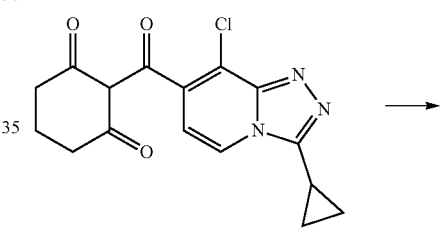

2

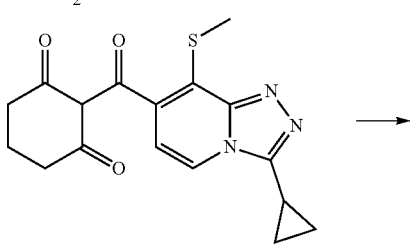

11

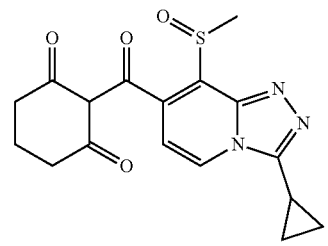

12

1 gram of compound 2 was dissolved in 10V of N,N-dimethylformamide, added with 8 eq of sodium methyl mercaptide aqueous solution, allowed to react at 90° C. for 3 hours. Upon the completion of the reaction, the reaction solution was diluted with water, and extracted with ethyl acetate, then the ethyl acetate phase was collected, and the product was mixed with silica gel and purified by column chromatography to obtain the target product 11 with yield of 56%.

The obtained product 11 was dissolved in dichloromethane, added with 1.0 eq of m-chloroperoxybenzoic acid, and allowed to react at room temperature for 1 hour. Upon the completion of the reaction, sodium bisulfite was added to quench the reaction, the product was mixed with silica gel and purified by column chromatography to obtain the target product 12 with yield of 52%.

4. Synthesis of Compound 38

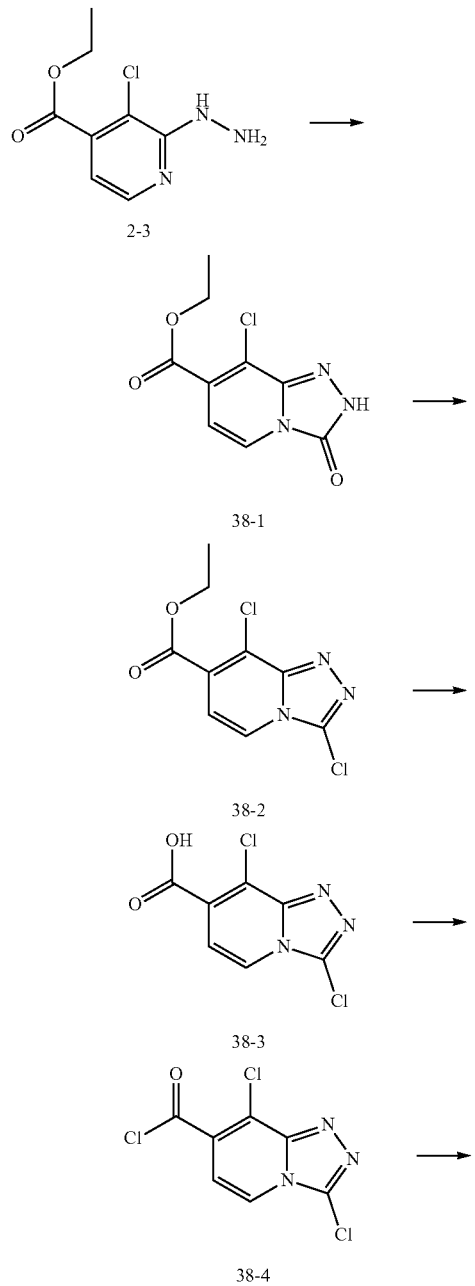

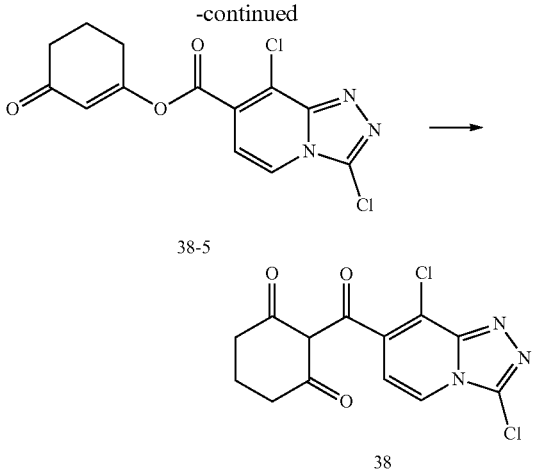

To a reactor was added compound 2-3, and 10V of DCM was added for dissolution, followed by the addition of 1.0 eq of N,N'-carbonyldiimidazole, and allowed to react at room temperature for 4 hours. Upon the completion of the reaction, pH was adjusted to 3~5. After being washed with water, the organic phase was subjected to rotatory evaporation and purified by beating with isopropyl ether to obtain product 38-1 with yield of 75%.

To a reactor were added the obtained product 38-1, 10V of 1,2 dichloroethane as a solvent, a catalytic amount of N,N-dimethylformamide, and 1.5 eq of phosphorus oxychloride, heated to 80° C., and allowed to react for 20 hours. Upon the completion of the reaction, the reaction solution was added into the aqueous phase in a dropwise manner, the organic phase was washed with sodium bicarbonate aqueous solution, the organic phase was subjected to rotatory evaporation and purified by beating with isopropyl ether to obtain product 38-2 with yield of 51%.

Compound 38-2 was dissolved in 5V of dioxane, and controlled to 15° C., the prepared sodium hydroxide aqueous solution (1.0 eq of sodium hydroxide dissolved in 5V of water) was added slowly to 38-2 in dioxane solution in a dropwise manner, and allowed to react for 0.5 hour. Upon the completion of the reaction, dioxane was removed, 1M aqueous hydrochloric acid solution was added to adjust the pH to 1 to 2. The stirring was continued for 1.5 hours after the precipitation of the solid, then filtration was performed, the filter cake was washed once with water, and the solid was dried to obtain product 38-3 with yield of 78%.

To a reactor were added compound 38-3 and 10V of dichloromethane, and 2.5 eq. of thionyl chloride was added in a dropwise manner with stirring at a controlled temperature of 15° C. and allowed to react for 1 hour. Upon the completion of the reaction, dichloromethane and thionyl chloride were removed under vacuum, then the residue was dissolved in 3V of dichloromethane for later use.

To a reactor were added 1,3-cyclohexanedionea, 10V of dichloromethane, and 2.5 eq of triethylamine, and then the above obtained acyl chloride in dichloromethane solution was added in a dropwise manner at a controlled temperature of 15° C., and allowed to react for 5 hours. Upon the completion of the reaction, dichloromethane and triethylamine were removed under vacuum to obtain crude product 38-5.

The crude product 38-5 was dissolved in 10V of acetonitrile, added with 3.0 eq of triethylamine, then a catalytic amount of acetone cyanohydrin was added under the protection of nitrogen, and allowed to react at 70° C. for 5 hours. Upon the completion of the reaction, the product was mixed with silica gel and purified by column chromatography to obtain the final product 38 with yield of 48%.

5. Synthesis of Compound 87

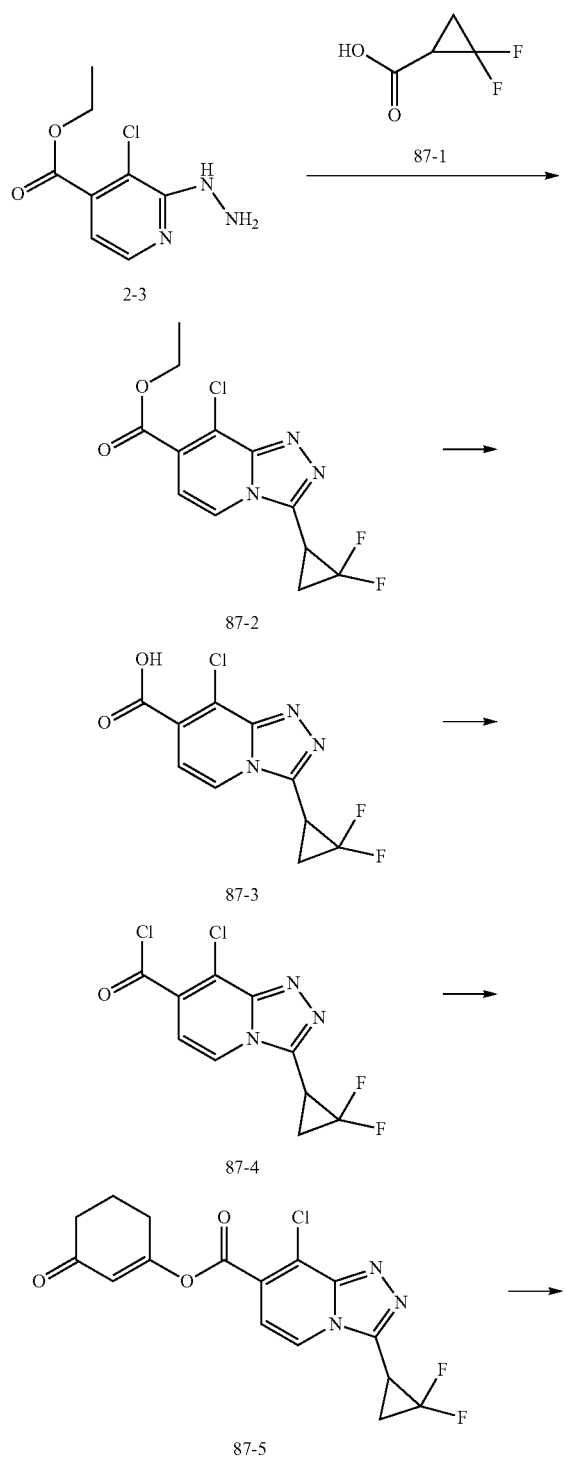

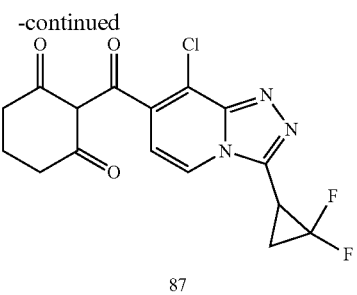

To a reactor were added compound 2-3, 10V of toluene as the solvent, and 87-1 (1.1 eq), the reaction system was heated to 80° C. and added with phosphorus oxychloride (2.5 eq), then allowed to react for 5 hours, then heated to 100° C. and allowed to react for 1 hour. Upon the completion of the reaction, the reaction system was controlled to 25° C., and added into water. Extraction and separation were performed, the toluene phase was collected. The aqueous phase was extracted twice with ethyl acetate (5V), and the organic phase was collected. After being washed with sodium bicarbonate solution (10V), the organic phase was removed under vacuum to obtain a solid product, then the product was purified by beating with isopropyl ether and filtered to obtain product 87-2 with yield of 75%.

The obtained product 87-2 was dissolved in 5V of dioxane and controlled to 25° C., followed by the addition of the prepared sodium hydroxide aqueous solution (1.2 eq of sodium hydroxide dissolved in 5V of water) in a dropwise manner, and then was allowed to react for 0.5 hour. Upon the completion of the reaction, dioxane was removed, pH was adjusted to 1 to 2 with 1M aqueous hydrochloric acid solution. The stirring was continued for 0.5 hour after the precipitation of the solid, then filtration was performed, the filter cake was washed once with water, and the solid was dried to obtain product 87-3 with yield of 82%.

To a reactor were added the obtained product 87-3 and 10V of dichloromethane, and 2.5 eq of thionyl chloride was added in a dropwise manner with stirring at a controlled temperature of 25° C., then allowed to react for 1 hour. Upon the completion of the reaction, dichloromethane and thionyl chloride were removed under vacuum, then the residue was dissolved in 3V of dichloromethane for later use.

To a reactor were added 1,3-cyclohexanedione, 10V of dichloromethane, and 2.5 eq of triethylamine, then the above obtained acyl chloride in dichloromethane solution was added in a dropwise manner at a controlled temperature of 25° C., and allowed to react for 3 hours. Upon the completion of the reaction, dichloromethane and triethylamine were removed under vacuum to obtain crude product 87-5.

The crude product 87-5 was dissolved into 10V of acetonitrile, added with 3.0 eq of triethylamine, then a catalytic amount of acetone cyanohydrin was added under nitrogen protection, and allowed to react at 20° C. for 24 hours. Upon the completion of the reaction, the product was mixed with silica gel and purified by column chromatography to obtain the target product 87 with yield of 42%.

6. Synthesis of Compound 114

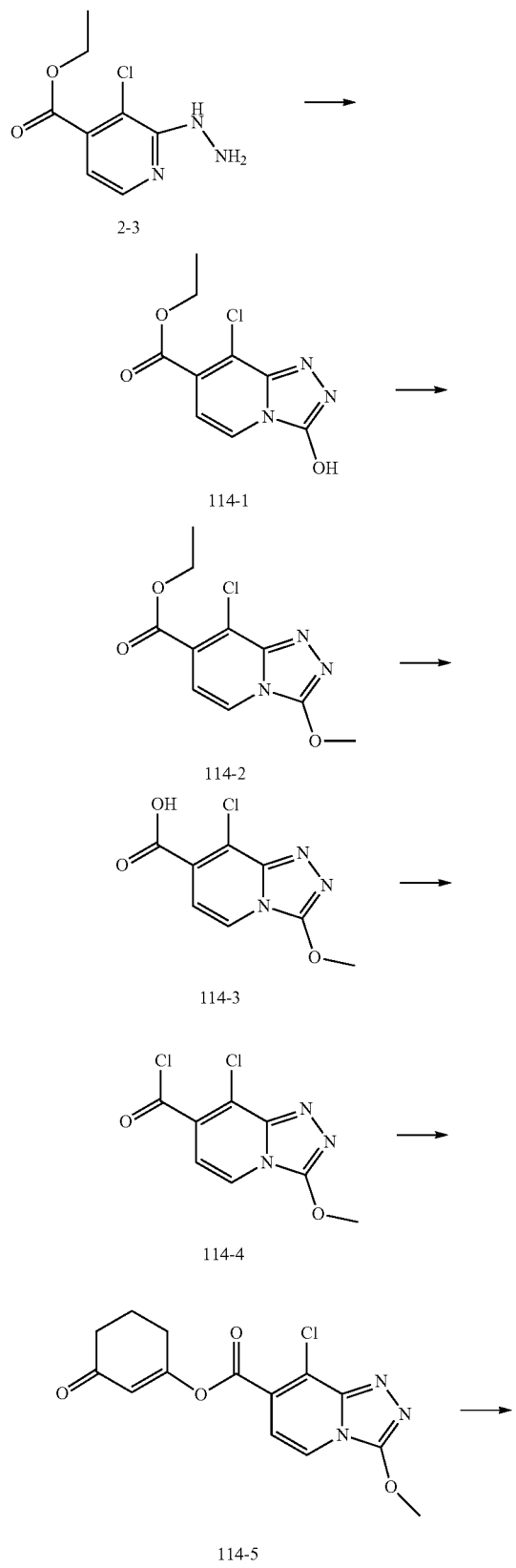

2-3

114-1

114-2

114-3

114-4

114-5

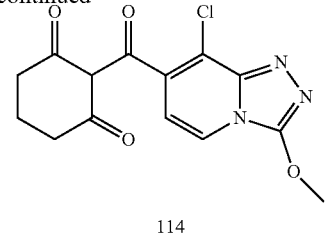

114

The product 2-3 was dissolved in 10 volumes of N,N-dimethylformamide, 1.2 equivalent of N,N-carbonyldiimidazole was added thereto, then heated to 80° C. and stirred for 3 hours. Upon the completion of the reaction, the reaction system was cooled to room temperature, and 20 volumes of the aqueous solution was added in a dropwise manner. The stirring was continued for 30 minutes after the precipitation of the solid. The solid was collected by filtration and dried to obtain the product with yield of 89%.

The product 114-1 was dissolved in 10 volumes of acetonitrile, and added with 1.5 equivalents of methyl iodide and 2 equivalents of potassium carbonate, then heated to 80° C. and allowed to react for 2 hours with stirring. Upon the completion of the reaction, acetonitrile was removed under vacuum, 10 volumes of water and 10 volumes of ethyl acetate were added, extraction was performed and the organic phase was collected, the organic solvent was removed by drying to obtain product 114-2 with yield of 80%.

The product 114-2 was dissolved in 5V of dioxane and controlled to 25° C., followed by the addition of the prepared sodium hydroxide aqueous solution (1.2 eq of sodium hydroxide dissolved in 5V of water) in a dropwise manner, and then was allowed to react for 3 hours. Upon the completion of the reaction, dioxane was removed, pH was adjusted to 1 to 2 with 1M aqueous hydrochloric acid solution. The stirring was continued for 3 hours after the precipitation of the solid, then filtration was performed, the filter cake was washed once with water, and the solid was dried to obtain product 114-3 with yield of 81%.

To a reactor were added the obtained product 114-3 and 10V of dichloromethane, 2.5 eq of thionyl chloride was added in a dropwise manner with stirring at a controlled temperature of 25° C., then heated to 40° C. and allowed to react for 1 hour. Upon the completion of the reaction, dichloromethane and thionyl chloride were removed under vacuum, then the residue was dissolved in 3V of dichloromethane for later use.

To a reactor were added 1.1 equivalents of 1,3-cyclohexanedione, 10V of dichloromethane, and 3.0 eq of triethylamine, then the above obtained 114-4 in dichloromethane solution was added in a dropwise manner at a controlled temperature of 10° C., and allowed to react for 1 hour. Upon the completion of the reaction, dichloromethane and triethylamine were removed under vacuum to obtain crude product 114-5.

The crude product 114-5 was dissolved in 10V of acetonitrile, added with 1.0 eq of triethylamine, then a catalytic amount of acetone cyanohydrin was added under nitrogen protection, and allowed to react at 70° C. for 10 hours. Upon the completion of the reaction, the insoluble solid was removed by filtration and the acetonitrile was removed under vacuum. The residue was dissolved with 10 volumes of dichloromethane, then added with 5 volumes of water, adjusted with 1M hydrochloric acid to a pH of 3 to 4, extraction and separation were then performed and the organic phase was collected; the organic phase was added with 5 volumes of water, and then adjusted with saturated sodium bicarbonate aqueous solution to a pH of 8, extraction and separation were then performed and the aqueous solution was collected; the aqueous phase was adjusted with 1M hydrochloric acid to a pH of 2 to 3, extraction with dichloromethane and separation were then performed and the organic phase was collected. The organic phase was subjected to rotatory evaporation to obtain product 114 with yield of 52%.

7. Synthesis of Compound 118

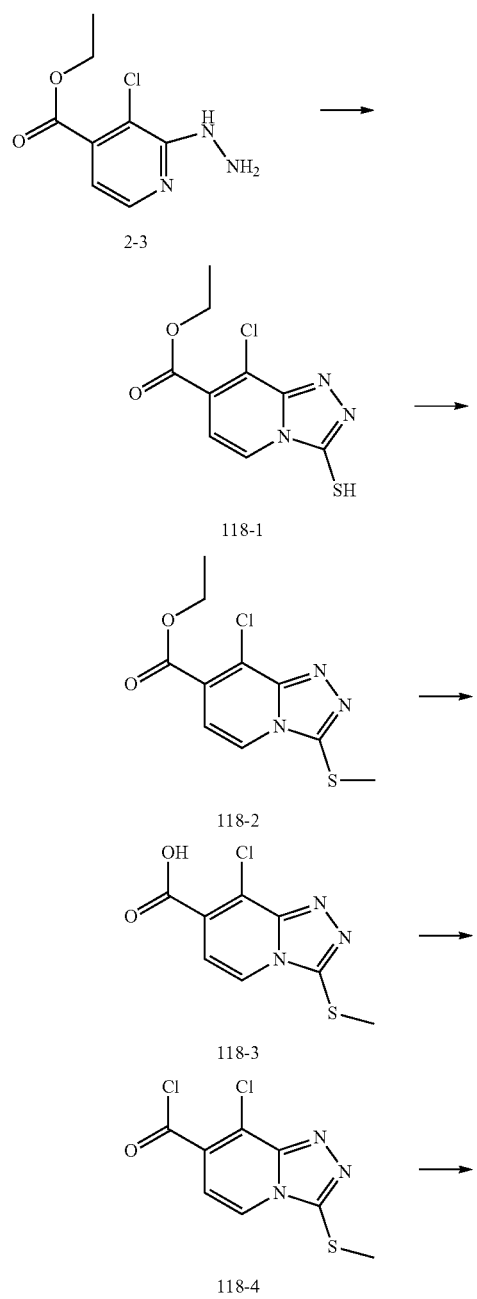

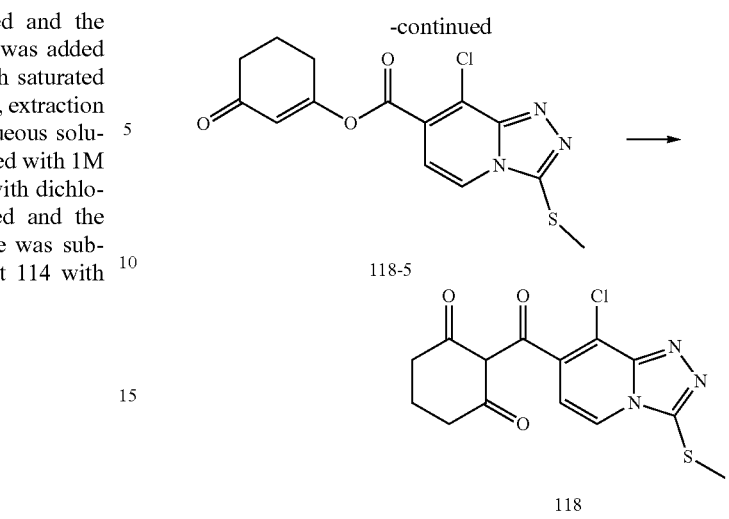

The product 2-3 was dissolved in 10 volumes of ethanol, added with 3 volumes of carbon disulfide, then heated to 80° C. and stirred for 20 hours. Upon the completion of the reaction, the reaction system was cooled to room temperature. Ethanol and carbon disulfide were removed under vacuum to obtain crude product 118-1 for later use.

The product 118-1 was dissolved in 10 volumes of acetonitrile, and added with 1.2 equivalents of methyl iodide and 2 equivalents of potassium carbonate, then heated to 80° C. and allowed to react with stirring for 3 hours. Upon the completion of the reaction, acetonitrile was removed under vacuum, and the product was mixed with silica gel and purified by column chromatography to obtain product 118-2 with yield of 55%.

The product 118-2 was dissolved in 5V of dioxane and controlled to 15° C., followed by the addition of the prepared sodium hydroxide aqueous solution (1.2 eq of sodium hydroxide dissolved in 5V of water) in a dropwise manner, and then was allowed to react for 2 hours. Upon the completion of the reaction, dioxane was removed, pH was adjusted to 1 to 2 with 1M hydrochloric acid aqueous solution, extraction and liquid separation were performed twice with 10 volumes of dichloromethane. The organic phase was collected and subjected to rotatory-evaporation to remove the solvent to obtain product 118-3 with yield of 70%.

To a reactor were added the product 118-3 and 10V of dichloromethane, 3.0 eq of thionyl chloride was added in a dropwise manner with stirring at a controlled temperature of 10° C., then heated to 50° C. and allowed to react for 1 hour. Upon the completion of the reaction, dichloromethane and thionyl chloride were removed under vacuum, then the residue was dissolved in 3V of dichloromethane for later use.

To a reactor were added 1.1 equivalents of 1,3-cyclohexanedione, 10V of dichloromethane, and 3.0 eq of triethylamine, then the above obtained 118-4 in dichloromethane solution was added in a dropwise manner at a controlled temperature of 10° C., and allowed to react for 0.5 hour. Upon the completion of the reaction, dichloromethane and triethylamine were removed under vacuum to obtain crude product 118-5.

The crude product 118-5 was dissolved into 10V of acetonitrile, added with 1.2 eq of triethylamine, then a catalytic amount of acetone cyanohydrin was added under nitrogen protection, and allowed to react at 50° C. for 5 hours. Upon the completion of the reaction, the insoluble solid was removed by filtration and the acetonitrile was removed under vacuum. The residue was added with 5 volumes of water, adjusted with 1M hydrochloric acid to a pH of 3 to 4, and purified by reversed-phase chromatography to obtain the target product 118 with yield of 45%.

8. Synthesis of Compound 122

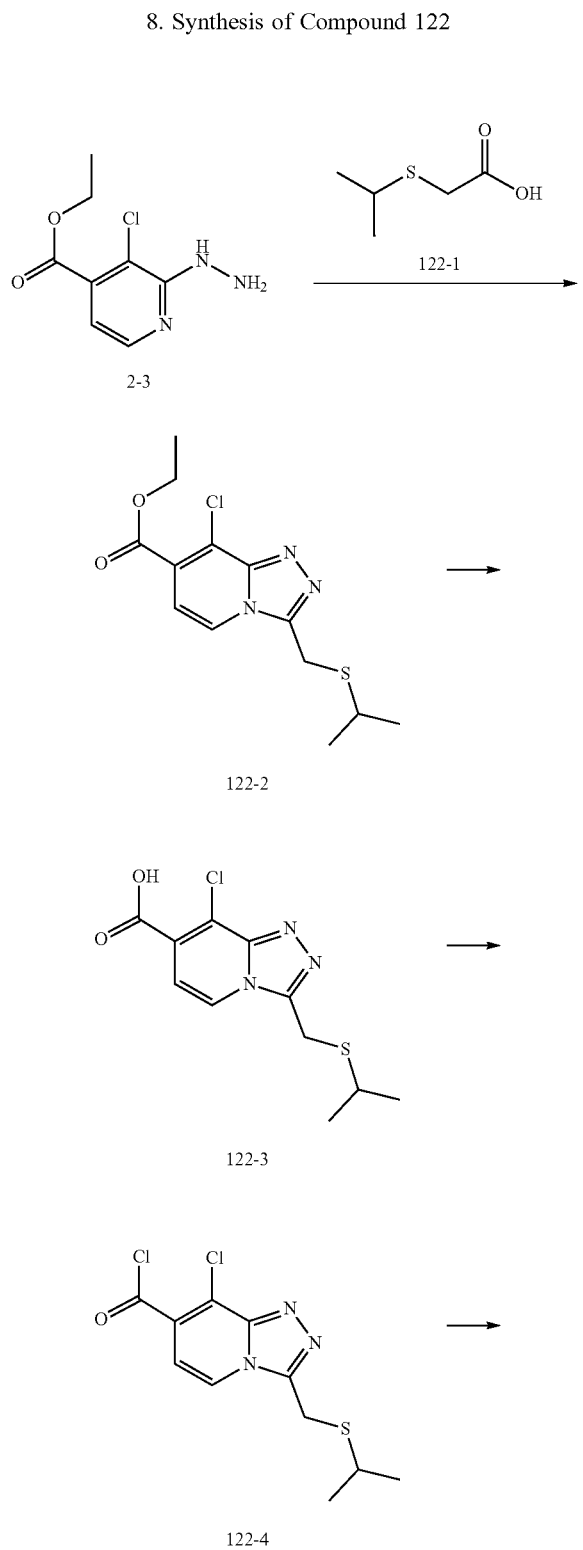

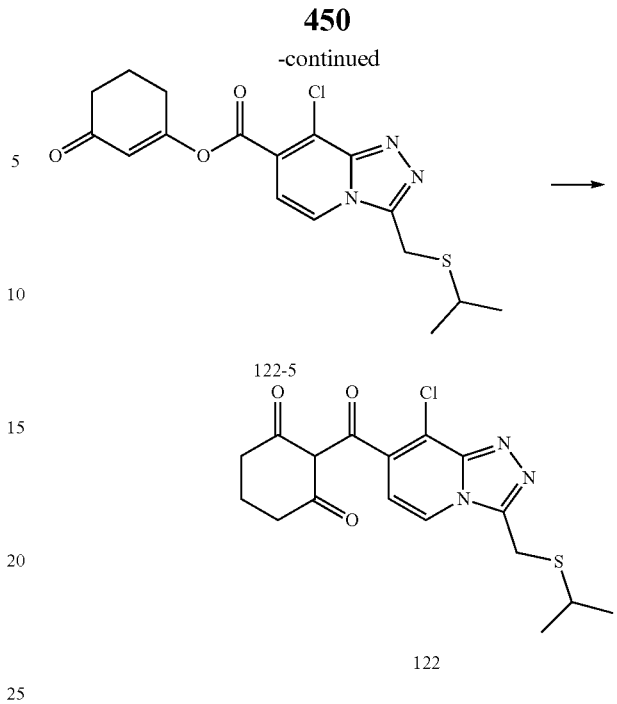

To a reactor were added compound 2-3, 8V of toluene as the solvent, and 122-1 (1.0 eq), the reaction system was heated to 80° C. and added with phosphorus oxychloride (2.5 eq), then allowed to react for 16 hours, then heated to 100° C. and allowed to react for an hour. Upon the completion of the reaction, the reaction system was controlled to 10° C., and added into water. Extraction and separation were performed, the toluene phase was collected. The aqueous phase was extracted twice with ethyl acetate (5V), and the organic phase was collected. After being washed with sodium bicarbonate solution (5V), the organic phase was removed under vacuum to obtain a solid product, which was purified by beating with isopropyl ether and filtered to obtain product 122-2 with yield of 93%.

The obtained product 122-2 was dissolved in 5V of ethanol and controlled to 10° C., followed by the addition of the prepared sodium hydroxide aqueous solution (1.2 eq of sodium hydroxide dissolved in 5V of water) in a dropwise manner, and then the system was allowed to react for 3 hours. Upon the completion of the reaction, ethanol was removed, pH was adjusted to 1 to 2 with 1M aqueous hydrochloric acid solution, and extraction was performed twice with 10V of dichloromethane. The organic phase was collected and subjected to rotatory-evaporation to remove dichloromethane to obtain product 122-3 with yield of 89%.

To a reactor were added the obtained product 122-3 and 10V of dichloromethane, 2.5 eq of thionyl chloride was added in a dropwise manner with stirring at a controlled temperature of 10° C., then allowed to react for 1 hour. Upon the completion of the reaction, dichloromethane and thionyl chloride were removed under vacuum, then the residue was dissolved in 3V of dichloromethane for later use.

To a reactor were added 1,3-cyclohexanedione, 10V of dichloromethane, and 2.5 eq of triethylamine, then the above obtained acyl chloride in dichloromethane solution was added in a dropwise manner at a controlled temperature of 10° C., and allowed to react for 3 hours. Upon the completion of the reaction, dichloromethane and triethylamine were removed under vacuum to obtain crude product 122-5.

The crude product 122-5 was dissolved into 10V of acetonitrile, added with 3.0 eq of triethylamine, then a catalytic amount of acetone cyanohydrin was added under nitrogen protection, and allowed to react at 60° C. for 12 hours. Upon the completion of the reaction, the product was mixed with silica gel and purified by column chromatography to obtain the target product 122 with yield of 61%.

9. Synthesis of Compound 274

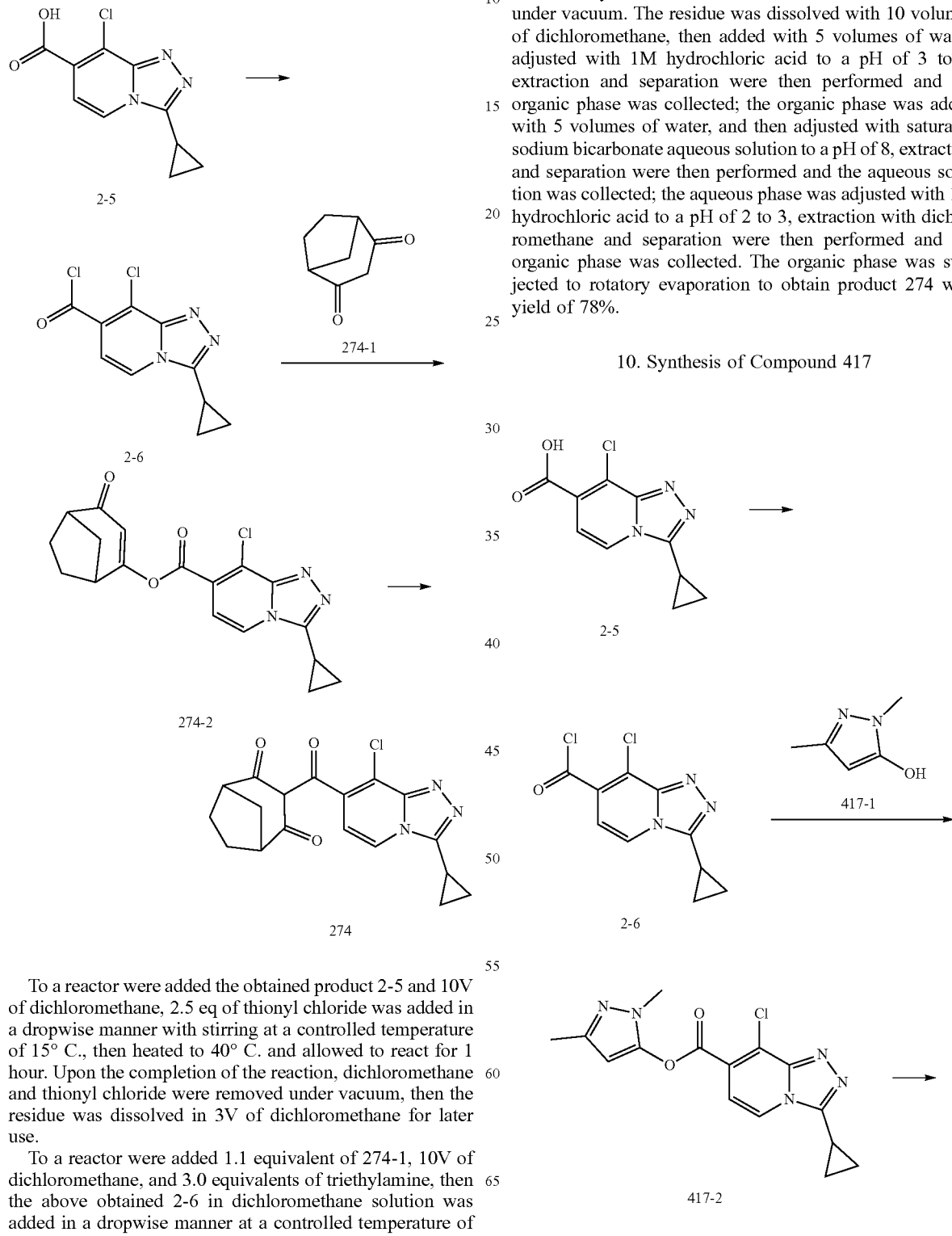

To a reactor were added the obtained product 2-5 and 10V of dichloromethane, 2.5 eq of thionyl chloride was added in a dropwise manner with stirring at a controlled temperature of 15° C., then heated to 40° C. and allowed to react for 1 hour. Upon the completion of the reaction, dichloromethane and thionyl chloride were removed under vacuum, then the residue was dissolved in 3V of dichloromethane for later use.

To a reactor were added 1.1 equivalent of 274-1, 10V of dichloromethane, and 3.0 equivalents of triethylamine, then the above obtained 2-6 in dichloromethane solution was added in a dropwise manner at a controlled temperature of 5° C., and allowed to react for 1 hour. Upon the completion of the reaction, dichloromethane and triethylamine were removed under vacuum to obtain crude product 274-2.

The crude product 274-2 was dissolved in 10V of acetonitrile, added with 1.2 eq of triethylamine, then a catalytic amount of acetone cyanohydrin was added under nitrogen protection, and allowed to react at 70° C. for 20 hours. Upon the completion of the reaction, the insoluble solid was removed by filtration and the acetonitrile was removed under vacuum. The residue was dissolved with 10 volumes of dichloromethane, then added with 5 volumes of water, adjusted with 1M hydrochloric acid to a pH of 3 to 4, extraction and separation were then performed and the organic phase was collected; the organic phase was added with 5 volumes of water, and then adjusted with saturated sodium bicarbonate aqueous solution to a pH of 8, extraction and separation were then performed and the aqueous solution was collected; the aqueous phase was adjusted with 1M hydrochloric acid to a pH of 2 to 3, extraction with dichloromethane and separation were then performed and the organic phase was collected. The organic phase was subjected to rotatory evaporation to obtain product 274 with yield of 78%.

10. Synthesis of Compound 417

-continued

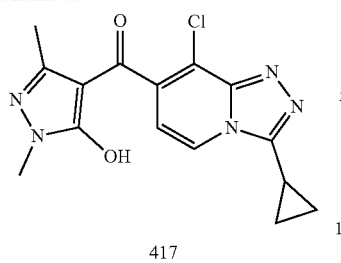

417

To a reactor were added the obtained product 2-5 and 10V of dichloromethane, 3.0 eq of thionyl chloride was added in a dropwise manner with stirring at a controlled temperature of 15° C., and allowed to react for 1 hour. Upon the completion of the reaction, dichloromethane and thionyl chloride were removed under vacuum, then the residue was dissolved in 3V of dichloromethane for later use.

To a reactor were added the raw material 417-1, 10V of dichloromethane, and 3.0 eq of triethylamine, then the above obtained acyl chloride in dichloromethane solution was added in a dropwise manner at a controlled temperature of 5° C., and allowed to react for 4 hours. Upon the completion of the reaction, dichloromethane and triethylamine were removed under vacuum to obtain crude product 417-2.

The crude product 417-2 was dissolved in 10V of acetonitrile, added with 3.0 eq of triethylamine, then a catalytic amount of acetone cyanohydrin was added under nitrogen protection, and allowed to react at 50° C. for 15 hours. Upon the completion of the reaction, the product was mixed with silica gel and purified by column chromatography to obtain the target product 417 with yield of 63%.

11. Synthesis of Compounds 418

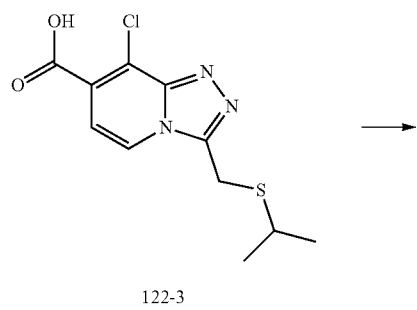

122-3

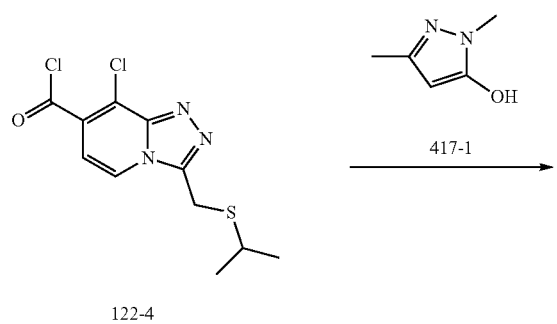

122-4

-continued

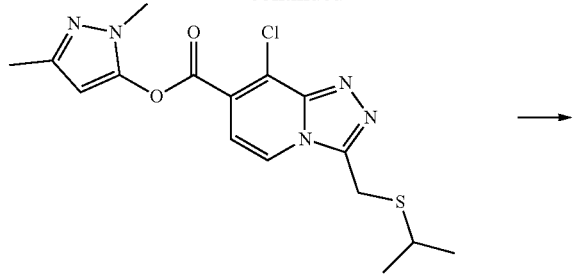

418-1

418

To a reactor were added the obtained product 122-3 and 10V of dichloromethane, 3.0 eq of thionyl chloride was added in a dropwise manner with stirring at a controlled temperature of 25° C., and allowed to react for 1 hour. Upon the completion of the reaction, dichloromethane and thionyl chloride were removed under vacuum, then the residue was dissolved in 3V of dichloromethane for later use.

To a reactor were added the raw material 417-1, 10V of dichloromethane, and 3.0 eq of triethylamine, then the above obtained acyl chloride in dichloromethane solution was added in a dropwise manner at a controlled temperature of 25° C., and allowed to react for 5 hours. Upon the completion of the reaction, dichloromethane and triethylamine were removed under vacuum to obtain crude product 418-1.

The crude product 418-1 was dissolved in 10V of acetonitrile, added with 3.0 eq of triethylamine, then a catalytic amount of acetone cyanohydrin was added under nitrogen protection, and allowed to react at 30° C. for 15 hours. Upon the completion of the reaction, the product was mixed with silica gel and purified by column chromatography to obtain the target product 418 with yield of 38%.

Biological Activity Evaluation:

The activity level criteria for plant damage (i.e., growth control rate) are as follows:
  Level 5: growth control rate is above 85%;
  Level 4: growth control rate is greater than or equal to 60% and less than 85%;
  Level 3: growth control rate is greater than or equal to 40% and less than 60%;
  Level 2: growth control rate is greater than or equal to 20% and less than 40%;
  Level 1: growth control rate is greater than or equal to 5% and less than 20%;
  Level 0: growth control rate is less than 5%.

The above growth control rates are fresh weight control rates.

(1) Experiment on weeding effect in post-emergence stage: monocotyledonous and dicotyledonous weed seeds and major crop seeds (wheat, corn, rice, soybean, cotton, oilseed rape, millet, *Sorghum*) were placed in plastic pots filled with soil, then covered with 0.5-2 cm of soil, allowed to grow in a good greenhouse environment. After 2 weeks of sowing, the test plants were treated. The tested compounds of the present invention were respectively dissolved in acetone, then added with Tween 80, diluted with a certain amount of water to obtain a solution with a certain concentration, added with 1000 g/ha of emulsified methyl oleate as a synergist, and sprayed with a spray tower onto the plants. After the application, the plants were cultured for 3 weeks in the greenhouse, and then the experimental results of the weeding were listed in Table 2-3.

TABLE 2

Results on weeding effect in post-emergence stage (weeds 2-3 leaf stage)

| Compound No. | Echinochloa crusgalli | Digitaria sanguinalis | Leptochloa chinensis | Amaranthus retroflexus L. | rice (indica rice huang-huazhan) |
|---|---|---|---|---|---|
| 2 | 5 | 5 | 5 | 5 | 0 |
| 41 | 5 | 5 | 5 | 5 | 0 |
| 43 | 5 | 5 | 5 | 5 | 0 |
| 45 | 5 | 5 | 5 | 5 | 0 |
| 68 | 3 | 4 | 4 | 3 | 1 |
| 69 | 5 | 4 | 5 | 5 | 0 |
| 70 | 5 | 5 | 5 | 5 | 0 |
| 83 | 5 | 5 | 5 | 5 | 0 |
| 87 | 4 | 4 | 5 | 5 | 0 |
| 88 | 3 | 3 | 4 | 3 | 0 |
| 114 | 5 | 5 | 5 | 5 | 0 |
| 115 | 5 | 5 | 5 | 5 | 0 |
| 118 | 5 | 5 | 5 | 5 | 0 |
| 133 | 4 | 4 | 5 | 5 | 0 |
| 263 | 5 | 5 | 5 | 5 | 1 |
| 264 | 4 | 5 | 4 | 4 | N |
| 265 | 3 | N | 3 | 3 | 0 |
| 271 | 5 | 5 | 5 | 5 | 1 |
| 274 | 5 | 5 | 5 | 5 | 0 |
| 297 | N | N | N | 3 | 0 |
| 305 | 3 | 3 | 3 | 4 | 0 |
| 317 | N | N | 3 | N | 0 |
| 622 | 3 | N | 5 | 4 | 1 |
| 628 | 3 | 3 | N | 3 | 1 |
| 630 | N | N | N | 3 | 0 |
| 632 | 3 | N | N | 3 | 0 |
| 638 | 4 | 5 | 3 | N | 0 |
| 643 | N | N | N | 3 | 1 |
| 647 | 3 | 3 | 3 | 4 | 1 |
| 652 | 3 | 3 | 4 | N | 0 |
| 669 | N | N | N | 3 | 0 |
| 671 | N | N | 3 | 3 | 0 |
| 700 | N | 3 | 3 | 3 | 0 |
| 701 | 4 | 4 | 5 | 4 | N |
| 702 | 3 | 4 | 5 | 3 | 1 |
| 703 | 3 | N | N | 3 | 0 |
| 707 | 3 | N | 3 | N | 0 |
| 708 | 3 | 3 | 5 | N | 0 |
| 711 | N | N | 3 | N | 0 |
| 712 | 3 | N | 5 | 4 | 0 |
| 721 | 3 | 3 | 3 | 3 | 1 |
| 724 | 3 | N | 3 | N | 0 |
| 725 | N | N | N | 3 | 1 |
| 727 | N | N | 4 | N | 0 |
| 731 | N | N | N | 3 | 0 |
| 741 | 4 | 3 | 5 | 3 | N |
| 743 | N | N | N | 3 | 0 |
| 745 | 4 | 3 | N | 4 | 0 |
| 746 | 3 | 3 | N | 3 | 0 |
| 749 | 3 | 3 | 3 | 3 | 1 |
| 750 | 3 | 5 | 4 | N | 0 |
| 751 | 4 | 5 | 4 | 4 | 0 |
| 752 | 3 | 4 | 4 | 4 | 1 |
| 753 | 4 | 5 | 4 | 3 | 0 |
| 754 | N | N | N | 3 | 0 |
| 755 | 3 | N | N | 3 | 0 |
| 756 | 4 | 4 | 5 | 3 | 1 |
| 760 | 3 | 4 | 3 | 4 | 0 |
| 761 | 3 | 4 | N | 4 | 0 |
| 764 | N | 3 | N | 3 | 1 |
| 765 | 4 | 5 | 4 | 3 | 0 |
| 767 | 3 | N | N | N | 0 |
| 768 | 4 | 5 | 5 | 3 | 0 |
| 771 | N | N | N | 3 | 1 |
| 776 | N | N | N | 3 | 0 |
| 789 | 3 | N | N | 3 | 0 |
| 791 | 3 | 3 | 3 | 3 | 0 |
| Control compound A | 3 | N | N | N | 2 |

Note:
N represented no data, the application dose was active ingredient 240 g/ha, plus water 450 kg/ha.
Control compound A:

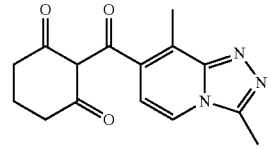 [SMILES: Cc1c(C(=O)C2C(=O)CCCC2=O)ccn2c(C)nnc12]

TABLE 3

Results on weeding effect in post-emergence stage

| Compound No. | Echinochloa crusgalli | Digitaria sanguinalis | Leptochloa chinensis | Setaria viridis | indica rice | japonica rice | Dose |
|---|---|---|---|---|---|---|---|
| 2 | 5 | 5 | 5 | 5 | 0 | 0 | 120 g/ha |
| 2 | 5 | 5 | 5 | 5 | 0 | 0 | 60 g/ha |
| 2 | 5 | 5 | 5 | 5 | 0 | 0 | 30 g/ha |
| 274 | 5 | 5 | 5 | 5 | 0 | 0 | 120 g/ha |
| 274 | 5 | 5 | 5 | 5 | 0 | 0 | 60 g/ha |
| 274 | 5 | 5 | 5 | 5 | 0 | 0 | 30 g/ha |

In addition, although the aforementioned patent application WO2008006540A1 listed many specific structures, the better efficacy data were given for only the compounds with ketone at meta-position of pyridine nitrogen and with trifluoromethyl at para-position of ketone; moreover, although a small amount of structures with ketone at para-position of pyridine nitrogen were also listed, neither their nuclear magnetic data nor their activity data were disclosed. However, the inventors unexpectedly finds that the compounds with ketone at para-position of the substituted pyridine nitrogen according to the present invention show good herbicidal activity and good selectivity for rice and other crops, especially compared with the compounds disclosed in the art and the commercialized HPPD herbicides.

Experiment on Weed Effect in Pre-Emergence Stage:

Seeds of monocotyledonous and dicotyledonous weeds and main crops (e.g. wheat, corn, rice, soybean, cotton, oilseed rape, millet and *Sorghum*) were put into a plastic pot loaded with soil and covered with 0.5-2 cm soil. The test compounds of the present invention was dissolved with acetone, then added with tween 80, diluted by a certain amount of water to reach a certain concentration, and sprayed immediately after sowing. The obtained seeds were incubated for 4 weeks in the greenhouse after spraying and the test results were observed. It was observed that the herbicide mostly had excellent effect at the application rate of 250 g a.i./ha, especially to weeds such as *Echinochloa crusgalli, Digitaria sanguinalis, Leptochloa chinensis*, and *Abutilon theophrasti*, etc. . . . And many compounds had good selectivity for corn, wheat, rice, soybean, and oilseed rape, etc. . . . In particular, the compound 2 and compound 274 of the present invention were safe and efficient for direct seeding of rice, and had excellent sealing effects on *Echinochloa crusgalli, Leptochloa chinensis, Digitaria sanguinalis*, and *Abutilon theophrasti*.

It is indicated from the experiment that the compounds of the present invention generally have good weed control efficacy, especially for the major cyperaceae weeds like *Echinochloa crusgalli, Digitaria sanguinalis*, and *Setaria viridis*, etc., and the major broad-leaved weeds like *Abutilon theophrasti, Rorippa indica*, and *Bidens pilosa* L., etc., which are widely occurring in corn, rice, and wheat fields, and have excellent commercial value. Above all, it is noted that they have extremely high activity to broad-leaved weeds, which are resistant to ALS inhibitor, like *Rorippa indica, Descurainia sophia, Capsella bursa-pastoris, Lithospermum arvense, Galium aparine* L., and *Stellaria media*, etc. . . .

Transplanted rice safety evaluation and weed control effect evaluation in rice field:

Rice field soil was loaded into a 1/1,000,000 ha pot. The seeds of *Echinochloa crusgalli, Scirpus juncoides*, and *Bidens tripartita* L. were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgalli, Scirpus juncoides*, and *Bidens tripartita* L. reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (japonica rice) was transplanted at 3 cm of transplanting depth the next day. The compound of the present invention was treated by the same way after 5 days of transplantation.

The fertility condition of *Echinochloa crusgalli, Scirpus juncoides, Bidens tripartita* L., and *Sagittaria trifolia* 14 days after the treatment of the compound of the invention and the fertility condition of rice 21 days after the treatment of the compound of the invention were observed respectively with the naked eye. Evaluate the weed control effect with the above activity standard level 1-5. Many compounds show excellent activity and selectivity.

Note: The seeds of *Echinochloa crusgalli, Scirpus juncoides, Sagittaria trifolia*, and *Bidens tripartita* L. were collected from Heilongjiang Province of China. The tests indicated that the weeds were resistant to the common doses of Pyrazosulfuron-ethyl.

It could be seen from this experiment that the compound of the present invention has excellent activity against the anti-ALS weeds which is a serious challenge in the production, and could solve the increasingly serious problem of resistance.

At the same time, it is found after several tests that the compounds of the present invention have good selectivity to many gramineae grasses such as *Zoysia japonica*, bermuda grass, tall fescue, bluegrass, ryegrass and seashore paspalum etc, and are able to control many important grass weeds and broad-leaved weeds. The compounds also show excellent selectivity and commercial value in the tests on sugarcane, soybean, cotton, oil sunflower, potato, orchards and vegetables in different herbicide application methods.

What is claimed is:

1. A substituted 1,2,4-triazolo[4,3-a]pyridine derivative of Formula I:

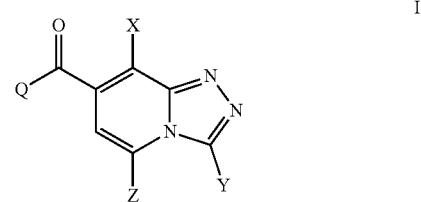

Q represents

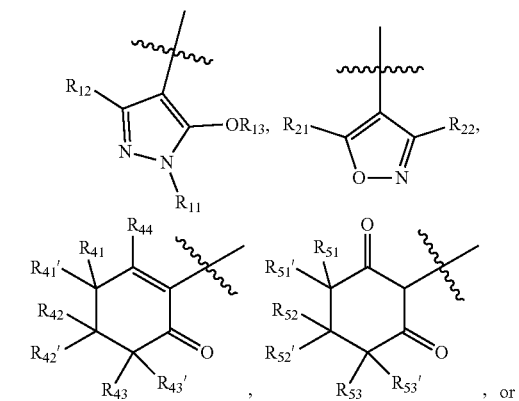
, or

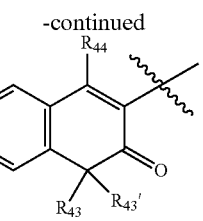

$R_{11}$ represents $C_1$-$C_6$ alkyl;
$R_{12}$ represents hydrogen, $C_1$-$C_6$ alkyl or $C_3$-$C_6$ cycloalkyl;
$R_{13}$ represents hydrogen, sodium ion or —(C=O)$R_{64}$;
$R_{21}$ and $R_{22}$ each independently represent hydrogen or $C_3$-$C_6$ cycloalkyl;
$R_{41}$, $R_{41}'$, $R_{42}$, $R_{42}'$, $R_{43}$ and $R_{43}'$ each independently represent hydrogen, $C_1$-$C_6$ alkyl or halogenated $C_1$-$C_6$ alkyl, or two of $R_{41}$, $R_{41}'$, $R_{42}$, $R_{42}'$, $R_{43}$ and $R_{43}'$ that are on different carbon atoms connect to form (CH$_2$)$_2$;
$R_{44}$ is selected from —ONa;
$R_{51}$, $R_{51}'$, $R_{52}$, $R_{52}'$, $R_{53}$ and $R_{53}'$ each independently represent hydrogen, $C_1$-$C_6$ alkyl or halogenated $C_1$-$C_6$ alkyl, or two of $R_{51}$, $R_{51}'$, $R_{52}$, $R_{52}'$, $R_{53}$ and $R_{53}'$ that are on different carbon atoms connect to form CH$_2$ or (CH$_2$)$_2$;
$R_{64}$ represents aryl or heterocyclyl;
X represents fluorine, chlorine, bromine, iodine, $C_3$-$C_6$ cycloalkyl, or $C_1$-$C_6$ alkylthio;
$R_1$ and $R_2$ each independently represent $C_1$-$C_6$ alkyl, or —NR$_1$R$_2$ represents butyrolactam group;
Y represents hydrogen; fluorine; chlorine; bromine; iodine; formyl; cyano-$C_1$-$C_3$ alkyl; a $C_1$-$C_{10}$ alkyl, $C_2$-$C_6$ alkenyl or $C_2$-$C_6$ alkynyl, each of which contains or does not contain a fluorine or chlorine; —OR$_3$; —COR$_4$; —SR$_3$; —SOR$_4$; —SO$_2$R$_4$; —(C$_1$-C$_3$ alkyl)-OR$_3$; —(C$_1$-C$_6$ alkyl)-OCOR$_4$; —(C$_1$-C$_3$ alkyl)-SR$_3$; —(C$_1$-C$_3$ alkyl)-SOR$_4$; —(C$_1$-C$_3$ alkyl)-SO$_2$R$_4$; an amino, amino-$C_1$-$C_3$ alkyl or aminoacyl, each of which is unsubstituted or substituted with 1 to 2 groups selected from $C_1$-$C_6$ alkyl, $C_2$-$C_6$ alkenyl, $C_2$-$C_6$ alkynyl and $C_1$-$C_6$ alkylacyl; a $C_3$-$C_6$ cycloalkyl, $C_3$-$C_6$ cycloalkyl-$C_1$-$C_3$ alkyl or $C_3$-$C_6$ cycloalkenyl, each of which is unsubstituted or substituted with 1 to 2 groups selected from $C_1$-$C_6$ alkyl, cyano and fluorine; aryl; heterocyclyl; aryl-$C_1$-$C_3$ alkyl or heterocyclyl-$C_1$-$C_3$ alkyl;
$R_3$ each independently represents hydrogen, sodium ion, $C_1$-$C_6$ alkyl, $C_2$-$C_6$ alkenyl or $C_2$-$C_6$ alkynyl;
$R_4$ each independently represents $C_1$-$C_6$alkyl;
Z represents hydrogen, fluorine or chlorine;
the aryl or heterocyclyl is substituted or unsubstituted, respectively, and said substituted refers to being substituted with 1 to 2 groups selected from fluorine, chlorine, cyano, $C_1$-$C_6$ alkyl and phenyl;
the aryl is selected from phenyl and naphthyl; the heterocyclyl is selected from

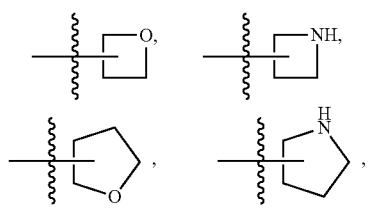

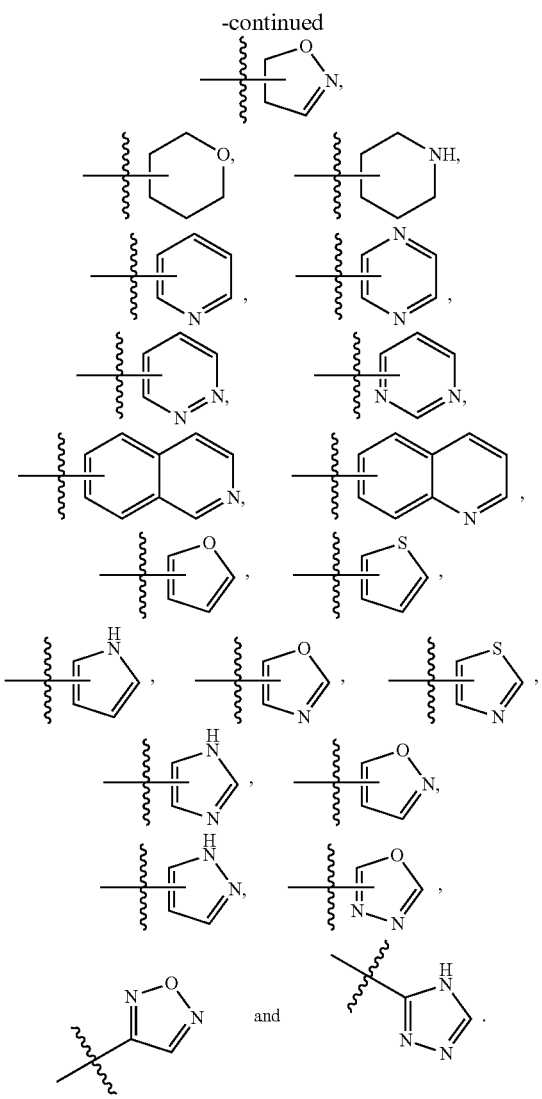

2. The substituted 1,2,4-triazolo[4,3-a]pyridine derivative according to claim 1, wherein Q represents

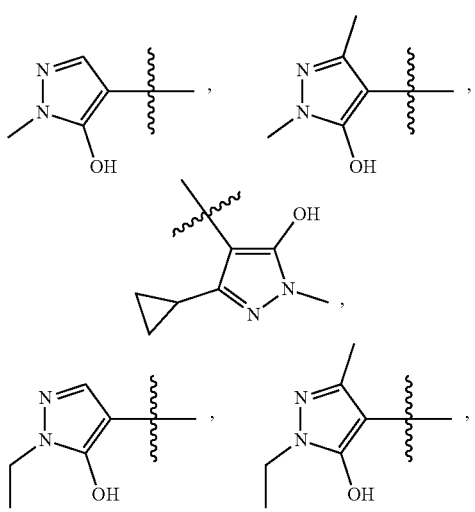

461
-continued
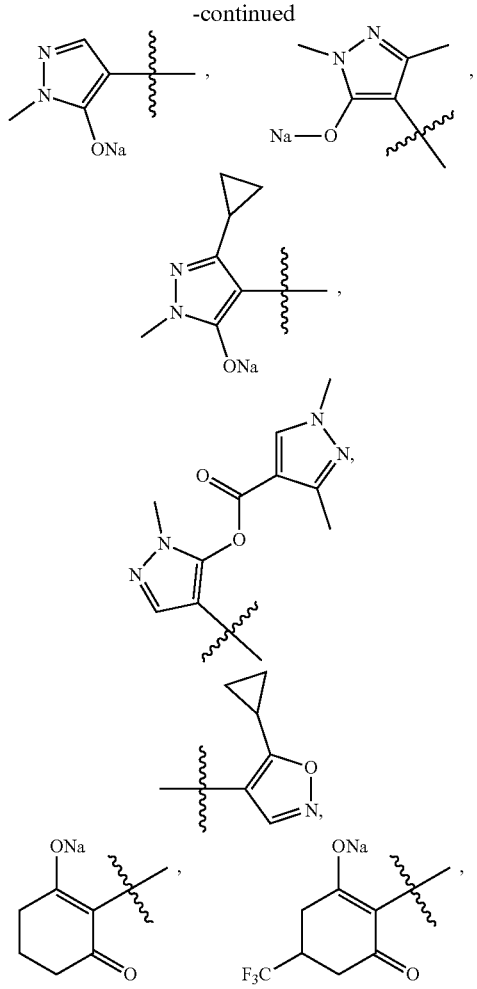
462
-continued
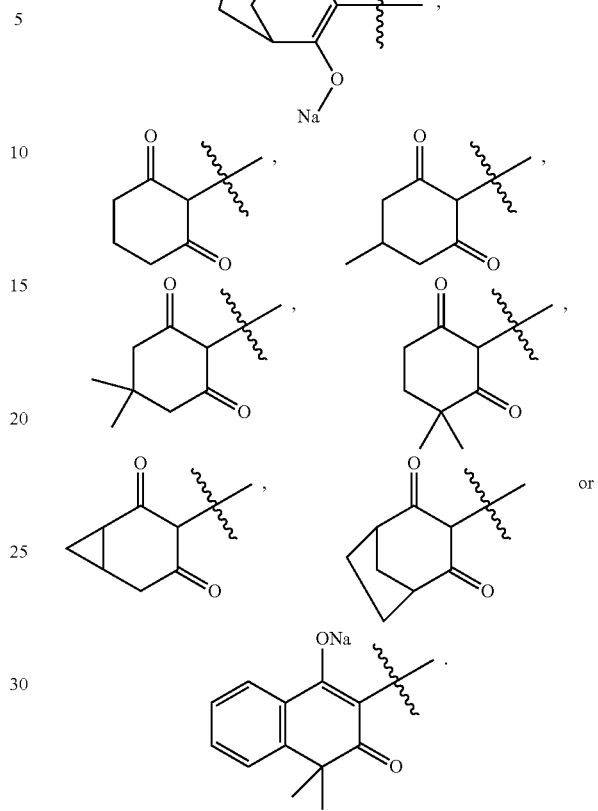
3. A substituted 1,2,4-triazolo[4,3-a]pyridine derivative of Formula I, which is selected from
| Compound No. | Q | X | Y | Z |
|---|---|---|---|---|
| 1 | | F | | H |
| 2 | | Cl | | H |
| 3 | | Br | | H |

-continued

| Compound No. | Q | X | Y | Z |
|---|---|---|---|---|
| 4 | 2,6-dioxocyclohexyl | I | cyclopropyl | H |
| 7 | 2,6-dioxocyclohexyl | cyclopropyl | cyclopropyl | H |
| 11 | 2,6-dioxocyclohexyl | -SCH$_3$ | cyclopropyl | H |
| 19 | 2,6-dioxocyclohexyl | F | CH$_3$ | H |
| 20 | 2,6-dioxocyclohexyl | Cl | CH$_3$ | H |
| 21 | 2,6-dioxocyclohexyl | Br | CH$_3$ | H |
| 22 | 2,6-dioxocyclohexyl | I | CH$_3$ | H |
| 25 | 2,6-dioxocyclohexyl | cyclopropyl | CH$_3$ | H |
| 29 | 2,6-dioxocyclohexyl | -SCH$_3$ | CH$_3$ | H |

-continued
| Compound No. | Q | X | Y | Z |
|---|---|---|---|---|
| 36 | 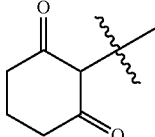 | Cl | H | H |
| 37 | 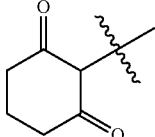 | Cl | F | H |
| 38 | 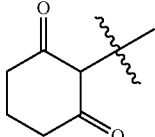 | Cl | Cl | H |
| 39 | 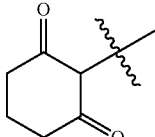 | Cl | Br | H |
| 40 | 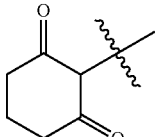 | Cl | I | H |
| 41 | 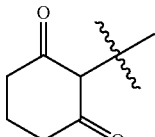 | Cl | $CH_2CH_3$ | H |
| 42 | 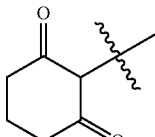 | Cl | 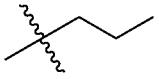 [SMILES: *CCC] | H |
| 43 | 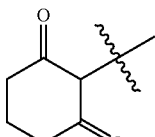 | Cl | 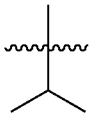 | H |
| 44 | 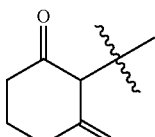 | Cl | 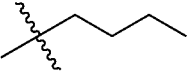 [SMILES: *CCCC] | H |

-continued

| Compound No. | Q | X | Y | Z |
|---|---|---|---|---|
| 45 | 2,6-dioxocyclohexyl | Cl | tert-butyl | H |
| 46 | 2,6-dioxocyclohexyl | Cl | sec-butyl | H |
| 47 | 2,6-dioxocyclohexyl | Cl | isobutyl | H |
| 48 | 2,6-dioxocyclohexyl | Cl | n-pentyl | H |
| 49 | 2,6-dioxocyclohexyl | Cl | 2-methylbutyl | H |
| 50 | 2,6-dioxocyclohexyl | Cl | 3-methylbutyl | H |
| 51 | 2,6-dioxocyclohexyl | Cl | 4-methylpentyl | H |
| 52 | 2,6-dioxocyclohexyl | Cl | 3-pentyl | H |
| 53 | 2,6-dioxocyclohexyl | Cl | 2,2-dimethylpropyl | H |

-continued
| Compound No. | Q | X | Y | Z |
|---|---|---|---|---|
| 54 | 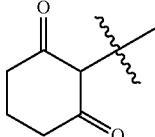 | Cl | 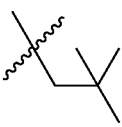 [SMILES: *CC(C)(C)C] | H |
| 55 | 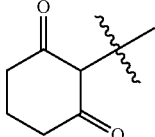 | Cl | 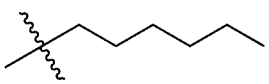 [SMILES: *CCCCCC] | H |
| 56 | 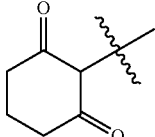 | Cl | 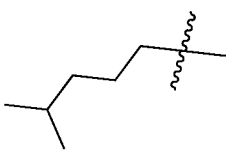 [SMILES: *CCCC(C)C] | H |
| 57 | 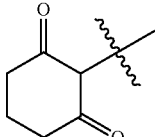 | Cl | 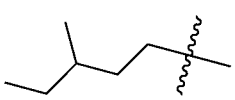 [SMILES: *CCC(C)CC] | H |
| 58 | 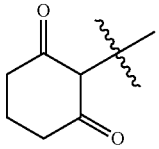 [SMILES: *C1C(=O)CCCC1=O] | Cl | 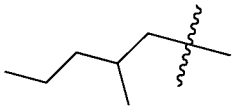 [SMILES: *CC(C)CCC] | H |
| 59 | 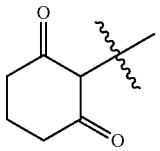 [SMILES: *C1C(=O)CCCC1=O] | Cl | 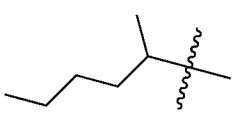 [SMILES: *C(C)CCCC] | H |
| 60 | 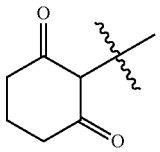 | Cl | 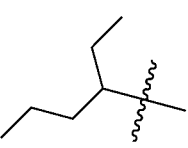 [SMILES: *C(CC)CCC] | H |
| 61 | 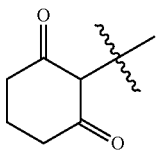 [SMILES: *C1C(=O)CCCC1=O] | Cl | 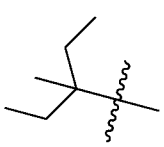 [SMILES: *C(C)(CC)CC] | H |
| 62 | 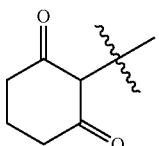 | Cl | 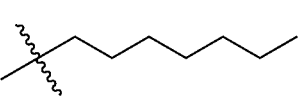 [SMILES: *CCCCCCC] | H |

-continued

| Compound No. | Q | X | Y | Z |
|---|---|---|---|---|
| 63 | 2,6-dioxocyclohexyl | Cl | 6-methylheptan-2-yl | H |
| 64 | 2,6-dioxocyclohexyl | Cl | 3-ethylhexyl | H |
| 65 | 2,6-dioxocyclohexyl | Cl | nonan-2-yl | H |
| 66 | 2,6-dioxocyclohexyl | Cl | decan-2-yl | H |
| 67 | 2,6-dioxocyclohexyl | Cl | undecan-2-yl | H |
| 68 | 2,6-dioxocyclohexyl | Cl | CHF$_2$ | H |
| 69 | 2,6-dioxocyclohexyl | Cl | CF$_3$ | H |
| 70 | 2,6-dioxocyclohexyl | Cl | CH$_2$CH$_2$CF$_3$ | H |
| 71 | 2,6-dioxocyclohexyl | Cl | CF$_2$CF$_2$CF$_3$ | H |

-continued

| Compound No. | Q | X | Y | Z |
|---|---|---|---|---|
| 72 | 2,6-dioxocyclohexyl | Cl | -CH₂CH₂Cl | H |
| 73 | 2,6-dioxocyclohexyl | Cl | -CH(CH₃)Cl | H |
| 74 | 2,6-dioxocyclohexyl | Cl | -CH₂CH₂CH₂Cl | H |
| 75 | 2,6-dioxocyclohexyl | Cl | -CH=CH₂ | H |
| 76 | 2,6-dioxocyclohexyl | Cl | -CH₂CH=CH₂ | H |
| 77 | 2,6-dioxocyclohexyl | Cl | -C(CH₃)=CH₂ | H |
| 78 | 2,6-dioxocyclohexyl | Cl | -CH=CHCH₃ | H |
| 79 | 2,6-dioxocyclohexyl | Cl | -CF=CF₂ (with F substituent) | H |
| 80 | 2,6-dioxocyclohexyl | Cl | -C≡CH | H |

-continued

| Compound No. | Q | X | Y | Z |
|---|---|---|---|---|
| 81 | 2,6-dioxocyclohexyl | Cl | ethynyl | H |
| 82 | 2,6-dioxocyclohexyl | Cl | 1-methylcyclopropyl | H |
| 83 | 2,6-dioxocyclohexyl | Cl | 2-methylcyclopropyl | H |
| 84 | 2,6-dioxocyclohexyl | Cl | 2-fluorocyclopropyl | H |
| 85 | 2,6-dioxocyclohexyl | Cl | 1-cyanocyclopropyl | H |
| 86 | 2,6-dioxocyclohexyl | Cl | 2,2-dimethylcyclopropyl | H |
| 87 | 2,6-dioxocyclohexyl | Cl | 2,2-difluorocyclopropyl | H |
| 88 | 2,6-dioxocyclohexyl | Cl | cyclobutyl | H |
| 89 | 2,6-dioxocyclohexyl | Cl | cyclopentyl | H |

| Compound No. | Q | X | Y | Z |
|---|---|---|---|---|
| 90 | 2,6-dioxocyclohexyl | Cl | cyclohexyl | H |
| 91 | 2,6-dioxocyclohexyl | Cl | cyclopent-1-en-1-yl | H |
| 92 | 2,6-dioxocyclohexyl | Cl | cyclohex-3-en-1-yl | H |
| 93 | 2,6-dioxocyclohexyl | Cl | cyclopropylmethyl | H |
| 94 | 2,6-dioxocyclohexyl | Cl | cyclopentylmethyl | H |
| 95 | 2,6-dioxocyclohexyl | Cl | cyclohexylmethyl | H |
| 96 | 2,6-dioxocyclohexyl | Cl | oxiran-2-yl | H |
| 97 | 2,6-dioxocyclohexyl | Cl | oxetan-3-yl | H |
| 98 | 2,6-dioxocyclohexyl | Cl | 1-methylazetidin-3-yl | H |

-continued

| Compound No. | Q | X | Y | Z |
|---|---|---|---|---|
| 99 | 2,6-dioxocyclohexyl | Cl | tetrahydrofuran-2-yl | H |
| 100 | 2,6-dioxocyclohexyl | Cl | tetrahydrofuran-3-yl | H |
| 101 | 2,6-dioxocyclohexyl | Cl | pyrrolidin-3-yl | H |
| 102 | 2,6-dioxocyclohexyl | Cl | 1,3-dioxolan-2-yl | H |
| 103 | 2,6-dioxocyclohexyl | Cl | 2,5-dihydrofuran-2-yl | H |
| 104 | 2,6-dioxocyclohexyl | Cl | 5,5-diphenyl-4,5-dihydroisoxazol-3-yl | H |
| 105 | 2,6-dioxocyclohexyl | Cl | tetrahydro-2H-pyran-4-yl | H |
| 106 | 2,6-dioxocyclohexyl | Cl | 1-methylpiperidin-4-yl | H |

-continued

| Compound No. | Q | X | Y | Z |
|---|---|---|---|---|
| 107 | 2,6-dioxocyclohexyl | Cl | 1,3-dioxan-5-yl | H |
| 108 | 2,6-dioxocyclohexyl | Cl | 1,4-dioxan-2-yl | H |
| 109 | 2,6-dioxocyclohexyl | Cl | morpholin-2-yl | H |
| 110 | 2,6-dioxocyclohexyl | Cl | piperazin-2-yl | H |
| 111 | 2,6-dioxocyclohexyl | Cl | 3,6-dihydro-2H-pyran-2-yl | H |
| 112 | 2,6-dioxocyclohexyl | Cl | 1,2,3,6-tetrahydropyridin-4-yl | H |
| 113 | 2,6-dioxocyclohexyl | Cl | —CH(CH₃)CN | H |
| 114 | 2,6-dioxocyclohexyl | Cl | —CH(CH₃)OCH₃ | H |
| 115 | 2,6-dioxocyclohexyl | Cl | —CH₂OCH₃ | H |

| Compound No. | Q | X | Y | Z |
|---|---|---|---|---|
| 116 | 2,6-dioxocyclohexyl | Cl | -C(CH₃)₂CH₂OEt | H |
| 117 | 2,6-dioxocyclohexyl | Cl | -C(CH₃)₂CH₂OMe (with wavy) | H |
| 118 | 2,6-dioxocyclohexyl | Cl | -C(CH₃)₂SMe | H |
| 119 | 2,6-dioxocyclohexyl | Cl | -C(CH₃)₂S(O)Me | H |
| 120 | 2,6-dioxocyclohexyl | Cl | -C(CH₃)₂S(O)₂Me | H |
| 121 | 2,6-dioxocyclohexyl | Cl | -CH₂SMe | H |
| 122 | 2,6-dioxocyclohexyl | Cl | -C(CH₃)₂S-iPr | H |
| 123 | 2,6-dioxocyclohexyl | Cl | -C(CH₃)₂S(O)-iPr | H |
| 124 | 2,6-dioxocyclohexyl | Cl | -C(CH₃)₂S(O)₂-iPr | H |

-continued

| Compound No. | Q | X | Y | Z |
|---|---|---|---|---|
| 125 | 2,6-dioxocyclohexyl | Cl | -CH₂N(CH₃)₂ | H |
| 126 | 2,6-dioxocyclohexyl | Cl | -CH(CH=O) | H |
| 127 | 2,6-dioxocyclohexyl | Cl | -CH(C(=O)CH₃) | H |
| 128 | 2,6-dioxocyclohexyl | Cl | -CH(C(=O)N(CH₃)₂) | H |
| 129 | 2,6-dioxocyclohexyl | Cl | -CH₂-phenyl | H |
| 130 | 2,6-dioxocyclohexyl | Cl | -CH₂-(pyridin-3-yl) | H |
| 131 | 2,6-dioxocyclohexyl | Cl | -CH₂-(thiophen-2-yl) | H |
| 132 | 2,6-dioxocyclohexyl | Cl | -CH₂-(thiophen-3-yl) | H |

-continued

| Compound No. | Q | X | Y | Z |
|---|---|---|---|---|
| 133 | 2,6-dioxocyclohexyl | Cl | phenyl | H |
| 134 | 2,6-dioxocyclohexyl | Cl | 4-fluorophenyl | H |
| 135 | 2,6-dioxocyclohexyl | Cl | 3-fluorophenyl | H |
| 136 | 2,6-dioxocyclohexyl | Cl | 2-fluorophenyl | H |
| 137 | 2,6-dioxocyclohexyl | Cl | 4-cyanophenyl | H |
| 138 | 2,6-dioxocyclohexyl | Cl | 3-cyanophenyl | H |
| 139 | 2,6-dioxocyclohexyl | Cl | 2-cyanophenyl | H |

| Compound No. | Q | X | Y | Z |
|---|---|---|---|---|
| 140 | 2,6-dioxocyclohexyl | Cl | 4-chlorophenyl | H |
| 141 | 2,6-dioxocyclohexyl | Cl | 3-chlorophenyl | H |
| 142 | 2,6-dioxocyclohexyl | Cl | 2-chlorophenyl | H |
| 143 | 2,6-dioxocyclohexyl | Cl | 2-bromophenyl | H |
| 144 | 2,6-dioxocyclohexyl | Cl | 3-methylphenyl | H |
| 145 | 2,6-dioxocyclohexyl | Cl | 4-(prop-1-en-1-yl)phenyl | H |
| 146 | 2,6-dioxocyclohexyl | Cl | 4-(2-chlorovinyl)phenyl | H |
| 147 | 2,6-dioxocyclohexyl | Cl | 3-ethynylphenyl | H |
| 148 | 2,6-dioxocyclohexyl | Cl | 4-(trifluoromethyl)phenyl | H |

-continued

| Compound No. | Q | X | Y | Z |
|---|---|---|---|---|
| 149 | 2,6-dioxocyclohexyl | Cl | 3-hydroxyphenyl | H |
| 150 | 2,6-dioxocyclohexyl | Cl | 3-methoxyphenyl | H |
| 151 | 2,6-dioxocyclohexyl | Cl | 3-(SO$_2$Me)phenyl | H |
| 152 | 2,6-dioxocyclohexyl | Cl | 2-(MeS)phenyl | H |
| 153 | 2,6-dioxocyclohexyl | Cl | 3-cyclopropylphenyl | H |
| 154 | 2,6-dioxocyclohexyl | Cl | 4-nitrophenyl | H |
| 155 | 2,6-dioxocyclohexyl | Cl | 4-(methoxycarbonyl)phenyl | H |
| 156 | 2,6-dioxocyclohexyl | Cl | 2-(acetoxy)phenyl | H |

-continued

| Compound No. | Q | X | Y | Z |
|---|---|---|---|---|
| 157 | 2,6-dioxocyclohexyl | Cl | 4-formylphenyl | H |
| 158 | 2,6-dioxocyclohexyl | Cl | 3-acetylphenyl | H |
| 159 | 2,6-dioxocyclohexyl | Cl | 3-(dimethylamino)phenyl | H |
| 160 | 2,6-dioxocyclohexyl | Cl | 4-acetamidophenyl | H |
| 161 | 2,6-dioxocyclohexyl | Cl | 4-(methylsulfinyl)phenyl | H |
| 162 | 2,6-dioxocyclohexyl | Cl | 3-(cyanomethyl)phenyl | H |
| 163 | 2,6-dioxocyclohexyl | Cl | 4-(hydroxymethyl)phenyl | H |
| 164 | 2,6-dioxocyclohexyl | Cl | 4-(methoxymethyl)phenyl | H |

-continued

| Compound No. | Q | X | Y | Z |
|---|---|---|---|---|
| 165 | 2,6-dioxocyclohexyl | Cl | 3-amino-5-methylphenyl | H |
| 166 | 2,6-dioxocyclohexyl | Cl | pyridin-2-yl | H |
| 167 | 2,6-dioxocyclohexyl | Cl | 3,6-dichloropyridin-2-yl | H |
| 168 | 2,6-dioxocyclohexyl | Cl | 4,6-dichloropyridin-2-yl | H |
| 169 | 2,6-dioxocyclohexyl | Cl | 3,5-dichloropyridin-2-yl | H |
| 170 | 2,6-dioxocyclohexyl | Cl | pyridin-2-yl | H |
| 171 | 2,6-dioxocyclohexyl | Cl | 2,4-dichloropyridin-3-yl | H |
| 172 | 2,6-dioxocyclohexyl | Cl | 2,5-dichloropyridin-3-yl | H |

-continued

| Compound No. | Q | X | Y | Z |
|---|---|---|---|---|
| 173 | 2,6-dioxocyclohexyl | Cl | 2,6-dichloropyridin-3-yl | H |
| 174 | 2,6-dioxocyclohexyl | Cl | 3,6-dichloropyridin-... | H |
| 175 | 2,6-dioxocyclohexyl | Cl | 5,6-dichloropyridin-3-yl | H |
| 176 | 2,6-dioxocyclohexyl | Cl | pyridin-4-yl | H |
| 177 | 2,6-dioxocyclohexyl | Cl | 2,3-dichloropyridin-4-yl | H |
| 178 | 2,6-dioxocyclohexyl | Cl | 2-chloro-3-fluoropyridin-4-yl | H |
| 179 | 2,6-dioxocyclohexyl | Cl | 2,6-dichloropyridin-4-yl | H |

-continued

| Compound No. | Q | X | Y | Z |
|---|---|---|---|---|
| 180 | 2,6-dioxocyclohexyl | Cl | 3,5-dichloropyridin-4-yl | H |
| 181 | 2,6-dioxocyclohexyl | Cl | 3,6-dichloropyridin-4-yl | H |
| 182 | 2,6-dioxocyclohexyl | Cl | pyrimidin-2-yl | H |
| 183 | 2,6-dioxocyclohexyl | Cl | pyrimidin-4-yl | H |
| 184 | 2,6-dioxocyclohexyl | Cl | pyrimidin-5-yl | H |
| 185 | 2,6-dioxocyclohexyl | Cl | pyridazin-3-yl | H |
| 186 | 2,6-dioxocyclohexyl | Cl | pyridazin-4-yl | H |
| 187 | 2,6-dioxocyclohexyl | Cl | pyrazin-2-yl | H |

-continued

| Compound No. | Q | X | Y | Z |
|---|---|---|---|---|
| 188 | 2,6-dioxocyclohexyl | Cl | 1,3,5-triazin-2-yl | H |
| 189 | 2,6-dioxocyclohexyl | Cl | 1,2,4-triazin-5-yl | H |
| 190 | 2,6-dioxocyclohexyl | Cl | 1,2,4,5-tetrazin-3-yl | H |
| 191 | 2,6-dioxocyclohexyl | Cl | furan-2-yl | H |
| 192 | 2,6-dioxocyclohexyl | Cl | thiophen-2-yl | H |
| 193 | 2,6-dioxocyclohexyl | Cl | furan-3-yl | H |
| 194 | 2,6-dioxocyclohexyl | Cl | thiophen-3-yl | H |
| 195 | 2,6-dioxocyclohexyl | Cl | 1-methyl-1H-pyrrol-2-yl | H |
| 196 | 2,6-dioxocyclohexyl | Cl | 1-methyl-1H-pyrrol-3-yl | H |

-continued

| Compound No. | Q | X | Y | Z |
|---|---|---|---|---|
| 197 | 2,6-dioxocyclohexyl | Cl | 1-methyl-1H-pyrazol-4-yl | H |
| 198 | 2,6-dioxocyclohexyl | Cl | 1,3-dimethyl-1H-pyrazol-4-yl | H |
| 199 | 2,6-dioxocyclohexyl | Cl | 1-methyl-1H-pyrazol-3-yl | H |
| 200 | 2,6-dioxocyclohexyl | Cl | 1-methyl-1H-pyrazol-5-yl | H |
| 201 | 2,6-dioxocyclohexyl | Cl | isoxazol-4-yl | H |
| 202 | 2,6-dioxocyclohexyl | Cl | isoxazol-5-yl | H |
| 203 | 2,6-dioxocyclohexyl | Cl | isoxazol-3-yl | H |
| 204 | 2,6-dioxocyclohexyl | Cl | isothiazol-5-yl | H |
| 205 | 2,6-dioxocyclohexyl | Cl | isothiazol-4-yl | H |

-continued

| Compound No. | Q | X | Y | Z |
|---|---|---|---|---|
| 206 | 2,6-dioxocyclohexyl | Cl | isothiazol-3-yl | H |
| 207 | 2,6-dioxocyclohexyl | Cl | oxazol-4-yl | H |
| 208 | 2,6-dioxocyclohexyl | Cl | oxazol-5-yl | H |
| 209 | 2,6-dioxocyclohexyl | Cl | thiazol-5-yl | H |
| 210 | 2,6-dioxocyclohexyl | Cl | thiazol-4-yl | H |
| 211 | 2,6-dioxocyclohexyl | Cl | thiazol-2-yl | H |
| 212 | 2,6-dioxocyclohexyl | Cl | 1-methyl-1H-imidazol-5-yl | H |
| 213 | 2,6-dioxocyclohexyl | Cl | 1-methyl-1H-imidazol-4-yl | H |

-continued

| Compound No. | Q | X | Y | Z |
|---|---|---|---|---|
| 214 | 2,6-dioxocyclohexyl | Cl | 1-methyl-1H-imidazol-5-yl | H |
| 215 | 2,6-dioxocyclohexyl | Cl | 1,2,5-oxadiazol-3-yl | H |
| 216 | 2,6-dioxocyclohexyl | Cl | 1,2,5-thiadiazol-3-yl | H |
| 217 | 2,6-dioxocyclohexyl | Cl | 1H-1,2,3-triazol-4-yl | H |
| 218 | 2,6-dioxocyclohexyl | Cl | 5-methyl-1,3,4-oxadiazol-2-yl | H |
| 219 | 2,6-dioxocyclohexyl | Cl | 1,3,4-thiadiazol-2-yl | H |
| 220 | 2,6-dioxocyclohexyl | Cl | 4H-1,2,4-triazol-3-yl | H |
| 221 | 2,6-dioxocyclohexyl | Cl | 1,2,4-oxadiazol-3-yl | H |
| 222 | 2,6-dioxocyclohexyl | Cl | 1,2,3-thiadiazol-5-yl | H |

-continued

| Compound No. | Q | X | Y | Z |
|---|---|---|---|---|
| 223 | cyclohexane-1,3-dione-2-yl | Cl | 1H-1,2,4-triazol-5-yl | H |
| 224 | cyclohexane-1,3-dione-2-yl | Cl | 1,2,3-oxadiazol-4-yl | H |
| 225 | cyclohexane-1,3-dione-2-yl | Cl | 1,2,3-thiadiazol-5-yl | H |
| 226 | cyclohexane-1,3-dione-2-yl | Cl | 1H-1,2,3-triazol-5-yl | H |
| 227 | cyclohexane-1,3-dione-2-yl | Cl | 1,2,3,4-oxatriazol-5-yl | H |
| 228 | cyclohexane-1,3-dione-2-yl | Cl | 1,2,3,4-thiatriazol-5-yl | H |
| 229 | cyclohexane-1,3-dione-2-yl | Cl | 1,2,3,4-oxatriazol-5-yl | H |
| 230 | cyclohexane-1,3-dione-2-yl | Cl | 1,2,3,4-thiatriazol-5-yl | H |
| 231 | cyclohexane-1,3-dione-2-yl | Cl | 1H-tetrazol-5-yl | H |

-continued

| Compound No. | Q | X | Y | Z |
|---|---|---|---|---|
| 232 | 2,6-dioxocyclohexyl | Cl | tetrazol-5-yl | H |
| 233 | 2,6-dioxocyclohexyl | Cl | naphthalen-1-yl | H |
| 234 | 2,6-dioxocyclohexyl | Cl | naphthalen-2-yl | H |
| 235 | 2,6-dioxocyclohexyl | Cl | quinolin-8-yl | H |
| 236 | 2,6-dioxocyclohexyl | Cl | quinolin-5-yl | H |
| 237 | 2,6-dioxocyclohexyl | Cl | quinolin-4-yl | H |
| 238 | 2,6-dioxocyclohexyl | Cl | isoquinolin-1-yl | H |
| 239 | 2,6-dioxocyclohexyl | Cl | 3,7-dichloroquinolin-8-yl | H |

-continued
| Compound No. | Q | X | Y | Z |
|---|---|---|---|---|
| 240 | 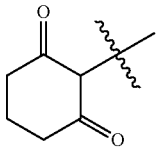 [SMILES: *C1C(=O)CCCC1=O] | Cl | 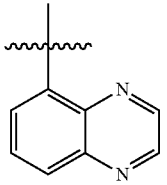 [SMILES: *c1cccc2nccnc12] | H |
| 241 | 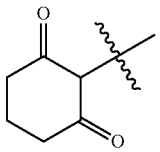 [SMILES: *C1C(=O)CCCC1=O] | Cl | 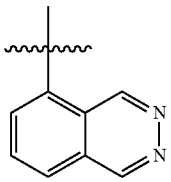 [SMILES: *c1cccc2cnncc12] | H |
| 242 | 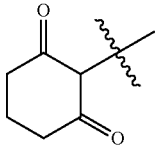 [SMILES: *C1C(=O)CCCC1=O] | Cl | 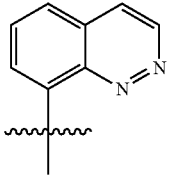 [SMILES: *c1cccc2ccnnc12] | H |
| 243 | 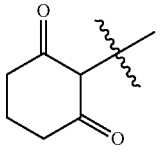 [SMILES: *C1C(=O)CCCC1=O] | Cl | 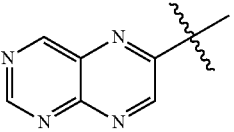 [SMILES: *c1cnc2ncncc2n1] | H |
| 244 | 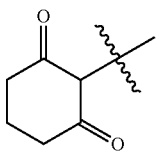 [SMILES: *C1C(=O)CCCC1=O] | Cl | 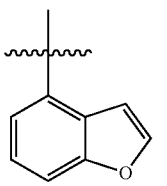 [SMILES: *c1cccc2occc12] | H |
| 245 | 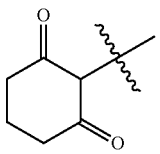 [SMILES: *C1C(=O)CCCC1=O] | Cl | 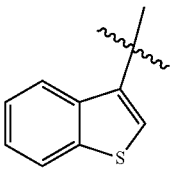 [SMILES: *c1csc2ccccc12] | H |
| 246 | 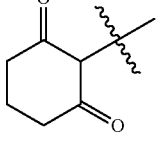 | Cl | 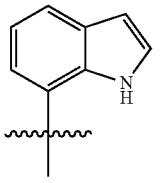 [SMILES: *c1cccc2cc[nH]c12] | H |
| 247 | 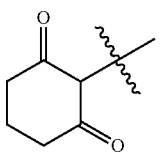 [SMILES: *C1C(=O)CCCC1=O] | Cl | 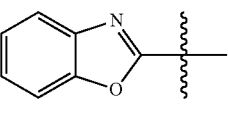 [SMILES: *c1nc2ccccc2o1] | H |

-continued

| Compound No. | Q | X | Y | Z |
|---|---|---|---|---|
| 248 | 2,6-dioxocyclohexyl | Cl | benzothiazol-6-yl | H |
| 249 | 2,6-dioxocyclohexyl | Cl | 1H-benzimidazol-5-yl | H |
| 250 | 2,6-dioxocyclohexyl | Cl | benzo[c]isoxazol-5-yl | H |
| 251 | 2,6-dioxocyclohexyl | Cl | imidazo[1,2-b]pyridazin-6-yl | H |
| 252 | 2,6-dioxocyclohexyl | Cl | 1H-benzotriazol-5-yl | H |
| 253 | 2,6-dioxocyclohexyl | Cl | 9H-purin-2-yl | H |
| 254 | 2,6-dioxocyclohexyl | Cl | [1,2,4]triazolo[1,5-a]pyrimidin-7-yl | H |
| 255 | 2,6-dioxocyclohexyl | Cl | [1,2,4]triazolo[1,5-c]pyrimidin-8-yl | H |
| 256 | 2,6-dioxocyclohexyl | Cl | anthracen-2-yl | H |

| Compound No. | Q | X | Y | Z |
|---|---|---|---|---|
| 257 | 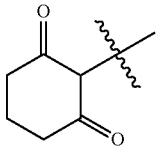 [SMILES: *C1C(=O)CCCC1=O] | Cl | 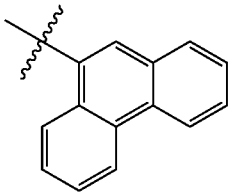 [SMILES: *c1cc2ccccc2c2ccccc12] | H |
| 258 | 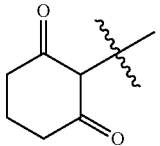 [SMILES: *C1C(=O)CCCC1=O] | Cl | 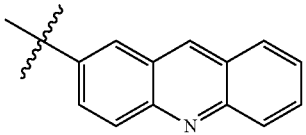 [SMILES: *c1ccc2nc3ccccc3cc2c1] | H |
| 259 | 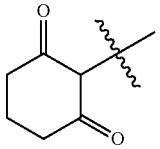 [SMILES: *C1C(=O)CCCC1=O] | Cl | 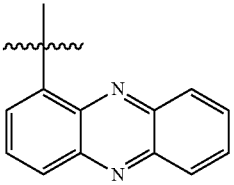 [SMILES: *c1cccc2nc3ccccc3nc12] | H |
| 260 | 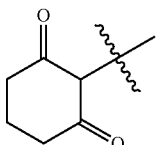 | Cl | 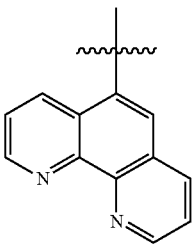 [SMILES: *c1cc2cccnc2c2ncccc12] | H |
| 261 | 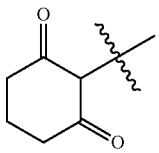 [SMILES: *C1C(=O)CCCC1=O] | Cl | 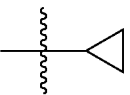 [SMILES: *C1CC1] | H |
| 262 | 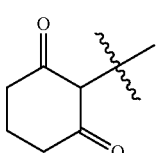 | Cl | 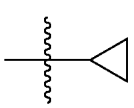 [SMILES: *C1CC1] | H |
| 263 | 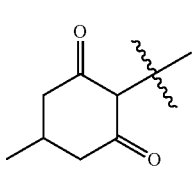 [SMILES: *C1C(=O)CC(C)CC1=O] | Cl | 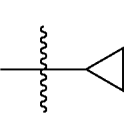 [SMILES: *C1CC1] | H |
| 264 | 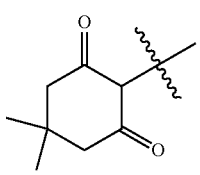 [SMILES: *C1C(=O)CC(C)(C)CC1=O] | Cl | 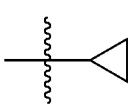 [SMILES: *C1CC1] | H |

| Compound No. | Q | X | Y | Z |
|---|---|---|---|---|
| 265 | 2,2-dimethyl-4,6-dioxocyclohexyl | Cl | cyclopropyl | H |
| 266 | 2,2,6,6-tetramethyl-3,5-dioxocyclohexyl | Cl | cyclopropyl | H |
| 267 | 4-ethyl-2,6-dioxocyclohexyl | Cl | cyclopropyl | H |
| 268 | 2,4,6-trioxocyclohexyl | Cl | cyclopropyl | H |
| 269 | 2,2,6,6-tetramethyl-3,4,5-trioxocyclohexyl | Cl | cyclopropyl | H |
| 270 | 1,3-dioxospiro[2.5]cyclohexyl | Cl | cyclopropyl | H |
| 271 | 2,4-dioxobicyclo[4.1.0]heptyl | Cl | cyclopropyl | H |
| 272 | 5,5-dimethyl-2,4-dioxobicyclo[4.1.0]heptyl | Cl | cyclopropyl | H |
| 273 | 2,4-dioxobicyclo[3.2.1]octyl | F | cyclopropyl | H |

-continued

| Compound No. | Q | X | Y | Z |
|---|---|---|---|---|
| 274 | bicyclic diketone | Cl | cyclopropyl | H |
| 275 | bicyclic diketone | Br | cyclopropyl | H |
| 276 | bicyclic diketone | I | cyclopropyl | H |
| 283 | bicyclic diketone | -S-CH₃ | cyclopropyl | H |
| 292 | 3-ONa-cyclohex-2-enone | Cl | isooctyl | H |
| 293 | 3-ONa-cyclohex-2-enone | Cl | 3-ethylheptyl | H |
| 294 | 3-ONa-cyclohex-2-enone | Cl | branched alkyl | H |
| 295 | 3-ONa-cyclohex-2-enone | Cl | branched alkyl | H |
| 296 | 3-ONa-cyclohex-2-enone | Cl | branched alkyl | H |

-continued

| Compound No. | Q | X | Y | Z |
|---|---|---|---|---|
| 297 | 3-ONa-cyclohex-2-enone | Cl | isopropenyl (2-methylprop-1-en-1-yl attachment) | H |
| 298 | 3-ONa-cyclohex-2-enone | Cl | 1,2,2-trifluorovinyl | H |
| 299 | 3-ONa-cyclohex-2-enone | Cl | 2-chloroethyl | H |
| 300 | 3-ONa-cyclohex-2-enone | Cl | 1-chloro-1-methylethyl (2-chloropropan-2-yl) | H |
| 301 | 3-ONa-cyclohex-2-enone | Cl | 3-chloropropyl | H |
| 302 | 3-ONa-cyclohex-2-enone | Cl | CHO (formyl) | H |
| 303 | 3-ONa-cyclohex-2-enone | Cl | acetyl (C(O)CH$_3$) | H |
| 304 | 3-ONa-cyclohex-2-enone | Cl | N,N-dimethylcarbamoyl | H |
| 305 | 3-ONa-cyclohex-2-enone | Cl | tetrahydrofuran-2-yl | H |

-continued

| Compound No. | Q | X | Y | Z |
|---|---|---|---|---|
| 306 | 3-ONa-2-yl-cyclohex-2-enone | Cl | tetrahydrofuran-3-yl | H |
| 307 | 3-ONa-2-yl-cyclohex-2-enone | Cl | 5,5-diphenyl-4,5-dihydroisoxazol-3-yl | H |
| 308 | 3-ONa-2-yl-cyclohex-2-enone | Cl | phenyl | H |
| 309 | 3-ONa-2-yl-cyclohex-2-enone | Cl | pyridin-3-yl | H |
| 310 | 3-ONa-2-yl-cyclohex-2-enone | Cl | thiophen-2-yl | H |
| 311 | 3-ONa-2-yl-cyclohex-2-enone | Cl | thiophen-3-yl | H |
| 312 | 3-phenoxy-2-yl-cyclohexanone | Cl | cyclopropyl | H |

-continued

| Compound No. | Q | X | Y | Z |
|---|---|---|---|---|
| 313 | 2-(phenylthio)cyclohex-2-en-1-one attached | Cl | cyclopropyl | H |
| 314 | 4-methoxy-bicyclo[4.1.0]heptan-2-one attached | Cl | cyclopropyl | H |
| 315 | acetoxy-bicyclo[2.2.1] ketone attached | Cl | cyclopropyl | H |
| 316 | 5-hydroxy-1-methyl-1H-pyrazol-4-yl | F | cyclopropyl | H |
| 317 | 5-hydroxy-1-methyl-1H-pyrazol-4-yl | Cl | cyclopropyl | H |
| 318 | 5-hydroxy-1-methyl-1H-pyrazol-4-yl | Br | cyclopropyl | H |
| 319 | 5-hydroxy-1-methyl-1H-pyrazol-4-yl | I | cyclopropyl | H |
| 322 | 5-hydroxy-1-methyl-1H-pyrazol-4-yl | cyclopropyl | cyclopropyl | H |
| 326 | 5-hydroxy-1-methyl-1H-pyrazol-4-yl | SCH$_3$ | cyclopropyl | H |

-continued

| Compound No. | Q | X | Y | Z |
|---|---|---|---|---|
| 334 | 1-methyl-5-hydroxy-pyrazol-4-yl | F | cyclopropyl | H |
| 335 | 1-methyl-5-hydroxy-pyrazol-4-yl | Cl | cyclopropyl | H |
| 336 | 1-methyl-5-hydroxy-pyrazol-4-yl | Br | CH₃ | H |
| 337 | 1-methyl-5-hydroxy-pyrazol-4-yl | I | CH₃ | H |
| 340 | 1-methyl-5-hydroxy-pyrazol-4-yl | cyclopropyl-CH₂ | CH₃ | H |
| 344 | 1-methyl-5-hydroxy-pyrazol-4-yl | -CH(SCH₃)- | CH₃ | H |
| 351 | 1-methyl-5-hydroxy-pyrazol-4-yl | Cl | H | H |
| 352 | 1-methyl-5-hydroxy-pyrazol-4-yl | Cl | F | H |
| 353 | 1-methyl-5-hydroxy-pyrazol-4-yl | Cl | Cl | H |
| 354 | 1-methyl-5-hydroxy-pyrazol-4-yl | Cl | Br | H |

-continued

| Compound No. | Q | X | Y | Z |
|---|---|---|---|---|
| 355 | 1-methyl-5-hydroxy-pyrazol-4-yl | Cl | I | H |
| 356 | 1-methyl-5-hydroxy-pyrazol-4-yl | Cl | CHF$_2$ | H |
| 357 | 1-methyl-5-hydroxy-pyrazol-4-yl | Cl | CF$_3$ | H |
| 358 | 1-methyl-5-hydroxy-pyrazol-4-yl | Cl | CH$_2$CH$_2$Cl | H |
| 359 | 1-methyl-5-hydroxy-pyrazol-4-yl | Cl | CH$_2$CH$_3$ | H |
| 360 | 1-methyl-5-hydroxy-pyrazol-4-yl | Cl | CH(CH$_3$)$_2$ | H |
| 361 | 1-methyl-5-hydroxy-pyrazol-4-yl | Cl | C(CH$_3$)$_3$ | H |
| 362 | 1-methyl-5-hydroxy-pyrazol-4-yl | Cl | CH$_2$CH=CH$_2$ | H |
| 363 | 1-methyl-5-hydroxy-pyrazol-4-yl | Cl | CF=CF$_2$ | H |
| 364 | 1-methyl-5-hydroxy-pyrazol-4-yl | Cl | C≡CH | H |

-continued

| Compound No. | Q | X | Y | Z |
|---|---|---|---|---|
| 365 | 1-methyl-5-hydroxy-pyrazol-4-yl | Cl | 1-methyl-cyclopropyl | H |
| 366 | 1-methyl-5-hydroxy-pyrazol-4-yl | Cl | 1,2-dimethyl-cyclopropyl | H |
| 367 | 1-methyl-5-hydroxy-pyrazol-4-yl | Cl | 2-fluoro-cyclopropyl | H |
| 368 | 1-methyl-5-hydroxy-pyrazol-4-yl | Cl | 1-cyano-cyclopropyl | H |
| 369 | 1-methyl-5-hydroxy-pyrazol-4-yl | Cl | 2-methyl-cyclopropyl | H |
| 370 | 1-methyl-5-hydroxy-pyrazol-4-yl | Cl | 2,2-difluoro-cyclopropyl | H |
| 371 | 1-methyl-5-hydroxy-pyrazol-4-yl | Cl | cyclobutyl | H |
| 372 | 1-methyl-5-hydroxy-pyrazol-4-yl | Cl | cyclopent-1-enyl | H |
| 373 | 1-methyl-5-hydroxy-pyrazol-4-yl | Cl | cyclopropylmethyl | H |
| 374 | 1-methyl-5-hydroxy-pyrazol-4-yl | Cl | 1-methyl-azetidin-3-yl | H |

-continued

| Compound No. | Q | X | Y | Z |
|---|---|---|---|---|
| 375 | 1-methyl-5-hydroxy-pyrazol-4-yl | Cl | tetrahydrofuran-2-yl | H |
| 376 | 1-methyl-5-hydroxy-pyrazol-4-yl | Cl | 5,5-diphenyl-4,5-dihydroisoxazol-3-yl | H |
| 377 | 1-methyl-5-hydroxy-pyrazol-4-yl | Cl | tetrahydro-2H-pyran-4-yl | H |
| 378 | 1-methyl-5-hydroxy-pyrazol-4-yl | Cl | 1-methylpiperidin-4-yl | H |
| 379 | 1-methyl-5-hydroxy-pyrazol-4-yl | Cl | -CH$_2$CN | H |
| 380 | 1-methyl-5-hydroxy-pyrazol-4-yl | Cl | -OCH$_3$ | H |
| 381 | 1-methyl-5-hydroxy-pyrazol-4-yl | Cl | -CH$_2$OC$_2$H$_5$ | H |
| 382 | 1-methyl-5-hydroxy-pyrazol-4-yl | Cl | -SCH$_3$ | H |
| 383 | 1-methyl-5-hydroxy-pyrazol-4-yl | Cl | -S(O)CH$_3$ | H |

-continued

| Compound No. | Q | X | Y | Z |
|---|---|---|---|---|
| 384 | 1-methyl-5-hydroxy-pyrazol-4-yl | Cl | methylsulfonyl-methyl | H |
| 385 | 1-methyl-5-hydroxy-pyrazol-4-yl | Cl | (isopropylthio)methyl | H |
| 386 | 1-methyl-5-hydroxy-pyrazol-4-yl | Cl | (isopropylsulfinyl)methyl | H |
| 387 | 1-methyl-5-hydroxy-pyrazol-4-yl | Cl | (isopropylsulfonyl)methyl | H |
| 388 | 1-methyl-5-hydroxy-pyrazol-4-yl | Cl | (dimethylamino)methyl | H |
| 389 | 1-methyl-5-hydroxy-pyrazol-4-yl | Cl | acetyl (CHO-methyl) | H |
| 390 | 1-methyl-5-hydroxy-pyrazol-4-yl | Cl | acetyl (C(O)CH$_3$) | H |
| 391 | 1-methyl-5-hydroxy-pyrazol-4-yl | Cl | N,N-dimethylcarbamoyl | H |
| 392 | 1-methyl-5-hydroxy-pyrazol-4-yl | Cl | benzyl | H |

-continued

| Compound No. | Q | X | Y | Z |
|---|---|---|---|---|
| 393 | 1-methyl-5-hydroxy-pyrazol-4-yl | Cl | pyridin-3-ylmethyl | H |
| 394 | 1-methyl-5-hydroxy-pyrazol-4-yl | Cl | thiophen-2-ylmethyl | H |
| 395 | 1-methyl-5-hydroxy-pyrazol-4-yl | Cl | phenyl | H |
| 396 | 1-methyl-5-hydroxy-pyrazol-4-yl | Cl | 4-fluorophenyl | H |
| 397 | 1-methyl-5-hydroxy-pyrazol-4-yl | Cl | 2-cyanophenyl | H |
| 398 | 1-methyl-5-hydroxy-pyrazol-4-yl | Cl | pyridin-4-yl | H |
| 399 | 1-methyl-5-hydroxy-pyrazol-4-yl | Cl | 3,6-dichloropyridin-2-yl | H |
| 400 | 1-methyl-5-hydroxy-pyrazol-4-yl | Cl | pyrimidin-5-yl | H |

| Compound No. | Q | X | Y | Z |
|---|---|---|---|---|
| 401 | 1-methyl-5-hydroxy-pyrazol-4-yl | Cl | pyridazin-4-yl | H |
| 402 | 1-methyl-5-hydroxy-pyrazol-4-yl | Cl | pyrazin-2-yl | H |
| 403 | 1-methyl-5-hydroxy-pyrazol-4-yl | Cl | furan-3-yl | H |
| 404 | 1-methyl-5-hydroxy-pyrazol-4-yl | Cl | thiophen-3-yl | H |
| 405 | 1-methyl-5-hydroxy-pyrazol-4-yl | Cl | 1-methyl-pyrrol-2-yl | H |
| 406 | 1-methyl-5-hydroxy-pyrazol-4-yl | Cl | 1,3-dimethyl-pyrazol-4-yl | H |
| 407 | 1-methyl-5-hydroxy-pyrazol-4-yl | Cl | isoxazol-3-yl | H |
| 408 | 1-methyl-5-hydroxy-pyrazol-4-yl | Cl | oxazol-5-yl | H |
| 409 | 1-methyl-5-hydroxy-pyrazol-4-yl | Cl | thiazol-4-yl | H |

-continued
| Compound No. | Q | X | Y | Z |
|---|---|---|---|---|
| 410 | 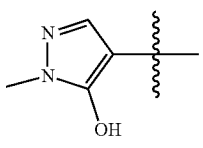 [SMILES: *c1cnn(C)c1O] | Cl | 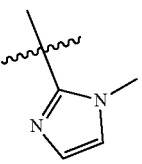 [SMILES: *c1nccn1C] | H |
| 411 | 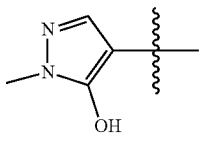 [SMILES: *c1cnn(C)c1O] | Cl | 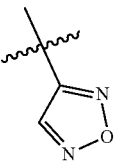 [SMILES: *c1cnon1] | H |
| 412 | 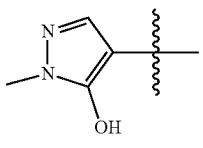 [SMILES: *c1cnn(C)c1O] | Cl | 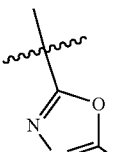 | H |
| 413 | 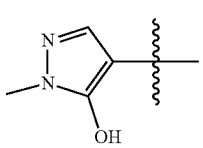 [SMILES: *c1cnn(C)c1O] | Cl | 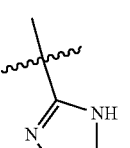 | H |
| 414 | 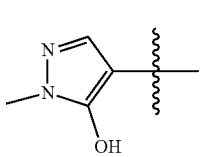 [SMILES: *c1cnn(C)c1O] | Cl | 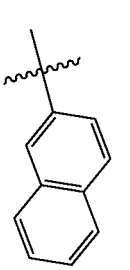 [SMILES: *c1ccc2ccccc2c1] | H |
| 415 | 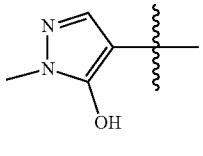 [SMILES: *c1cnn(C)c1O] | Cl | 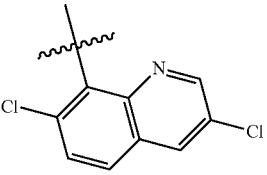 [SMILES: *c1c(Cl)ccc2cc(Cl)cnc12] | H |
| 416 | 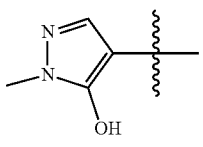 [SMILES: *c1cnn(C)c1O] | Cl | 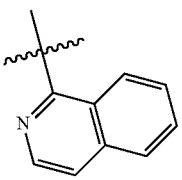 [SMILES: *c1nccc2ccccc12] | H |
| 417 | 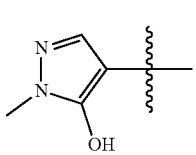 [SMILES: *c1cnn(C)c1O] | Cl | 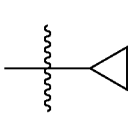 [SMILES: *C1CC1] | H |

-continued

| Compound No. | Q | X | Y | Z |
|---|---|---|---|---|
| 418 | 1-methyl-5-hydroxy-pyrazol-4-yl | Cl | -CH(CH₃)-S-CH(CH₃)₂ | H |
| 419 | 3-cyclopropyl-1-methyl-5-hydroxy-pyrazol-4-yl | Cl | cyclopropyl | H |
| 420 | 3-CF₃-1-methyl-5-hydroxy-pyrazol-4-yl | Cl | cyclopropyl | H |
| 421 | 1-ethyl-5-hydroxy-pyrazol-4-yl | Cl | cyclopropyl | H |
| 422 | 3-methyl-1-ethyl-5-hydroxy-pyrazol-4-yl | Cl | cyclopropyl | H |
| 423 | 1-(difluoromethyl)-5-hydroxy-pyrazol-4-yl | Cl | cyclopropyl | H |
| 424 | 3-CF₃-1-phenyl-5-hydroxy-pyrazol-4-yl | Cl | cyclopropyl | H |
| 425 | isoxazol-4-yl | Cl | cyclopropyl | H |
| 426 | 5-methyl-isoxazol-4-yl | Cl | cyclopropyl | H |

-continued
| Compound No. | Q | X | Y | Z |
|---|---|---|---|---|
| 427 | 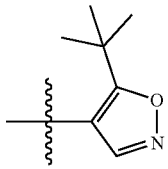 | Cl | 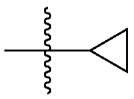 [SMILES: *C1CC1] | H |
| 428 | 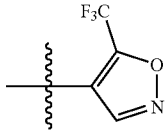 | Cl | 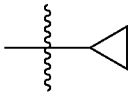 [SMILES: *C1CC1] | H |
| 429 | 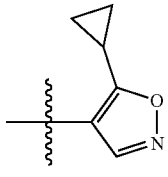 [SMILES: *c1cnoc1C1CC1] | F | 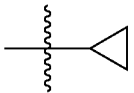 [SMILES: *C1CC1] | H |
| 430 | 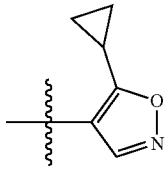 [SMILES: *c1cnoc1C1CC1] | Cl | 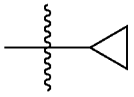 | H |
| 431 | 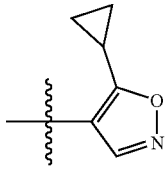 [SMILES: *c1cnoc1C1CC1] | Br | 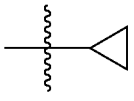 | H |
| 432 | 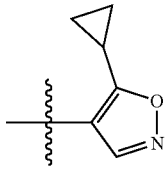 [SMILES: *c1cnoc1C1CC1] | I | 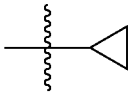 | H |
| 435 | 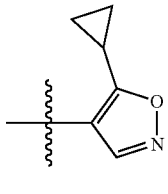 [SMILES: *c1cnoc1C1CC1] | 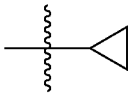 | 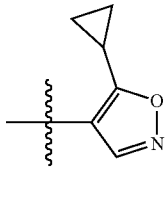 [SMILES: *c1cnoc1C1CC1] | H |
| 439 | 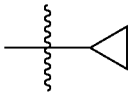 |  |  | H |

-continued
| Compound No. | Q | X | Y | Z |
|---|---|---|---|---|
| 446 | 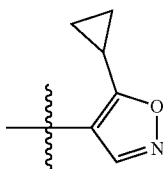 | F | CH₃ | H |
| 447 | 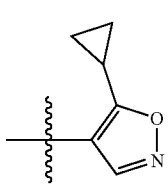 [SMILES: *c1cnoc1C1CC1] | F | CH₃ | H |
| 448 | 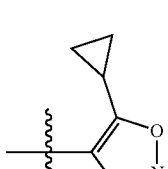 | Cl | CH₃ | H |
| 449 | 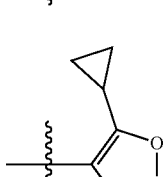 | Br | CH₃ | H |
| 450 | 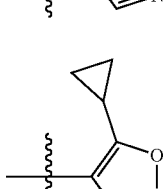 | I | CH₃ | H |
| 453 | 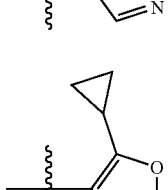 | 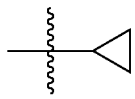 [SMILES: *C1CC1] | CH₃ | H |
| 457 | 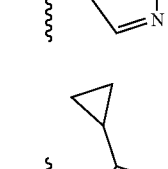 | 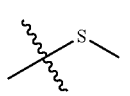 | CH₃ | H |
| 464 | 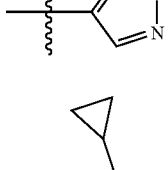 | Cl | H | H |

-continued
| Compound No. | Q | X | Y | Z |
|---|---|---|---|---|
| 465 | 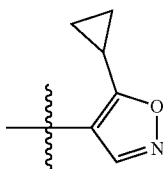 | Cl | F | H |
| 466 | 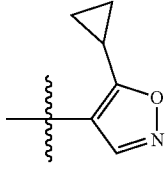 [SMILES: *c1cnoc1C1CC1] | Cl | Cl | H |
| 467 | 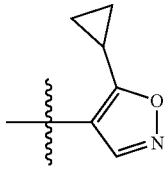 | Cl | Br | H |
| 468 | 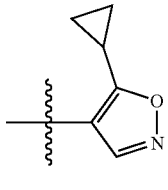 [SMILES: *c1cnoc1C1CC1] | Cl | I | H |
| 469 | 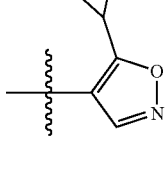 | Cl | 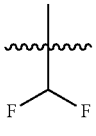 | H |
| 470 | 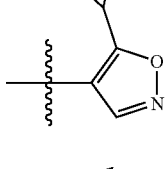 | Cl | CF$_3$ | H |
| 471 | 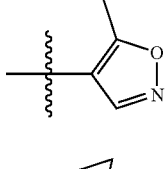 | Cl | 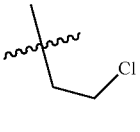 | H |
| 472 | 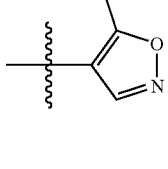 | Cl | CH$_2$CH$_3$ | H |

-continued
| Compound No. | Q | X | Y | Z |
|---|---|---|---|---|
| 473 | 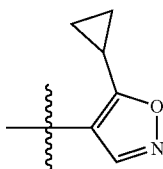 | Cl | 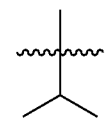 | H |
| 474 | 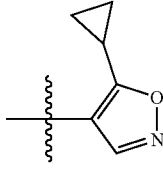 | Cl | 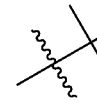 | H |
| 475 | 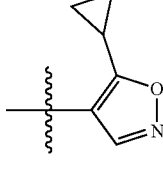 | Cl |  | H |
| 476 | 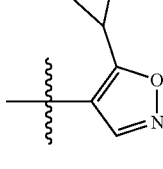 | Cl | 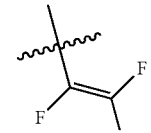 | H |
| 477 | 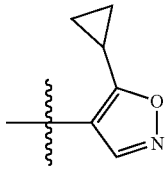 [SMILES: *c1cnoc1C1CC1] | Cl | 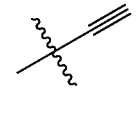 [SMILES: *C#C] | H |
| 478 | 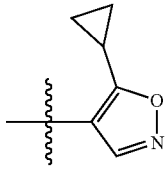 [SMILES: *c1cnoc1C1CC1] | Cl |  | H |
| 479 | 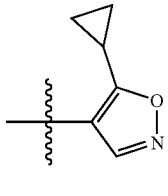 [SMILES: *c1cnoc1C1CC1] | Cl | 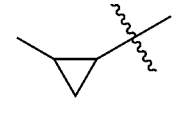 [SMILES: *C1CC1C] | H |
| 480 | 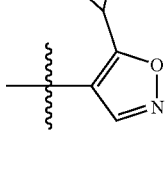 | Cl | 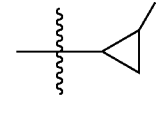 | H |

-continued
| Compound No. | Q | X | Y | Z |
|---|---|---|---|---|
| 481 | 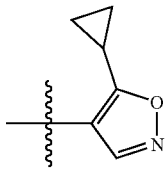 [SMILES: *c1cnoc1C1CC1] | Cl | 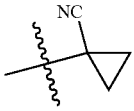 [SMILES: *C1(C#N)CC1] | H |
| 482 | 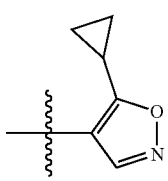 [SMILES: *c1cnoc1C1CC1] | Cl | 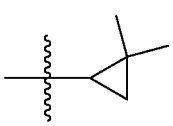 [SMILES: *C1CC1(C)C] | H |
| 483 | 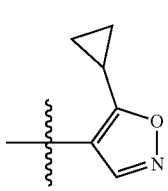 | Cl | 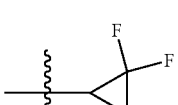 | H |
| 484 | 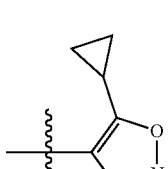 | Cl | 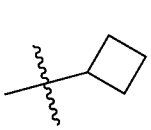 [SMILES: *C1CCC1] | H |
| 485 | 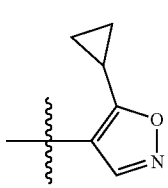 [SMILES: *c1cnoc1C1CC1] | Cl | 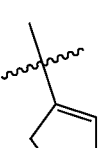 | H |
| 486 | 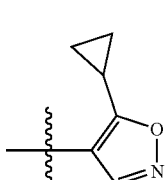 | Cl |  | H |
| 487 | 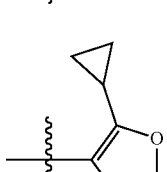 | Cl | 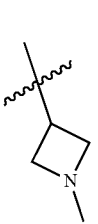 [SMILES: *C1CN(C)C1] | H |
| 488 | 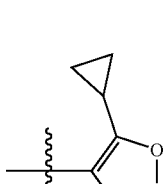 | Cl |  | H |

-continued
| Compound No. | Q | X | Y | Z |
|---|---|---|---|---|
| 489 | 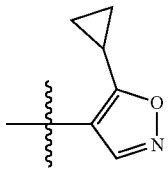 [SMILES: *c1cnoc1C1CC1] | Cl | 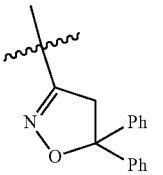 [SMILES: *C1=NOC(c2ccccc2)(c2ccccc2)C1] | H |
| 490 | 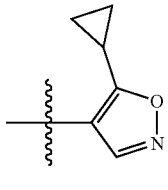 [SMILES: *c1cnoc1C1CC1] | Cl | 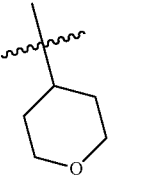 [SMILES: *C1CCOCC1] | H |
| 491 | 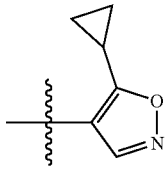 [SMILES: *c1cnoc1C1CC1] | Cl | 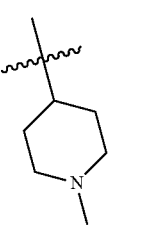 [SMILES: *C1CCN(C)CC1] | H |
| 492 | 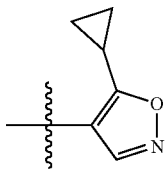 [SMILES: *c1cnoc1C1CC1] | Cl | 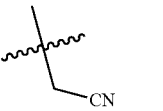 | H |
| 493 | 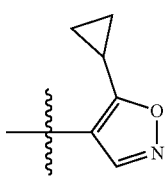 | Cl | 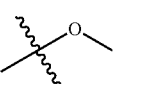 | H |
| 494 | 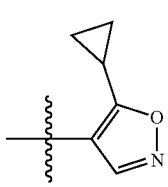 | Cl | 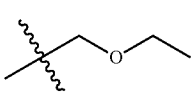 | H |
| 495 | 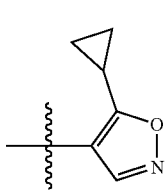 [SMILES: *c1cnoc1C1CC1] | Cl | 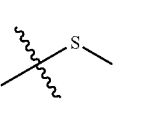 | H |
| 496 | 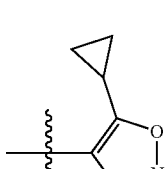 | Cl | 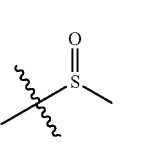 | H |

| Compound No. | Q | X | Y | Z |
|---|---|---|---|---|
| 497 | 4-cyclopropyl-isoxazol-3-yl | Cl | -S(O)₂CH₃ | H |
| 498 | 4-cyclopropyl-isoxazol-3-yl | Cl | -CH₂-S-CH(CH₃)₂ | H |
| 499 | 4-cyclopropyl-isoxazol-3-yl | Cl | -CH₂-S(O)-CH(CH₃)₂ | H |
| 500 | 4-cyclopropyl-isoxazol-3-yl | Cl | -C(CH₃)₂-S(O)₂-CH(CH₃)₂ | H |
| 501 | 4-cyclopropyl-isoxazol-3-yl | Cl | -C(CH₃)₂-N(CH₃)₂ | H |
| 502 | 4-cyclopropyl-isoxazol-3-yl | Cl | -CH(CH₃)-CHO | H |
| 503 | 4-cyclopropyl-isoxazol-3-yl | Cl | -C(CH₃)₂-C(O)CH₃ | H |
| 504 | 4-cyclopropyl-isoxazol-3-yl | Cl | -C(CH₃)₂-C(O)N(CH₃)₂ | H |

| Compound No. | Q | X | Y | Z |
|---|---|---|---|---|
| 505 | 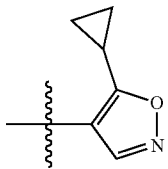 [SMILES: *c1cnoc1C1CC1] | Cl | 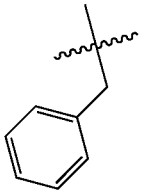 [SMILES: *Cc1ccccc1] | H |
| 506 | 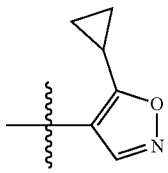 | Cl | 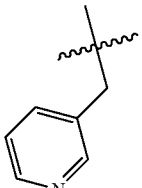 | H |
| 507 | 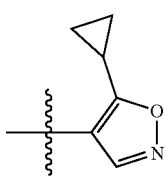 [SMILES: *c1cnoc1C1CC1] | Cl | 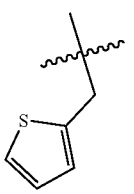 [SMILES: *Cc1cccs1] | H |
| 508 | 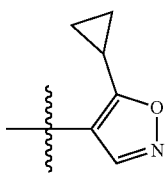 [SMILES: *c1cnoc1C1CC1] | Cl | 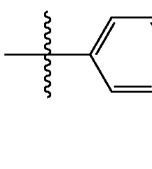 | H |
| 509 | 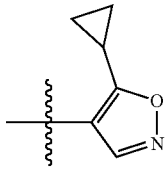 [SMILES: *c1cnoc1C1CC1] | Cl | 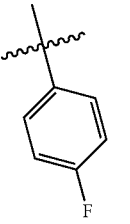 [SMILES: *c1ccc(F)cc1] | H |
| 510 | 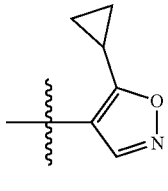 | Cl | 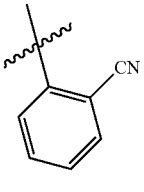 [SMILES: *c1ccccc1C#N] | H |
| 511 | 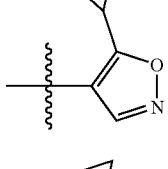 | Cl | 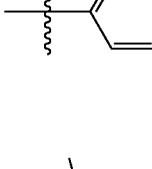 | H |
| 512 | 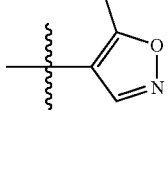 | Cl | 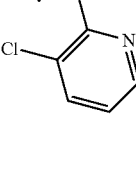 | H |

-continued

| Compound No. | Q | X | Y | Z |
|---|---|---|---|---|
| 513 | 4-cyclopropylisoxazol-3-yl | Cl | pyrimidin-5-yl | H |
| 514 | 4-cyclopropylisoxazol-3-yl | Cl | pyridazin-4-yl | H |
| 515 | 4-cyclopropylisoxazol-3-yl | Cl | pyrazin-2-yl | H |
| 516 | 4-cyclopropylisoxazol-3-yl | Cl | furan-3-yl | H |
| 517 | 4-cyclopropylisoxazol-3-yl | Cl | thiophen-3-yl | H |
| 518 | 4-cyclopropylisoxazol-3-yl | Cl | 1-methyl-1H-pyrrol-2-yl | H |
| 519 | 4-cyclopropylisoxazol-3-yl | Cl | 1,3-dimethyl-1H-pyrazol-4-yl | H |
| 520 | 4-cyclopropylisoxazol-3-yl | Cl | isoxazol-3-yl | H |

-continued

| Compound No. | Q | X | Y | Z |
|---|---|---|---|---|
| 521 | 5-cyclopropyl-isoxazol-4-yl | Cl | oxazol-5-yl | H |
| 522 | 5-cyclopropyl-isoxazol-4-yl | Cl | thiazol-4-yl | H |
| 523 | 5-cyclopropyl-isoxazol-4-yl | Cl | 1-methyl-imidazol-2-yl | H |
| 524 | 5-cyclopropyl-isoxazol-4-yl | Cl | 1,2,5-oxadiazol-3-yl | H |
| 525 | 5-cyclopropyl-isoxazol-4-yl | Cl | 5-methyl-1,3,4-oxadiazol-2-yl | H |
| 526 | 5-cyclopropyl-isoxazol-4-yl | Cl | 4H-1,2,4-triazol-3-yl | H |
| 527 | 5-cyclopropyl-isoxazol-4-yl | Cl | naphthalen-2-yl | H |
| 528 | 5-cyclopropyl-isoxazol-4-yl | Cl | 3,7-dichloroquinolin-8-yl | H |

-continued

| Compound No. | Q | X | Y | Z |
|---|---|---|---|---|
| 529 | 4-cyclopropyl-isoxazol-5-yl (attached at 4-position) | Cl | isoquinolin-1-yl | H |
| 530 | 5-cyclopropyl-3-(methylthio)isoxazol-4-yl | Cl | cyclopropyl | H |
| 531 | 5-cyclopropyl-3-(methylthio)isoxazol-4-yl | Cl | cyclopropyl | H |
| 532 | 5-cyclopropyl-3-(methoxycarbonyl)isoxazol-4-yl | Cl | cyclopropyl | H |
| 533 | 5-cyclopropyl-3-(ethoxycarbonyl)isoxazol-4-yl | Cl | cyclopropyl | H |
| 534 | 2-cyano-1-(2,2-dimethylpropanoyl) substituent | Cl | cyclopropyl | H |
| 535 | 2-cyano-1-(cyclopropanecarbonyl) substituent | Cl | cyclopropyl | H |
| 536 | 2-cyano-1-(cyclopropanecarbonyl) substituent | F | cyclopropyl | H |

-continued

| Compound No. | Q | X | Y | Z |
|---|---|---|---|---|
| 537 | cyclopropyl-C(O)-CH(CN)- | Cl | cyclopropyl | H |
| 538 | cyclopropyl-C(O)-CH(CN)- | Br | cyclopropyl | H |
| 539 | cyclopropyl-C(O)-CH(CN)- | I | cyclopropyl | H |
| 542 | cyclopropyl-C(O)-CH(CN)- | cyclopropyl | cyclopropyl | H |
| 546 | cyclopropyl-C(O)-CH(CN)- | -S-CH₃ | cyclopropyl | H |
| 553 | cyclopropyl-C(O)-CH(CN)- | Cl | H | H |
| 554 | cyclopropyl-C(O)-CH(CN)- | Cl | F | H |
| 555 | cyclopropyl-C(O)-CH(CN)- | Cl | Cl | H |
| 556 | cyclopropyl-C(O)-CH(CN)- | Cl | Br | H |
| 557 | cyclopropyl-C(O)-CH(CN)- | Cl | I | H |
| 558 | cyclopropyl-C(O)-CH(CN)- | Cl | -CHF₂ | H |

-continued

| Compound No. | Q | X | Y | Z |
|---|---|---|---|---|
| 559 | cyclopropyl-C(=O)-CH(CN)- | Cl | CF₃ | H |
| 560 | cyclopropyl-C(=O)-CH(CN)- | Cl | -C(CH₃)₂CH₂Cl | H |
| 561 | cyclopropyl-C(=O)-CH(CN)- | Cl | CH₃ | H |
| 562 | cyclopropyl-C(=O)-CH(CN)- | Cl | CH₂CH₃ | H |
| 563 | cyclopropyl-C(=O)-CH(CN)- | Cl | -CH(CH₃)₂ | H |
| 564 | cyclopropyl-C(=O)-CH(CN)- | Cl | -C(CH₃)₃ | H |
| 565 | cyclopropyl-C(=O)-CH(CN)- | Cl | -CH₂CH=CH₂ | H |
| 566 | cyclopropyl-C(=O)-CH(CN)- | Cl | -C(F)=CF₂ | H |
| 567 | cyclopropyl-C(=O)-CH(CN)- | Cl | -C≡CH | H |
| 568 | cyclopropyl-C(=O)-CH(CN)- | Cl | cyclopropyl | H |

-continued

| Compound No. | Q | X | Y | Z |
|---|---|---|---|---|
| 569 | cyclopropyl-C(=O)-CH(CN)- | Cl | methylcyclopropyl | H |
| 570 | cyclopropyl-C(=O)-CH(CN)- | Cl | 2-fluorocyclopropyl-methyl | H |
| 571 | cyclopropyl-C(=O)-CH(CN)- | Cl | 1-cyanocyclopropyl-methyl | H |
| 572 | cyclopropyl-C(=O)-CH(CN)- | Cl | 2-methylcyclopropyl-methyl | H |
| 573 | cyclopropyl-C(=O)-CH(CN)- | Cl | 2,2-difluorocyclopropyl-methyl | H |
| 574 | cyclopropyl-C(=O)-CH(CN)- | Cl | cyclobutyl | H |
| 575 | cyclopropyl-C(=O)-CH(CN)- | Cl | cyclopentenyl | H |
| 576 | cyclopropyl-C(=O)-CH(CN)- | Cl | cyclopropylmethyl | H |
| 577 | cyclopropyl-C(=O)-CH(CN)- | Cl | 1-methylazetidin-3-yl | H |
| 578 | cyclopropyl-C(=O)-CH(CN)- | Cl | tetrahydrofuran-2-yl | H |

-continued

| Compound No. | Q | X | Y | Z |
|---|---|---|---|---|
| 579 | cyclopropyl-C(O)-CH(CN)- | Cl | 3-yl-5,5-diphenyl-4,5-dihydroisoxazole | H |
| 580 | cyclopropyl-C(O)-CH(CN)- | Cl | tetrahydro-2H-pyran-4-yl | H |
| 581 | cyclopropyl-C(O)-CH(CN)- | Cl | 1-methylpiperidin-4-yl | H |
| 582 | cyclopropyl-C(O)-CH(CN)- | Cl | -CH₂CN | H |
| 583 | cyclopropyl-C(O)-CH(CN)- | Cl | -OCH₃ | H |
| 584 | cyclopropyl-C(O)-CH(CN)- | Cl | -CH₂OCH₂CH₃ | H |
| 585 | cyclopropyl-C(O)-CH(CN)- | Cl | -SCH₃ | H |
| 586 | cyclopropyl-C(O)-CH(CN)- | Cl | -S(O)CH₃ | H |
| 587 | cyclopropyl-C(O)-CH(CN)- | Cl | -S(O)₂CH₃ | H |

-continued
| Compound No. | Q | X | Y | Z |
|---|---|---|---|---|
| 588 | 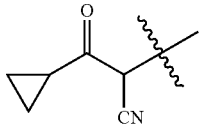 [SMILES: *C(C#N)C(=O)C1CC1] | Cl | 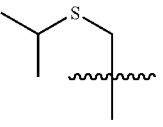 [SMILES: *CSC(C)C] | H |
| 589 | 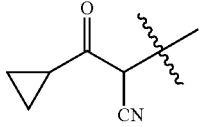 [SMILES: *C(C#N)C(=O)C1CC1] | Cl | 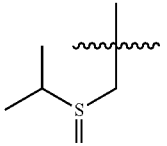 | H |
| 590 | 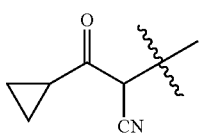 [SMILES: *C(C#N)C(=O)C1CC1] | Cl | 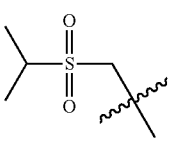 [SMILES: *CS(=O)(=O)C(C)C] | H |
| 591 | 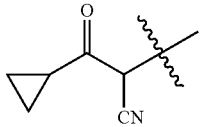 [SMILES: *C(C#N)C(=O)C1CC1] | Cl | 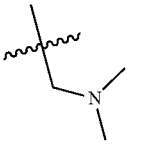 [SMILES: *CN(C)C] | H |
| 592 | 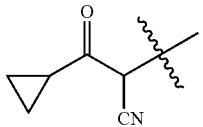 [SMILES: *C(C#N)C(=O)C1CC1] | Cl | 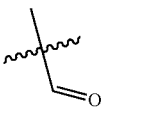 [SMILES: *C=O] | H |
| 593 | 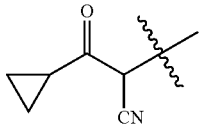 [SMILES: *C(C#N)C(=O)C1CC1] | Cl | 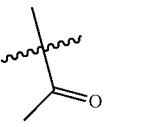 [SMILES: *C(C)=O] | H |
| 594 | 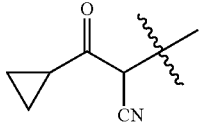 | Cl | 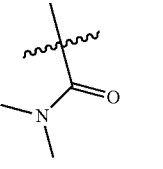 [SMILES: *C(=O)N(C)C] | H |
| 595 | 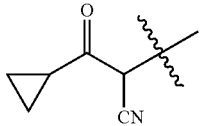 | Cl | 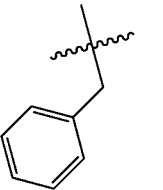 [SMILES: *Cc1ccccc1] | H |
| 596 | 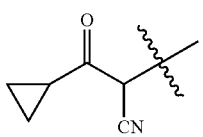 [SMILES: *C(C#N)C(=O)C1CC1] | Cl | 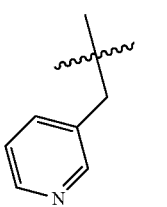 | H |

-continued

| Compound No. | Q | X | Y | Z |
|---|---|---|---|---|
| 597 | cyclopropyl-C(O)-CH(CN)-C(CH3) | Cl | thiophen-2-yl | H |
| 598 | cyclopropyl-C(O)-CH(CN)-C(CH3) | Cl | phenyl | H |
| 599 | cyclopropyl-C(O)-CH(CN)-C(CH3) | Cl | 4-fluorophenyl | H |
| 600 | cyclopropyl-C(O)-CH(CN)-C(CH3) | Cl | 2-cyanophenyl | H |
| 601 | cyclopropyl-C(O)-CH(CN)-C(CH3) | Cl | 3,6-dichloropyridin-2-yl | H |
| 602 | cyclopropyl-C(O)-CH(CN)-C(CH3) | Cl | pyridin-4-yl | H |
| 603 | cyclopropyl-C(O)-CH(CN)-C(CH3) | Cl | pyrimidin-5-yl | H |
| 604 | cyclopropyl-C(O)-CH(CN)-C(CH3) | Cl | pyridazin-4-yl | H |

-continued

| Compound No. | Q | X | Y | Z |
|---|---|---|---|---|
| 605 | cyclopropyl-C(O)-CH(CN)- | Cl | pyrazin-2-yl | H |
| 606 | cyclopropyl-C(O)-CH(CN)- | Cl | 1-methyl-1H-pyrrol-2-yl | H |
| 607 | cyclopropyl-C(O)-CH(CN)- | Cl | furan-3-yl | H |
| 608 | cyclopropyl-C(O)-CH(CN)- | Cl | thiophen-3-yl | H |
| 609 | cyclopropyl-C(O)-CH(CN)- | Cl | 1,3-dimethyl-1H-pyrazol-4-yl | H |
| 610 | cyclopropyl-C(O)-CH(CN)- | Cl | isoxazol-3-yl | H |
| 611 | cyclopropyl-C(O)-CH(CN)- | Cl | oxazol-5-yl | H |
| 612 | cyclopropyl-C(O)-CH(CN)- | Cl | thiazol-4-yl | H |
| 613 | cyclopropyl-C(O)-CH(CN)- | Cl | 1-methyl-1H-imidazol-2-yl | H |

-continued

| Compound No. | Q | X | Y | Z |
|---|---|---|---|---|
| 614 | cyclopropyl-C(O)-CH(CN)- | Cl | 1,2,5-oxadiazol-3-yl | H |
| 615 | cyclopropyl-C(O)-CH(CN)- | Cl | 5-methyl-1,3,4-oxadiazol-2-yl | H |
| 616 | cyclopropyl-C(O)-CH(CN)- | Cl | 4H-1,2,4-triazol-3-yl | H |
| 617 | cyclopropyl-C(O)-CH(CN)- | Cl | naphthalen-2-yl | H |
| 618 | cyclopropyl-C(O)-CH(CN)- | Cl | 3,7-dichloroquinolin-8-yl | H |
| 619 | cyclopropyl-C(O)-CH(CN)- | Cl | isoquinolin-1-yl | H |
| 622 | 2-(2,6-dioxocyclohexyl)- | -S-CH$_3$ | CH$_2$CH$_3$ | H |
| 623 | 2-(2,6-dioxocyclohexyl)- | -S-CH$_3$ | n-propyl | H |

-continued

| Compound No. | Q | X | Y | Z |
|---|---|---|---|---|
| 626 | 3-ONa-cyclohex-2-enone | Cl | Cl | H |
| 627 | 3-ONa-cyclohex-2-enone | Cl | Br | H |
| 628 | 3-ONa-cyclohex-2-enone | Cl | sec-butyl | H |
| 629 | 3-ONa-cyclohex-2-enone | Cl | 3-pentyl | H |
| 630 | 3-ONa-cyclohex-2-enone | Cl | neopentyl | H |
| 631 | 3-ONa-cyclohex-2-enone | Cl | 2-heptyl | H |
| 632 | 3-ONa-cyclohex-2-enone | Cl | 4-methylpent-2-yl | H |
| 633 | 3-ONa-cyclohex-2-enone | Cl | n-octyl | H |
| 634 | 3-ONa-cyclohex-2-enone | Cl | 2-methylbut-2-en-yl | H |

-continued

| Compound No. | Q | X | Y | Z |
|---|---|---|---|---|
| 635 | 3-ONa-cyclohex-2-enone-2-yl (methyl) | Cl | -C≡CH | H |
| 636 | 3-ONa-cyclohex-2-enone-2-yl (methyl) | Cl | -CH₂Cl | H |
| 637 | 3-ONa-cyclohex-2-enone-2-yl (methyl) | Cl | -(CH₂)₄Cl | H |
| 638 | 3-ONa-cyclohex-2-enone-2-yl (methyl) | Cl | -CH₂CF₃ | H |
| 639 | 3-ONa-cyclohex-2-enone-2-yl (methyl) | Cl | -CF₂CH₃ | H |
| 640 | 3-ONa-cyclohex-2-enone-2-yl (methyl) | Cl | -C(CH₃)₂CF₃ | H |
| 641 | 3-ONa-cyclohex-2-enone-2-yl (methyl) | Cl | -CH=CHCl (cis) | H |
| 642 | 3-ONa-cyclohex-2-enone-2-yl (methyl) | Cl | cyclopropyl | H |
| 643 | 3-ONa-cyclohex-2-enone-2-yl (methyl) | Cl | cyclopentyl | H |

US 12,240,843 B2
589                                                                  590
-continued
| Compound No. | Q | X | Y | Z |
|---|---|---|---|---|
| 644 | 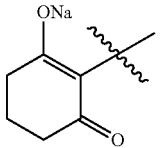 | Cl | 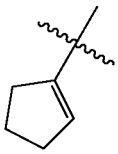 [SMILES: *C1=CCCC1] | H |
| 645 | 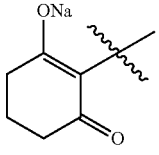 | Cl | 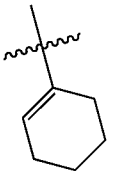 | H |
| 646 | 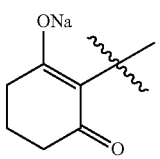 | Cl | 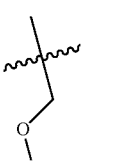 | H |
| 647 | 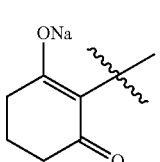 | Cl | 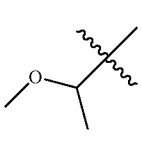 [SMILES: *C(C)OC] | H |
| 648 | 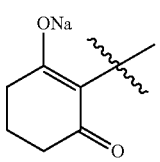 | Cl | 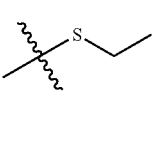 [SMILES: *SCC] | H |
| 649 | 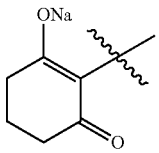 | Cl | 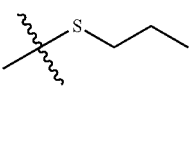 [SMILES: *SCCC] | H |
| 650 | 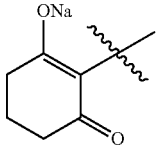 | Cl | 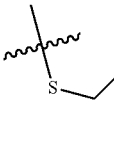 | H |
| 651 | 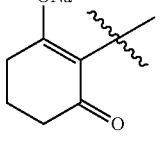 | Cl | 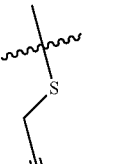 | H |
| 652 | 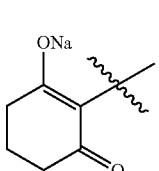 | Cl | 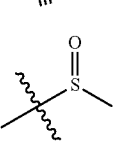 | H |

-continued

| Compound No. | Q | X | Y | Z |
|---|---|---|---|---|
| 653 | 3-ONa-2-yl-cyclohex-2-enone | Cl | NH$_2$ | H |
| 654 | 3-ONa-2-yl-cyclohex-2-enone | Cl | -N(CH$_3$)$_2$ (on CH) | H |
| 655 | 3-ONa-2-yl-cyclohex-2-enone | Cl | -N(CH$_2$CH=CH$_2$)$_2$ (on CH) | H |
| 656 | 3-ONa-2-yl-cyclohex-2-enone | Cl | -N(CH$_2$C≡CH)$_2$ (on CH) | H |
| 657 | 3-ONa-2-yl-cyclohex-2-enone | Cl | -NHC(O)CH$_3$ (on CH) | H |
| 658 | 3-ONa-2-yl-cyclohex-2-enone | Cl | -CH(OH)CH$_3$ | H |
| 659 | 3-ONa-2-yl-cyclohex-2-enone | Cl | -CH$_2$SCH$_3$ | H |
| 660 | 3-ONa-2-yl-cyclohex-2-enone | Cl | -CH$_2$N(CH$_3$)$_2$ (on CH) | H |
| 661 | 3-ONa-2-yl-cyclohex-2-enone | Cl | -CH$_2$OC(O)CH$_3$ | H |

-continued
| Compound No. | Q | X | Y | Z |
|---|---|---|---|---|
| 662 | 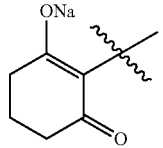 | Cl |  | H |
| 663 | 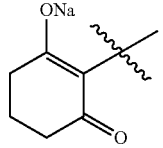 | Cl | 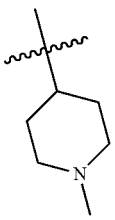 [SMILES: *C1CCN(C)CC1] | H |
| 664 | 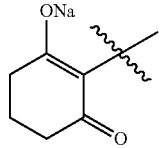 | Cl | 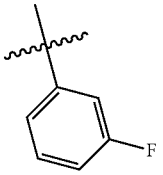 [SMILES: *c1cccc(F)c1] | H |
| 665 | 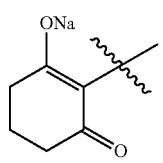 | Cl | 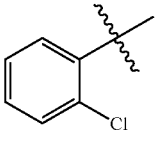 [SMILES: *c1ccccc1Cl] | H |
| 666 | 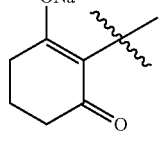 | Cl | 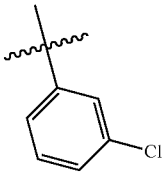 [SMILES: *c1cccc(Cl)c1] | H |
| 667 | 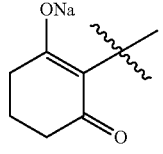 | Cl | 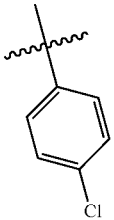 [SMILES: *c1ccc(Cl)cc1] | H |
| 668 | 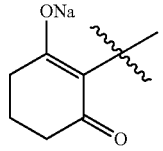 | Cl | 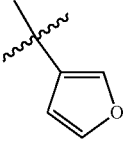 [SMILES: *c1ccoc1] | H |
| 669 | 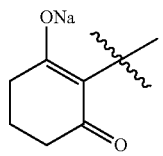 | Cl | 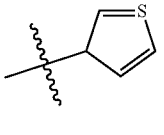 | H |

-continued

| Compound No. | Q | X | Y | Z |
|---|---|---|---|---|
| 670 | 3-ONa-cyclohex-2-enone-2-yl | Cl | isoxazol-3-yl | H |
| 671 | 3-ONa-cyclohex-2-enone-2-yl | Cl | oxazol-4-yl | H |
| 672 | 3-ONa-cyclohex-2-enone-2-yl | Cl | thiazol-2-yl | H |
| 673 | 3-ONa-cyclohex-2-enone-2-yl | Cl | thiazol-5-yl | H |
| 674 | 3-ONa-cyclohex-2-enone-2-yl | Cl | thiazol-4-yl | H |
| 675 | 3-ONa-cyclohex-2-enone-2-yl | Cl | 1-methyl-imidazol-5-yl | H |
| 676 | 3-ONa-cyclohex-2-enone-2-yl | Cl | 1-methyl-imidazol-4-yl | H |
| 677 | 3-ONa-cyclohex-2-enone-2-yl | Cl | 1-methyl-imidazol-2-yl | H |
| 678 | 3-ONa-cyclohex-2-enone-2-yl | Cl | pyridin-4-yl | H |

-continued
| Compound No. | Q | X | Y | Z |
|---|---|---|---|---|
| 679 | 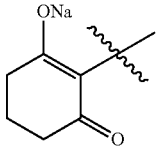 | Cl | 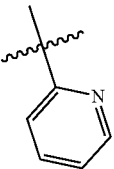 [SMILES: *c1ccccn1] | H |
| 680 | 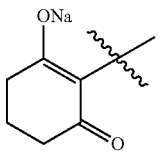 | Cl | 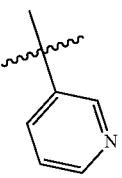 | H |
| 681 | 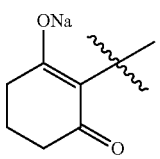 | Cl | 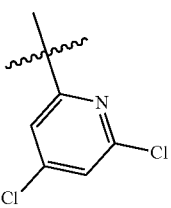 [SMILES: *c1cc(Cl)cc(Cl)n1] | H |
| 682 | 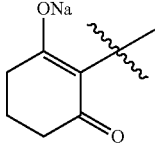 | Cl | 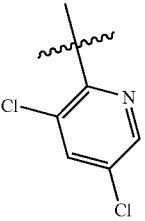 | H |
| 683 | 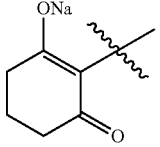 | Cl | 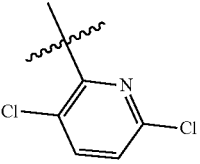 [SMILES: *c1nc(Cl)ccc1Cl] | H |
| 684 | 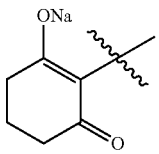 | Cl | 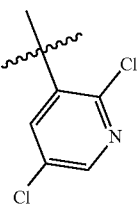 | H |
| 685 | 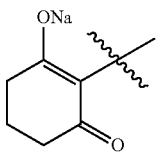 | Cl | 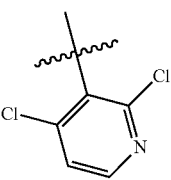 [SMILES: *c1c(Cl)ccnc1Cl] | H |

-continued

| Compound No. | Q | X | Y | Z |
|---|---|---|---|---|
| 686 | 3-ONa-2-yl-cyclohex-2-enone | Cl | 5,6-dichloropyridin-3-yl | H |
| 687 | 3-ONa-2-yl-cyclohex-2-enone | Cl | 2,6-dichloropyridin-3-yl | H |
| 688 | 3-ONa-2-yl-cyclohex-2-enone | Cl | 4,6-dichloropyridin-3-yl | H |
| 689 | 3-ONa-2-yl-cyclohex-2-enone | Cl | 2-chloro-3-fluoropyridin-4-yl | H |
| 690 | 3-ONa-2-yl-cyclohex-2-enone | Cl | pyridazin-4-yl | H |
| 691 | 3-ONa-2-yl-cyclohex-2-enone | Cl | pyrimidin-5-yl | H |
| 692 | 3-ONa-2-yl-cyclohex-2-enone | Cl | quinolin-8-yl | H |

-continued

| Compound No. | Q | X | Y | Z |
|---|---|---|---|---|
| 693 | 3-ONa-2-yl-cyclohex-2-enone | Cl | 7,3-dichloroquinolin-8-yl | H |
| 699 | 3-ONa-2-yl-cyclohex-2-enone | SMe | cyclopropyl | H |
| 700 | 3-ONa-2-yl-cyclohex-2-enone | SMe | OMe | H |
| 701 | 3-ONa-2-yl-cyclohex-2-enone | SMe | 3-ONa-2-yl-cyclohex-2-enone | H |
| 702 | 3-ONa-2-yl-cyclohex-2-enone | SPr | cyclopropyl | H |
| 703 | 3-ONa-2-yl-cyclohex-2-enone | SPr | cyclopropyl | H |
| 707 | 3-ONa-5-CF₃-2-yl-cyclohex-2-enone | Cl | cyclopropyl | H |
| 708 | bicyclo[2.2.2]octenone-ONa | Cl | CH₃ | H |
| 709 | bicyclo[2.2.2]octenone-ONa | Cl | n-butyl | H |

-continued

| Compound No. | Q | X | Y | Z |
|---|---|---|---|---|
| 710 | bicyclic ketone with ONa | Cl | pentyl | H |
| 711 | bicyclic ketone with ONa | Cl | hexyl | H |
| 712 | bicyclic ketone with ONa | Cl | sec-butyl branched | H |
| 713 | bicyclic ketone with ONa | Cl | neopentyl branched | H |
| 714 | bicyclic ketone with ONa | Cl | 3-methylbutyl branched | H |
| 715 | bicyclic ketone with ONa | Cl | 3-methylpentyl branched | H |
| 716 | bicyclic ketone with ONa | Cl | heptyl | H |

-continued

| Compound No. | Q | X | Y | Z |
|---|---|---|---|---|
| 717 | bicyclic ketone with ONa substituent | Cl | nonyl chain | H |
| 718 | bicyclic ketone with ONa substituent | Cl | undecyl chain | H |
| 719 | bicyclic ketone with ONa substituent | Cl | 2-methylprop-1-enyl | H |
| 720 | bicyclic ketone with ONa substituent | Cl | cyclopentyl | H |
| 721 | bicyclic ketone with ONa substituent | Cl | 2,2-difluorobutyl | H |
| 722 | bicyclic ketone with ONa substituent | Cl | 3,3,3-trifluoropropyl-substituted | H |
| 723 | bicyclic ketone with ONa substituent | Cl | pentafluoroethyl-substituted alkyl | H |

-continued

| Compound No. | Q | X | Y | Z |
|---|---|---|---|---|
| 724 | bicyclic ketone with ONa, attached via wavy bond | Cl | CH₂CH₂Cl with wavy bond | H |
| 725 | bicyclic ketone with ONa | Cl | CH₂OCH₃ with wavy bond | H |
| 726 | bicyclic ketone with ONa | Cl | CH₂CH₂OEt with wavy bond | H |
| 727 | bicyclic ketone with ONa | Cl | CH(CH₃)OCH₃ with wavy bond | H |
| 728 | bicyclic ketone with ONa | Cl | CH₂SCH₃ with wavy bond | H |
| 729 | bicyclic ketone with ONa | Cl | tetrahydrofuran-2-yl | H |
| 730 | bicyclic ketone with ONa | Cl | tetrahydropyran-4-yl | H |

-continued

| Compound No. | Q | X | Y | Z |
|---|---|---|---|---|
| 731 | bicyclic ketone with O-Na substituent | Cl | oxazol-4-yl | H |
| 732 | bicyclic ketone with O-Na substituent | Cl | thiazol-4-yl | H |
| 733 | 1,3-dimethyl-5-(NaO)-pyrazol-4-yl | Cl | sec-butyl (2-methylbutyl via CH) | H |
| 734 | 1,3-dimethyl-5-(NaO)-pyrazol-4-yl | Cl | 3-pentyl (CH(Et)₂) | H |
| 735 | 1,3-dimethyl-5-(NaO)-pyrazol-4-yl | Cl | 2-methylpentyl branch | H |
| 736 | 1,3-dimethyl-5-(NaO)-pyrazol-4-yl | Cl | heptyl branch | H |
| 737 | 1,3-dimethyl-5-(NaO)-pyrazol-4-yl | Cl | 3-cyanophenyl | H |
| 738 | 1,3-dimethyl-5-(NaO)-pyrazol-4-yl | Cl | thiophen-2-yl | H |

-continued

| Compound No. | Q | X | Y | Z |
|---|---|---|---|---|
| 739 | 4-ONa, 1,1-dimethyl-3,4-dihydronaphthalen-2(1H)-one-3-yl | Cl | pyrrolidin-1-yl | H |
| 741 | 3-ONa-2-yl-cyclohex-2-enone (methyl attachment) | Cl | cyclopropyl (methyl attachment) | H |
| 742 | 3-ONa-2-yl-cyclohex-2-enone (methyl attachment) | Cl | H | H |
| 743 | 3-ONa-2-yl-cyclohex-2-enone (methyl attachment) | Cl | $CF_3$ | H |
| 744 | 3-ONa-2-yl-cyclohex-2-enone (methyl attachment) | Cl | $CF_2CH_3$ | H |
| 745 | 3-ONa-2-yl-cyclohex-2-enone (methyl attachment) | Cl | $CF(CF_3)_2$ | H |
| 746 | 3-ONa-2-yl-cyclohex-2-enone (methyl attachment) | Cl | $CH_2CH_2CF_3$ | H |
| 747 | 3-ONa-2-yl-cyclohex-2-enone (methyl attachment) | Cl | $CH(CH_2Cl)CH_2CH_2Cl$ | H |
| 748 | 3-ONa-2-yl-cyclohex-2-enone (methyl attachment) | Cl | $C(=CH_2)CH_2CH_2Cl$ | H |

-continued

| Compound No. | Q | X | Y | Z |
|---|---|---|---|---|
| 749 | 3-ONa-cyclohex-2-enone | Cl | 1-fluorocyclopropyl | H |
| 750 | 3-ONa-cyclohex-2-enone | Cl | CH$_3$ | H |
| 751 | 3-ONa-cyclohex-2-enone | Cl | CH$_2$CH$_3$ | H |
| 752 | 3-ONa-cyclohex-2-enone | Cl | CH(CH$_3$)CH$_2$CH$_3$ | H |
| 753 | 3-ONa-cyclohex-2-enone | Cl | CH(CH$_3$)$_2$ | H |
| 754 | 3-ONa-cyclohex-2-enone | Cl | n-butyl | H |
| 755 | 3-ONa-cyclohex-2-enone | Cl | CH$_2$CH(CH$_3$)$_2$ | H |
| 756 | 3-ONa-cyclohex-2-enone | Cl | C(CH$_3$)$_3$ | H |
| 757 | 3-ONa-cyclohex-2-enone | Cl | n-pentyl | H |

-continued

| Compound No. | Q | X | Y | Z |
|---|---|---|---|---|
| 758 | 3-ONa-cyclohex-2-enone | Cl | tert-butyl | H |
| 759 | 3-ONa-cyclohex-2-enone | Cl | sec-butyl | H |
| 760 | 3-ONa-cyclohex-2-enone | Cl | 2-methylcyclopropyl | H |
| 761 | 3-ONa-cyclohex-2-enone | Cl | cyclopropylmethyl | H |
| 762 | 3-ONa-cyclohex-2-enone | Cl | cyclohexyl | H |
| 763 | 3-ONa-cyclohex-2-enone | Cl | tetrahydropyran-4-yl | H |
| 764 | 3-ONa-cyclohex-2-enone | Cl | methoxymethyl | H |
| 765 | 3-ONa-cyclohex-2-enone | Cl | methoxyethyl | H |
| 766 | 3-ONa-cyclohex-2-enone | Cl | ethoxymethyl | H |

-continued

| Compound No. | Q | X | Y | Z |
|---|---|---|---|---|
| 767 | 3-ONa, 2-yl cyclohex-2-enone | Cl | -CH(CH₃)CH₂OCH₃ | H |
| 768 | 3-ONa, 2-yl cyclohex-2-enone | Cl | -CH(CH₃)SCH₃ | H |
| 769 | 3-ONa, 2-yl cyclohex-2-enone | Cl | -CH(CH₃)CH₂SCH₃ | H |
| 770 | 3-ONa, 2-yl cyclohex-2-enone | Cl | 2-fluorophenyl | H |
| 771 | 3-ONa, 2-yl cyclohex-2-enone | Cl | 4-fluorophenyl | H |
| 772 | 3-ONa, 2-yl cyclohex-2-enone | Cl | 3-cyanophenyl | H |
| 773 | 3-ONa, 2-yl cyclohex-2-enone | Cl | 4-cyanophenyl | H |
| 774 | 3-ONa, 2-yl cyclohex-2-enone | Cl | 2,3-dichloropyridin-4-yl | H |

-continued
| Compound No. | Q | X | Y | Z |
|---|---|---|---|---|
| 775 | 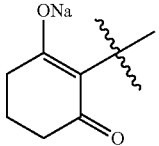 | Cl | 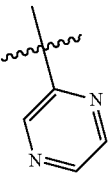 [SMILES: *c1cnccn1] | H |
| 776 | 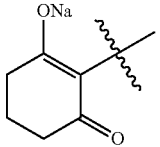 | Cl | 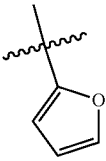 | H |
| 777 | 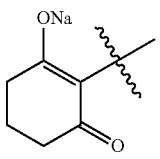 | Cl | 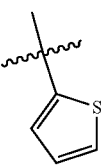 [SMILES: *c1cccs1] | H |
| 778 | 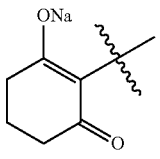 | Cl | 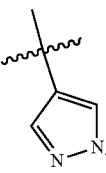 | H |
| 779 | 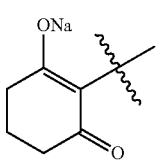 | Cl | 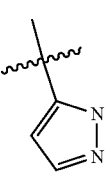 | H |
| 780 | 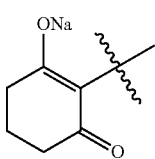 | Cl | 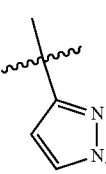 | H |
| 781 | 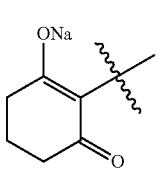 | Cl | 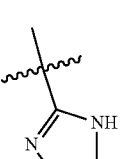 | H |
| 782 | 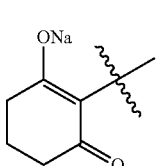 | Cl | 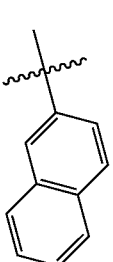 | H |

-continued

| Compound No. | Q | X | Y | Z |
|---|---|---|---|---|
| 783 | 3-ONa-2-yl-cyclohex-2-enone | Cl | isoquinolin-1-yl | H |
| 784 | 2,6-dioxocyclohexyl | SMe | isopropyl | H |
| 786 | 2,6-dioxocyclohexyl | Cl | CH₂OC(O)CH₃ | H |
| 787 | 2,6-dioxocyclohexyl | Cl | CH(CH₂Cl) | H |
| 789 | 3-ONa-bicyclo[2.2.2]oct-2-en-2-yl-one | Cl | sec-pentyl (CH(CH₃)CH₂CH₂CH₃) | H |
| 790 | 3-ONa-bicyclo[2.2.2]oct-2-en-2-yl-one | Cl | tert-butyl-CH | H |
| 791 | 3-ONa-bicyclo[2.2.2]oct-2-en-2-yl-one | Cl | cyclopropyl | H |
| 792 | 3-ONa-bicyclo[2.2.2]oct-2-en-2-yl-one | Cl | 1-methylcyclopropyl | H |
| 793 | 3-ONa-bicyclo[2.2.2]oct-2-en-2-yl-one | Cl | cyclohexyl-CH | H |

-continued

| Compound No. | Q | X | Y | Z |
|---|---|---|---|---|
| 794 | bicyclic enone with ONa | Cl | cyclopentenyl | H |
| 795 | bicyclic enone with ONa | Cl | thiophen-3-yl | H |
| 796 | bicyclic enone with ONa | Cl | thiophen-2-yl | H |
| 797 | bicyclic enone with ONa | Cl | isoxazol-3-yl | H |
| 798 | 1,3-dimethyl-5-ONa-pyrazol-4-yl | Cl | -C(CH$_3$)$_2$CH$_2$CF$_3$ | H |
| 799 | 1,3-dimethyl-5-ONa-pyrazol-4-yl | Cl | -C(CH$_3$)$_2$CH$_2$CH$_3$ | H |
| 800 | 1,3-dimethyl-5-ONa-pyrazol-4-yl | Cl | -C(CH$_3$)$_2$CH(CH$_3$)CH$_2$CH$_3$ | H |
| 801 | 1,3-dimethyl-5-ONa-pyrazol-4-yl | Cl | -C(CH$_3$)$_2$C(CH$_3$)$_3$ | H |

-continued

| Compound No. | Q | X | Y | Z |
|---|---|---|---|---|
| 802 | 1,3-dimethyl-5-ONa pyrazol-4-yl | Cl | 2-methyloctan-2-yl | H |
| 803 | 1,3-dimethyl-5-ONa pyrazol-4-yl | Cl | 2-methoxypropan-2-yl | H |
| 804 | 1,3-dimethyl-5-ONa pyrazol-4-yl | Cl | 1-ethoxy-2-methylpropan-2-yl | H |
| 805 | 1,3-dimethyl-5-ONa pyrazol-4-yl | Cl | 2-(4-cyanophenyl)propan-2-yl | H |
| 806 | 1,3-dimethyl-5-ONa pyrazol-4-yl | Cl | 2-(pyrazin-2-yl)propan-2-yl | H |
| 807 | 1,3-dimethyl-5-ONa pyrazol-4-yl | Cl | 2-(furan-2-yl)propan-2-yl | H |
| 808 | 1,3-dimethyl-5-ONa pyrazol-4-yl | Cl | 2-(thiophen-3-yl)propan-2-yl | H |
| 809 | 1,3-dimethyl-5-ONa pyrazol-4-yl | Cl | 2-(1-methyl-1H-pyrazol-4-yl)propan-2-yl | H |

-continued

| Compound No. | Q | X | Y | Z |
|---|---|---|---|---|
| 810 | 3-methyl-5-ONa-1-methyl-pyrazol-4-yl | Cl | 1-methyl-pyrazol-3-yl | H |
| 811 | 3-methyl-5-ONa-1-methyl-pyrazol-4-yl | Cl | 1-methyl-pyrazol-5-yl | H |
| 812 | 3-methyl-5-ONa-1-methyl-pyrazol-4-yl | Cl | 2,3-dichloropyridin-4-yl | H |
| 814 | 3-cyclopropyl-5-ONa-1-methyl-pyrazol-4-yl | Cl | cyclopropyl | H |
| 815 | (1,3-dimethylpyrazol-5-yl) 1-methyl-3-methyl-pyrazole-4-carboxylate linked | Cl | cyclopropyl | H |

4. A herbicidal composition, comprising (i) one or more of the substituted 1,2,4-triazolo[4,3-a]pyridine derivatives according to claim 1; optionally, further comprising (ii) one or more further herbicides and/or safeners, and/or (iii) one or more agrochemically acceptable formulation auxiliaries.

5. A method for controlling a weed comprising applying a herbicidally effective amount of at least one of the substituted 1,2,4-triazolo[4,3-a]pyridine derivatives according to claim 1 to a plant or a weed area.

6. A method for controlling a weed comprising applying a herbicidally effective amount of the herbicidal composition according to claim 4 to a plant or a weed area.

7. A method for controlling a weed comprising applying at least one of the substituted 1,2,4-triazolo[4,3-a]pyridine derivatives according to claim 1.

8. A method for controlling a weed comprising applying the herbicidal composition according to claim 4.

9. The method of claim 7, wherein the substituted 1,2,4-triazolo[4,3-a]pyridine derivatives being used for preventing and/or controlling a weed in a useful crop, wherein the useful crop is a transgenic crop or a crop treated by gene editing technique.

* * * * *

UNITED STATES PATENT AND TRADEMARK OFFICE
CERTIFICATE OF CORRECTION

PATENT NO. : 12,240,843 B2
APPLICATION NO. : 17/414501
DATED : March 4, 2025
INVENTOR(S) : Lei Lian et al.

It is certified that error appears in the above-identified patent and that said Letters Patent is hereby corrected as shown below:

In the Claims

In Claim 1, Column 459, Line 50, "$C_1$-$C_6$alkyl;" should read --$C_1$-$C_6$ alkyl;--.

In Claim 3, Column 530, Compound No. 334, column Y, "  " should read as --$CH_3$--.

In Claim 3, Column 530, Compound No. 335, column Y, "  " should read as --$CH_3$--.

In Claim 3, Column 544, Compound No. 413, column Y, " 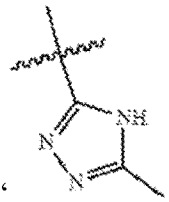 " should read as -- 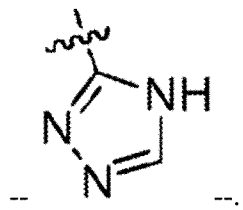 --.

Signed and Sealed this
Twenty-third Day of September, 2025

John A. Squires
*Director of the United States Patent and Trademark Office*

CERTIFICATE OF CORRECTION (continued)

In Claim 3, Column 567, Compound No. 531, column Q, " 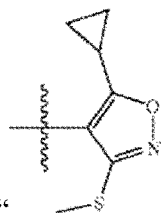 " should read as 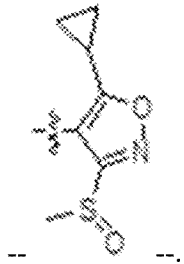 --.

In Claim 3, Column 627, Compound No. 812, column Q, " 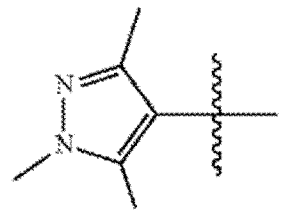 " should read as 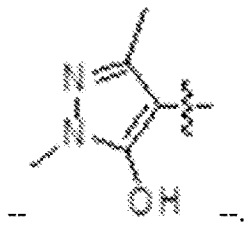 --.